(12) United States Patent
Boyd et al.

(10) Patent No.: US 7,153,855 B2
(45) Date of Patent: *Dec. 26, 2006

(54) PYRAZOLOPYRIDINYL PYRIMIDINE THERAPEUTIC COMPOUNDS

(75) Inventors: F. Leslie Boyd, Durham, NC (US); Kristjan Gudmundsson, Durham, NC (US); Brian A Johns, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 349 days.

This patent is subject to a terminal disclaimer.

(21) Appl. No.: 10/468,729

(22) PCT Filed: Mar. 5, 2002

(86) PCT No.: PCT/US02/06552

§ 371 (c)(1),
(2), (4) Date: Aug. 22, 2003

(87) PCT Pub. No.: WO02/072581

PCT Pub. Date: Sep. 19, 2002

(65) Prior Publication Data

US 2005/0049260 A1 Mar. 3, 2005

Related U.S. Application Data

(60) Provisional application No. 60/274,297, filed on Mar. 8, 2001.

(51) Int. Cl.
*C07D 471/04* (2006.01)
*A61K 31/435* (2006.01)
*C07D 401/04* (2006.01)

(52) U.S. Cl. .............. 514/235.8; 514/252.18; 514/274; 514/275; 544/122; 544/316; 544/331

(58) Field of Classification Search .............. 544/122, 544/316, 331; 514/235.8, 274, 252.18, 275
See application file for complete search history.

(56) References Cited

U.S. PATENT DOCUMENTS

| | | |
|---|---|---|
| 4,576,952 A | 3/1986 | Hurst et al. |
| 4,621,089 A | 11/1986 | Ward et al. |
| 4,670,432 A | 6/1987 | Ward et al. |
| 4,985,444 A | 1/1991 | Shiokawa et al. |
| 5,155,114 A | 10/1992 | Shiokawa et al. |
| 5,204,346 A | 4/1993 | Shiokawa et al. |
| 5,234,930 A | 8/1993 | Shiokawa et al. |
| 5,296,490 A | 3/1994 | Shiokawa et al. |
| 5,300,478 A | 4/1994 | Michaely et al. |
| 5,498,774 A | 3/1996 | Mitsudera et al. |
| 5,552,422 A | 9/1996 | Gauthier et al. |
| 5,700,816 A | 12/1997 | Isakson et al. |
| 5,773,530 A | 6/1998 | Akahane et al. |
| 5,990,148 A | 11/1999 | Isakson et al. |
| 6,136,839 A | 10/2000 | Isakson et al. |
| 6,207,675 B1 | 3/2001 | Carry et al. |
| 6,919,352 B1 | 7/2005 | Chamberlain et al. |
| 6,962,914 B1 | 11/2005 | Gudmundsson et al. |
| 2004/0053942 A1 | 3/2004 | Alberti et al. |

FOREIGN PATENT DOCUMENTS

| | | |
|---|---|---|
| EP | 0 364 204 A1 | 10/1989 |
| EP | 0 404 190 A1 | 6/1990 |
| EP | 0 404 190 B1 | 6/1990 |
| EP | 0 379 979 | 8/1990 |
| EP | 0 467 248 B1 | 7/1991 |
| EP | 0 497 258 A2 | 1/1992 |
| FR | 2 757 059 | 6/1998 |
| WO | WO 91 00092 | 1/1991 |
| WO | WO 91 19497 | 12/1991 |
| WO | WO 95 00501 | 1/1995 |
| WO | WO 96 06840 | 3/1996 |
| WO | WO 96 21667 | 7/1996 |
| WO | WO 96 31509 | 10/1996 |
| WO | WO 96 41625 | 12/1996 |
| WO | WO 96 41626 | 12/1996 |
| WO | WO 96 41645 | 12/1996 |
| WO | WO 98 56377 | 12/1998 |
| WO | WO 99 12930 | 3/1999 |
| WO | WO 99/58523 | 11/1999 |
| WO | WO 99/59585 | 11/1999 |

(Continued)

OTHER PUBLICATIONS

Bosseray et al., PubMed Abstract (Pathol Biol (Paris) 50(8):483-92), Oct. 2002.*

(Continued)

*Primary Examiner*—Deepak Rao
(74) *Attorney, Agent, or Firm*—Lorie Ann Morgan

(57) ABSTRACT

The present invention provides compounds of formula (I):

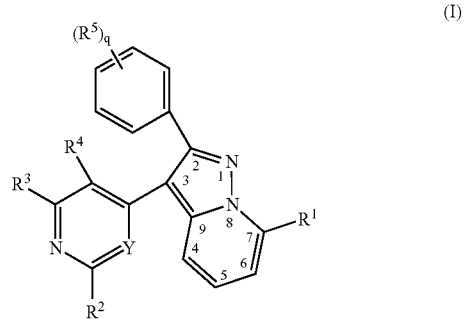

pharmaceutical compositions containing the same, processes for preparing the same and their use as pharmaceutical agents.

20 Claims, No Drawings

FOREIGN PATENT DOCUMENTS

| WO | WO 99 64419 | 12/1999 |
|---|---|---|
| WO | WO 00/26216 | 5/2000 |
| WO | WO 00/52008 | 9/2000 |
| WO | WO 01/00615 | 1/2001 |
| WO | WO 01 14375 | 3/2001 |
| WO | WO 02/16359 | 2/2002 |
| WO | WO 02 16359 | 2/2002 |
| WO | WO 02/18382 | 3/2002 |
| WO | WO 02 48147 | 6/2002 |
| WO | WO 02/048148 | 6/2002 |
| WO | WO 02 066481 | 8/2002 |
| WO | WO 03/00682 | 1/2003 |

OTHER PUBLICATIONS

Razonable et al., PubMed Abstract (Herpes 10(3):60-5), Dec. 2003.*

Vippagunta et al., Crystalline Solids, Advanced Drug Delivery Reviews 48:3-26, 2001.*

West, Solid Solutions, Solid State Chemistry and Its Applications, pp. 365, 1988.*

Douglas, Jr. Introduction to Viral Diseases, Cecil Textbook of Medicine, 20th Edition, vol. 2, pp. 1739-1747, 1996.*

Vane, J. et al. "Towards a Better Aspirin." Nature, vol. 367, Jan. 20, 1994, pp. 215-216.

Carter, J. et al. "Recently Reported Inhibitors of Cyclooxygenase-2." Exp. Opin. Ther. Patents (1998), 8(1), pp. 21-29.

Talley, J.J., "Review, Pulmonary-Allergy, Dermatological, Gastrointestinal & Arthritis, Selective Inhibitors of Cyclooxygenase-2." Exp. Opin. Ther. Patents (1997) 7(1), pp. 55-62.

Roy, P., "A New Series of Selective Cox-2 Inhibitors: 5,6-Diarylthiazolo [3,2-b][1,22,4] Triazoles," *Bioorganiz & Med. Chem. Ltrs.*, vol. 7, No. 1, 1997, pp. 57-62.

Therien, Michael, Synthesis and Biological Evaluation of 5, 6-Diarylimidazo[2.1-b]Thiazole As Selective Cox-2 Inhibitors, *Bioorganic & Med. Chem. Ltrs.*, vol 7, No. 1, 1997, pp. 47-52.

Akahane, Atsushi, "Discovery of 6-Oxo-3-(2-Phenlypyrazolo[1,5-a]pyridin-3-yl)-1(6H)-pyridazinebutanoic Acid (FR 838): A Novel Xanthine Adenosine $A_1$ Receptor Antagonist with Potent Diuretic Activity," *Journal of Medicinal Chemistry*, vol. 42, No. 5, 1999, pp. 779-783.

Talley, John J., 5 Selective Inhibitors of Cyclooxygenase-2 (COX-2) *Progress in Medicinal Chemistry*, vol. 36, (1999): pp. 201-234.

Boehm, J.C., et al. "1-Substituted 4-Aryl-5-pyridinylimidazoles: A New Class of Cytokine Suppressive Drugs with Low 5-Lipoxygenase and Cyclooxygenase Inhibitory Potency." J. Med. Chem. 1996, 39, pp. 3929-3937.

Hanson, G.J., et al. "Pulmonary-Allergy, Dermatological, Gastrointestinal & Arthritis, Inhibitors of p38 kinase." Expert Opinion Ther. Patents, 1997, 7(7):729-733.

Roizman et al., "The Family Herpesviridae: A Brief Introduction," *Fields Virology* vol. 2, 4th Edition, pp. 2381-2397, 2001.

* cited by examiner

PYRAZOLOPYRIDINYL PYRIMIDINE THERAPEUTIC COMPOUNDS

CROSS REFERENCES TO RELATED APPLICATIONS

This application is a 371 Application of PCT/US02/06552, filed 5 Mar. 2002, which claims priority to U.S. Application Ser. No. 60/274,297, filed 8 Mar. 2001.

BACKGROUND OF THE INVENTION

The present invention relates to novel compounds, pharmaceutical formulations comprising these compounds, and the use of these compounds in therapy. More particularly, the present invention relates to compounds for the prophylaxis and treatment of herpes viral infections.

Of the DNA viruses, those of the herpes group are the sources of the most common viral illnesses in man. The group includes herpes simplex virus types 1 and 2 (HSV), varicella zoster virus (VZV), cytomegalovirus (CMV), Epstein-Barr virus (EBV), human herpes virus type 6 (HHV-6), human herpes virus type 7 (HHV-7) and human herpes virus type 8 (HHV-8). HSV-1 and HSV-2 are some of the most common infectious agents of man. Most of these viruses are able to persist in the host's neural cells; once infected, individuals are at risk of recurrent clinical manifestations of infection which can be both physically and psychologically distressing.

Herpes simplex viruses (HSV-1 and -2) are the causative agents of herpes labialis and genital herpes. HSV infection is often characterised by extensive and debilitating lesions of the skin, mouth and/or genitals. Primary infections may be subclinical although tend to be more severe than infections in individuals previously exposed to the virus. Ocular infection by HSV can lead to keratitis or cataracts thereby endangering the host's sight. Infection in the new-born, in immunocompromised patients or penetration of the infection into the central nervous system can prove fatal. In the US alone, 40 million individuals are infected with HSV-2, a number that is expected to increase to 60 million by 2007. Over 80% of individuals infected with HSV-2 are unaware they carry and spread the virus, and of those diagnosed less than 20% received oral therapies. The net result is that less than 5% of the infected population are treated. Likewise of the 530 million individuals worldwide who carry HSV-1, 81% of the symptomatic population remain untreated. No cure exists for HSV infection, and once infected, individuals carry the virus for life in a dormant state. Reactivation of the virus from latency occurs periodically and may be triggered by stress, environmental factors, and/or suppression of the host immune system. Currently, the use of nucleoside analogs such as valaciclovir (VALTREX®) and aciclovir (ZOVIRAX®) is the standard of care for managing genital herpes virus outbreaks.

Varacella zoster virus (VZV) (also know as herpes zoster virus) is a herpes virus which causes chickenpox and shingles. Chickenpox is the primary disease produced in a host without immunity, and in young children is usually a mild illness characterised by a vesicular rash and fever. Shingles or zoster is the recurrent form of the disease which occurs in adults who were previously infected with VZV. The clinical manifestations of shingles are characterised by neuralgia and a vesicular skin rash that is unilateral and dermatomal in distribution. Spread of inflammation may lead to paralysis or convulsions. Coma can occur if the meninges become affected. VZV is of serious concern in patients receiving immunosuppressive drugs for transplant purposes or for treatment of malignant neoplasia and is a serious complication of AIDS patients due to their impaired immune system.

In common with other herpes viruses, infection with CMV leads to a lifelong association of virus and host. Congenital infection following infection of the mother during pregnancy may give rise to clinical effects such as death or gross disease (microcephaly, hepatosplenomegaly, jaundice, mental retardation), retinitis leading to blindness or, in less severe forms, failure to thrive, and susceptibility to chest and ear infections. CMV infection in patients who are immunocompromised for example as a result of malignancy, treatment with immunosuppressive drugs following transplantation or infection with Human Immunodeficiency Virus, may give rise to retinitis, pneumonitis, gastrointestinal disorders and neurological diseases. CMV infection is also associated with cardiovascular diseases and conditions including restenosis and atherosclerosis.

The main disease caused by EBV is acute or chronic infectious mononucleosis (glandular fever). Examples of other EBV or EBV associated diseases include lymphoproliferative disease which frequently occurs in persons with congenital or acquired cellular immune deficiency, X-linked lymphoproliferative disease which occurs namely in young boys, EBV-associated B-cell tumours, Hodgkin's disease, nasopharyngeal carcinoma, Burkitt lymphoma, non-Hodgkin lymphoma, thymomas and oral hairy leukoplakia. EBV infections have also been found in association with a variety of epithelial-cell-derived tumours of the upper and lower respiratory tracts including the lung. EBV infection has also been associated with other diseases and conditions including chronic fatigue syndrome, multiple sclerosis and Alzheimer's disease.

HHV-6 has been shown to be a causative agent of infantum subitum in children and of kidney rejection and interstitial pneumonia in kidney and bone marrow transplant patients, respectively, and may be associated with other diseases such as multiple sclerosis. There is also evidence of repression of stem cell counts in bone marrow transplant patients. HHV-7 is of undetermined disease aetiology.

Hepatitis B virus (HBV) is a viral pathogen of world-wide major importance. The virus is aetiologically associated with primary hepatocellular carcinoma and is thought to cause 80% of the world's liver cancer. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

BRIEF SUMMARY OF THE INVENTION

According to a first aspect of the invention there is provided the compound of formula (I):

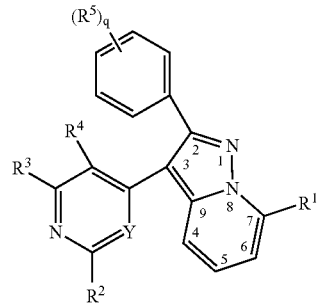

wherein:

R¹ is selected from the group consisting of halo, —NR⁷R⁸, Ay, —NR⁷Ay, Het, —NHR¹⁰Het, NHHet and —NHR¹⁰Ay;

each R⁷ and R⁸ are the same or different and are independently selected from the group consisting of H, alkyl, cycloalkyl, alkenyl, cycloalkenyl, —R¹⁰cycloalkyl, —R¹⁰OR⁹, —R¹⁰NR⁹R¹¹, —R¹⁰C(O)R⁹, —C(O)R⁹, —C(O)R¹⁰Ay, —C(O)R¹⁰Het, —CO₂R⁹, —R¹⁰CO₂R⁹, —C(O)NR⁹R¹¹, —R¹⁰C(O)NR⁹R¹¹, —R¹⁰C(O)Ay, —R¹⁰C(O)Het, —C(S)NR⁹R¹¹, —R¹⁰C(S)NR⁹R¹¹, —R¹⁰NHC(NH)NR⁹R¹¹, —R¹⁰NHC(O)R¹⁰Het, —R¹⁰NHC(O)R¹⁰CO₂R⁹, —R¹⁰NHC(NCO₂R⁹)NHCO₂R⁹, —R¹⁰NHC(O)NHSO₂R⁹, —R¹⁰NHC(O)NHSO₂Ay, —R¹⁰NHC(O)NHSO₂Het, —R¹⁰C(NH)NR⁹R¹¹, —C(NH)NR⁹R¹¹, —SO₂NR⁹R¹¹, —R¹⁰SO₂NR⁹R¹¹, —R¹⁰NHSO₂R⁹, —SO₂R¹⁰, —R¹⁰SO₂R¹⁰, —R¹⁰NHCOR⁹, —R¹⁰SO₂NHCOR⁹, —R¹⁰NHP(O)(OR⁹)₂, —R₁₀OP(O)(OR⁹)₂ and —R¹⁰OP(O)(OR¹⁰Ay)₂;

each R⁹ and R¹¹ are the same or different and are independently selected from the group consisting of H, alkyl, cycloalkyl, —R¹⁰cycloalkyl, —R¹⁰OH, —R₁₀(OR¹⁰)ᵥᵥ where w is 1–10, and —R¹⁰NR¹⁰R¹⁰;

each R¹⁰ is the same or different and is independently selected from the group consisting of alkyl, cycloalkyl, alkenyl, cycloalkenyl, and alkynyl;

Ay is aryl;

Het is a 5- or 6-membered heterocyclic or heteroaryl group;

R² is selected from the group consisting of halo, alkyl, cycloalkyl, alkenyl, cycloalkenyl, —NR⁷R⁸, —OR⁷, —OAy, —S(O)ₙR⁹, —S(O)ₙAy, —R¹⁰NR⁷R⁸, —R¹⁰NR⁷Ay, Ay, Het, —NHHet, —NHR¹⁰Het, —OHet and —OR¹⁰Het;

n is 0, 1 or 2;

Y is N or CH;

R³ and R⁴ are the same or different and are each independently selected from the group consisting of H, halo, alkyl, cycloalkyl, alkenyl, Ay, —OR⁷, —OAy, —R¹⁰OR⁷, —R¹⁰OAy, —NR⁷R⁸, —NR⁷Ay, —R¹⁰NR⁷R⁸, —R¹⁰NR⁷Ay, —C(O)R⁷, —C(O)Ay, —CO₂R⁷, —CO₂Ay, —SO₂NHR⁹, Het, —NHHet and NHR¹⁰Het;

q is 0, 1, 2, 3, 4 or 5; and each R⁵ is the same or different and is independently selected from the group consisting of halo, alkyl, alkenyl, alkynyl, cycloalkyl, cycloalkenyl, —R¹⁰cycloalkyl, Ay, —NHR¹⁰Ay, Het, —NHHet, —NHR¹⁰Het, —OR⁷, —OAy, —OHet, —R¹⁰OR⁹, —NR⁷R⁸, —NR⁷Ay, —R¹⁰NR⁷R⁸, —R¹⁰NR⁷Ay, —R¹⁰C(O)R⁹, —C(O)R⁹, —CO₂R⁹, —R¹⁰CO₂R⁹, —C(O)NR⁷R⁸, —C(O)Ay, —C(O)NR⁷Ay, —C(O)Het, —C(O)NHR¹⁰Het, —R¹⁰C(O)NR⁹R¹¹, —C(S)NR⁹R¹¹, —R¹⁰C(S)NR⁹R¹¹, —R¹⁰NHC(NH)NR⁹R¹¹, —C(NH)NR⁷R⁸, —R¹⁰C(NH)NR⁹R¹¹, —S(O)₂NR⁷R⁸, —S(O)₂NR⁷Ay, —R¹⁰SO₂NHCOR⁹, —R¹⁰SO₂NR⁹R¹¹, —R¹⁰SO₂R⁹, —S(O)ₙR⁹, cyano, nitro and azido; or two adjacent R⁵ groups together with the atoms to which they are attached form a C₅₋₆ cycloalkyl or aryl;

wherein when q is 1 and R⁵ is in the para position, R⁵ is not halo;

wherein when Y is CH, R³ is not —NR⁷Ay;

and pharmaceutically acceptable salts, solvates and physiologically functional derivatives thereof.

In another aspect of the invention there is provided a pharmaceutical composition comprising a compound of formula (I). In one embodiment, the pharmaceutical composition further comprises a pharmaceutically acceptable carrier or diluent. In one embodiment, the pharmaceutical composition further comprises an antiviral agent selected from the group consisting of aciclovir and valacicilovir.

In a third aspect of the invention, there is provided a method for the prophylaxis or treatment of herpes viral infections in an animal. The method comprises administering to the animal a therapeutically effective amount of a compound of formula (I) or a pharmaceutically acceptable salt, solvate or physiologically functional derivative thereof. The herpes viral infection can be any of herpes simplex virus 1, herpes simplex virus 2, cytomegalovirus, Epstein Barr virus, varacella zoster virus, human herpes virus 6, human herpes virus 7, and human herpes virus 8.

In a fourth aspect, there is provided a method for the treatment or prophylaxis of conditions or diseases associated with herpes viral infections in an animal. The method comprises administering to the animal a therapeutically effective amount of a compound of formula (I) or a salt, solvate or physiologically functional derivative thereof.

In another aspect, there is provided a process for preparing the compounds of formula (I) wherein Y is N, R² is selected from the group consisting of alkyl, cycloalkyl, alkenyl, cycloalkenyl, Ay, —NR⁷R⁸, —OR⁷, —OAy, —S(O)ₙR⁹, —S(O)ₙAy, —R¹⁰NR⁷R⁸, —R¹⁰NR⁷Ay, Het, —NHHet, —NHR¹⁰Het, —OHet, and —OR¹⁰Het; and R³ and R⁴ are H. The process comprises reacting a compound of formula (IX):

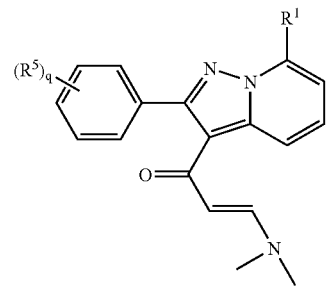

IX with an amine of formula (X):

X

In another aspect, the present invention provides a process for preparing the compounds of formula (I) wherein Y is N, R² is selected from the group consisting of H, alkyl, cycloalkyl, alkenyl, cycloalkenyl, Ay, —NR⁷R⁸, —OR⁷, —OAy, —S(O)ₙR⁹, —S(O)ₙAy, —R¹⁰NR⁷R⁸, —R¹⁰NR⁷Ay, Het, —NHHet, —NHR¹⁰Het, —OHet, and —OR¹⁰Het; R³ is selected from the group consisting of H, alkyl, cycloalkyl, alkenyl, —R¹⁰OR⁷, —R¹⁰OAy, —NR⁷R⁸ where R⁷ and R⁸ are not H, Ay, —NR⁷Ay where R⁷ is not H, —R¹⁰NR⁷R⁸, —R¹⁰NR⁷Ay, —C(O)R⁷, —C(O)Ay, —CO₂R⁷, —CO₂Ay, —SO₂NHR⁹ and Het; and R⁴ is H. The process comprises reacting a compound of formula (XVI):

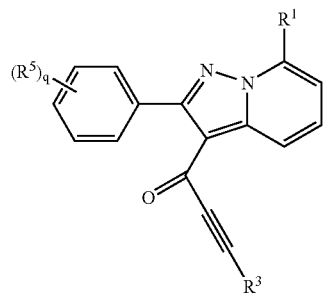

XVI with an amine of formula (X):

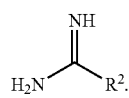

X

In another aspect, the present invention provides a process for preparing the compounds of formula (I) wherein Y is N and R² is selected from the group consisting of alkyl, cycloalkyl, alkenyl, cycloalkenyl, Ay, —NR⁷R⁸, —OR⁷, —OAy, —S(O)ₙR⁹, —S(O)ₙAy, —R¹⁰NR⁷R⁸, R¹⁰NR⁷R⁸, Het, —NHHet, —NHR¹⁰Het, —OHet, and —OR¹⁰Het. The process comprises the steps of:

a) reacting a compound of formula (XX):

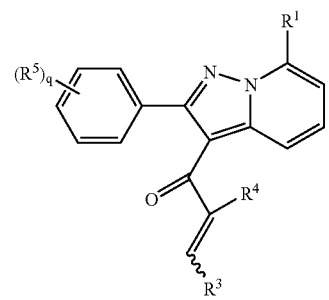

XX with an amine of formula (X):

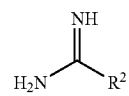

X to prepare an intermediate compound; and b) oxidizing the intermediate compound.

In another aspect, the present invention provides a process for preparing the compounds of formula (I). The process comprises reacting a compound of formula (XXII):

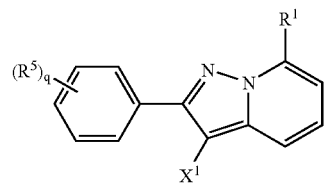

XXII with a compound of formula XXIV:

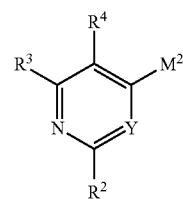

XXIV wherein X¹ is chloro, bromo or iodo; and M² is selected from the group consisting of —B(OH)₂, —B(ORa)₂, —B(Ra)₂, —Sn(Ra)₃, Zn-halide, ZnRa, and Mg-halide, where Ra is alkyl or cycloalkyl and halide is halo.

In another aspect, the present invention provides a process for preparing compounds of formula (VI):

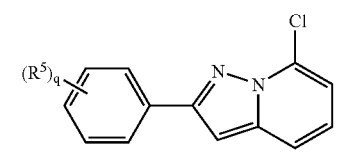

VI wherein when q is 1 and R⁵ is in the para position, R⁵ is not halo.

The process comprises rearranging the compound of formula (V):

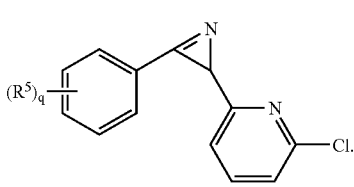

V

As another aspect, the present invention provides a process for preparing compounds of formula (XXII-B)

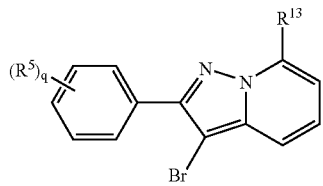

XXII-B wherein R$^{13}$ is selected from the group consisting of —NR$^7$R$^8$, —NR$^7$Ay, Het, —NHR$^{10}$Het, —NHHet and —NHR$^{10}$Ay and wherein when q is 1 and R$^5$ is in the para position, R$^5$ is not halo. The process comprises reacting a compound of formula (XXII-A):

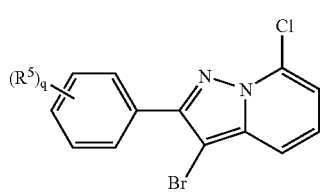

XXII-A with a compound of formula H—R$^{13}$.

In another aspect, the present invention provides a radiolabeled compound of formula (I) or a pharmaceutically acceptable salt, solvate or physiologically functional derivative thereof. In one embodiment, the present invention provides a tritiated compound of formula (I) or a pharmaceutically acceptable salt, solvate or physiologically functional derivative thereof. In another aspect, the present invention provides a biotinylated compound of formula (I) or a pharmaceutically acceptable salt, solvate or physiologically functional derivative thereof.

In another aspect, the present invention provides a compound of formula (I) for use in therapy.

In yet another aspect, the present invention provides the use of a compound of formula (I) for the prophylaxis or treatment of herpes viral infections.

In yet another aspect, the present invention provides a compound of formula (I) for the prophylaxis or treatment of conditions or diseases associated with herpes viral infections in an animal.

In yet another aspect, the present invention provides the use of a compound of formula (I) for the preparation of a medicament for the prophylaxis or treatment of herpes viral infections in animals, preferrably humans.

In yet another aspect, the present invention provides the use of a compound of formula (I) for the preparation of a medicament for the treatment or prophylaxis of diseases or conditions associated with herpes viral infections in animals, preferrably humans.

In yet another aspect, the present invention provides a pharmaceutical composition comprising a compound of formula (I) for use in the prophylaxis or treatment of herpes viral infections in an animal.

DETAILED DESCRIPTION OF THE INVENTION

As used herein, "a compound of the invention" means a compound of formula (I) or a pharmaceutically acceptable salt, solvate, or physiologically functional derivative thereof. Similarly, with respect to isolatable intermediates such as compounds of formula (VI), (IX), (XVI), (XX), (XXII) and (XXII-B), the phrase "a compound of formula (number)" means a compound having that formula and pharmaceutically acceptable salts, solvates and physiologically functional derivatives thereof.

As used herein, the terms "alkyl" and "alkylene" refer to straight or branched hydrocarbon chains containing from 1 to 8 carbon atoms. Examples of "alkyl" as used herein include, but are not limited to, methyl, ethyl, n-propyl, n-butyl, n-pentyl, isobutyl, isopropyl, and tert-butyl. Examples of "alkylene" as used herein include, but are not limited to, methylene, ethylene, propylene, butylene, and isobutylene. "Alkyl also includes substituted alkyl (alkylene). The alkyl groups may be optionally substituted one or more times with a substituent selected from the group consisting of mercapto, nitro, cyano and halo. Trihalomethyl, such as trifluoromethyl is one particularly preferred alkyl group.

As used herein, the term "cycloalkyl" refers to a non-aromatic carbocyclic ring having from 3 to 8 carbon atoms and no carbon-carbon double bonds. "Cycloalkyl" includes by way of example cyclopropyl, cyclobutyl, cyclopentyl, cyclohexyl, cycloheptyl and cyclooctyl. "Cycloalkyl" also includes substituted cycloalkyl. The cycloalkyl may optionally be substituted on an available carbon with one or more substituents selected from the group consisting of mercapto, nitro, cyano, halo, and alkyl.

As used herein, the term "alkenyl" refers to straight or branched hydrocarbon chains containing from 2 to 8 carbon atoms and at least one and up to three carbon-carbon double bonds. Examples of "alkenyl" as used herein include, but are not limited to ethenyl and propenyl. "Alkenyl" also includes substituted alkenyl. The alkenyl groups may optionally be substituted on an available carbon with one or more substituents selected from the group consisting of mercapto, nitro, cyano, halo, and alkyl.

As used herein, the term "cycloalkenyl" refers to refers to a non-aromatic carbocyclic ring having from 3 to 8 carbon atoms (unless otherwise specified) and up to 3 carbon-carbon double bonds. "Cycloalkenyl" includes by way of example cyclobutenyl, cyclopentenyl and cyclohexenyl. "Cycloalkenyl" also includes substituted cycloalkenyl. The cycloalkenyl may optionally be substituted on an available carbon with one or more substituents selected from the group consisting of mercapto, nitro, cyano, halo, and alkyl.

As used herein, the term "alkynyl" refers to straight or branched hydrocarbon chains containing from 2 to 8 carbon atoms and at least one and up to three carbon-carbon triple bonds. Examples of "alkynyl" as used herein include, but are not limited to ethynyl and propynyl. "Alkynyl" also includes substituted alkynyl. The alkynyl groups may optionally be substituted on an available carbon with one or more substituents selected from the group consisting of mercapto, nitro, cyano, and halo.

The term "halo" or "halogen" refers to the elements fluorine, chlorine, bromine and iodine.

The term "aryl" refers to monocyclic carbocyclic groups and fused bicyclic carbocyclic groups having from 5 to 12 carbon atoms and having at least one aromatic ring. Examples of particular aryl groups include but are not limited to phenyl, and naphthyl. "Aryl" also includes substituted aryl. Aryl groups may be optionally substituted on an available carbon with one or more substituents selected from the group consisting of halo, alkyl (including perhaloalkyl), alkenyl, cycloalkyl, cycloalkenyl, alkoxy, cycloalkoxy, amino, mercapto, hydroxy, alkylhydroxy, alkylamine, cycloalkylamine, carboxy, carboxamide, sulfonamide, Het, amidine, cyano, nitro and azido. Preferred aryl groups according to the invention include but are not limited to phenyl and substituted phenyl.

The term "heterocyclic" (or "heterocycle") refers to a monocyclic saturated or unsaturated non-aromatic groups and fused bicyclic non-aromatic groups, having the specified number of members (total carbon atoms and heteroatoms) and containing 1, 2, 3 or 4 heteroatoms selected from N, O and S. Examples of particular heterocyclic groups include but are not limited to tetrahydrofuran, dihydropyran, tetrahydropyran, pyran, oxetane, thietane, 1,4-dioxane, 1,3-dioxane, 1,3-dioxalane, piperidine, piperazine, tetrahydropyrimidine, pyrrolidine, morpholine, thiomorpholine, thiazolidine, oxazolidine, tetrahydrothiopyran, tetrahydrothiophene, and the like. "Heterocyclic" also refers to substituted heterocyclic. The heterocyclic group may be optionally substituted on any available carbon or heteroatom, with one or more substituents selected from the group consisting of halo, alkyl (including perhaloalkyl), alkenyl, cycloalkyl, cycloalkenyl, alkoxy, cycloalkoxy, amino, mercapto, hydroxy, alkylhydroxy, alkylamine, cycloalkylamine, carboxy, carboxamide, sulfonamide, Het, amidine, cyano, nitro and azido. Preferred heterocyclic groups according to the invention include but are not limited to pyrrolidine, piperidine, morpholine, thiomorpholine and piperazine and substituted variants thereof.

The term "heteroaryl" refers to aromatic monocyclic groups and aromatic fused bicyclic groups having the specified number of members (total carbon atoms and heteroatoms) and containing 1, 2, 3, or 4 heteroatoms selected from N, O and S. Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole. "Heteroaryl" also includes substituted heteroaryl. The heteroaryl group may be optionally substituted on any available carbon or heteroatom with one or more substituents selected from the group consisting of halo, alkyl (including perhaloalkyl), alkenyl, cycloalkyl, cycloalkenyl, alkoxy, cycloalkoxy, amino, mercapto, hydroxy, alkylhydroxy, alkylamine, cycloalkylamine, carboxy, carboxamide, sulfonamide, Het, amidine cyano, nitro and azido. Preferred heteroaryl groups according to the invention include but are not limited to pyridine, furan, thiophene, pyrrole, imidazole, pyrazole, and pyrimidine and substituted variants thereof.

As used herein, the term "optionally" means that the subsequently described event(s) may or may not occur, and includes both event(s) which occur and events that do not occur.

The present invention provides compounds of formula (I):

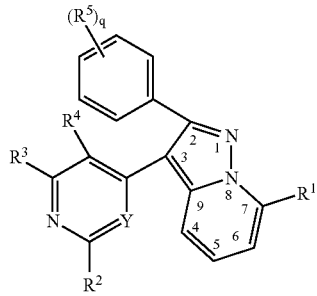

wherein:

$R^1$ is selected from the group consisting of halo, —$NR^7R^8$, Ay, —$NR^7Ay$, Het, —$NHR^{10}Het$, —NHHet and —$NHR^{10}Ay$;

each $R^7$ and $R^8$ are the same or different and are independently selected from the group consisting of H, alkyl, cycloalkyl, alkenyl, cycloalkenyl, —$R^{10}$cycloalkyl, —$R^{10}OR^9$, —$R^{10}NR^9R^{11}$, —$R^{10}C(O)R^9$, —C(O)$R^9$, —C(O)$R^{10}Ay$, —C(O)$R^{10}Het$, —$CO_2R^9$, —$R^{10}CO_2R^9$, —C(O)$NR^9R^{11}$, —$R^{10}C(O)NR^9R^{11}$, —$R^{10}OC(O)Ay$, —$R^{10}C(O)Het$, —C(S)$NR^9R^{11}$, —$R^{10}C(S)NR^9R^{11}$, —$R^{10}NHC(NH)NR^9R^{11}$, —$R^{10}NHC(O)R^{10}Het$, —$R^{10}NHC(O)R^{10}CO_2R^9$, —$R^{10}NHC(NCO_2R^9)NHCO_2R^9$, —$R^{10}NHC(O)NHSO_2R^9$, —$R^{10}NHC(O)NHSO_2Ay$, —$R^{10}NHC(O)NHSO_2Het$, —$R^{10}C(NH)NR^9R^{11}$, —C(NH)$NR^9R^{11}$, —$SO_2NR^9R^{11}$, —$R^{10}SO_2NR^9R^{11}$, —$R^{10}NHSO_2R^9$, —$SO_2R^{10}$, —$R^{10}SO_2R^{10}$, —$R^{10}NHCOR^9$, —$R^{10}SO_2NHCOR^9$, —$R^{10}NHP(O)(OR^9)_2$, —$R_{10}OP(O)(OR^9)_2$ and —$R^{10}OP(O)(OR^{10}Ay)_2$;

each $R^9$ and $R^{11}$ are the same or different and are independently selected from the group consisting of H, alkyl, cycloalkyl, —$R^{10}$cycloalkyl, —$R^{10}OH$, —$R_{10}(OR^{10})_w$ wherein w is 1–10, and —$R^{10}NR^{10}R^{10}$;

each $R^{10}$ is the same or different and is independently selected from the group consisting of alkyl, cycloalkyl, alkenyl, cycloalkenyl and alkynyl;

Ay is aryl;

Het is a 5- or 6-membered heterocyclic or heteroaryl group;

$R^2$ is selected from the group consisting of halo, alkyl, cycloalkyl, alkenyl, cycloalkenyl, —$NR^7R^9$, —$OR^7$, —OAy, —S(O)$_nR^9$, —S(O)$_nAy$, —$R^{10}NR^7R^8$, —$R^{10}NR^7Ay$, Ay, Het, —NHHet, —$NHR^{10}Het$, —OHet and —$OR^{10}Het$;

n is 0, 1 or 2;

Y is N or CH;

$R^3$ and $R^4$ are the same or different and are each independently selected from the group consisting of H, halo, alkyl, cycloalkyl, alkenyl, Ay, —$OR^7$, —OAy, —$R^{10}OR^7$, —$R^{10}OAy$, —$NR^7R^8$, —$NR^7Ay$, —$R^{10}NR^7R^8$, —$R^{10}NR^7Ay$, —C(O)$R^7$, —C(O)Ay, —$CO_2R^7$, —$CO_2Ay$, —$SO_2NHR^9$, Het, —NHHet and —$NHR^{10}Het$; and q is 0, 1, 2, 3, 4 or 5; and each $R^5$ is the same or different and is independently selected from the group consisting of halo, alkyl, alkenyl, alkynyl, cycloalkyl, cycloalkenyl, —$R^{10}$cycloalkyl, Ay, —NHR$^{10}$Ay, Het, —NHHet, —NHR$^{10}$Het, —OR$^7$, —OAy, —OHet, —$R^{10}$OR$^9$, —NR$^7$R$^9$, —NR$^7$Ay, —$R^{10}$NR$^7$R$^8$, —$R^{10}$NR$^7$Ay, —$R^{10}$C(O)R$^9$, —C(O)R$^9$, —CO$_2$R$^9$, —$R^{10}$CO$_2$R$^9$, —C(O)NR$^7$R$^8$, —C(O)Ay, —C(O)NR$^7$Ay, —C(O)Het, —C(O)NHR$^{10}$Het —$R^{10}$C(O)NR$^9$R$^{11}$, —C(S)NR$^9$R$^{11}$, —$R^{10}$C(S)NR$^9$R$^{11}$, —$R^{10}$NHC(NH)NR$^9$R$^{11}$, —C(NH)NR$^7$R$^8$, —C(NH)NR$^7$Ay, —$R^{10}$C(NH)NR$^9$R$^{11}$, —S(O)$_2$NR$^7$R$^8$, —S(O)$_2$NR$^7$Ay, —$R^{10}$SO$_2$NHCOR$^9$, —$R^{10}$SO$_2$NR$^9$R$^{11}$, —$R^{10}$SO$_2$R$^9$, —S(O)$_n$R$^9$, cyano, nitro and azido; or two adjacent $R^5$ groups together with the atoms to which they are bonded form a $C_{5-6}$ cycloalkyl or aryl;

wherein when q is 1 and $R^5$ is in the para position, $R^5$ is not halo; and wherein when Y is CH, $R^3$ is not —NR$^7$Ay; and pharmaceutically acceptable salts, solvates and physiologically functional derivatives thereof.

Preferred compounds of formula (I) include those compounds defined wherein at least one of $R^1$ and $R^2$ contains an aryl, heterocyclic or heteroaryl moiety. The groups Ay, —NR$^7$Ay, Het, —NHR$^{10}$Het, NHHet, —NHR$^{10}$Ay, —OAy, —S(O)$_n$Ay, $R^{10}$NR$^7$Ay, —OHet and —OR$^{10}$Het are groups containing an aryl, heterocyclic or heteroaryl moieties. In another embodiment, preferred compounds of the present invention include those compounds defined wherein at least one of $R^1$ and $R^2$ contain a heterocyclic or heteroaryl moiety such as Het, —NHHet, —NHR$^{10}$Het, —OHet, and —OR$^{10}$Het.

Another preferred class of compounds of formula (I) include those compounds defined wherein neither $R^1$ nor $R^2$ contain an aryl, heterocyclic or heteroaryl moiety. In such embodiments, $R^1$ is preferably —NR$^7$R$^8$, and $R^2$ is preferably selected from the group consisting of H, halo, alkyl, cycloalkyl, alkenyl, cycloalkenyl, —NR$^7$R$^8$, —OR$^7$, —S(O)$_n$R$^9$, and —$R^{10}$NR$^7$R$^8$. More particularly preferred compounds include those defined wherein neither $R^1$ nor $R^2$ contain a heterocyclic or heteroaryl moiety but may contain an aryl moiety.

In another embodiment, the compounds of formula (I) include those compounds defined where at least one of $R^3$ and $R^4$ contain a heterocyclic or heteroaryl moiety. A further embodiment includes those compounds of formula (I) where neither $R^3$ nor $R^4$ contain a heterocyclic or heteroaryl moiety.

Another class of compounds of formula (I) includes those compounds defined wherein at least one $R^5$ group contains an aryl, heterocyclic or heteroaryl moiety (preferably a heterocyclic or heteroaryl moiety) and two adjacent $R^5$ groups together with the atoms to which they are bonded do not form a $C_{5-6}$ cycloalkyl or aryl. Another class of compounds of formula (I) includes those compounds defined wherein q is 3, 4 or 5, at least one $R^5$ group contains an aryl, heterocyclic or heteroaryl moiety (preferably a heterocyclic or heteroaryl moiety) and two adjacent $R^5$ groups together with the atoms to which they are bonded form a $C_{5-6}$ cycloalkyl or aryl. Another class of compounds of formula (I) includes those compounds defined where no $R^5$ group contains an aryl, heterocyclic or heteroaryl moiety (or in one embodiment no $R^5$ group contains a heterocyclic or heteroaryl moiety) and two adjacent $R^5$ groups together with the atoms to which they are bonded do not form a $C_{5-6}$ cycloalkyl or aryl. Another class of compounds of formula (I) includes those compounds defined wherein q is 2, 3, 4 or 5, no $R^5$ group contains an aryl, heterocyclic or heteroaryl moiety (or in one embodiment no $R^5$ group contains a heterocyclic or heteroaryl moiety) and two adjacent $R^5$ groups together with the atoms to which they are bonded form a $C_{5-6}$ cycloalkyl or aryl.

In one preferred class of compounds of formula (I), Y is CH. In another preferred class of compounds of formula (I), Y is N.

Preferably, $R^1$ is selected from the group consisting of —NR$^7$R$^8$, Ay, —NR$^7$Ay, Het, —NHR$^{10}$Het, —NHHet, and —NHR$^{10}$Ay, or any subset thereof. More preferably, $R^1$ is selected from the group consisting of —NR$^7$R$^8$, Het, —NHR$^{10}$Het and —NHHet, or any subset thereof. Particularly preferred compounds of formula (I) are defined wherein $R^1$ is —NR$^7$R$^8$ or Het.

In one preferred embodiment, $R^1$ is selected from the group consisting of —NH$_2$, —NH-alkyl, —NH-cycloalkyl, —N(alkyl)(alkyl), Het and —NHAy, or any subset thereof. More preferably, $R^1$ is selected from the group consisting of —NH-alkyl, —NH-cycloalkyl and pyrrolidone or any subset thereof.

Specific examples of some prefered $R^1$ groups are selected from the group consisting of —NH$_2$, —NH-methyl, —N(CH$_3$)$_2$, —NH-cyclopentyl, —NH-cyclopropyl, —NH-isopropyl, —NH-butyl, —NH-phenyl and pyrrolidine, or any subset thereof.

$R^2$ is preferably selected from the group consisting of —NR$^7$R$^8$, Ay, —OR$^7$, —OAy, —S(O)$_n$R$^9$, —S(O)$_n$Ay, —$R^{10}$NR$^7$R$^8$, —$R^{10}$NR$^7$Ay, Het, —NHR$^{10}$Het, —NHHet, —OHet and —OR$^{10}$Het, or any subset thereof. More preferably, $R^2$ is selected from the group consisting of —NR$^7$R$^8$, Het, —NHHet and —NHR$^{10}$Het, or any subset thereof. Particularly preferred compounds of formula (I) are defined where $R^2$ is selected from the group consisting of —NR$^7$R$^8$ and Het.

In one preferred embodiment, $R^2$ is selected from the group consisting of —NH$_2$, —NH-alkyl, —NH-cycloalkyl, —N(alkyl)(alkyl) and Het, or any subset thereof. More preferably, $R^2$ is selected from the group consisting of —NH-alkyl and —NH-cycloalkyl, or any subset thereof.

Specific examples of some preferred $R^2$ groups are selected from the group consisting of —NH$_2$, —NH-methyl, —NH-ethyl, —NH-cyclopentyl, —NH-cyclopropyl, —NH-isopropyl, —NH-butyl and pyrrolidine, or any subset thereof.

Preferably, $R^7$ and $R^8$ are each the same or different and are independently selected from the group consisting of H, alkyl, cycloalkyl, $R^{10}$-cycloalkyl, —$R^{10}$OR$^9$, —$R^{10}$NR$^9$R$^{11}$, —C(O)R$^9$, and $R^{10}$CO$_2$R$^9$, or any subset thereof. More preferably, $R^7$ and $R^8$ are each the same or different and are independently selected from the group consisting of H, alkyl, cycloalkyl and $R^{10}$-cycloalkyl, or any subset thereof. In one embodiment, $R^7$ and $R^8$ are each the same or different and are independently selected from the group consisting of H, alkyl and cycloalkyl, or any subset thereof.

Preferably $R^9$ and $R^{11}$ are each the same or different and are independently selected from the group consisting of H, alkyl, cycloalkyl and —$R^{10}$-cycloalkyl, or any subset thereof. More preferably, $R^9$ and $R^{11}$ are each the same or different and are independently selected from the group consisting of H and alkyl.

Preferably $R^{10}$ is alkyl or cycloalkyl; more preferably alkyl.

$R^3$ is preferably selected from the group consisting of H, halo, alkyl, —OR$^7$, —$R^{10}$OR$^7$, —NR$^7$R$^8$, —$R^{10}$NR$^7$R$^8$, —CO$_2$R$^7$ and Ay, or any subset thereof. More preferably, $R^3$ is H, halo, alkyl, —OR$^7$ and —NR$^7$R$^8$, or any subset thereof. Most preferably R$^3$ is H or alkyl. In one embodiment, R$^3$ is H.

R$^4$ is preferably H, halo, alkyl, —OR$^7$, —R$^{10}$OR$^7$, —NR$^7$R$^8$, —R$^{10}$NR$^7$R$^8$, —CO$_2$R$^7$, or any subset thereof. More preferably R$^4$ is H, halo, alkyl, —OR$^7$ and —NR$^7$R$^8$, or any subset thereof. Most preferably, R$^4$ is H or alkyl. In one embodiment, R$^4$ is H.

More particularly, R$^3$ and R$^4$ are preferably each independently selected from the group consisting of H, F, Cl, Br, methyl, ethyl, propyl, O-methyl, O-ethyl, O-isopropyl, —CH$_2$—O—methyl, —NH$_2$, —NH(alkyl), —N(alkyl)(alkyl), —CH$_2$—NH$_2$, CH$_2$—NH(alkyl), —CH$_2$—N(alkyl)(alkyl), —CO$_2$H, —CO$_2$-methyl and phenyl, or any subset thereof. More preferably, R$^3$ and R$^4$ are each independently selected from the group consisting of H, F, Cl, Br, methyl, ethyl, propyl, O-methyl, O-ethyl, O-isopropyl, —NH$_2$, —NH(alkyl) and —N(alkyl)(alkyl), or any subset thereof.

Preferably q is 0, 1 or 2. In one embodiment, q is 0. In one preferred embodiment, q is 1. In one embodiment, q is 2 and the two R$^5$ groups are bonded two adjacent carbon atoms, and optionally they together with the atoms to which they are bonded form a cycloalkyl or aryl. The phrase "two adjacent R$^5$ groups" refers to two R$^5$ groups, each bonded to adjacent carbon atoms on the phenyl ring. In the embodiment where two adjacent R$^5$ groups together with the atoms to which they are bonded form a cycloalkyl or aryl group, q is preferably 2, 3, 4 or 5; more preferably 2.

R$^5$ may be in the ortho, meta or para position.

In the embodiments where two adjacent R$^5$ groups together with the atoms to which they are attached form a cycloalkyl or aryl group, each R$^5$ group may be the same or different and is preferably selected from the group consisting of alkyl and alkenyl. In one embodiment, two adjacent R$^5$ groups are alkyl and together with the atoms to which they are attached, they form a cycloalkyl group such as:

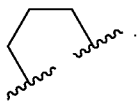

From this example, additional embodiments, including those where two adjacent R$^5$ groups together with the atoms to which they are bonded form an aryl group, can be readily ascertained by those skilled in the art. Preferably, the compounds of formula (I) are defined wherein two adjacent R$^5$ groups together with the atoms to which they are bonded do not form a C$_{5-6}$ cycloalkyl or aryl group.

Preferably, each R$^5$ group is the same or different and is independently selected from the group consisting of halo, alkyl, alkenyl, —OR$^7$, —CO$_2$R$^9$, —NR$^7$R$^8$, C(O)NR$^7$R$^8$, Ay, —NHR$^{10}$Ay, Het, —S(O)$_2$NR$^7$R$^8$, cyano, nitro and azido, or any subset thereof. More preferably, each R$^5$ group is the same or different and is independently selected from the group consisting of halo, alkyl, alkenyl, —OR$^7$, —NR$^7$R$^8$, Ay, Het —S(O)$_2$NR$^7$R$^8$, cyano, nitro and azido, or any subset thereof. Most preferably, each R$^5$ group is the same or different and is independently selected from the group consisting of halo, —OR$^7$, NR$^7$R$^8$, alkyl, and cyano, or any subset thereof. In particular, preferred embodiments of the compounds of formula (I) are defined where R$^5$ is selected from the group consisting of halo (e.g., fluoro, chloro or bromo), alkyl (e.g., methyl), O-alkyl (e.g., O-methyl, O-isobutyl, and

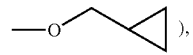

O-allyl, cyano, —NH—CH$_3$, —N(CH$_3$)$_2$, nitro and azido or any subset thereof.

It is to be understood that the present invention includes all combinations and subsets of the particular and preferred groups defined hereinabove.

Preferred compounds of formula (I) include but are not limited to:

N-Cyclopentyl-3-[2-(cyclopentylamino)-4-pyrimidinyl]-2-(4-methoxyphenyl)-pyrazolo[1,5-a]pyridin-7-amine, N-Cyclopentyl-4-[2-(4-methoxyphenyl)-7-(1-pyrrolidinyl)pyrazolo[1,5-a]pyridin-3-yl]-2-pyrimidinamine, 4-[2-(4-Methoxyphenyl)-7-(1-pyrrolidinyl)pyrazolo[1,5-a]pyridin-3-yl]-2-pyrimidinamine, 4-{7-(Cyclopentylamino)-3-[2-(cyclopentylamino)-4-pyrimidinyl]pyrazolo-[1,5-a]pyridin-2-yl}phenol, 4-[3-[2-(Cyclopentylamino)-4-pyrimidinyl]-7-(1-pyrrolidinyl)pyrazolo[1,5-a]pyridin-2-yl]phenol, 4-[3-(2-Amino-4-pyrimidinyl)-7-(1-pyrrolidinyl)pyrazolo[1,5-a]pyridin-2-yl]phenol, 2-[4-(Allyloxy)phenyl]-N-cyclopentyl-3-[2-(cyclopentylamino)-4-pyrimidinyl]pyrazolo-[1,5-a]pyridin-7-amine, Ethyl (4-{7-(cyclopentylamino)-3-[2-(cyclopentylamino)-4-pyrimidinyl]-pyrazolo[1,5-a]pyridin-2-yl}phenoxy)acetate, 2-(4-Butoxyphenyl)-N-cyclopentyl-3-[2-(cyclopentylamino)-4-pyrimidinyl]-pyrazolo[1,5-a]pyridin-7-amine, N-Cyclopentyl-3-[2-(cyclopentylamino)-4-pyrimidinyl]-2-(4-isobutoxyphenyl)pyrazolo-[1,5-a]pyridin-7-amine, N-Cyclopentyl-3-[2-(cyclopentylamino)-4-pyrimidinyl]-2-[4-(cyclopropyl-methoxy)-phenyl]pyrazolo[1,5-a]pyridin-7-amine, 2-[4-(Cyclobutylmethoxy)phenyl]-N-cyclopentyl-3-[2-(cyclopentylamino)-4-pyrimidinyl]pyrazolo[1,5-a]pyridin-7-amine, N-Cyclopentyl-3-[2-(cyclopentylamino)-4-pyrimidinyl]-2-(4-phenoxyphenyl)-pyrazolo[1,5-a]pyridin-7-amine, 2-[1,1'-Biphenyl]-4-yl-N-butyl-3-[2-(butylamino)-4-pyrimidinyl]pyrazolo-[1,5-a]pyridin-7-amine, N-{4-[2-(4-Aminophenyl)-7-(butylamino)pyrazolo[1,5-a]pyridin-3-yl]-2-pyrimidinyl}-N-butylamine, N-Butyl-3-[2-(butylamino)-4-pyrimidinyl]-2-[4-(cyclohexylamino)phenyl]-pyrazolo[1,5-a]pyridin-7-amine, N-Butyl-3-[2-(butylamino)-4-pyrimidinyl]-2-(4-isoprope-nylphenyl)-pyrazolo[1,5-a]pyridin-7-amine, 2-(4-Anilinophenyl)-N-butyl-3-[2-(butylamino)-4-pyrimidinyl]pyrazolo[1,5-a]pyridin-7-amine, 2-(4-Anilinophenyl)-N-butyl-3-[2-(butylamino)-4-pyrimidinyl]-N-phenylpyrazolo[1,5-a]pyridin-7-amine, 2-{4-[Bis(cyclopropylmethyl)amino]phenyl}-N-butyl-3-[2-(butylamino)-4-pyrimidinyl]pyrazolo[1,5-a]pyridin-7-amine, N-Butyl-3-[2-(butylamino)-4-pyrimidinyl]-2-{4-[(cyclopropylmethyl)amino]phenyl}-pyrazolo[1,5-a]pyridin-7-amine, N-Butyl-3-[2-(butylamino)-4-pyrimidinyl]-2-[4-(dimethylamino)phenyl]-pyrazolo[1,5-a]pyridin-7-amine, 2-(2-Bromophenyl)-N-cyclopentyl-3-[2-(cyclopentylamino)-4-pyrimidinyl]pyrazolo[1,5-a]pyridin-7-amine, 2-(3-Bromophenyl)-N-cyclopentyl-3-[2-(cyclopentylamino)-4-pyrimidinyl]pyrazolo[1,5-a]pyridin-7-amine, 4-[2-(3-Bromophenyl)-7-(1-pyrrolidinyl)pyrazolo[1,5-a]pyridin-3-yl]-N-cyclopentyl-2-pyrimidinamine,
N-[3-(2-Amino-4-pyrimidinyl)-2-(3-bromophenyl)pyrazolo[1,5-a]pyridin-7-yl]-N-cyclopentylamine,
4-[2-(3-Bromophenyl)-7-(1-pyrrolidinyl)pyrazolo[1,5-a]pyridin-3-yl]-2-pyrimidinamine,
2-[1,1'-Biphenyl]-3-yl-N-cyclopentyl-3-[2-(cyclopentylamino)-4-pyrimidinyl]pyrazolo-[1,5-a]pyridin-7-amine,
4-[2-[1,1'-Biphenyl]-3-yl-7-(1-pyrrolidinyl)pyrazolo[1,5-a]pyridin-3-yl]-N-cyclopentyl-2-pyrimidinamine,
N-Cyclopentyl-3-[2-(cyclopentylamino)-4-pyrimidinyl]-2-[3-(4-pyridinyl)phenyl]-pyrazolo[1,5-a]pyridin-7-amine,
N-Cyclopentyl-3-[2-(cyclopentylamino)-4-pyrimidinyl]-2-[3-(3-thienyl)phenyl]pyrazolo-[1,5-a]pyridin-7-amine,
N-Cyclopentyl-3-[2-(cyclopentylamino)-4-pyrimidinyl]-2-[3-(2-thienyl)-phenyl]pyrazolo[1,5-a]pyridin-7-amine,
2-(3-Aminophenyl)-N-cyclopentyl-3-[2-(cyclopentylamino)-4-pyrimidinyl]pyrazolo[1,5-a]pyridin-7-amine,
N-(3-{7-(Cyclopentylamino)-3-[2-(cyclopentylamino)-4-pyrimidinyl]pyrazolo[1,5-a]pyridin-2-yl}phenyl)acetamide,
N-(3-{7-(Cyclopentylamino)-3-[2-(cyclopentylamino)-4-pyrimidinyl]-pyrazolo[1,5-a]pyridin-2-yl}phenyl)methanesulfonamide,
4-[2-(3-Aminophenyl)-7-(1-pyrrolidinyl)pyrazolo[1,5-a]pyridin-3-yl]-N-cyclopentyl-2-pyrimidinamine,
N-Cyclopentyl-3-[2-(cyclopentylamino)-4-pyrimidinyl]-2-phenylpyrazolo-[1,5-a]pyridin-7-amine,
3-{(7-(Cyclopentylamino)-3-[2-(cyclopentylamino)-4-pyrimidinyl]pyrazolo[1,5-a]pyridin-2-yl}benzonitrile,
3-{7-(Cyclopentylamino)-3-[2-(cyclopentylamino)-4-pyrimidinyl]-pyrazolo[1,5-a]pyridin-2-yl}benzamide,
3-{7-(Cyclopentylamino)-3-[2-(cyclopentylamino)-4-pyrimidinyl]pyrazolo-[1,5-a]pyridin-2-yl}benzoic acid,
N-{4-[2-(3-Bromo-4-methoxyphenyl)-7-(cyclopentylamino)pyrazolo[1,5-a]pyridin-3-yl]-2-pyrimidinyl}-N-cyclopentylamine,
2-(3-Bromo-4-chlorophenyl)-N-cyclopentyl-3-[2-(cyclopentylamino)-4-pyrimidinyl]-pyrazolo[1,5-a]pyridin-7-amine,
2-(3-Amino-4-chlorophenyl)-N-cyclopentyl-3-[2-(cyclopentylamino)-4-pyrimidinyl]pyrazolo[1,5-a]pyridin-7-amine,
2-[4-(Benzylamino)phenyl]-N-butyl-3-[2-(butylamino)-4-pyrimidinyl]-pyrazolo[1,5-a]pyridin-7-amine,
N-Cyclopentyl-3-[2-(cyclopentylamino)-4-pyrimidinyl]-2-(3-methylphenyl)pyrazolo[1,5-a]pyridin-7-amine,
4-[7-Chloro-2-(3-methylphenyl)pyrazolo[1,5-a]pyridin-3-yl]-N-cyclopentyl-5,6-dimethyl-2-pyrimidinamine,
N-cyclopentyl-3-[2-(cyclopentylamino)-5,6-dimethyl-4-pyrimidinyl]-2-(3-methylphenyl)pyrazolo[1,5-a]pyridin-7-amine,
3-[2-(Cyclopentylamino)-4-pyrimidinyl]-N-isopropyl-2-(3-methylphenyl)pyrazolo[1,5-a]pyridin-7-amine,
4-[7-Chloro-2-(3-methoxyphenyl)pyrazolo[1,5-a]pyridin-3-yl]-N-cyclopentyl-2-pyrimidinamine,
N-Cyclopentyl-3-[2-(cyclopentylamino)-4-pyrimidinyl]-2-(3-methoxyphenyl)-pyrazolo[1,5-a]pyridin-7-amine,
3-[2-(Cyclopentylamino)-4-pyrimidinyl]-N-isopropyl-2-(3-methoxyphenyl)-pyrazolo[1,5-a]pyridin-7-amine,
3-[2-(Cyclopentylamino)-4-pyrimidinyl]-2-(3-methoxyphenyl)-N,N-dimethylpyrazolo-[1,5-a]pyridin-7-amine,
3-{7-(Cyclopentylamino)-3-[2-(cyclopentylamino)-4-pyrimidinyl]pyrazolo[1,5-a]pyridin-2-yl}phenol,
N-Cyclopentyl-3-[2-(cyclopentylamino)-4-pyrimidinyl]-2-[3-(cyclopropylmethoxy)phenyl]pyrazolo[1,5-a]pyridin-7-amine,
N-Cyclopentyl-3-[2-(cyclopentylamino)-4-pyrimidinyl]-2-(3-fluorophenyl)pyrazolo[1,5-a]pyridin-7-amine,
2-(3-Chlorophenyl)-N-cyclopentyl-3-[2-(cyclopentylamino)-4-pyrimidinyl]pyrazolo[1,5-a]pyridin-7-amine,
N-Cyclopentyl-3-[2-(cyclopropylamino)-4-pyrimidinyl]-2-(4-methoxyphenyl)pyrazolo[1,5-a]pyridin-7-amine,
3-[2-(Cyclopentylamino)-4-pyrimidinyl]-2-(4-methoxyphenyl)-N-[2-(4-morpholinyl)ethyl]pyrazolo[1,5-a]pyridin-7-amine,
3-[2-(Cyclopentylamino)-4-pyrimidinyl]-N-cyclopropyl-2-(4-methoxyphenyl)pyrazolo[1,5-a]pyridin-7-amine,
N-Cyclopentyl-4-[2-(4-methoxyphenyl)-7-(4-morpholinyl)pyrazolo[1,5-a]pyridin-3-yl]-2-pyrimidinamine,
3-[2-(Cyclopentylamino)-4-pyrimidinyl]-N-(2-methoxyethyl)-2-(4-methoxyphenyl)pyrazolo[1,5-a]pyridin-7-amine,
N-Cyclopropyl-4-[2-(4-methoxyphenyl)-7-(4-morpholinyl)pyrazolo[1,5-a]pyridin-3-yl]-2-pyrimidinamine,
3-[2-(Cyclopropylamino)-4-pyrimidinyl]-N-(2-methoxyethyl)-2-(4-methoxyphenyl)pyrazolo[1,5-a]pyridin-7-amine,
3-[2-(Cyclopropylamino)-4-pyrimidinyl]-2-(4-methoxyphenyl)-N-[2-(4-morpholinyl)ethyl]pyrazolo[1,5-a]pyridin-7-amine,
N-Cyclopropyl-3-[2-(cyclopropylamino)-4-pyrimidinyl]-2-(4-methoxyphenyl)pyrazolo[1,5-a]pyridin-7-amine,
4-[3-[2-(Cyclopentylamino)-4-pyrimidinyl]-7-(cyclopropylamino)pyrazolo[1,5-a]pyridin-2-yl]phenol,
4-{7-(Cyclopentylamino)-3-[2-(cyclopropylamino)-4-pyrimidinyl]pyrazolo[1,5-a]pyridin-2-yl}phenol,
4-{7-(Cyclopropylamino)-3-[2-(cyclopropylamino)-4-pyrimidinyl]pyrazolo[1,5-a]pyridin-2-yl}phenol,
3-[2-(Cyclopentylamino)-4-pyrimidinyl]-N-cyclopropyl-2-[4-(cyclopropylmethoxy)phenyl]pyrazolo[1,5-a]pyridin-7-amine,
2-[4-(Allyloxy)phenyl]-N-cyclopentyl-3-[2-(cyclopropylamino)-4-pyrimidinyl]pyrazolo[1,5-a]pyridin-7-amine,
N-Cyclopropyl-3-[2-(cyclopropylamino)-4-pyrimidinyl]-2-[4-(cyclopropylmethoxy)phenyl]pyrazolo[1,5-a]pyridin-7-amine,
2-[4-(Allyloxy)phenyl]-N-cyclopropyl-3-[2-(cyclopropylamino)-4-pyrimidinyl]pyrazolo[1,5-a]pyridin-7-amine,
N-Butyl-3-[2-(butylamino)pyrimidin-4-yl]-2-{4-[(4-methoxybenzyl)amino]phenyl}pyrazolo[1,5-a]pyridin-7-amine,
N-Butyl-3-[2-(butylamino)pyrimidin-4-yl]-2-(4-morpholin-4-ylphenyl)pyrazolo[1,5-a]pyridin-7-amine,
2-(3-Bromophenyl)-N-cyclopentyl-3-[2-(cyclopropylamino)-4-pyrimidinyl]pyrazolo[1,5-a]pyridin-7-amine,
2-(3-Bromophenyl)-3-[2-(cyclopentylamino)-4-pyrimidinyl]-N-cyclopropylpyrazolo[1,5-a]pyridin-7-amine,
2-(3-Bromophenyl)-N-cyclopropyl-3-[2-(cyclopropylamino)-4-pyrimidinyl]pyrazolo[1,5-a]pyridin-7-amine,
Methyl N-[3-[2-(cyclopentylamino)pyrimidin-4-yl]-2-(4-methoxyphenyl)pyrazolo[1,5-a]pyridin-7-yl]glycinate,
5-[(3aS,4S,6aR)-2-Oxohexahydro-1H-thieno[3,4-d]imidazol-4-yl]-N-(4-{(7-(butylamino)-3-[2-(butylamino)pyrimidin-4-yl]pyrazolo[1,5-a]pyridin-2-yl}phenyl)pentanamide,
N-[3-[2-(Cyclopentylamino)pyrimidin-4-yl]-2-(4-methoxyphenyl)pyrazolo[1,5-a]pyridin-7-yl]butane-1,4-diamine,
5-[(3aS,4S,6aR)-2-Oxohexahydro-1H-thieno[3,4-d]imidazol-4-yl]-N-(4-{[3-[2-(cyclopentylamino)pyrimidin-4-yl]-2-(4-methoxyphenyl)pyrazolo[1,5-a]pyridin-7-yl]amino}butyl)pentanamide,
3-[2-(Cyclopentylamino)pyrimidin-4-yl]-2-(4-methoxyphenyl)pyrazolo[1,5-a]pyridin-7-amine, N,N'-di-tert-butoxycarbonyl-N'-(4-{[3-[2-(cyclopentylamino)pyrimidin-4-yl]-2-(4-methoxyphenyl)pyrazolo[1,5-a]pyridin-7-yl]amino}butyl)guanidine,
N-(4-{[3-[2-(Cyclopentylamino)pyrimidin-4-yl]-2-(4-methoxyphenyl)pyrazolo[1,5-a]pyridin-7-yl]amino}butyl) guanidine,
N-(4-{[3-[2-(Cyclopentylamino)pyrimidin-4-yl]-2-(4-methoxyphenyl)pyrazolo[1,5-a]pyridin-7-yl]amino}butyl) methanesulfonamide,
N-{[(4-{[3-[2-(Cyclopentylamino)pyrimidin-4-yl]-2-(4-methoxyphenyl)pyrazolo-[1,5-a]pyridin-7-yl]amino)}butyl)amino]carbonyl}-4-methylbenzenesulfonamide,
4-[(4-{[3-[2-(Cyclopentylamino)pyrimidin-4-yl]-2-(4-methoxyphenyl)pyrazolo[1,5-a]pyridin-7-yl]amino}butyl)amino]-4-oxobutanoic acid,
Diethyl 4-{[3-[2-(cyclopentylamino)pyrimidin-4-yl]-2-(4-methoxyphenyl)pyrazolo[1,5-a]pyridin-7-yl]amino}butylamidophosphate,
4-{[3-[2-(Cyclopentylamino)pyrimidin-4-yl]-2-(4-methoxyphenyl)pyrazolo[1,5-a]pyridin-7-yl]amino}butan-1-ol,
Dibenzyl 4-{[3-[2-(cyclopentylamino)pyrimidin-4-yl]-2-(4-methoxyphenyl)pyrazolo[1,5-a]pyridin-7-yl]amino}butyl phosphate,
4-{[3-[2-(Cyclopentylamino)pyrimidin-4-yl]-2-(4-methoxyphenyl)pyrazolo[1,5-a]pyridin-7-yl]amino}butyl phosphate diammonium salt,
2-(3-Azidophenyl)-N-cyclopentyl-3-[2-(cyclopentylamino)pyrimidin-4-yl]pyrazolo[1,5-a]pyridin-7-amine,
3-[2-(Cyclopentylamino)-4-pyrimidinyl]-2-(4-methoxyphenyl)-N-[2-oxo-2-(1-pyrrolidinyl)ethyl]pyrazolo[1,5-a]pyridin-7-amine,
N-(2-{[3-[2-(Cyclopentylamino)-4-pyrimidinyl]-2-(4-methoxyphenyl)pyrazolo[1,5-a]pyridin-7-yl]amino}ethyl) methanesulfonamide,
N'-[3-[2-(Cyclopentylamino)-4-pyrimidinyl]-2-(4-methoxyphenyl)pyrazolo[1,5-a]pyridin-7-yl]-1,2-ethanediamine,
N-Cyclopentyl-4-[2-(3-fluorophenyl)-7-(4-morpholinyl) pyrazolo[1,5-a]pyridin-3-yl]-2-pyrimidinamine,
N-Cyclopentyl-3-[2-(cyclopentylamino)-4-pyrimidinyl]-2-[3-(trifluoromethyl)phenyl]pyrazolo[1,5-a]pyridin-7-amine,
2-(3-Chlorophenyl)-N-cyclopropyl-3-[2-(cyclopropylamino)-4-pyrimidinyl]pyrazolo[1,5-a]pyridin-7-amine,
2-(3-Chlorophenyl)-N-cyclopentyl-3-[2-(cyclopropylamino)-4-pyrimidinyl]pyrazolo[1,5-a]pyridin-7-amine,
2-(3-Chlorophenyl)-3-[2-(cyclopentylamino)-4-pyrimidinyl]-N-cyclopropylpyrazolo[1,5-a]pyridin-7-amine,
N-Cyclopentyl-3-[2-(cyclopropylamino)-4-pyrimidinyl]-2-(3-fluorophenyl)pyrazolo[1,5-a]pyridin-7-amine,
4-[2-(3-Chlorophenyl)-7-(4-morpholinyl)pyrazolo[1,5-a]pyridin-3-yl]-N-cyclopentyl-2-pyrimidinamine,
2-(3-Chlorophenyl)-3-[2-(cyclopentylamino)-4-pyrimidinyl]-N-(2-methoxyethyl)pyrazolo[1,5-a]pyridin-7-amine,
3-[2-(Cyclopentylamino)-4-pyrimidinyl]-N-cyclopropyl-2-(3-fluorophenyl)pyrazolo[1,5-a]pyridin-7-amine,
3-[2-(Cyclopentylamino)-4-pyrimidinyl]-2-(3-fluorophenyl)-N-(2-methoxyethyl)pyrazolo[1,5-a]pyridin-7-amine, and pharmaceutically acceptable salts, solvates and physiologically functional derivatives thereof.

Particularly preferred compounds of formula (I) include but are not limited to:

N-Cyclopentyl-3-[2-(cyclopentylamino)-4-pyrimidinyl]-2-(4-methoxyphenyl)-pyrazolo[1,5-a]pyridin-7-amine,
2-[4-(Allyloxy)phenyl]-N-cyclopentyl-3-[2-(cyclopentylamino)-4-pyrimidinyl]pyrazolo[1,5- a]pyridin-7-amine,
N-Cyclopentyl-3-[2-(cyclopentylamino)-4-pyrimidinyl]-2-[4-(cyclopropyl-methoxy)phenyl]pyrazolo[1,5-a]pyridin-7-amine,
2-(3-Bromophenyl)-N-cyclopentyl-3-[2-(cyclopentylamino)-4-pyrimidinyl]pyrazolo[1,5-a]pyridin-7-amine,
N-Cyclopentyl-3-[2-(cyclopentylamino)-4-pyrimidinyl]-2-phenylpyrazolo-[1,5-a]pyridin-7-amine,
N-Cyclopentyl-3-[2-(cyclopentylamino)-4-pyrimidinyl]-2-(3-methylphenyl)pyrazolo[1,5-a]pyridin-7-amine;
N-Cyclopentyl-3-[2-(cyclopentylamino)-4-pyrimidinyl]-2-(3-methoxyphenyl)pyrazolo[1,5-a]pyridin-7-amine;
N-Cyclopentyl-3-[2-(cyclopentylamino)-4-pyrimidinyl]-2-[3-(cyclopropylmethoxy)phenyl]pyrazolo[1,5-a]pyridin-7-amine;
N-Cyclopentyl-3-[2-(cyclopentylamino)-4-pyrimidinyl]-2-(3-fluorophenyl)pyrazolo[1,5-a]pyridin-7-amine;
2-(3-Chlorophenyl)-N-cyclopentyl-3-[2-(cyclopentylamino)-4-pyrimidinyl]pyrazolo[1,5-a]pyridin-7-amine;
N-Cyclopentyl-3-[2-(cyclopropylamino)-4-pyrimidinyl]-2-(4-methoxyphenyl)pyrazolo[1,5-a]pyridin-7-amine;
3-[2-(Cyclopentylamino)-4-pyrimidinyl]-2-(4-methoxyphenyl)-N-[2-(4-morpholinyl)ethyl]pyrazolo[1,5-a]pyridin-7-amine;
3-[2-(Cyclopentylamino)-4-pyrimidinyl]-N-cyclopropyl-2-(4-methoxyphenyl)pyrazolo[1,5-a]pyridin-7-amine;
N-Cyclopentyl-4-[2-(4-methoxyphenyl)-7-(4-morpholinyl)pyrazolo[1,5-a]pyridin-3-yl]-2-pyrimidinamine;
3-[2-(Cyclopentylamino)-4-pyrimidinyl]-N-(2-methoxyethyl)-2-(4-methoxyphenyl)pyrazolo[1,5-a]pyridin-7-amine;
3-[2-(Cyclopropylamino)-4-pyrimidinyl]-N-(2-methoxyethyl)-2-(4-methoxyphenyl)pyrazolo[1,5-a]pyridin-7-amine;
4-[3-[2-(Cyclopentylamino)-4-pyrimidinyl]-7-(cyclopropylamino)pyrazolo[1,5-a]pyridin-2-yl]phenol;
5-[(3aS,4S,6aR)-2-Oxohexahydro-1H-thieno[3,4-d]imidazol-4-yl]-N-(4-{[3-[2-(cyclopentylamino)pyrimidin-4-yl]-2-(4-methoxyphenyl)pyrazolo[1,5-a]pyridin-7-yl]amino}butyl)pentanamide;
4-{[3-[2-(Cyclopentylamino)pyrimidin-4-yl]-2-(4-methoxyphenyl)-pyrazolo[1,5-a]pyridin-7-yl]amino}butan-1-ol;
4-{[3-[2-(Cyclopentylamino)pyrimidin-4-yl]-2-(4-methoxy-phenyl)pyrazolo[1,5-a]pyridin-7-yl]amino}butyl phosphate diammonium salt;
N-(2-{[3-[2-(Cyclopentylamino)-4-pyrimidinyl]-2-(4-methoxy-phenyl)pyrazolo[1,5-a]pyridin-7-yl]amino}ethyl) methanesulfonamide;
N-Cyclopentyl-3-[2-(cyclopentylamino)-4-pyrimidinyl]-2-[3-(trifluoromethyl)phenyl]pyrazolo[1,5-a]pyridin-7-amine;
2-(3-Chlorophenyl)-N-cyclopentyl-3-[2-(cyclopropylamino)-4-pyrimidinyl]pyrazolo[1,5-a]pyridin-7-amine;
2-(3-Chlorophenyl)-3-[2-(cyclopentylamino)-4-pyrimidinyl]-N-cyclopropylpyrazolo[1,5-a]pyridin-7-amine;
2-(3-Chlorophenyl)-3-[2-(cyclopentylamino)-4-pyrimidinyl]-N-(2-methoxyethyl)pyrazolo[1,5-a]pyridin-7-amine; and
3-[2-(Cyclopentylamino)-4-pyrimidinyl]-2-(3-fluorophenyl)-N-(2-methoxyethyl)pyrazolo[1,5-a]pyridin-7-amine; and
pharmaceutically acceptable salts, solvates and physiologically functional derivatives thereof.

It will be appreciated by those skilled in the art that the compounds of the present invention may also be utilized in the form of a pharmaceutically acceptable salt or solvate thereof. The pharmaceutically acceptable salts of the compounds of formula (I) include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

The term "solvate" as used herein refers to a complex of variable stoichiometry formed by a solute (a compound of formula (I)) and a solvent. Solvents, by way of example, include water, methanol, ethanol, or acetic acid.

The term "physiologically functional derivative" as used herein refers to any pharmaceutically acceptable derivative of a compound of the present invention, for example, an ester or an amide of a compound of formula (I), which upon administration to an animal, particularly a mammal, such as a human, is capable of providing (directly or indirectly) a compound of the present invention or an active metabolite thereof. See for example, Burger's Medicinal Chemistry And Drug Discovery, 5th Edition, Vol 1: Principles And Practice.

Processes for preparing pharmaceutically acceptable salts, solvates and physiologically functional derivatives of the compounds of formula (I) are conventional in the art. See, e.g., Burger's Medicinal Chemistry And Drug Discovery 5th Edition, Vol 1: Principles And Practice.

As will be apparent to those skilled in the art, in the processes described below for the preparation of compounds of formula (I), certain intermediates, may be in the form of pharmaceutically acceptable salts, solvates or physiologically functional derivatives of the compound. Those terms as applied to any intermediate employed in the process of preparing compounds of formula (I) have the same meanings as noted above with respect to compounds of formula (I). Processes for preparing pharmaceutically acceptable salts, solvates and physiologically functional derivatives of such intermediates are known in the art and are analogous to the process for preparing pharmaceutically acceptable salts, solvates and physiologically functional derivatives of the compounds of formula (I).

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centers are inverted. Likewise, it is understood that compounds of formula (I) may exist in tautomeric forms other than that shown in the formula and these are also included within the scope of the present invention.

The present invention further provides compounds of formula (I) for use in medical therapy, e.g. in the treatment or prophylaxis, including suppression of recurrence of symptoms, of a viral disease in an animal, e.g. a mammal such as a human. The compounds of formula (I) are especially useful for the treatment or prophylaxis of viral diseases such as herpes viral infections. Herpes viral infections include, for example, herpes simplex virus 1 (HSV-1), herpes simplex virus 2 (HSV-2), cytomegalovirus (CMV), Epstein Barr virus (EBV), varacella zoster virus (VZV), human herpes virus 6 (HHV-6), human herpes virus 7 (HHV-7), and human herpes virus 8 (HHV-8). Thus, the compounds of the invention are also useful in the treatment or prophylaxis of the symptoms or effects of herpes virus infections.

The compounds of the invention are useful in the treatment or prophylaxis of conditions or diseases associated with herpes virus infections, particularly conditions or diseases associated with latent herpes virus infections in an animal, e.g., a mammal such as a human. By conditions or diseases associated with herpes viral infections is meant a condition or disease, excluding the viral infection per se, which results from the presence of the viral infection, such as chronic fatigue syndrome which is associated with EBV infection; and multiple sclerosis which has been associated with herpes viral infections such as EBV and HHV-6. Further examples of such conditions or diseases are described in the background section above.

In addition to those conditions and diseases, the compounds of the present invention may also be used for the treatment or prophylaxis of cardiovascular diseases and conditions associated with herpes virus infections, in particular atherosclerosis, coronary artery disease and restenosis and specifically restenosis following angioplasty (RFA). Restenosis is the narrowing of the blood vessels which can occur after injury to the vessel wall, for example injury caused by balloon angioplasty or other surgical and/or diagnostic techniques, and is characterized by excessive proliferation of smooth muscle cells in the walls of the blood vessel treated. It is thought that in many patients suffering from RFA, viral infection, particularly by CMV and/or HHV-6 of the patient plays a pivotal role in the proliferation of the smooth muscle cells in the coronary vessel treated. Restenosis can occur following a number of surgical and/or diagnostic techniques, for example, transplant surgery, vein grafting, coronary by-pass grafting and, most commonly following angioplasty.

There is evidence from work done both in vitro and in vivo, indicating that restenosis is a multifactorial process. Several cytokines and growth factors, acting in concert, stimulate the migration and proliferation of vascular smooth muscle cells (SMC) and production of extracellular matrix material, which accumulate to occlude the blood vessel. In addition growth suppressors act to inhibit the proliferation of SMC's and production of extracellular matrix material.

In addition, compounds of formula (I) may be useful in the treatment or prophylaxis of hepatitis B or hepatitis C viruses, human papilloma virus (HPV) and HIV.

The present invention provides a method for the treatment or prophylaxis of a viral infection in an animal such as a mammal (e.g., a human), particularly a herpes viral infection, which comprises administering to the animal a therapeutically effective amount of the compound of formula (I).

As used herein, the term "prophylaxis" refers to the complete prevention of infection, the prevention of occurrence of symptoms in an infected subject, the prevention of recurrence of symptoms in an infected subject, or a decrease in severity or frequency of symptoms of viral infection, condition or disease in the subject.

As used herein, the term "treatment" refers to the partial or total elimination of symptoms or decrease in severity of symptoms of viral infection, condition or disease in the subject, or the elimination or decrease of viral presence in the subject.

As used herein, the term "therapeutically effective amount" means an amount of a compound of formula (I) which is sufficient, in the subject to which it is administered, to treat or prevent the stated disease, condition or infection. For example, a therapeutically effective amount of a compound of formula (I) for the treatment of a herpes virus infection is an amount sufficient to treat the herpes virus infection in the subject.

The present invention also provides a method for the treatment or prophylaxis of conditions or diseases associated with herpes viral infections in an animal such as a mammal (e.g., a human), which comprises administering to the animal a therapeutically effective amount of the compound of formula (I). In one embodiment, the present invention provides a method for the treatment or prophylaxis of chronic fatigue syndrome and multiple sclerosis in an animal such as a mammal (e.g., a human), which comprises administering to the animal a therapeutically effective amount of a compound of formula (I). The foregoing method is particularly useful for the treatment or prophylaxis of chronic fatigue syndrome and multiple sclerosis associated with latent infection with a herpes virus.

In another embodiment, the present invention provides a method for the treatment or prophylaxis of a cardiovascular condition such as atherosclerosis, coronary artery disease or restenosis (particularly restenosis following surgery such as angioplasty), which comprises administering to the animal a therapeutically effective antiviral amount of the compound of formula (I).

The present invention further provides a method for the treatment or prophylaxis of hepatitis B or hepatitis C viruses in an animal such as a mammal (e.g., a human), which comprises administering to the animal a therapeutically effective amount of the compound of formula (I).

The present invention further provides a method for the treatment or prophylaxis of human papilloma virus in an animal such as a mammal (e.g., a human), which comprises administering to the animal a therapeutically effective amount of the compound of formula (I).

The present invention further provides a method for the treatment or prophylaxis of HIV in an animal such as a mammal (e.g., a human), which comprises administering to the animal a therapeutically effective amount of the compound of formula (I).

The present invention also provides the use of the compound of formula (I) in the preparation of a medicament for the treatment or prophylaxis of a viral infection in an animal such as a mammal (e.g., a human), particularly a herpes viral infection; the use of the compound of formula (I) in the preparation of a medicament for the treatment of conditions or disease associated with a herpes viral infection; and the use of the compound of formula (I) in the preparation of a medicament for the treatment or prophylaxis of hepatitis B or hepatitis C viruses, human papilloma virus and HIV. In particular, the present invention also provides the use of a compound of formula (I) in the preparation of a medicament for the treatment or prophylaxis of chronic fatigue syndrome or multiple sclerosis. In one embodiment, the present invention provides the use of a compound of formula (I) in the preparation of a medicament for the treatment or prophylaxis of cardiovascular disease, such as restenosis and atherosclerosis.

The compounds of formula (I) are conveniently administered in the form of pharmaceutical compositions. Such compositions may conveniently be presented for use in conventional manner in admixture with one or more physiologically acceptable carriers or diluents.

While it is possible that compounds of the present invention may be therapeutically administered as the raw chemical, it is preferable to present the active ingredient as a pharmaceutical formulation. The pharmaceutical formulation may comprise a carrier or diluent. The carrier(s) or diluent(s) must be "acceptable" in the sense of being compatible with the other ingredients of the formulation and not deleterious to the recipient thereof.

Accordingly, the present invention further provides for a pharmaceutical composition or formulation comprising a compound of formula (I). In one embodiment, the pharmaceutical formulation further comprises one or more pharmaceutically acceptable carriers or dilents and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition, age, and disorder of the recipient as well as the viral infection or disease being treated. The formulations may conveniently be presented in unit dosage form and may be prepared by any of the methods well known in the art of pharmacy. All methods include the step of bringing into association the compound(s) ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation. Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. A tablet may be made by compression or moulding, optionally with one or more accessory ingredients. Compressed tablets may be prepared by compressing in a suitable machine the active ingredient in a free-flowing form such as a powder or granules, optionally mixed with other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured base such as sucrose and acacia or tragacanth, and pastilles comprising the active ingredient in a base such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 100–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The compound of formula (I) for use in the instant invention may be used in combination with other therapeutic agents for example, non-nucleotide reverse transcriptase inhibitors, nucleoside reverse transcriptase inhibitors, protease inhibitors and/or other antiviral agents. The invention thus provides in a further aspect the use of a combination comprising a compound of formula (I) with a further therapeutic agent in the treatment of viral infections. Particular antiviral agents which may be combined with the compounds of the present invention include aciclovir, valaciclovir, famcyclovir, docosanol, gancyclovir, miribavir, amprenavir, lamivudine, zidovudine, and abacavir. Preferred antiviral agents for combining with the compounds of the present invention include aciclovir and valaciclovir. Thus the present invention provides in a further aspect, a combination comprising a compound of formula (I) and an antiviral agent selected from the group consisting of aciclovir and valaciclovir; the use of such combination in the treatment of viral infections and the preparation of a medicament for the treatment of viral infections, and a method of treating viral infections comprising administering a compound of formula (I) and an antiviral agent selected from the group consisting of aciclovir and valaciclovir.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optionally together with a pharmaceutically acceptable carrier or diluent comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, in such a manner as are known for such compounds in the art.

When a compound of formula (I) is used in combination with a second therapeutic agent active against the viral infection, the dose of each compound may differ from that when the compound is used alone. Appropriate doses will be readily appreciated by those skilled in the art.

Compounds of formula (I) wherein Y is N and $R^2$ is selected from the group consisting of alkyl, cycloalkyl, alkenyl, cycloalkenyl, —$NR^7R^8$, —$OR^7$, Ay, —OAy, —$S(O)_nR^9$, —$S(O)_n$Ay, —$R^{10}NR^7R^8$, —$R^{10}NR^7$Ay, Het, —NHHet, —$NHR^{10}$Het, —OHet, and —$OR^{10}$Het, and $R^3$ and $R^4$ are H, may be conveniently prepared by the general process outlined in Scheme 1 below.

Scheme 1

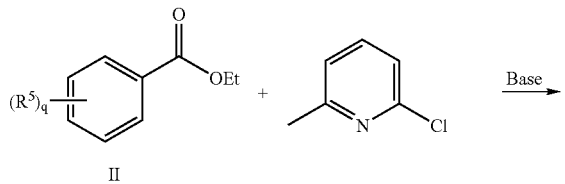

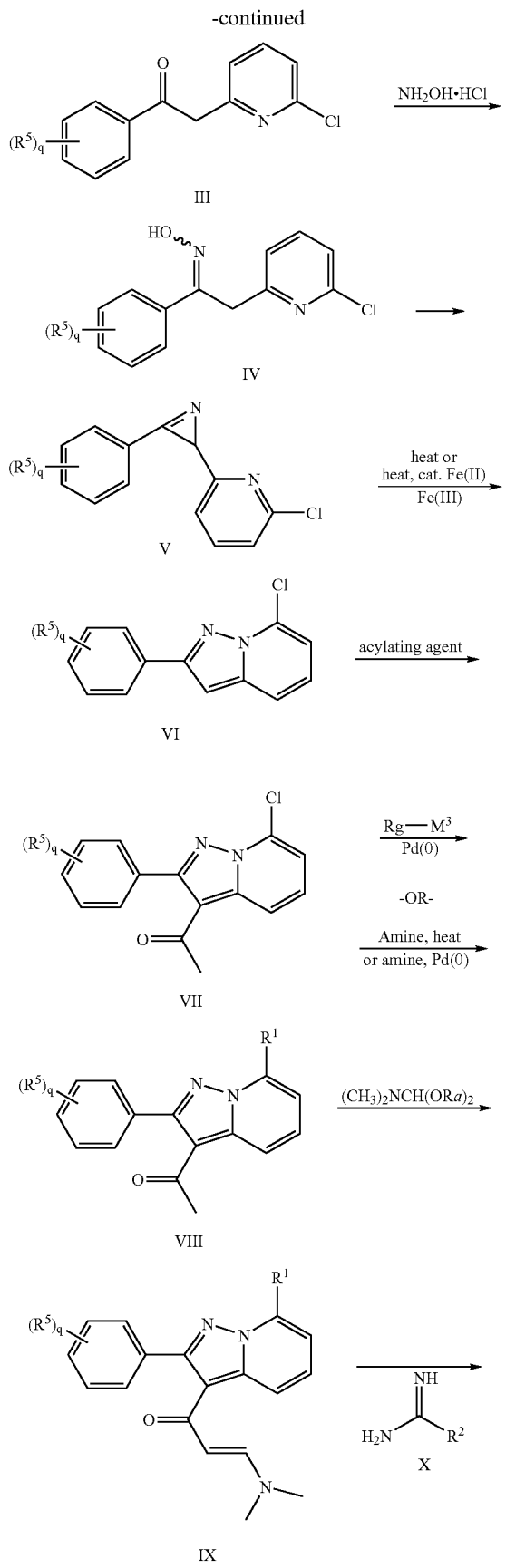

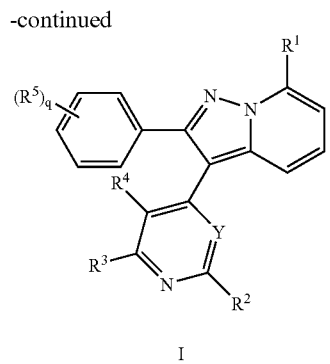

wherein:
R[1] is selected from the group consisting of halo, —NR[7]R[8], Ay, —NR[7]Ay, Het, —NHR[10]Het, —NHHet and —NHR[10]Ay;
  each R[7] and R[8] are the same or different and are independently selected from the group consisting of H, alkyl, cycloalkyl, alkenyl, cycloalkenyl, —R[10]cycloalkyl, —R[10]OR[9], —R[10]NR[9]R[11], —R[10]C(O)R[9], —C(O)R[9], —C(O)R[10]Ay, —C(O)R[10]Het, —CO$_2$R[9], —R[10]CO$_2$R[9], —C(O)NR[9]R[11], —R[10]C(O)NR[9]R[11], —R[10]C(O)Ay, —R[10]C(O)Het, —C(S)NR[9]R[11], —R[10]C(S)NR[9]R[11], —R[10]NHC(NH)NR[9]R[11], —R[10]NHC(O)R[10]Het, —R[10]NHC(O)R[10]CO$_2$R[9], —R[10]NHC(NCO$_2$R[9])NHCO$_2$R[9], —R[10]NHC(O)NHSO$_2$R[9], —R[10]NHC(O)NHSO$_2$Ay, —R[10]NHC(O)NHSO$_2$Het, —R[10]C(NH)NR[9]R[11], —C(NH)NR[9]R[11], —SO$_2$NR[9]R[11], —R[10]SO$_2$NR[9]R[11], —R[10]NHSO$_2$R[9], —SO$_2$R[10], —R[10]SO$_2$R[10], —R[10]NHCOR[9], —R[10]SO$_2$NHCOR[9], —R[10]NHP(O)(OR[9])$_2$, —R[10]OP(O)(OR[9])$_2$ and —R[10]OP(O)(OR[10]Ay)$_2$;
  each R[9] and R[11] are the same or different and are independently selected from the group consisting of H, alkyl, cycloalkyl, —R[10]cycloalkyl, —R[10]OH, —R[10](OR[10])$_w$ where w is 1–10, and —R[10]NR[10]R[10];
  each R[10] is the same or different and is independently selected from the group consisting of alkyl, cycloalkyl, alkenyl, cycloalkenyl and alkynyl;
  Ay is aryl;
  Het is a 5- or 6-membered heterocyclic or heteroaryl group;
R[2] is selected from the group consisting of alkyl, cycloalkyl, alkenyl, cycloalkenyl, Ay, —NR[7]R[8], —OR[7], —OAy, —S(O)$_n$R[9], —S(O)$_n$Ay, —R[10]NR[7]R[8], —R[10]NR[7]Ay, Het, —NHHet, —NHR[10]Het, —OHet and —OR[10]Het;
n is 0, 1 or 2;
Y is N;
R[3] and R[4] are both H;
q is 0, 1, 2, 3, 4 or 5;
  each R[5] is the same or different and is independently selected from the group consisting of halo, alkyl, alkenyl, alkynyl, cycloalkyl, cycloalkenyl, —R[10]cycloalkyl, Ay, —NHR[10]Ay, Het, —NHHet, —NHR[10]Het, —OR[7], —OAy, —OHet, —R[10]OR[9], —NR[7]R[8], —NR[7]Ay, —R[10]NR[7]R[8], —R[10]NR[7]Ay, —R[10]C(O)R[9], —C(O)R[9], —CO$_2$R[9], —R[10]CO$_2$R[9], —C(O)NR[7]R[8], —C(O)Ay, —C(O)NR[7]Ay, —C(O)Het, —C(O)NHR[10]Het —R[10]C(O)NR[9]R[11], —C(S)NR[9]R[11], —R[10]C(S)NR[9]R[11], —R[10]NHC(NH)NR[9]R[11], —C(NH)NR[7]R[8], —C(NH)

NR⁷Ay, —R¹⁰C(NH)NR⁹R¹¹, —S(O)₂NR⁷R⁸, —S(O)₂NR⁷Ay, —R¹⁰SO₂NHCOR⁹, —R¹⁰SO₂NR⁹R¹¹, —R¹⁰SO₂R⁹, —S(O)ₙR⁹, cyano, nitro and azido; or two adjacent R⁵ groups together with the atoms to which they are bonded form a C₅₋₆ cycloalkyl or aryl;

wherein when q is 1 and R⁵ is in the para position, R⁵ is not halo; and

Rg is Ay or Het as defined above;

M³ is B(OH)₂, B(ORa)₂, B(Ra)₂, Sn(Ra)₃, Zn-halide, Zn—Ra or Mg-halide;

Ra is alkyl or cycloalkyl; and halide is halo.

Generally, the process for preparing the compounds of formula (I) wherein Y is N and R² is selected from the group consisting of alkyl, cycloalkyl, alkenyl, cycloalkenyl, —NR⁷R⁸, —OR⁷, Ay, —OAy, —S(O)ₙR⁹, —S(O)ₙAy, —R¹⁰NR⁷R⁸, —R¹⁰NR⁷Ay, Het, —NHHet, —NHR¹⁰Het, —OHet, and —OR¹⁰Het, and R³ and R⁴ are H, (all formulas and all other variables having been defined above in connection with Scheme 1) comprises the steps of:

(a) reacting 2-chloro-6-picoline with a benzoylating agent of formula (II) to prepare a compound of formula (III);
(b) reacting the compound of formula (III) with a hydroxylamine source to prepare a compound of formula (IV);
(c) reacting the compound of formula (IV) with an acylating or sulfonylating agent to prepare a compound of formula (V);
(d) rearranging the compound of formula (V) to prepare a compound of formula (VI);
(e) acylating the compound of formula (VI) to prepare a compound of formula (VII);
(f) either:
    (1) replacing the C-7 halogen of the compound of formula (VII) with an amine; or
    (2) coupling the compound of formula (VII) with a metal compound of the formula Rg-M³ to prepare a compound of formula (VIII);
(g) reacting the compound of formula (VIII) with a dimethylformamide dialkyl acetal of formula (CH₃)₂NCH(ORa)₂ to prepare a compound of formula (IX); and
(h) reacting the compound of formula (IX) with a compound of formula (X) to prepare the compounds of formula (I).

More specifically, compounds of formula (I) wherein Y is N and R² is selected from the group consisting of alkyl, cycloalkyl, alkenyl, cycloalkenyl, —NR⁷R⁸, —OR⁷, Ay, —OAy, —S(O)ₙR⁹, —S(O)ₙAy, —R¹⁰NR⁷R⁸, —R¹⁰NR⁷Ay, Het, —NHHet, —NHR¹⁰Het, —OHet, and —OR¹⁰Het, and R³ and R⁴ are H can be prepared by reacting a compound of formula (IX) with a compound of formula (X).

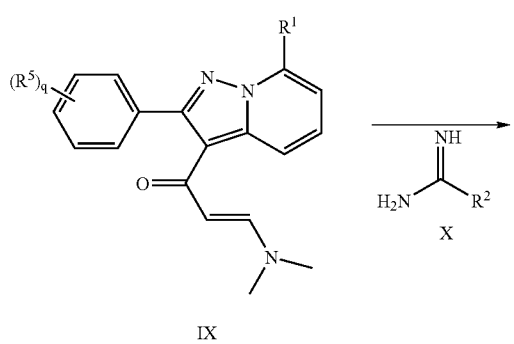

IX

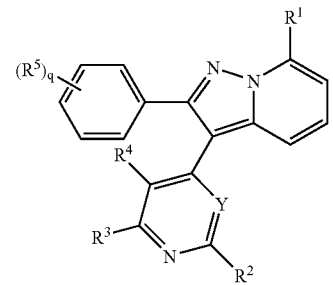

I wherein all variables are as defined above in connection with Scheme 1.

This method can be readily carried out by mixing a compound of formula (IX) with a compound of formula (X) in a suitable solvent, optionally in the presence of a base (preferably when the amidine is in a salt form), and heating the reaction to 50–150° C. Typical solvents include lower alcohols such as methanol, ethanol, isopropanol, dimethylformamide, or the like. The base is typically a sodium alkoxide, potassium carbonate, or an amine base such as triethylamine. In one embodiment, the solvent is dimethylformamide and the base is potassium carbonate, or an amine base such as triethylamine.

Compounds of the formula (IX) may be conveniently prepared by reacting a compound of formula (VIII) with a dimethylformamide dialkyl acetal.

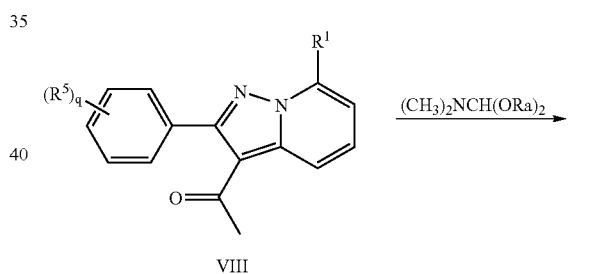

VIII

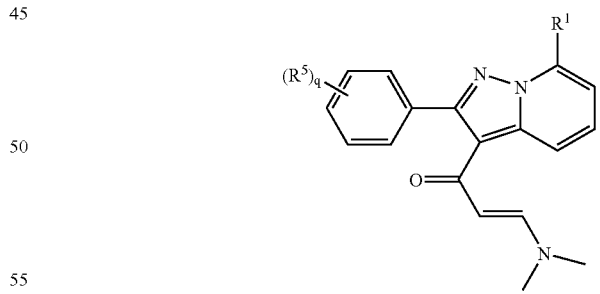

IX wherein all variables are as defined above in connection with Scheme 1.

Typical dimethylformamide dialkylacetal compounds for use in this method include but are not limited to dimethylformamide dimethylacetal and dimethylformamide di-tert-butylacetal. The reaction is carried out by mixing a compound of formula (VIII) with the dimethylformamide dialkyl acetal, optionally with heating.

Compounds of the formula (VIII) may be prepared by two methods. According to one method, compounds of formula (VIII) are prepared from compounds of formula (VII) by replacement of the C-7 halogen (chloro is depicted in formula (VII) but other halogens are similarly useful) with an amine nucleophile.

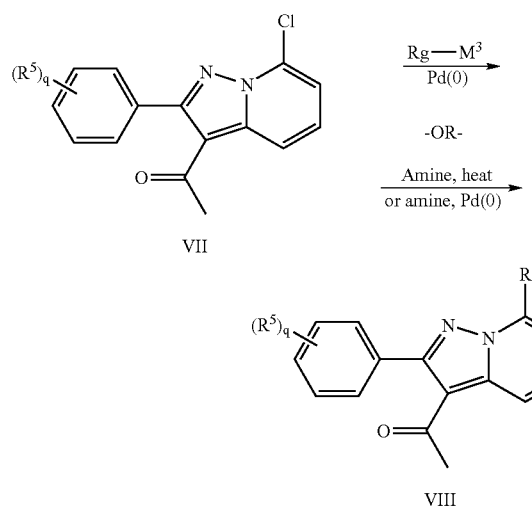

wherein all variables are as defined above in connection with Scheme 1.

Typically the replacement is carried out by mixing the compound of formula (VII) with an amine nucleophile of formula $R^{1a}$ where $R^{1a}$ is selected from the group consisting of —$NR^7R^8$, —$NR^7Ay$, Het, —$NHR^{10}$Het, NHHet, and —$NHR^{10}Ay$; and optionally heating the reaction.

The reaction can also be carried out via an adaptation of procedures found in the literature (Wolfe, J. P.; Buchwald, S. L. *J. Org. Chem.* 2000, 65, 1144) wherein a compound of formula (VII) is treated with an amine, a palladium (0) or nickel (0) source and a base in a suitable solvent. Suitable sources of palladium (0) include but are not limited to palladium(II) acetate and tris(dibenzylideneacetone) dipalladium (0). Typical bases for use in the reaction include, for example sodium tert-butoxide and cesium carbonate. Toluene is an example of a suitable solvent.

According to the second method, compounds of formula (VIII) are prepared from compounds of formula (VII) by coupling with metal compounds of the formula Rg-$M^3$ wherein Rg is Ay or Het as defined above and $M^3$ is $B(OH)_2$, $B(ORa)_2$, $B(Ra)_2$, $Sn(Ra)_3$, Zn-halide, Zn—Ra or Mg-halide, wherein Ra is alkyl or cycloalkyl and halide is halo. This general method can be conveniently performed in an inert solvent, in the presence of a palladium (0) catalyst, optionally with heating. Preferably the reaction is performed by reacting equimolar amounts of a compound of formula (VII) with the metal compound of formula Rg-$M^3$ or optionally adding an excess of the metal compound. The palladium catalyst is preferably present in 1–10 mol % compared to the compound of formula (VII). Palladium catalysts that may be used may include, but are not limited to, tetrakistriphenylphosphine palladium (0) dichlorobis(triphenylphosphine)palladium(II), and bis(diphenylphosphinoferrocene)-palladium (II) dichloride. Inert solvents for use in the reaction include but are not limited to, N,N-dimethylformamide, toluene, tetrahydrofuran, dioxane, and 1-methyl-2-pyrrolidinone.

When the metal compound of formula Rg-$M^3$ is an arylboronic acid or ester or an arylborinate, the reaction is more conveniently carried out by adding a base in a proportion equivalent to, or greater than, that of the metal compound.

Metal compounds of the formula Rg-$M^3$ can be purchased from commercial sources or prepared either as discreet isolated compounds or generated in situ by using methods known to one skilled in the art. (Suzuki, A. *J. Organomet. Chem.* 1999, 576, 147; Stille, J. Angew. *Chem. Int. Ed. Engl.* 1986, 25, 508; Snieckus, V. *J. Org. Chem.* 1995, 60, 292.)

Compounds of formula (VII) may be conveniently prepared from compounds of formula (VI) using an acylation procedure.

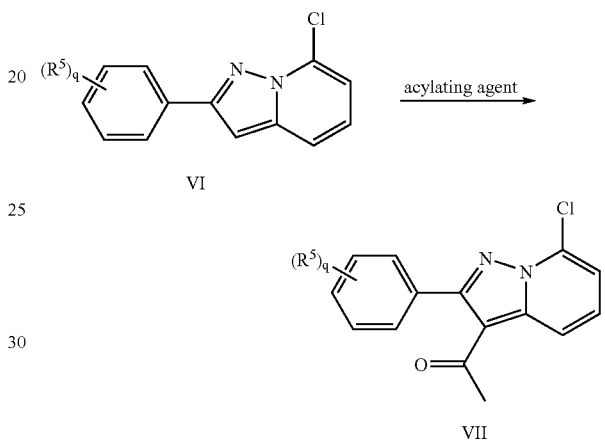

wherein all variables are as defined above in connection with Scheme 1.

Typically the acylation is carried out by treating the compounds of formula (VI) with an acylating agent, optionally in the presence of an acid or Lewis acid catalyst in an inert solvent with optional heating. Typical acylating agents will be readily determined by those skilled in the art. One preferred acylating agent is acetic anhydride. Lewis acid catalysts are also known to those skilled in the art. One preferred Lewis acid catalyst for use in this reaction is boron trifluoride diethyl etherate. A suitable solvent is toluene.

Compounds of formula (VI) are conveniently prepared by rearranging an azirine compound of formula (V).

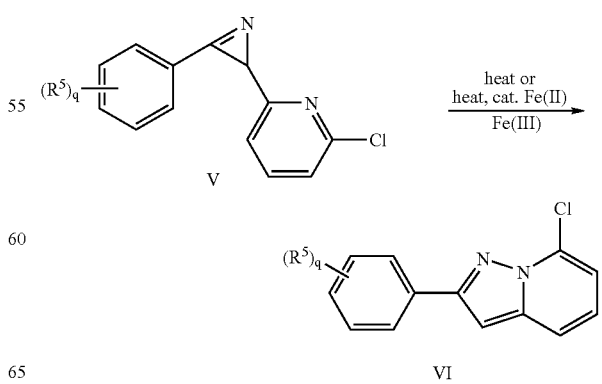

wherein all variables are as defined above in connection with Scheme 1.

The rearrangement of the azirines of formula (V) can be accomplished by heating a solution of the azirine of formula (V) in a suitable solvent at a temperature of about 160–200° C. Suitable inert solvents include, but are not limited to, 1-methyl-2-pyrrolidinone, and 1,2,4-trichlorobenzene. A more preferred method for rearrangement of the azirine of formula (V) to compounds of formula (VI) involves reacting the compound of formula (V) with ferrous chloride ($FeCl_2$) or ferric chloride ($FeCl_3$). This reaction is typically done in an inert solvent with heating. A preferred solvent for this reaction is 1,2-dimethoxyethane and the like.

Typically the azirines of formula (V) are prepared from oxime compounds of formula (IV) by treatment with acylating or sulfonylating agents in the presence of a base.

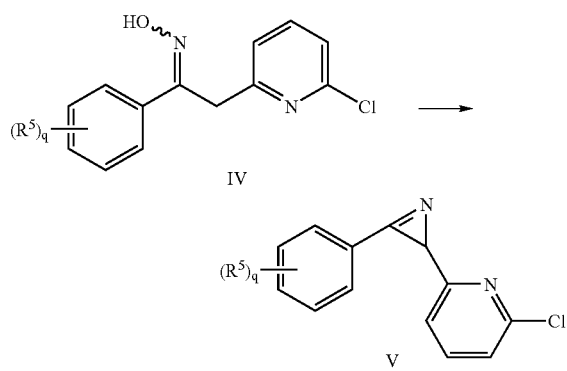

wherein all variables are as defined above in connection with Scheme 1.

Typical acylating or sulfonylating agents include but are not limited to, acetic anhydride, trifluoroacetic anhydride, methanesulfonyl chloride, toluenesulfonyl chloride and the like. Typical bases include, but are not limited to, triethylamine, diisopropylethylamine, pyridine, or the like. The reaction may be carried out in an inert solvent such as for example, chloroform, dichloromethane, toluene or the like.

The oxime compounds of formula (IV) are readily prepared by treating ketone compounds of formula (III) with a hydroxylamine source, in a suitable solvent, and optionally with a base.

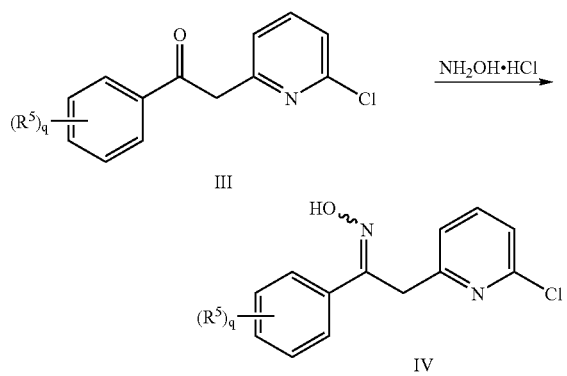

wherein all variables are as defined above in connection with Scheme 1.

Preferably the hydroxylamine is hydroxylamine hydrochloride and the base is an aqueous solution of sodium hydroxide. Suitable solvents include lower alcohols such as methanol, ethanol, or isopropanol.

The ketone compounds of formula (III) can be prepared by treatment of 2-chloro-6-picoline with a benzoylating agent of formula (II) in the presence of a base.

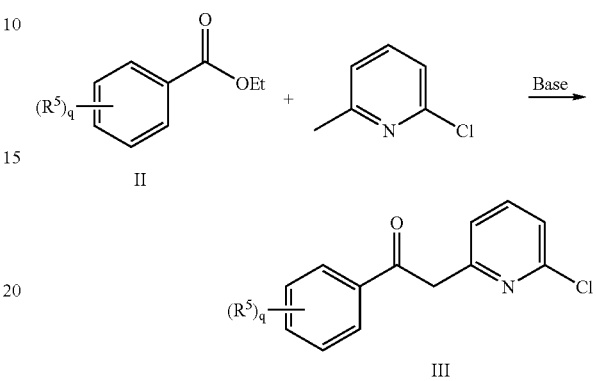

wherein all variables are as defined above in connection with Scheme 1.

Preferred benzoylating agents of formula (II) include, but are not limited to, benzoyl esters. An example of a suitable base is lithium bis(trimethylsilyl)amide in an inert solvent such as tetrahydrofuran. Ketones such as those of formula (III) can be readily prepared using procedures known to one skilled in the art and/or described in the literature (Cassity, R. P.; Taylor, L. T.; Wolfe, J. F. *J.Org. Chem.* 1978, 2286).

In addition to the foregoing process for preparing certain compounds of formula (I), the present invention also provides certain intermediate compounds for use in the preparation of such compounds of formula (I) according to the foregoing process.

Thus, as one aspect, the present invention provides compounds of formula (II)

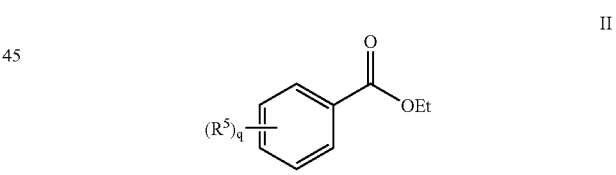

wherein all variables are as defined above in connection with Scheme 1 and Et is ethyl.

As another aspect, the present invention provides compounds of formula (III)

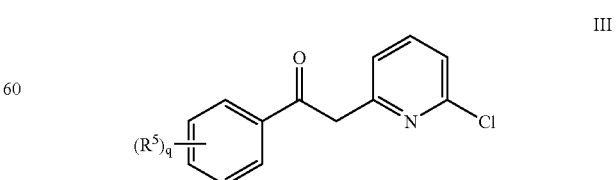

wherein all variables are as defined above in connection with Scheme 1.

As another aspect, the present invention provides compounds of formula (IV)

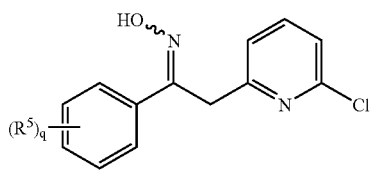

IV wherein all variables are as defined above in connection with Scheme 1.

As another aspect, the present invention provides compounds of formula (V)

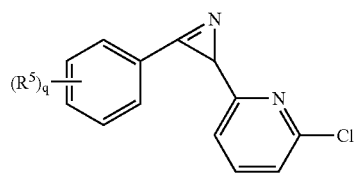

V wherein all variables are as defined above in connection with Scheme 1.

As another aspect, the present invention provides compounds of formula (VI)

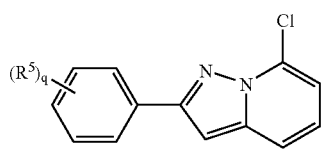

VI wherein all variables are as defined above in connection with Scheme 1.

As another aspect, the present invention provides compounds of formula (VII)

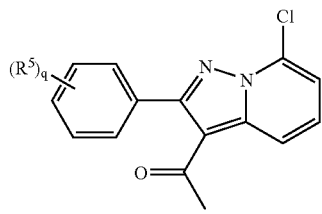

VII wherein all variables are as defined above in connection with Scheme 1.

As another aspect, the present invention provides compounds of formula (VIII)

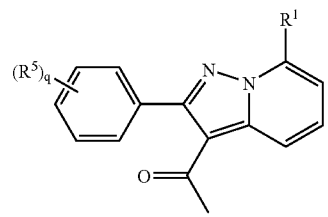

VIII wherein all variables are as defined above in connection with Scheme 1.

As another aspect, the present invention provides compounds of formula (IX)

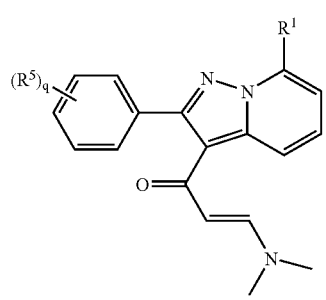

IX wherein all variables are as defined above in connection with Scheme 1.

In a further embodiment of the present invention, compounds of formula (I) wherein Y is N; $R^2$ is selected from the group consisting of H, alkyl, cycloalkyl, alkenyl, cycloalkenyl, —$NR^7R^8$, —$OR^7$, Ay, —OAy, —$S(O)_nR^9$, —$S(O)_n$Ay, —$R^{10}NR^7R^8$, —$R^{10}NR^7$Ay, Het, —NHHet, —$NHR^{10}$Het, —OHet, and —$OR^{10}$Het; $R^3$ is selected from the group consisting of H, alkyl, cycloalkyl, alkenyl, —$R^{10}OR^7$, —$R^{10}$OAy, —$NR^7R^8$ where $R^7$ and $R^8$ are not H, Ay, —$NR^7$Ay where $R^7$ is not H, —$R^{10}NR^7R^8$, —$R^{10}NR^7$Ay, —$C(O)R^7$, —C(O)Ay, —$CO_2R^7$, —$CO_2$Ay, —$SO_2NHR^9$ and Het; and $R^4$ is H, may be conveniently prepared by a general process outlined in Scheme 2 below.

Scheme 2

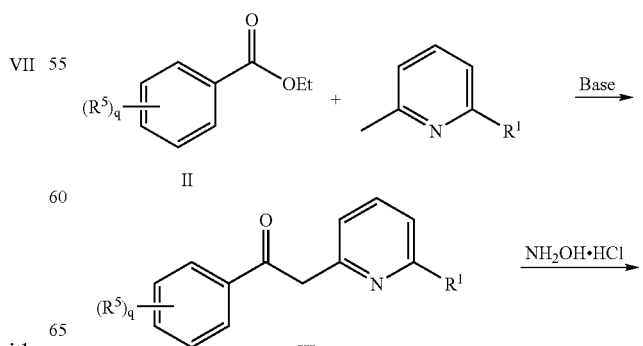

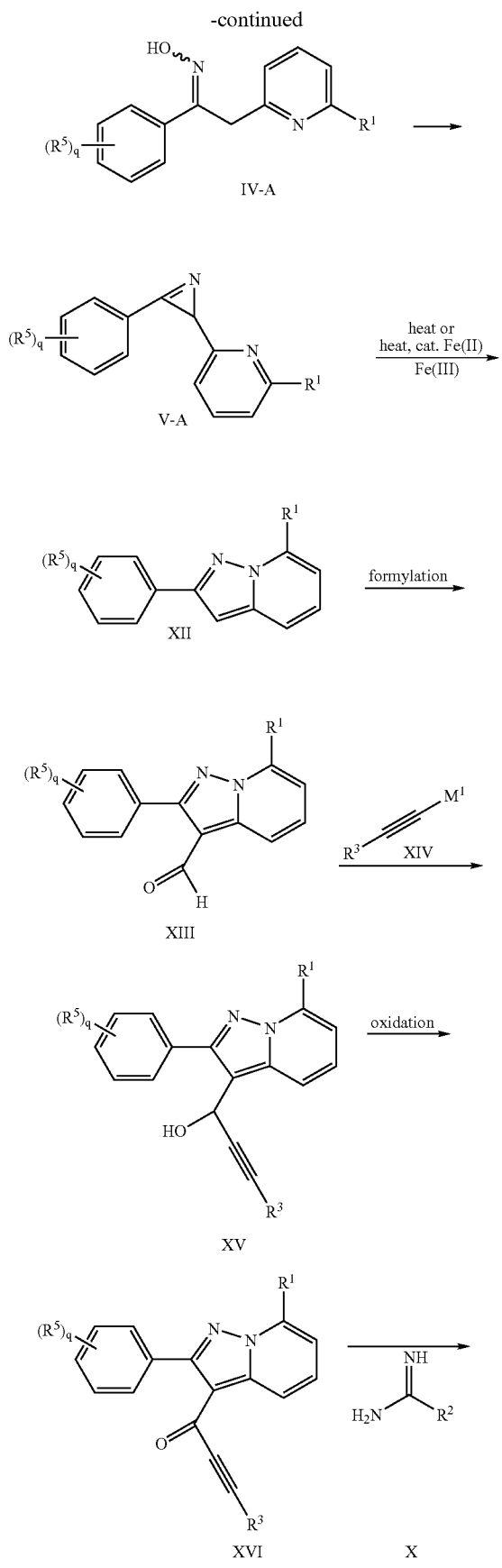

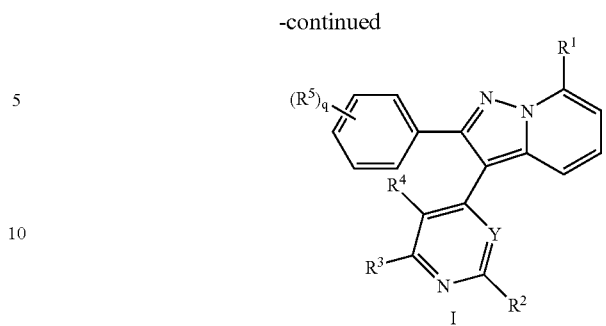

wherein:

R¹ is selected from the group consisting of halo, —NR⁷R⁸, Ay, —NR⁷Ay, Het, —NHR¹⁰Het, —NHHet and —NHR¹⁰Ay;

each R⁷ and R⁸ are the same or different and are independently selected from the group consisting of H, alkyl, cycloalkyl, alkenyl, cycloalkenyl, —R¹⁰cycloalkyl, —R¹⁰OR⁹, —R¹⁰NR⁹R¹¹, —R¹⁰C(O)R⁹, —C(O)R⁹, —C(O)R¹⁰Ay, —C(O)R¹⁰Het, —CO₂R⁹, —R¹⁰OC₂R⁹, —C(O)NR⁹R¹¹, —R¹⁰C(O)NR⁹R¹¹, —R¹⁰C(O)Ay, —R¹⁰C(O)Het, —C(S)NR⁹R¹¹, —R¹⁰C(S)NR⁹R¹¹, —R¹⁰NHC(NH)NR⁹R¹¹, —R¹⁰NHC(O)R¹⁰Het, —R¹⁰NHC(O)R¹⁰CO₂R⁹, —R¹⁰NHC(NCO₂R⁹)NHCO₂R⁹, —R¹⁰NHC(O)NHSO₂R⁹, —R¹⁰NHC(O)NHSO₂Ay, —R¹⁰NHC(O)NHSO₂Het, —R¹⁰C(NH)NR⁹R¹¹, —C(NH)NR⁹R¹¹, —SO₂NR⁹R¹¹, —R¹⁰SO₂NR⁹R¹¹, —R¹⁰NHSO₂R⁹, —SO₂R¹⁰, —R¹⁰SO₂R¹⁰, —R¹⁰NHCOR⁹, —R¹⁰SO₂NHCOR⁹, —R¹⁰NHP(O)(OR⁹)₂, —R₁₀OP(O)(OR⁹)₂ and —R¹⁰OP(O)(OR¹⁰Ay)₂;

each R⁹ and R¹¹ are the same or different and are independently selected from the group consisting of H, alkyl, cycloalkyl, —R¹⁰cycloalkyl, —R¹⁰OH, —R₁₀(OR¹⁰)_w where w is 1–10, and —R¹⁰NR¹⁰R¹⁰;

each R¹⁰ is the same or different and is independently selected from the group consisting of alkyl, cycloalkyl, alkenyl, cycloalkenyl and alkynyl;

Ay is aryl;

Het is a 5- or 6-membered heterocyclic or heteroaryl group;

R² is selected from the group consisting of alkyl, cycloalkyl, alkenyl, cycloalkenyl, Ay, —NR⁷R⁸, —OR⁷, —OAy, —S(O)ₙR⁹, —S(O)ₙAy, —R¹⁰NR⁷R⁸, —R¹⁰NR⁷Ay, Het, —NHHet, —NHR¹⁰Het, —OHet and —OR¹⁰Het;

n is 0, 1 or 2;

Y is N;

R³ is selected from the group consisting of H, alkyl, cycloalkyl, alkenyl, Ay, —R¹⁰OR⁷, —R¹⁰OAy, —NR⁷R⁸ where R⁷ and R⁸ are not H, —NR⁷Ay where R⁷ is not H, —R¹⁰NR⁷R⁸, —R¹⁰NR⁷Ay, —C(O)R⁷, —C(O)Ay, —CO₂R⁷, —CO₂Ay, —SO₂NHR⁹ and Het;

R⁴ is H;

q is 0, 1, 2, 3, 4 or 5;

each $R^5$ is the same or different and is independently selected from the group consisting of halo, alkyl, alkenyl, alkynyl, cycloalkyl, cycloalkenyl, —$R^{10}$cycloalkyl, Ay, —$NHR^{10}$Ay, Het, —NHHet, —$NHR^{10}$Het, —$OR^7$, —OAy, —OHet, —$R^{10}OR^9$, —$NR^7R^8$, —$NR^7$Ay, —$R^{10}NR^7R^8$, —$R^{10}NR^7$Ay, —$R^{10}C(O)R^9$, —$C(O)R^9$, —$CO_2R^9$, —$R^{10}CO_2R^9$, —$C(O)NR^7R^8$, —C(O)Ay, —$C(O)NR^7$Ay, —C(O)Het, —$C(O)NHR^{10}$Het —$R^{10}C(O)NR^9R^{11}$, —$C(S)NR^9R^{11}$, —$R^{10}C(S)NR^9R^{11}$, —$R^{10}NHC(NH)NR^9R^{11}$, —$C(NH)NR^7R^8$, —$C(NH)NR^7$Ay, —$R^{10}C(NH)NR^9R^{11}$, —$S(O)_2NR^7R^8$, —$S(O)_2NR^7$Ay, —$R^{10}SO_2NHCOR^9$, —$R^{10}SO_2NR^9R^{11}$, —$R^{10}SO_2R^9$, —$S(O)_nR^9$, cyano, nitro and azido; or two adjacent $R^5$ groups together with the atoms to which they are bonded form a $C_{5-6}$ cycloalkyl or aryl;

wherein when q is 1 and $R^5$ is in the para position, $R^5$ is not halo; and $M^1$ is Li, Mg-halide or cerium-halide, wherein halide is halo.

Generally, the process for preparing compounds of formula (I) wherein Y is N; $R^2$ is selected from the group consisting of alkyl, cycloalkyl, alkenyl, cycloalkenyl, —$NR^7R^8$, —$OR^7$, Ay, —OAy, —$S(O)_nR^9$, —$S(O)_n$Ay, —$R^{10}NR^7R^8$, —$R^{10}NR^7$Ay, Het, —NHHet, —$NHR^{10}$Het, —OHet, and —$OR^{10}$Het; $R^3$ is selected from the group consisting of H, alkyl, cycloalkyl, alkenyl, —$R^{10}OR^7$, —$R^{10}$OAy, —$NR^7R^8$ where $R^7$ and $R^8$ are not H, Ay, —$NR^7$Ay where $R^7$ is not H, —$R^{10}NR^7R^8$, —$R^{10}NR^7$Ay, —$C(O)R^7$, —C(O)Ay, —$CO_2R^7$, —$CO_2$Ay, —$SO_2NHR^9$ and Het; and $R^4$ is H (all other variables having been defined above in connection with Scheme 2), comprises the following steps:

(a) reacting a compound of formula (IV-A) with an acylating or sulfonylating agent to prepare a compound of formula (V-A);

(b) rearranging the compound of formula (V-A) to prepare a compound of formula (XII);

(c) formylating the compound of formula (XII) to prepare a compound of formula (XIII);

(d) reacting the compound of formula (XIII) with a compound of formula (XIV) to prepare a compound of formula (XV);

(e) oxidizing the compound of formula (XV) to prepare a compound of formula (XVI); and (f) reacting the compound of formula (XVI) with a compound of formula (X) to prepare the compounds of formula (I).

More specifically, compounds of formula (I) wherein Y is N; $R^2$ is selected from the group consisting of alkyl, cycloalkyl, alkenyl, cycloalkenyl, —$NR^7R^8$, —$OR^7$, Ay, —OAy, —$S(O)_nR^9$, —$S(O)_n$Ay, —$R^{10}NR^7R^8$, —$R^{10}NR^7$Ay, Het, —NHHet, —$NHR^{10}$Het, —OHet, and —$OR^{10}$Het; $R^3$ is selected from the group consisting of H, alkyl, cycloalkyl, alkenyl, —$R^{10}OR^7$, —$R^{10}$OAy, —$NR^7R^8$ where $R^7$ and $R^8$ are not H, Ay, —$NR^7$Ay where $R^7$ is not H, —$R^{10}NR^7R^8$, —$R^{10}NR^7$Ay, —$C(O)R^7$, —C(O)Ay, —$CO_2R^7$, —$CO_2$Ay, —$SO_2NHR^9$ and Het; and $R^4$ is H, may be prepared by reacting a compound of formula (XVI) with a compound of formula (X).

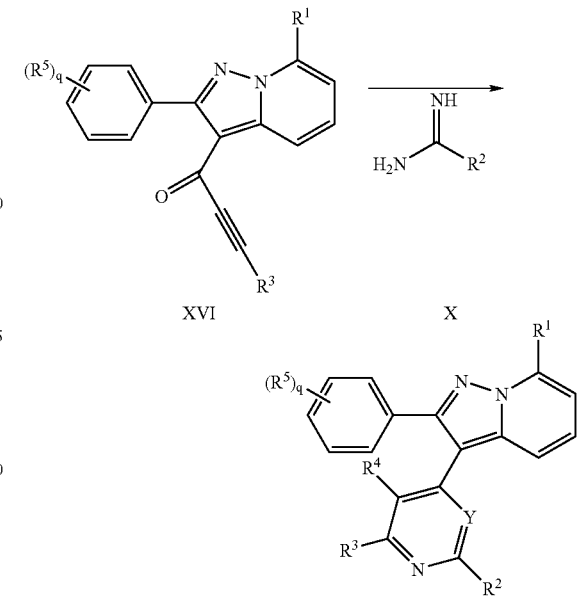

wherein all variables are as defined above in connection with Scheme 2.

This method can be readily carried out by mixing a compound of formula (XVI) with a compound of formula (X) in a suitable solvent, optionally in the presence of a base. The reaction may be heated to 50–150° C. or performed at ambient temperature. Typical solvents include but are not limited to lower alcohols such as methanol, ethanol, isopropanol and the like. Typical bases include for example, sodium alkoxide, potassium carbonate, or an amine base such as triethylamine. In another embodiment, the solvent is N,N-dimethylformamide and the base is potassium carbonate, or an amine base such as triethylamine.

Compounds of formula (XVI) may be conveniently prepared by oxidation of a compound of formula (XV).

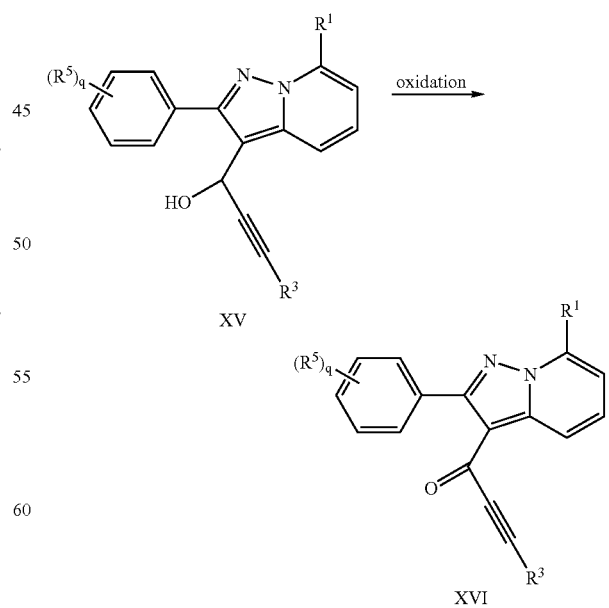

wherein all variables are as defined above in connection with Scheme 2.

Preferred oxidizing agents include but are not limited to, manganese dioxide, and the like, in an inert solvent. Suitable inert solvents include but are not limited to, dichloromethane, chloroform, N,N-dimethylformamide, ether, and the like.

Compounds of formula (XV) may be conveniently prepared by reacting a compound of formula (XIII) with a compound of formula (XIV).

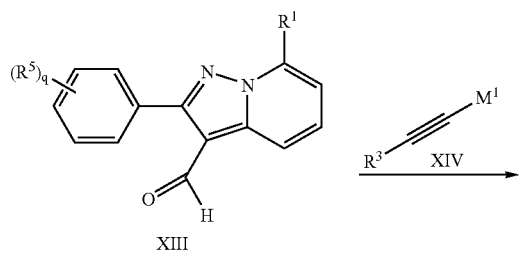

wherein all variables are as defined above in connection with Scheme 2.

Preferred metals ($M^1$) in the compounds of formula (XIV) include but are not limited to, lithium, magnesium(II) halides, cerium(III) halides, and the like. Compounds of formula (XIV) may be purchased from commercial sources or prepared by methods known to one skilled in the art.

Compounds of formula (XIII) may be conveniently prepared from compounds of formula (XII) by a formylation procedure.

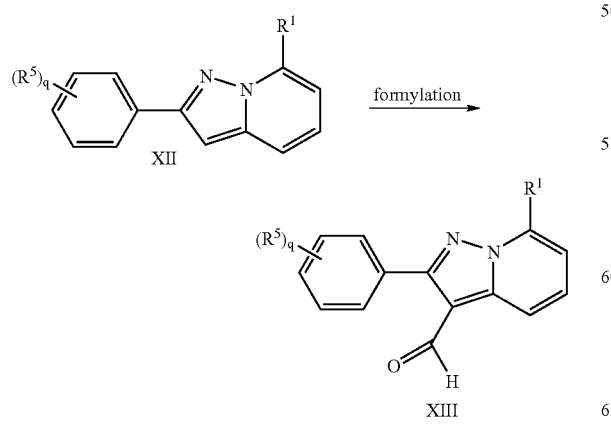

wherein all variables are as defined above in connection with Scheme 2.

Typically the formylation is carried out via the Vilsmeier-Haack reaction. The Vilsmeier-Haack reagents can be purchased from commercial sources or prepared in situ. Preferable conditions include, but are not limited to treating compounds of formula (XII) with a premixed solution of phosphorous oxychloride in N,N-dimethylformamide optionally with heating the reaction to 50–150° C.

The compounds of formula (XII) are prepared by a process analogous to the process employed for the preparation of compounds of formula (VI) in Scheme 1 above.

In addition to the foregoing process for preparing certain compounds of formula (I), the present invention also provides certain intermediate compounds for use in the preparation of such compounds of formula (I) according to the foregoing process. Thus, as one aspect, the present invention provides compounds of formula (III-A)

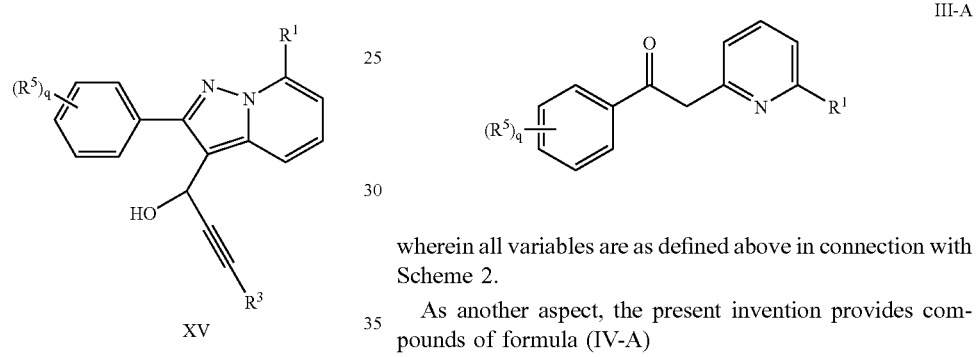

wherein all variables are as defined above in connection with Scheme 2.

As another aspect, the present invention provides compounds of formula (IV-A)

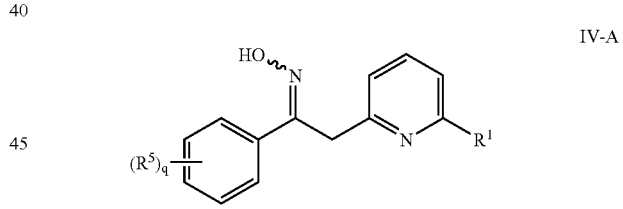

wherein all variables are as defined above in connection with Scheme 2.

As another aspect, the present invention provides compounds of formula (V-A)

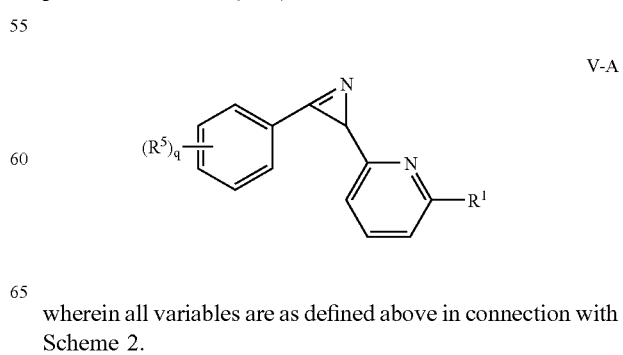

wherein all variables are as defined above in connection with Scheme 2.

As another aspect, the present invention provides compounds of formula (XII)

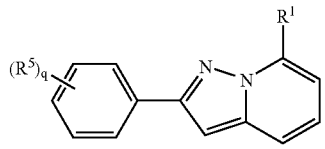

XII wherein all variables are as defined above in connection with Scheme 2.

In another aspect, the present invention provides compounds of formula (XIII)

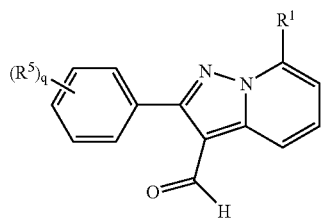

XIII wherein all variables are as defined above in connection with Scheme 2.

In another aspect, the present invention provides compounds of formula (XV)

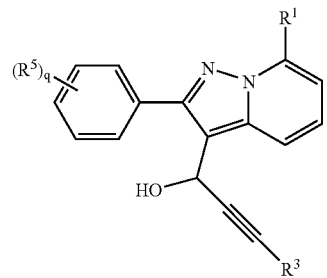

XV wherein all variables are as defined above in connection with Scheme 2.

In another aspect, the present invention provides compounds of formula (XVI)

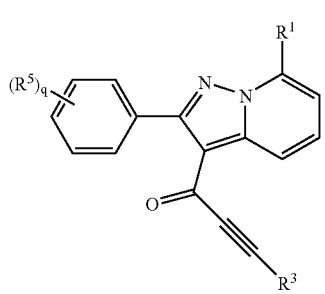

XVI wherein all variables are as defined above in connection with Scheme 2.

Compounds of formula (I) wherein Y is N and $R^2$ is selected from the group consisting of alkyl, cycloalkyl, alkenyl, cycloalkenyl, —$NR^7R^8$, —$OR^7$, Ay, —OAy, —$S(O)_nR^9$, —$S(O)_n$Ay, —$R^{10}NR^7R^8$, —$R^{10}NR^7$Ay, Het, —NHHet, —$NHR^{10}$Het, —OHet, and —$OR^{10}$Het, may be conveniently prepared by the process outlined in Scheme 3 below.

Scheme 3

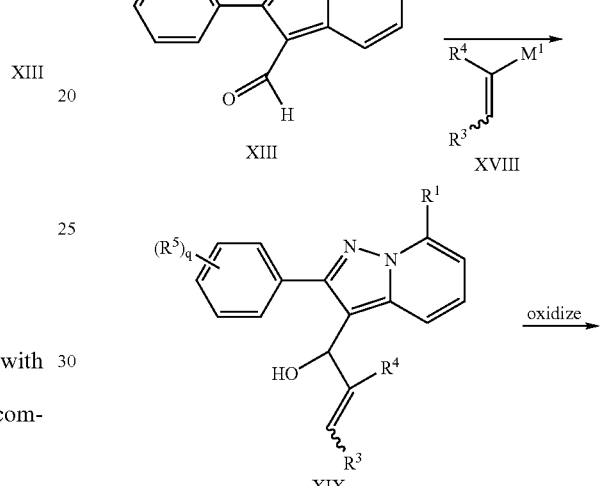

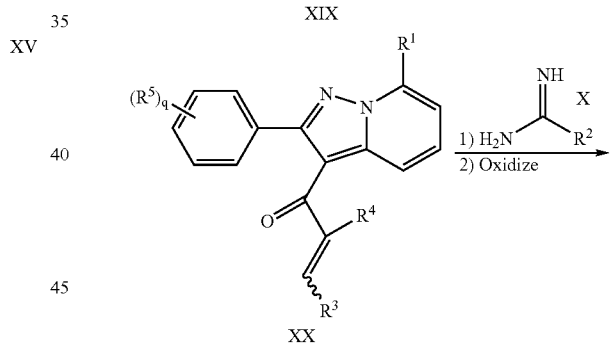

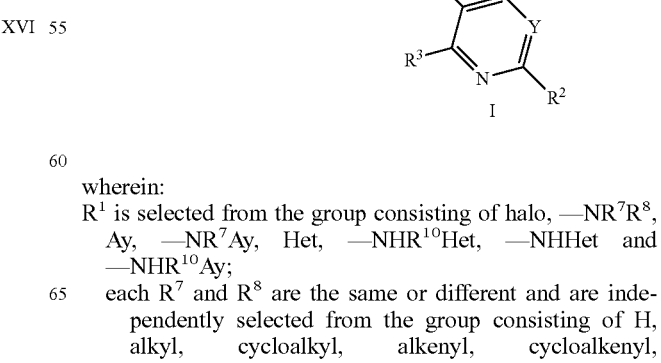

wherein:
$R^1$ is selected from the group consisting of halo, —$NR^7R^8$, Ay, —$NR^7$Ay, Het, —$NHR^{10}$Het, —NHHet and —$NHR^{10}$Ay;
each $R^7$ and $R^8$ are the same or different and are independently selected from the group consisting of H, alkyl, cycloalkyl, alkenyl, cycloalkenyl, —$R^{10}$cycloalkyl, —$R^{10}OR^9$, —$R^{10}NR^9R^{11}$, —$R^{10}C(O)R^9$, —$C(O)R^9$, —$C(O)R^{10}Ay$, —$C(O)R^{10}Het$, —$CO_2R^9$, —$R^{10}CO_2R^9$, —$C(O)NR^9R^{11}$, —$R^{10}C(O)NR^9R^{11}$, —$R^{10}C(O)Ay$, —$R^{10}C(O)Het$, —$C(S)NR^9R^{11}$, —$R^{10}C(S)NR^9R^{11}$, —$R^{10}NHC(NH)NR^9R^{11}$, —$R^{10}NHC(O)R^{10}Het$, —$R^{10}NHC(O)R^{10}CO_2R^9$, —$R^{10}NHC(NCO_2R^9)NHCO_2R^9$, —$R^{10}NHC(O)NHSO_2R^9$, —$R^{10}NHC(O)NHSO_2Ay$, —$R^{10}NHC(O)NHSO_2Het$, —$R^{10}C(NH)NR^9R^{11}$, —$C(NH)NR^9R^{11}$, —$SO_2NR^9R^{11}$, —$R^{10}SO_2NR^9R^{11}$, —$R^{10}NHSO_2R^9$, —$SO_2R^{10}$, —$R^{10}SO_2R^{10}$, —$R^{10}NHCOR^9$, —$R^{10}SO_2NHCOR^9$, —$R^{10}NHP(O)(OR^9)_2$, —$R_{10}OP(O)(OR^9)_2$ and —$R^{10}OP(O)(OR^{10}Ay)_2$;

each $R^9$ and $R^{11}$ are the same or different and are independently selected from the group consisting of H, alkyl, cycloalkyl, —$R^{10}$ cycloalkyl, —$R^{10}OH$, —$R_{10}(OR^{10})_w$ wherein w is 1–10, and —$R^{10}NR^{10}R^{10}$;

each $R^{10}$ is the same or different and is independently selected from the group consisting of alkyl, cycloalkyl, alkenyl, cycloalkenyl and alkynyl;

Ay is aryl;

Het is a 5- or 6-membered heterocyclic or heteroaryl group;

$R^2$ is selected from the group consisting of alkyl, cycloalkyl, alkenyl, cycloalkenyl, Ay, —$NR^7R^8$, —$OR^7$, —OAy, —$S(O)_nR^9$, —$S(O)_nAy$, —$R^{10}NR^7R^8$, —$R^{10}NR^7Ay$, Het, —NHHet, —$NHR^{10}$Het, —OHet and —$OR^{10}$ Het;

n is 0, 1 or 2;

Y is N;

$R^3$ and $R^4$ are the same or different and are each independently selected from the group consisting of H, halo, alkyl, cycloalkyl, alkenyl, Ay, —$OR^7$, —OAy, —$R^{10}OR^7$, —$R^{10}Ay$, —$NR^7R^8$, —$NR^7Ay$, —$R^{10}NR^7R^8$, —$R^{10}NR^7Ay$, —$C(O)R^7$, —$C(O)Ay$, —$CO_2R^7$, —$CO_2Ay$, —$SO_2NHR^9$, Het, —NHHet and —$NHR^{10}$Het;

q is 0, 1, 2, 3, 4 or 5;

each $R^5$ is the same or different and is independently selected from the group consisting of halo, alkyl, alkenyl, alkynyl, cycloalkyl, cycloalkenyl, —$R^{10}$cycloalkyl, Ay, —$NHR^{10}Ay$, Het, —NHHet, —$NHR^{10}$Het, —$OR^7$, —OAy, —OHet, —$R^{10}OR^9$, —$NR^7R^8$, —$NR^7Ay$, —$R^{10}NR^7R^8$, —$R^{10}NR^7Ay$, —$R^{10}C(O)R^9$, —$C(O)R^9$, —$CO_2R^9$, —$R^{10}CO_2R^9$, —$C(O)NR^7R^8$, —$C(O)Ay$, —$C(O)NR^7Ay$, —$C(O)Het$, —$C(O)NHR^{10}Het$ —$R^{10}C(O)NR^9R^{11}$, —$C(S)NR^9R^{11}$, —$R^{10}C(S)NR^9R^{11}$, —$R^{10}NHC(NH)NR^9R^{11}$, —$C(NH)NR^7R^8$, —$C(NH)NR^7Ay$, —$R^{10}C(NH)NR^9R^{11}$, —$S(O)_2NR^7R^8$, —$S(O)_2NR^7Ay$, —$R^{10}SO_2NHCOR^9$, —$R^{10}SO_2NR^9R^{11}$, —$R^{10}SO_2R^9$, —$S(O)_nR^9$, cyano, nitro and azido; or two adjacent $R^5$ groups together with the atoms to which they are bonded form a $C_{5-6}$ cycloalkyl or aryl;

wherein when q is 1 and $R^5$ is in the para position, $R^5$ is not halo; and $M^1$ is Li, Mg-halide or cerium-halide, wherein halide is halo.

Generally, the process for preparing compounds of formula (I) wherein Y is N and $R^2$ is selected from the group consisting of alkyl, cycloalkyl, alkenyl, cycloalkenyl, —$NR^7R^8$, —$OR^7$, Ay, —OAy, —$S(O)_nR^9$, —$S(O)_nAy$, —$R^{10}NR^7R^8$, —$R^{10}NR^7Ay$, Het, —NHHet, —$NHR^{10}$Het, —OHet, and —$OR^{10}$Het, (all formulas and all other variables having been defined above in connection with Scheme 3), comprises the following steps:

(a) reacting a compound of formula (XIII) with a compound of formula (XVIII) to prepare a compound of formula (XIX);

(b) oxidizing the compound of formula (XIX) to prepare a compound of formula (XX); and (c) reacting a compound of formula (XX) with a compound of formula (X) followed by oxidative aromatization to prepare the compounds of formula (I).

More specifically, compounds of formula (I) wherein Y is N and $R^2$ is selected from the group consisting of alkyl, cycloalkyl, alkenyl, cycloalkenyl, —$NR^7R^8$, —$OR^7$, Ay, —OAy, —$S(O)_nR^9$, —$S(O)_nAy$, —$R^{10}NR^7R^8$, —$R^{10}NR^7Ay$, Het, —NHHet, —$NHR^{10}$Het, —OHet, and —$OR^{10}$Het can be prepared by reacting a compound of formula (XX) with a compound of formula (X) followed by oxidative aromatization.

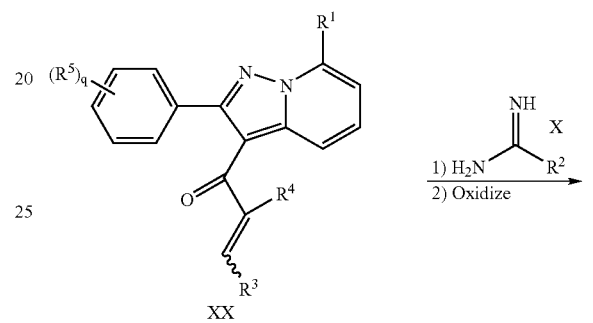

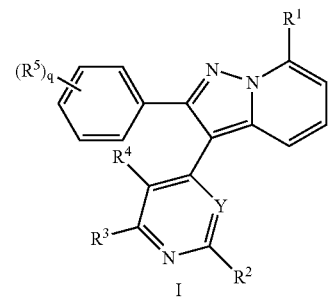

wherein all variables are as defined above in connection with Scheme 3.

The condensation is conveniently carried out by treating the compound of formula (XX) with a compound of formula (X) in an inert solvent, optionally in the presence of a base. The reaction may be heated to 50–150° C. or performed at ambient temperature. Suitable inert solvents include lower alcohols such as, for example, methanol, ethanol, isopropanol and the like. The base is typically sodium alkoxide, potassium carbonate, or an amine base such as triethylamine. In another embodiment, the solvent is N,N-dimethylformamide and the base is potassium carbonate, or an amine base such as triethylamine. The reaction produces a dihydropyrimidine intermediate.

Preferably in the same reaction vessel, the dihydropyrimidine intermediate may be oxidized to a compound of formula (I) by the addition of an oxidizing agent. The reaction may be heated to 50–150° C. or performed at ambient temperature. Preferably, the oxidizing agent is oxygen ($O_2$), palladium on carbon, 2,3-dichloro-5,6-dicyano-1,4-benzoquinone, or the like.

Compounds of formula (XX) may be conveniently prepared by oxidation of compounds of formula (XIX).

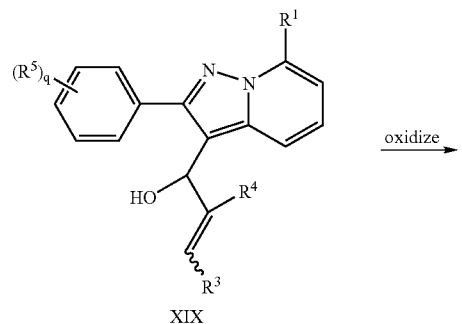

XIX

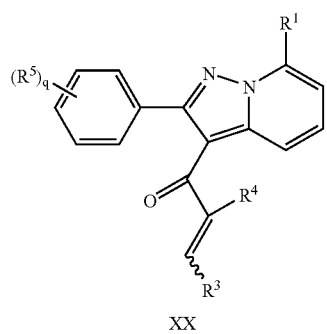

XX wherein all variables are as defined above in connection with Scheme 3.

Preferred oxidizing agents for the oxidation of compounds of formula (XIX) include but are not limited to manganese dioxide, and the like. The oxidation is typically carried out in an inert solvent such as for example, dichloromethane, chloroform, N,N-dimethylformamide, ether, and the like.

Compounds of formula (XIX) may be conveniently prepared by reacting a compound of formula (XIII) with a compound of formula (XVIII).

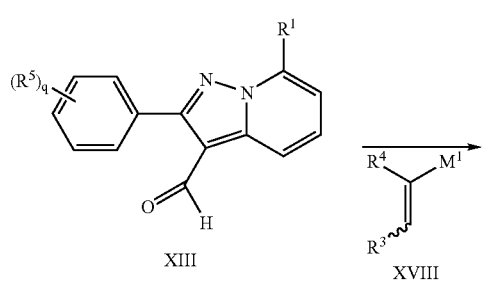

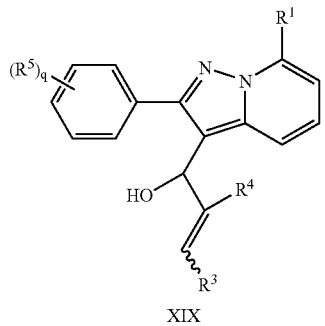

XIX wherein $M^1$ is a metal such as for example, lithium, magnesium(II) halides, cerium(III) halides, and the like and all other variables are as defined above in connection with Scheme 3. Compounds of formula (XVIII) may be purchased from commercial sources or prepared by methods known to one skilled in the art. The compounds of formula (XIII) may be prepared using the methods described in connection with Schemes 1 and 2 above.

In addition to the foregoing process for preparing certain compounds of formula (I), the present invention also provides certain intermediate compounds for use in the preparation of such compounds of formula (I) according to the foregoing process. Thus, as one aspect, the present invention provides compounds of formula (XIX)

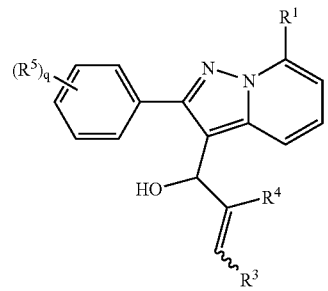

XIX wherein all variables are as described above in connection with Scheme 3.

In another aspect, the present invention provides compounds of formula (XX)

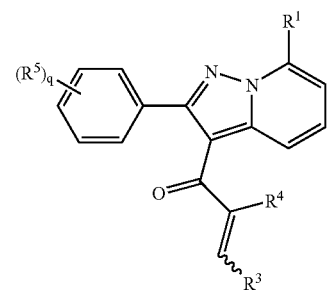

XX wherein all variables are as described above in connection with Scheme 3.

Compounds of formula (I) wherein Y is CH or N, may be conveniently prepared by the process outlined in Scheme 4 below.

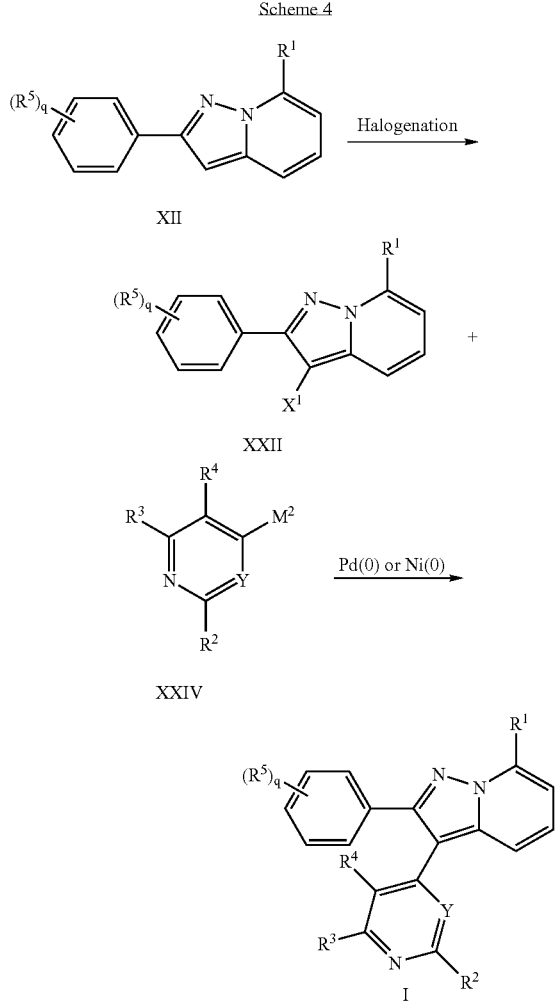

wherein:
$R^1$ is selected from the group consisting of halo, —$NR^7R^8$, Ay, —$NR^7$Ay, Het, —$NHR^{10}$Het, —NHHet and —$NHR^{10}$Ay;

each $R^7$ and $R^8$ are the same or different and are independently selected from the group consisting of H, alkyl, cycloalkyl, alkenyl, cycloalkenyl, —$R^{10}$cycloalkyl, —$R^{10}OR^9$, —$R^{10}NR^9R^{11}$, —$R^{10}C(O)R^9$, —$C(O)R^9$, —$C(O)R^{10}$Ay, —$C(O)R^{10}$Het, —$CO_2R^9$, —$R^{10}CO_2R^9$, —$C(O)NR^9R^{11}$, —$R^{10}C(O)NR^9R^{11}$, —$R^{10}C(O)$Ay, —$R^{10}C(O)$Het, —$C(S)NR^9R^{11}$, —$R^{10}C(S)NR^9R^{11}$, —$R^{10}NHC(NH)NR^9R^{11}$, —$R^{10}NHC(O)R^{10}$Het, —$R^{10}NHC(O)R^{10}CO_2R^9$, —$R^{10}NHC(NCO_2R^9)NHCO_2R^9$, —$R^{10}NHC(O)NHSO_2R^9$, —$R^{10}NHC(O)NHSO_2$Ay, —$R^{10}NHC(O)NHSO_2$Het, —$R^{10}C(NH)NR^9R^{11}$, —$C(NH)NR^9R^{11}$, —$SO_2NR^9R^{11}$, —$R^{10}SO_2NR^9R^{11}$, —$R^{10}NHSO_2R^9$, —$SO_2R^{10}$, —$R^{10}SO_2R^{10}$, —$R^{10}NHCOR^9$, —$R^{10}SO_2NHCOR^9$, —$R^{10}NHP(O)(OR^9)_2$, —$R^{10}OP(O)(OR^9)_2$ and —$R^{10}OP(O)(OR^{10}Ay)_2$;

each $R^9$ and $R^{11}$ are the same or different and are independently selected from the group consisting of H, alkyl, cycloalkyl, —$R^{10}$cycloalkyl, —$R^{10}OH$, —$R^{10}(OR^{10})_w$ where w is 1–10, and —$R^{10}NR^{10}R^{10}$;

each $R^{10}$ is the same or different and is independently selected from the group consisting of alkyl, cycloalkyl, alkenyl, cycloalkenyl and alkynyl;

Ay is aryl;

Het is a 5- or 6-membered heterocyclic or heteroaryl group;

$R^2$ is selected from the group consisting of halo, alkyl, cycloalkyl, alkenyl, cycloalkenyl, —$NR^7R^8$, —$OR^7$, —OAy, —$S(O)_nR^9$, —$S(O)_n$Ay, —$R^{10}NR^7R^8$, —$R^{10}NR^7$Ay, Ay, Het, —NHHet, —$NHR^{10}$Het, —OHet and —$OR^{10}$Het;

n is 0, 1 or 2;

Y is N or CH;

$R^3$ and $R^4$ are the same or different and are each independently selected from the group consisting of H, halo, alkyl, cycloalkyl, alkenyl, Ay, —$OR^7$, —OAy, —$R^{10}OR^7$, —$R^{10}$OAy, —$NR^7R^8$, —$NR^7$Ay, —$R^{10}NR^7R^8$, —$R^{10}NR^7$Ay, —$C(O)R^7$, —C(O)Ay, —$CO_2R^7$, —$CO_2$Ay, —$SO_2NHR^9$, Het, —NHHet and —$NHR^{10}$Het;

q is 0, 1, 2, 3, 4 or 5;

each $R^5$ is the same or different and is independently selected from the group consisting of halo, alkyl, alkenyl, alkynyl, cycloalkyl, cycloalkenyl, —$R^{10}$cycloalkyl, Ay, —$NHR^{10}$Ay, Het, —NHHet, —$NHR^{10}$Het, —$OR^7$, —OAy, —OHet, —$R^{10}OR^9$, —$NR^7R^8$, —$NR^7$Ay, —$R^{10}NR^7R^8$, —$R^{10}NR^7$Ay, —$R^{10}C(O)R^9$, $C(O)R^9$, —$CO_2R^9$, —$R^{10}CO_2R^9$, —$C(O)NR^7R^8$, —C(O)Ay, —$C(O)NR^7$Ay, —C(O)Het, —$C(O)NHR^{10}$Het —$R^{10}C(O)NR^9R^{11}$, —$C(S)NR^9R^{11}$, —$R^{10}C(S)NR^9R^{11}$, —$R^{10}NHC(NH)NR^9R^{11}$, —$C(NH)NR^7R^8$, —$C(NH)NR^7$Ay, —$R^{10}C(NH)NR^9R^{11}$, —$S(O)_2NR^7R^8$, —$S(O)_2NR^7$Ay, —$R^{10}SO_2NHCOR^9$, —$R^{10}SO_2NR^9R^{11}$, —$R^{10}SO_2R^9$, —$S(O)_nR^9$, cyano, nitro and azido; or two adjacent $R^5$ groups together with the atoms to which they are bonded form a $C_{5-6}$ cycloalkyl or aryl;

wherein when q is 1 and $R^5$ is in the para position, $R^5$ is not halo;

wherein when Y is CH, $R^3$ is not —$NR^7$Ay;

$X^1$ is chloro, bromo, or iodo; and $M^2$ is —$B(OH)_2$, —$B(ORa)_2$, —$B(Ra)_2$, —$Sn(Ra)_3$, Zn-halide, ZnRa, or Mg-halide where Ra is alkyl or cycloalkyl and halide is halo.

Generally, the process for preparing compounds of formula (I) (all formulas and variables having been defined above in connection with Scheme 4), comprises the following steps:

a) halogenating a compound of formula (XII) to prepare a compound of formula (XXII); and b) reacting the compound of formula (XXII) with a compound of formula (XXIV) to prepare the compounds of formula (I).

More specifically, compounds of formula (I) wherein Y is N or CH can be prepared by reacting a compound of formula (XXII) with a compound of formula (XXIV).

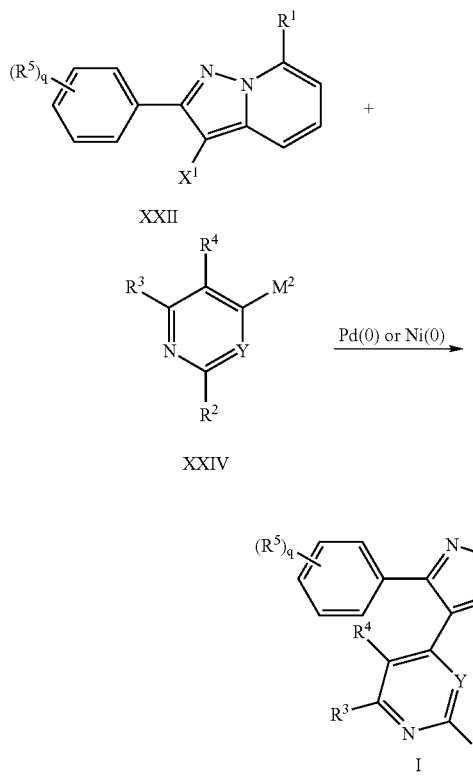

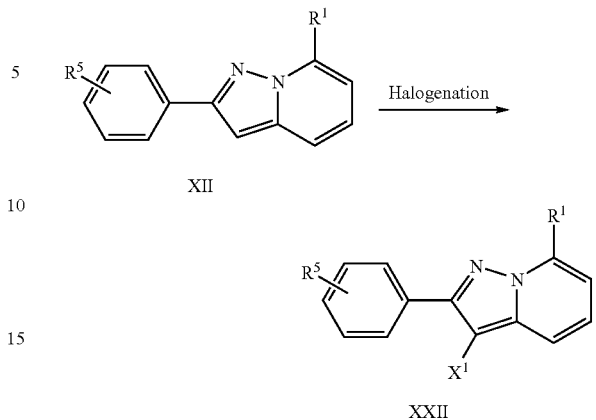

wherein all variables are as defined above in connection with Scheme 4.

The reaction may be carried out in an inert solvent, in the presence of a palladium (0) or nickel (0) catalyst. The reaction may optionally be heated to about 50–150° C. Preferably the reaction is performed by reacting equimolar amounts of a compound of formula (XXII) with a Het-metal compound of formula (XXIV), but the reaction may also be performed in the presence of an excess of compound of the formula (XXIV). The palladium or nickel catalyst is preferably present in 1–10 mol % compared to the compound of formula (XXII). Examples of suitable palladium catalysts include but are not limited to, tetrakis(triphenylphosphine)palladium (0), dichlorobis(triphenyl-phosphine)palladium (II), tris(dibenzylideneacetone)dipalladium (0), and bis(diphenylphosphinoferrocene)palladium (II) dichloride. Suitable solvents include but are not limited to, N,N-dimethylformamide, toluene, tetrahydrofuran, dioxane, and 1-methyl-2-pyrrolidinone. When the Het-metal compound of formula (XXIV) is an arylboronic acid or ester or an arylborinate the reaction is more conveniently carried out by adding a base in a proportion equivalent to, or greater than, that of the compound of formula (XXIV). Het-metal compounds of formula (XXIV) may be obtained from commercial sources or prepared either as discreet isolated compounds or generated in situ using methods known to one skilled in the art. (Suzuki, A. *J. Organomet. Chem.* 1999, 576, 147; Stille, J. *Angew. Chem. Int. Ed. Engl.* 1986, 25, 508; Snieckus, V. *J. Org. Chem.* 1995, 60, 292.)

Compounds of formula (XXII) can be prepared from compounds of formula (XII) by a halogenation procedure.

wherein all variables are as defined above in connection with Scheme 4.

Typically, the halogenation reaction is carried out by subjecting the compounds of formula (XII) to a halogenating agent in a suitable solvent. Suitable halogenating agents include but are not limited to, N-bromosuccinimide, trialkylammonium tribromides, bromine, N-chlorosuccinimide, N-iodosuccinimide, iodine monochloride, and the like. Suitable solvents include, for example, N,N-dimethylformamide, tetrahydrofuran, dioxane, 1-methyl-2-pyrrolidinone, carbon tetrachloride, toluene, dichloromethane, diethyl ether, and the like.

In the embodiments wherein the compound of formula (XXII) is defined where $R^1$ is chloro, (i.e., compounds of formula (XXII-A)) and compounds of formula (I) where $R^1$ is other than chloro are desired, it may be desireable to convert the compounds of formula (XXII-A) to compounds of formula (XXII-B) prior to reacting with the Het-metal compound of formula (XXIV). Compounds of formula (XXII-B) can be conveniently and surprisingly prepared from compounds of formula (XXII-A) by an amination procedure.

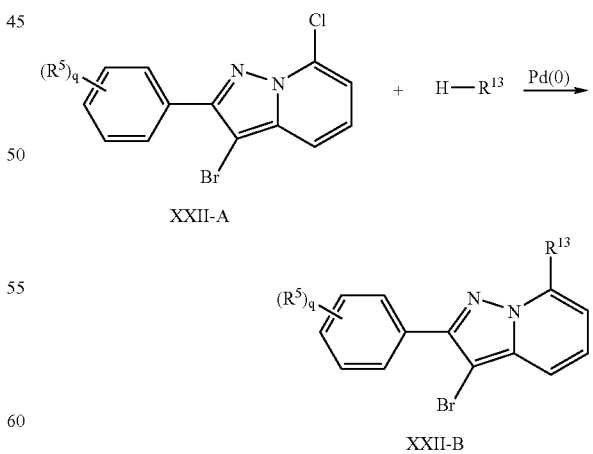

wherein $R^{13}$ is selected from the group consisting of —$NR^7R^8$, —$NR^7Ay$, Het, —$NHR^{10}Het$, —NHHet and —$NHR^{10}Ay$, and all other variables are as defined above in connection with Scheme 4.

The ability to replace the chlorine in preference to the bromine of the heterocyclic ring system is unexpected. Preferably, a compound of formula (XXII-A) is reacted with a primary or secondary amine having substitutions corresponding to those of R¹, in the presence of a palladium catalyst and a base. The procedure represents a modification of procedures found in the literature (Wolfe, J. P.; Buchwald, S. L. *J. Org. Chem.* 2000, 65, 1144) wherein amines are cross-coupled to aryl halides. Suitable palladium (0) catalysts include palladium(II) acetate and tris(dibenzylideneacetone) dipalladium (0). Suitable bases include sodium tert-butoxide and cesium carbonate. Solvents such as toluene may be employed.

In addition to the foregoing process for preparing compounds of formula (I), the present invention also provides certain intermediate compounds for use in the preparation of compounds of formula (I) according to the foregoing process. Thus, as one aspect, the present invention provides compounds of formula (XXII)

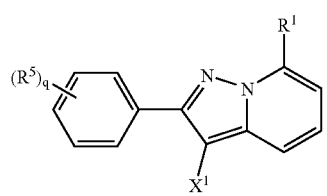

XXII wherein $X^1$ is chloro, bromo, or iodo, and all other variables are as defined above in connection with Scheme 4.

As will be apparent to those skilled in the art, the compounds of formula (I) may be converted to other compounds of formula (I) using techniques well known in the art. For example, one method of converting compounds of formula (I) to other compounds of formula (I) comprises a) oxidizing the compound of formula (I-A) to prepare a compound of formula (I-B) and then b) optionally reacting a compound of formula (I-B) with an oxygen or amine nucleophile of formula $R^2$, wherein $R^2$ is selected from the group consisting of —NR⁷R⁸, —OR⁷, —OAy, Het attached through N, —NHHet, —NHR¹⁰Het, —OHet and —OR¹⁰Het to produce a compound of formula I wherein $R^2$ is selected from the group consisting of —NR⁷R⁸, —OR⁷, —OAy, Het attached through N, —NHHet, —NHR¹⁰Het, —OHet and —OR¹⁰Het.

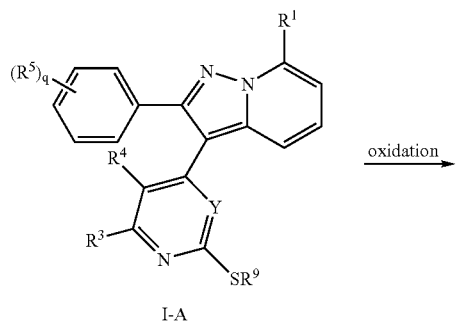

I-A

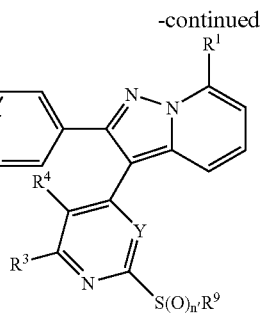

I-B

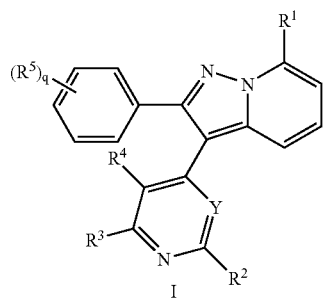

I wherein n' is 1 or 2 and all other variables are as defined according to any of the processes described above.

More specifically, compounds of formula (I) can be prepared by reacting a compound of formula (I-B) (i.e., compounds of formula I wherein $R^2$ is $S(O)_{n'}R^9$ where n' is 1 or 2) with an oxygen or amine nucleophile of formula $R^2$, wherein $R^2$ is selected from the group consisting of —NR⁷R⁸, —OR⁷, —OAy, Het linked through N, —NHHet, —NHR¹⁰Het, —OHet, and —OR¹⁰Het. The reaction may be carried out neat or in a suitable solvent and may be heated to 50–150° C. Typically the solvent is a lower alcohol such as methanol, ethanol, isopropanol or the like or a solvent such as N,N-dimethylformamide or tetrahydrofuran, or the like. Optionally a base may be used to facilitate the reaction. Typically the base can be potassium carbonate, or an amine base such as triethylamine.

Compounds of formula (I-B) may be conveniently prepared by reacting a compound of formula (I-A) (i.e., compounds of formula I wherein $R^2$ is $S(O)_{n'}R^9$ where n is 0) with an oxidizing agent in an inert solvent, optionally in the presence of a base. Typically the oxidizing agent is a peracid such as m-chloroperbenzoic acid or the like optionally with a base such as sodium bicarbonate. Careful monitoring of the stoichiometry between the oxidizing agent and the substrate allows the product distribution between sulfoxide (n=1), and sulfone (n=2) to be controlled. Suitable solvents include but are not limited to, dichloromethane, chloroform and the like.

Compounds of formula (I-A) are prepared by methods described above wherein $R^2=SR^9$ from the reaction of compounds selected from the group consisting of compounds of formula (XVI), compounds of formula (IX) and compounds of formula (XX) with a compound of formula (X-A) (i.e., the compound of formula (X) wherein $R^2$ is $SR^9$). The requisite compound of formula (X-A) can be obtained from commercial sources or prepared by methods known to one skilled in the art.

Another particularly useful method for converting compounds of formula (I) to other compounds of formula (I)

comprises reacting a compound of formula (I-C) (i.e., a compound of formula (I) wherein $R^2$ is fluoro) with an amine, and optionally heating the mixture to 50–150° C. to prepare a compound of formula (I-D) (i.e., a compound of formula (I) wherein $R^2$ is $NR^7R^8$).

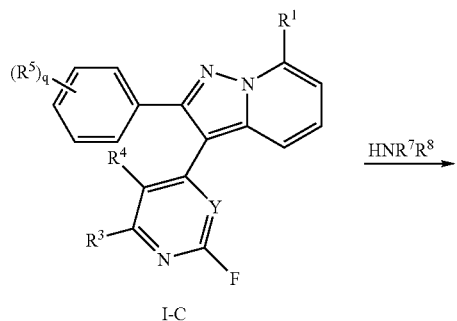

I-C $\xrightarrow{HNR^7R^8}$

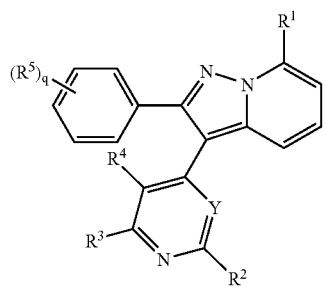

I-F wherein $M^3$ is $B(OH)_2$, $B(ORa)_2$, $B(Ra)_2$, $Sn(Ra)_3$, Zn-halide, Zn—Ra or Mg-halide, where Ra is alkyl or cycloalkyl, halide is halo, and all other variables are as defined in connection with any process described above.

Such method can be carried out using the reaction and conditions described above in connection with Scheme 1 and the conversion of compounds of formula VII to compounds of formula VIII. Thus, the present invention provides a process for converting compounds of formula (I-E) to compounds of formula (I-F) which comprises either: (1) replacing the C-7 halogen of the compound of formula (I-E) with an amine; or (2) coupling the compound of formula (I-E) with an aryl metal of the formula Ay-$M^3$ where $M^3$ is $B(OH)_2$, $B(ORa)_2$, $B(Ra)_2$, $Sn(Ra)_3$, Zn-halide, Zn—Ra or Mg-halide.

I-D wherein all variables are as defined in connection with any of the processes described above.

This procedure may be carried out by mixing a compound of formula (I-C) in an amine neat, or in a suitable solvent with an excess of amine to produce a compound of formula (I-D). Typically the solvent is a lower alcohol such as methanol, ethanol, isopropanol or the like. Other suitable solvents may include N,N-dimethylformamide, 1-methyl-2-pyrrolidine or the like.

As a further example, compounds of formula (I-E) may be converted to compounds of formula (I-F) using either of two methods.

As a further example, compounds of formula (I-G) (i.e., compounds of formula (I) wherein q is 1 or more and at least one $R^5$ is O-methyl) may be converted to compounds of formula (I-H) (i.e., compounds of formula (I) wherein q is 1 or more and at least one $R^5$ is OH) using conventional demethylation techniques. Additionally, compounds of formula (I-H) may optionally be converted to compounds of formula (I-J) (i.e., compounds of formula (I) wherein q is 1 or more and at least one $R^5$ is $OR^{10}$). For example, the foregoing conversions are represented schematically as follows:

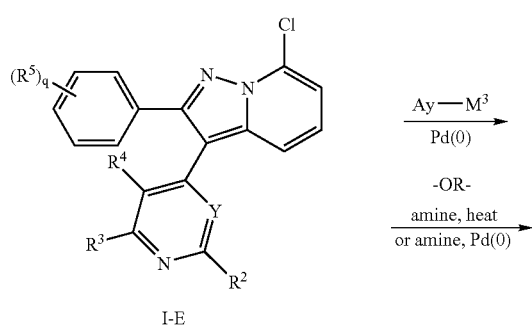

I-E $\xrightarrow[\text{or amine, Pd(0)}]{\text{Ay—}M^3 \atop Pd(0) \atop \text{-OR-} \atop \text{amine, heat}}$

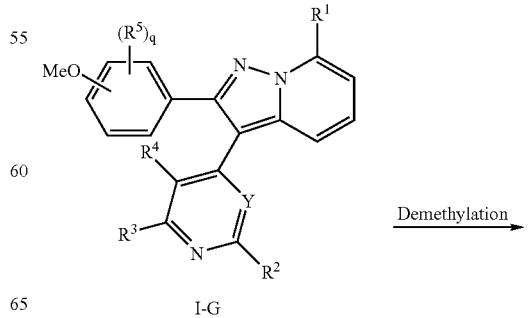

I-G $\xrightarrow{\text{Demethylation}}$

-continued

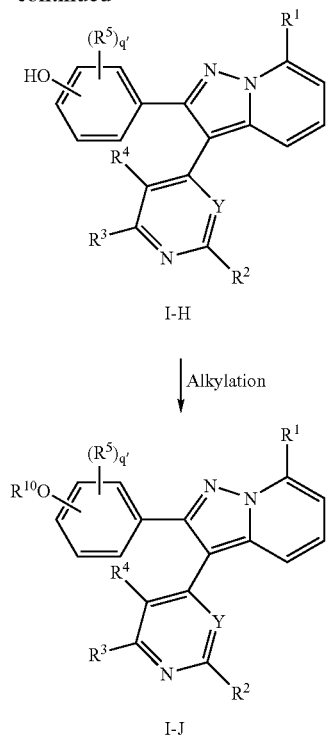

I-H

↓ Alkylation

I-J wherein q' is 0 1, 2, or 3, Me is methyl and all other variables are as defined in connection with any process described above.

The demethylation reaction may be carried out by treating a compound of formula (I-G) in a suitable solvent with a Lewis acid at a temperature of −78° C. to room temperature, to produce a compound of formula (I-H). Typically the solvent is an inert solvent such as dichloromethane, chloroform, acetonitrile, toluene and the like. The Lewis acid may be boron tribromide, trimethylsilyl iodide or the like.

Optionally, the compounds of formula (I-H) may be further converted to compounds of formula (I-J) by an alkylation reaction. The alkylation reaction may be carried out by treating a compound of formula (I-H) in suitable solvent with an alkyl halide of formula $R^{10}$-Halo where $R^{10}$ is as defined above, to form another compound of formula (I-J). The reaction is preferably carried out in the presence of a base and with optionally heating to 50–200° C. The reaction may be carried out in solvents such as N,N-dimethylformamide, dimethylsulfoxide and the like. Typically the base is potassium carbonate, cesium carbonate, sodium hydride or the like. Additionally, as will be apparent to those skilled in the art, the alkylation reaction can be carried out under Mitsunobu conditions.

As a further example of methods for converting compounds of formula (I) to other compounds of formula (I), compounds of formula (I-K) (i.e., compounds of formula (I) wherein q is 1 or more and at least one $R^5$ is halo) may be converted to compounds of formula (I-L) (i.e., compounds of formula (I) wherein q is 1 or more and at least one $R^5$ is Het) or compounds of formula (I-M) (i.e., compounds of formula (I) wherein q is 1 or more and at least one $R^5$ is Ay). For example, the conversion of compounds of formula (I-K) to compounds of formula (I-L) or compounds of formula (I-M) is shown schematically below.

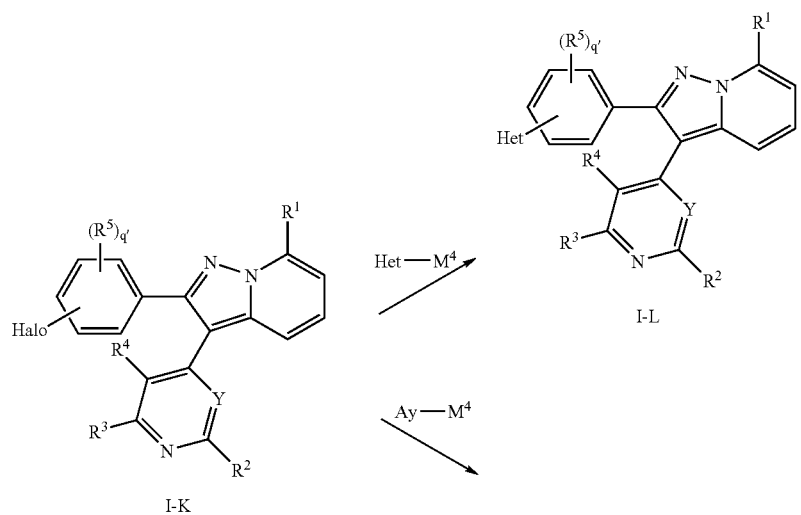

-continued

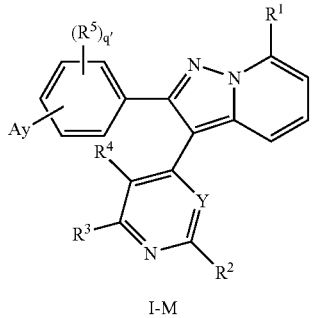

I-M wherein q' is 0, 1, 2 or 3;

$M^4$ is selected from the group consisting of —B(OH)$_2$, —B(ORa)$_2$, —B(Ra)$_2$, and —Sn(Ra)$_2$ wherein Ra is alkyl or cycloalkyl; and all other variables are as defined in connection with any of the processes described above.

The conversion of compounds of formula (I-K) to compounds of formula (I-L) or (I-M) is carried out by coupling the compound of formula (I-K) with a compound of formula Het-$M^4$ to make compounds of formula (I-L) or a compound of formula Ay-$M^4$ to make compounds of formula (I-M). The reaction may be carried out in an inert solvent, in the presence of a palladium (0) source. The reaction may optionally be heated to 50–150° C. Preferably the reaction is performed by reacting equimolar amounts of a compound of formula (I-K) with a compound of formula Het-$M^4$ or Ay-$M^4$ (depending upon whether compounds of formula (I-L) or compounds of formula (I-M) are desired). The reaction may also be performed in the presence of an excess Het-$M^4$ or Ay-$M^4$. The palladium (0) catalyst is preferably present in 1–25 mol % compared to the compound of formula (I-K). Examples of suitable palladium catalysts include but are not limited to, tetrakis(triphenylphosphine)palladium (0), dichlorobis(triphenyl-phosphine)palladium(II), and bis(diphenylphosphinoferrocene)palladium (II) dichloride. Suitable solvents include but are not limited to, N,N-dimethylformamide, toluene, tetrahydrofuran, dioxane, and 1-methyl-2-pyrrolidinone. When the compound of formula Het-$M^4$ or Ay-$M^4$ is a boronic acid or ester or a borinate the reaction is more conveniently carried out by adding a base in a proportion equivalent to, or greater than, that of the compound of formula Het-$M^4$ or Ay-$M^4$. Compounds of formula Het-$M^4$ and Ay-$M^4$ may be obtained from commercial sources or prepared either as discreet isolated compounds or generated in situ using methods known to one skilled in the art. (Suzuki, A. *J. Orgonomet. Chem.* 1999, 576, 147; Stille, J. *Angew. Chem. Int. Ed. Engl.* 1986, 25, 508; Snieckus, V. *J. Org. Chem.* 1995, 60, 292.)

In yet another example, compounds of formula (I-K) (i.e., compounds of formula (I) wherein q is 1 or more and at least one $R^5$ is halo) are converted to compounds of formula (I-N) (i.e., compounds of formula (I) wherein q is 1 or more and at least one $R^5$ is NH$_2$). Optionally, compounds of formula (I-N) may then be converted to compounds of formula (I-O) (i.e., compounds of formula (I) wherein q is 1 or more and at least one $R^5$ is —NR$^7$R$^8$). For example, the foregoing conversions are represented schematically as follows:

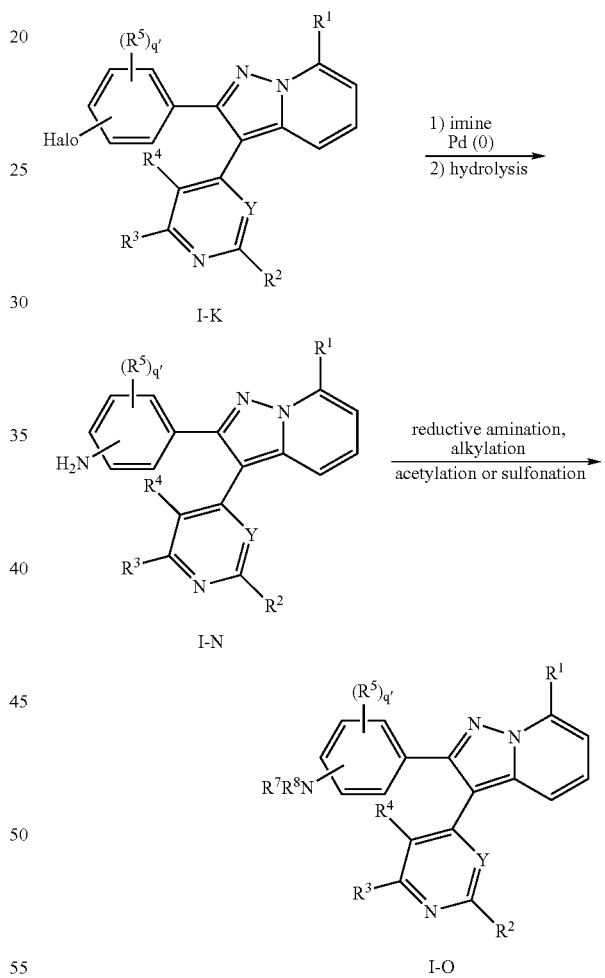

wherein q' is 0, 1, 2 or 3 and all other variables are as defined above in connection with any process described above.

The process of converting compounds of formula (I-K) to compounds of formula (I-N) is carried out by reacting a compound of formula (I-K) with an imine in the presence of a palladium (0) source, a base and a suitable ligand, followed by hydrolysis to give a compound of formula (I-N). See J. Wolfe, et al., *Tetrahedron Letters* 38:6367–6370 (1997). Typically the imine is benzophenoneimine, the palladium (0) source is tris(dibenzylideneacetone)dipalladium(0), the base is sodium tert-butoxide and the ligand is racemic-2,2'-bis(diphenylphosphino)-1,1'-binaphthyl. Suitable solvents include N,N-dimethylformamide and the like.

Reaction of a compound of formula (I-N) with compound of formula R<sup>7</sup>-halogen in a suitable solvent in the presence of base, optionally with heating may be used to prepare compounds of formula (I-O). Typically the base is triethylamine or pyridine and the solvent is N,N-dimethylformamide and the like. Other transformations well known to those skilled in the art for use with anilines may be used to convert compounds of formula (I-N) to compounds of formula (I-O).

Additional compounds of formula (I-O) can be obtained by reductive amination of compounds of formula (I-N) with ketones or aldehydes. See, A. Abdel-Magid, et al., *J. Org. Chem.* 61:3849–3862 (1996). Typically a compound of formula (I-N) is treated with an aldehyde or a ketone in the presence of an acid, such as acetic acid, and a reducing agent, such as sodium triacetoxyborohydride and the like, in an inert solvent such as dichloroethane and the like.

Based upon this disclosure and the examples contained herein one skilled in the art can readily convert compounds of formula (I) or a pharmaceutically accetpable salt, solvate or physiologically functional derivative thereof into other compounds of formula (I), or pharmaceutically acceptable salts, solvates or physiologically functional derivatives thereof.

The present invention also provides radiolabeled compounds of formula (I) and biotinylated compounds of formula (I) (e.g., examples 80 and 82 below). Radiolabeled compounds of formula (I) and biotinylated compounds of formula (I) can be prepared using conventional techniques. For example, radiolabeled compounds of formula (I) can be prepared by reacting the compound of formula (I) with tritium gas in the presence of an appropriate catalyst to produce radiolabeled compounds of formula (I). Biotinylated compounds of formula (I) can be prepared using the methods described in examples 80 and 82 below.

In one preferred embodiment, the compounds of formula (I) are tritiated.

The radiolabeled compounds of formula (I) and biotinylated compounds of formula (I) are useful in assays for the identification of compounds for the treatment or prophylaxis of viral infections such as herpes viral infections. Accordingly, the present invention provides an assay method for identifying compounds which have activity for the treatment or prophylaxis of viral infections such as herpes viral infections, which method comprises the step of specifically binding the radiolabeled compound of formula (I) or the biotinylated compound of formula (I) to the target protein. More specifically, suitable assay methods will include competition binding assays. The radiolabeled compounds of formula (I) or biotinylated compounds of formula (I) can be employed in assays according to the methods conventional in the art.

The following examples are intended for illustration only and are not intended to limit the scope of the invention in any way. Reagents are commercially available or are prepared according to procedures in the literature. Example numbers refer to those compounds listed in the tables above. <sup>1</sup>H and <sup>13</sup>C NMR spectra were obtained on Varian Unity Plus NMR spectrophotometers at 300 or 400 MHz, and 75 or 100 MHz respectively. <sup>19</sup>F NMR were recorded at 282 MHz. Mass spectra were obtained on Micromass Platform, or ZMD mass spectrometers from Micromass Ltd. Altrincham, UK, using either Atmospheric Chemical Ionization (APCI) or Electrospray Ionization (ESI). Analytical thin layer chromatography was used to verify the purity of some intermediates which could not be isolated or which were too unstable for full characterization, and to follow the progress of reactions. Unless otherwise stated, this was done using silica gel (Merck Silica Gel 60 F254). Unless otherwise stated, column chromatography for the purification of some compounds, used Merck Silica gel 60 (230–400 mesh), and the stated solvent system under pressure. All compounds were characterized as their free-base form unless otherwise stated. On occasion the corresponding hydrochloride salts were formed to generate solids where noted.

EXAMPLE 1

N-Cyclopentyl-3-[2-(cyclopentylamino)-4-pyrimidinyl]-2-(4-methoxyphenyl)-pyrazolo[1,5-a]pyridin-7-amine

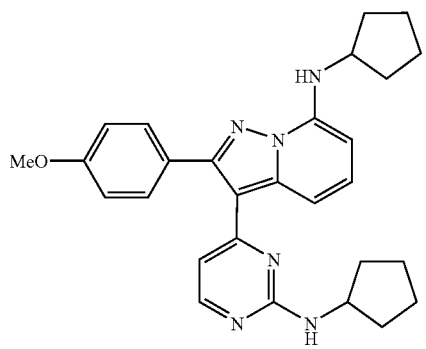

a) 2-(6-Chloro-2-pyridinyl)-1-(4-methoxyphenyl) ethanone

To a cold (0° C.) solution of 6-chloro-2-picoline (18.3 mL, 166.5 mmol) and ethyl 4-methoxybenzoate (30.0 g, 166.5 mmol) in tetrahydrofuran (300 mL) was added lithium bis(trimethylsilyl)amide (333 mL, 1.0 M in tetrahydrofuran, 332.7 mmol) dropwise via a pressure equalizing funnel over 1 hour. Upon complete addition, the cold bath was removed and the resulting solution was heated at 45° C. for hours. The mixture was cooled to room temperature, and the solution was concentrated. Methanol was added to quench the reaction, resulting in the formation of a yellow precipitate. The precipitate was collected by filtration and dried to give 2-(6-chloro-2-pyridinyl)-1-(4-methoxyphenyl)ethanone (37.4 g, 86%) as a yellow solid. <sup>1</sup>H NMR (CDCl<sub>3</sub>): δ 7.99 (d, 2H), 7.57 (t, 1H), 7.22–7.19 (m, 2H), 6.90 (d, 2H), 4.39 (s, 2H), 3.83 (s, 3H); MS m/z 262 (M+1).

b) 2-(6-Chloro-2-pyridinyl)-1-(4-methoxyphenyl) ethanone oxime

To a solution of 2-(6-chloro-2-pyridinyl)-1-(4-methoxyphenyl)ethanone (37.4 g, 142.9 mmol) in methanol (500 mL) was added hydroxylamine hydrochloride (49.7 g, 714.5 mmol) followed by the addition of a sodium hydroxide solution (28.6 g, 714.5 mmol in 50 mL of water). The resulting suspension was heated at reflux for 2 hours and then allowed to cool to room temperature. The mixture was concentrated and water was added to the resulting slurry. A white precipitate formed, which was collected by filtration, washed with water and dried to give 2-(6-chloro-2-pyridinyl)-1-(4-methoxyphenyl)ethanone oxime (38.7 g, 97%) as a white solid. $^1$H NMR (CDCl$_3$): δ 8.23 (b, 1H), 7.63 (d, 2H), 7.48 (d, 1H), 7.12 (m, 2H), 6.83 (dd, 2H), 4.33 (s, 2H), 3.76 (s, 3H); MS m/z 277 (M+1).

c) 7-Chloro-2-(4-methoxyphenyl)pyrazolo[1,5-a]pyridine

To a solution of 2-(6-chloro-2-pyridinyl)-1-(4-methoxyphenyl)ethanone oxime (38.7 g, 140 mmol) in 1,2-dimethoxyethane (150 mL) at 0° C. was added trifluoroacetic anhydride (20 mL, 140 mmol), keeping the temperature below 10° C. during the addition. After the addition was complete, the reaction was warmed to 15° C. The solution was then cooled to 4° C. and a solution of triethylamine (39 mL, 280 mmol) in 1,2-dimethoxyethane (15 mL) was added over a period of 0.5 hours. The mixture was allowed to warm to room temperature and was stirred at room temperature for 1.5 hours. To this mixture was added iron(II) chloride (0.18 g, 1.4 mmol) and the reaction was heated at 75° C. for 15 hours. The reaction mixture was poured into water (300 mL). The resulting suspension was extracted with ethyl acetate. The organic phase was dried (magnesium sulfate), filtered and concentrated to a solid. This solid was recrystallized from methanol to give 7-chloro-2-(4-methoxyphenyl)pyrazolo[1,5-a]pyridine (18.7 g, 52%) as pale yellow needles. $^1$H NMR (CDCl$_3$): δ 7.91 (d, 2H), 7.43 (d, 1H), 7.01 (t,1H), 6.95 (d, 2H), 6.81 (d, 1H), 6.80 (s, 1H), 3.83 (s, 3H); MS m/z 259 (M+1).

d) 1-[7-(Chloro)-2-(4-methoxyphenyl)pyrazolo[1,5-a]pyridin-3-yl]ethanone

To a solution of 7-chloro-2-(4-methoxyphenyl)pyrazolo[1,5-a]pyridine (18.7 g, 72.4 mmol) in toluene (300 mL) at room temperature was added acetic anhydride (8.2 mL, 86.9 mmol). Boron trifluoride diethyletherate (10.1 mL, 79.6 mmol) was then added dropwise and the resulting solution was heated at reflux for 4 hours. The reaction mixture was cooled to room temperature and quenched by the dropwise addition of saturated aqueous sodium bicarbonate. The reaction was extracted with ethyl acetate, and the ethyl acetate phase washed with brine, dried (magnesium sulfate), filtered and concentrated. The residue was purified by recrystallization from ethyl acetate-hexanes to give 1-[7-(chloro)-2-(4-methoxyphenyl)pyrazolo[1,5-a]pyridin-3-yl]ethanone (14.2 g, 65%) as reddish needles. $^1$H NMR (CDCl$_3$): δ 8.37 (dd, 1H), 7.49 (dd, 2H), 7.39 (dd, 1H), 7.10 (dd, 1H), 6.98 (dd, 2H), 3.84 (s, 3H), 2.13 (s, 3H); MS m/z 301 (M+1).

e) 1-[7-(Cyclopentylamino)-2-(4-methoxyphenyl)pyrazolo[1,5-a]pyridin-3-yl]ethanone To a solution of 1-[7-(chloro)-2-(4-methoxyphenyl)pyrazolo[1,5-a]pyridin-3-yl]ethanone (5.0 g, 16.6 mmol) in toluene (100 mL) was added successively racemic-2,2'-bis(diphenylphosphino)-1,1'-binaphthyl (620 mg, 1.0 mmol), cesium carbonate (8.12 g, 24.9 mmol), cyclopentylamine (8.2 mL, 83.1 mmol), and palladium (II) acetate (150 mg, 0.66 mmol). The resulting mixture was stirred at 95° C. for 4 hours, at which time the reaction was judged complete by thin layer chromatography. The solution was cooled to room temperature and diethyl ether and water were added to the reaction mixture. The phases were separated, and the aqueous phase again extracted with diethyl ether. The combined organic phases were dried (magnesium sulfate), filtered and concentrated. The resulting residue was purified by flash chromatography (4:1 hexanes:ethyl acetate) to give 1-[7-(cyclopentylamino)-2-(4-methoxyphenyl)pyrazolo[1,5-a]pyridin-3-yl]ethanone (5.66 g, 97%) as a yellow foam. $^1$H NMR (CDCl$_3$): δ 7.65 (d, 1H), 7.48 (d, 2H), 7.39 (t, 1H), 6.99 (d, 2H), 6.09 (d, 1H), 6.01 (d, 1H), 3.95 (m, 1H), 3.84 (s, 3H), 2.09 (s, 3H), 2.09–2.00 (m, 2H) 1.76–1.22 (m, 6H); MS m/z 350 (M+1).

f) (2E)-1-[7-(Cyclopentylamino)-2-(4-methoxyphenyl)pyrazolo[1,5-a]pyridin-3-yl]-3-(dimethylamino)-2-propen-1-one A solution of 1-[7-(cyclopentylamino)-2-(4-methoxyphenyl)pyrazolo[1,5-a]pyridin-3-yl]ethanone (5.56 g, 15.9 mmol) in N,N-dimethylformamide dimethyl acetal (25 mL) was heated at reflux for 5 days. The mixture was allowed to cool to room temperature. Water was added and the resulting mixture was extracted with ethyl acetate. The organic phase was dried (magnesium sulfate), filtered and concentrated. The resulting residue was purified by flash chromatography (7:3 ethyl acetate:acetone) to give (2E)-1-[7-(cyclopentylamino)-2-(4-methoxyphenyl)pyrazolo[1,5-a]pyridin-3-yl]-3-(dimethylamino)-2-propen-1-one (5.97 g, 93%) as a colored syrup. $^1$H NMR (CDCl$_3$): δ 7.96–7.59 (m, 3H), 7.53 (d, 1H), 7.23 (dd, 1H), 6.93 (d, 2H), 5.97–5.94 (m, 2H), 5.07 (d, 1H), 3.95 (m, 1H), 3.81 (s, 3H), 3.0–2.3 (b, 6H), 2.07 (m, 2H), 1.76–1.60 (m, 2H); MS m/z 405 (M+1).

g) N-Cyclopentyl-3-[2-(cyclopentylamino)-4-pyrimidinyl]-2-(4-methoxyphenyl)-pyrazolo[1,5-a]pyridin-7-amine To a solution of (2E)-1-[7-(cyclopentylamino)-2-(4-methoxyphenyl)pyrazolo[1,5-a]pyridin-3-yl]-3-(dimethylamino)-2-propen-1-one (5.97 g, 14.7 mmol) in dimethylformamide (80 mL) was added N-cyclopentyl guanidine hydrochloride (4.33 g, 26.5 mmol; Prepared by modification of a procedure from Bannard, R. A. B. et al., *Can. J. Chem.* 1958, 36, 1541–1549), followed by potassium carbonate (2.03 g, 14.7 mmol). The resulting solution was heated at reflux for 6 hours. Upon cooling to room temperature, water was added. The mixture was extracted with ethyl acetate. The ethyl acetate phase was washed with brine, dried (magnesium sulfate), filtered and concentrated in vacuo. The resulting residue was purified by flash chromatography (4:6 ethyl acetate:hexane) to give N-cyclopentyl-3-[2-(cyclopentylamino)-4-pyrimidinyl]-2-(4-methoxyphenyl)-pyrazolo[1,5-a]pyridin-7-amine (5.02 g, 73%) as a yellow solid. $^1$H NMR (CDCl$_3$): δ 7.95 (d, 1H), 7.72 (d, 1H), 7.54 (dd, 2H), 7.25 (t, 1H), 6.94 (dd, 2H), 6.28 (d, 1H), 6.00–5.97 (m, 2H), 5.03 (d, 1H), 4.33–4.31 (m, 1H), 3.96 (m, 1H), 3.83 (s, 3H), 2.10–2.01 (m, 4H), 1.77–1.50 (m, 12H); MS m/z 469 (M+1); Anal. Calcd for $C_{28}H_{32}N_6O$: C, 71.77; H, 6.88; N17.93. Found: C, 71.41; H, 7.02; N, 17.89.

EXAMPLE 2

N-Cyclopentyl-4-[2-(4-methoxyphenyl)-7-(1-pyrrolidinyl)pyrazolo[1,5-a]pyridin-3-yl]-2-pyrimidinamine

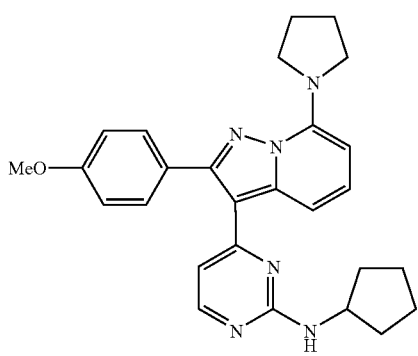

a) 1-[2-(4-Methoxyphenyl)-7-(1-pyrrolidinyl)pyrazolo[1,5-a]pyridin-3-yl]ethanone In a similar manner as described in Example 1 from 1-[7-(chloro)-2-(4-methoxyphenyl)pyrazolo[1,5-a]pyridin-3-yl]ethanone (5.00 g, 16.6 mmol) and pyrrolidine, 1-[2-(4-methoxyphenyl)-7-(1-pyrrolidinyl)pyrazolo[1,5-a]pyridin-3-yl]ethanone (4.68 g, 84%) was obtained as a yellow crystalline solid. $^1$H NMR (CDCl$_3$): δ 7.79 (d, 1H), 7.50 (dd, 2H), 7.33 (t, 1H), 6.97 (dd, 2H), 6.12 (d, 1H), 3.84 (s, 3H), 3.74–3.70 (m, 4H), 2.11 (s, 3H), 1.99–1.95 (m, 4H); MS m/z 336 (M+1).

b) (2E)-3-(Dimethylamino)-1-[2-(4-methoxyphenyl)-7-(1-pyrrolidinyl)pyrazolo[1,5-a]pyridin-3-yl]-2-propen-1-one In a similar manner as described in Example 1 from 1-[2-(4-methoxyphenyl)-7-(1-pyrrolidinyl)pyrazolo[1,5-a]pyridin-3-yl]ethanone (4.0 g, 11.9 mmol), (2E)-3-(dimethylamino)-1-[2-(4-methoxyphenyl)-7-(1-pyrrolidinyl)pyrazolo[1,5-a]pyridin-3-yl]-2-propen-1-one (4.18 g, 90%) was obtained as a brown syrup. $^1$H NMR (CDCl$_3$): δ 7.76 (d, 1H), 7.65 (dd, 2H), 7.53 (d, 1H), 7.20 (t, 1H), 6.93 (dd, 2H), 6.03 (d, 1H), 5.13 (d, 1H), 3.81 (s, 3H), 3.71–3.68 (m, 4H), 3.10–2.35 (b, 6H), 2.00–1.96 (m, 4H); MS m/z 391 (M+1).

c) N-Cyclopentyl-4-[2-(4-methoxyphenyl)-7-(1-pyrrolidinyl)pyrazolo[1,5-a]pyridin-3-yl]-2-pyrimidinamine In a similar manner as described in Example 1 from (2E)-3-(dimethylamino)-1-[2-(4-methoxyphenyl)-7-(1-pyrrolidinyl)pyrazolo[1,5-a]pyridin-3-yl]-2-propen-1-one (500 mg, 1.28 mmol), N-cyclopentyl-4-[2-(4-methoxyphenyl)-7-(1-pyrrolidinyl)pyrazolo[1,5-a]pyridin-3-yl]-2-pyrimidinamine (420 mg, 70%) was obtained as a solid. $^1$H NMR (CDCl$_3$): δ 7.97 (d, 1H), 7.84 (d, 1H), 7.57 (d, 2H), 7.19 (t,1H), 6.91 (d, 2H), 6.33 (d, 1H), 6.04 (d1H), 4.99 (d, 1H), 4.33 (m, 1H), 3,82 (s, 3H), 3.73–3.70 (m, 4H), 2.07–1.97 (m, 6H), 1.73–1.48 (m, 6H); MS m/z 455 (M+1); Anal. Calcd for C$_{27}$H$_{30}$N$_6$O: C, 71.34; H, 6.65; N18.49. Found: C, 71.58; H, 6.73; N, 18.28.

EXAMPLE 3

4-[2-(4-Methoxyphenyl)-7-(1-pyrrolidinyl)pyrazolo[1,5-a]pyridin-3-yl]-2-pyrimidinamine

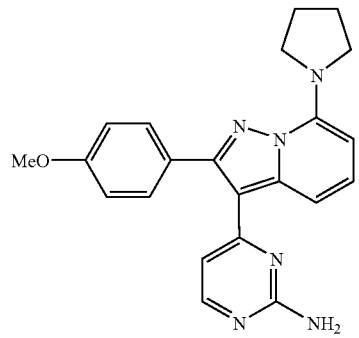

To a solution of (2E)-3-(dimethylamino)-1-[2-(4-methoxyphenyl)-7-(1-pyrrolidinyl)pyrazolo[1,5-a]pyridin-3-yl]-2-propen-1-one (500 mg, 1.28 mmol) in dimethylformamide (10 mL) was added guanidine sulfate (277 mg, 1.28 mmol), followed by potassium carbonate (195 mg, 1.41 mmol). The resulting solution was heated at reflux for 6 hours. After cooling to room temperature, ethyl acetate and water were added. The phases were separated and aqueous phase extracted with additional ethyl acetate. The combined organics were dried (magnesium sulfate), filtered and concentrated in vacuo to give 4-[2-(4-methoxyphenyl)-7-(1-pyrrolidinyl)pyrazolo[1,5-a]pyridin-3-yl]-2-pyrimidinamine (440 mg, 89%) as a yellow solid. $^1$H NMR (CDCl$_3$): δ 7.98 (d, 1H), 7.80 (d, 1H), 7.56 (dd, 2H), 7.20 (t, 1H), 6.92 (d, 2H), 6.43 (d, 1H), 6.05 (d, 1H), 4.95 (b, 2H), 3.83 (s, 3H), 3.74–3.70 (m, 4H), 2.01–1.98 (m, 4H); MS m/z 387 (M+1).

EXAMPLE 4

4-{7-(Cyclopentylamino)-3-[2-(cyclopentylamino)-4-pyrimidinyl]pyrazolo-[1,5-a]pyridin-2-yl}phenol

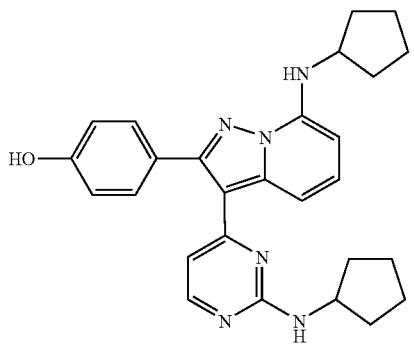

To a solution of N-cyclopentyl-3-[2-(cyclopentylamino)-4-pyrimidinyl]-2-(4-methoxyphenyl)pyrazolo[1,5-a]pyridin-7-amine (1.16 g, 2.48 mmol) in dichloromethane (50 mL) at −78° C. was added boron tribromide (9.92 mL, 1.0 M in dichloromethane, 9.92 mmol) dropwise. The resulting solution was allowed to warm to room temperature. After stirring for 15 hours at room temperature, the mixture was cooled to 0° C. and quenched by the addition of water. The mixture was extracted with ethyl acetate. The organic phase was dried (magnesium sulfate), filtered and concentrated to give a solid residue which was purified by flash chromatography (95:5 chloroform-methanol). 4-{7-(Cyclopentylamino)-3-[2-(cyclopentylamino)-4-pyrimidinyl]pyrazolo[1,5-a]pyridin-2-yl}phenol was obtained as a yellow solid (0.80 g, 71%). $^1$H NMR (CDCl$_3$): δ 7.91 (d, 1H), 7.70 (d, 1H), 7.46 (d, 2H), 7.26 (t, 1H), 6.86 (d, 2H), 6.27 (d, 1H), 6.00–5.97 (m, 2H), 5.06 (d, 1H), 4.33 (m, 1H), 3.96 (m, 1H), 2.10–2.03 (m, 4H), 1.78–1.47 (m, 12H); MS m/z 455 (M+1). U157430-190

EXAMPLE 5

4-[3-[2-(Cyclopentylamino)-4-pyrimidinyl]-7-(1-pyrrolidinyl)pyrazolo[1,5-a]pyridin-2-yl]phenol

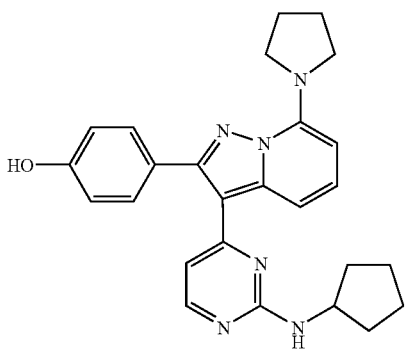

In a similar manner as described in Example 4 from N-cyclopentyl-4-[2-(4-methoxyphenyl)-7-(1-pyrrolidinyl)pyrazolo[1,5-a]pyridin-3-yl]-2-pyrimidinamine (300 mg, 0.66 mmol) was obtained 4-[3-[2-(cyclopentylamino)-4-pyrimidinyl]-7-(1-pyrrolidinyl)pyrazolo[1,5-a]pyridin-2-yl]phenol (190 mg, 66%) as an orange solid. $^1$H NMR (CD$_3$OD): δ 7.74 (d, 1H), 7.63 (d, 1H), 7.33 (dd, 2H), 7.10 (t, 1H), 6.79 (dd, 2H), 6.23 (d, 1H), 5.84 (d, 1H), 4.20–4.12 (m, 1H), 3.52 (m, 1H), 3.30–3.27 (m, 2H), 3.13–3.10 (m, 2H), 1.95–1.41 (m, 12H); MS m/z 441 (M+1).

EXAMPLE 6

4-[3-(2-Amino-4-pyrimidinyl)-7-(1-pyrrolidinyl)pyrazolo[1,5-a]pyridin-2-yl]phenol

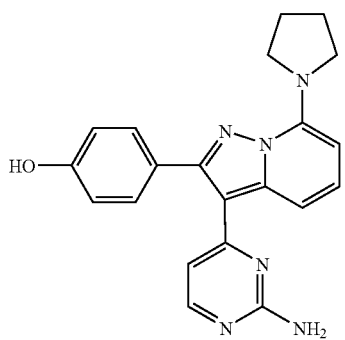

In a similar manner as described in Example 4 from 4-[2-(4-methoxyphenyl)-7-(1-pyrrolidinyl)pyrazolo[1,5-a]pyridin-3-yl]-2-pyrimidinamine (310 mg, 0.80 mmol) was obtained 4-[3-(2-amino-4-pyrimidinyl)-7-(1-pyrrolidinyl)pyrazolo[1,5-a]pyridin-2-yl]phenol (180 mg, 60%) as a yellow solid. $^1$H NMR (d$_6$-DMSO): δ 9.68 (s, 1H), 7.95–7.90 (m, 2H), 7.40 (d, 2H), 7.28 (t, 1H), 6.84 (d, 2H), 6.51 (b, 2H), 6.23–6.17 (m, 2H), 3.72–3.70 (m, 4H), 1.99–1.92 (m, 4H); MS m/z 373 (M+1).

EXAMPLE 7

2-[4-(Allyloxy)phenyl]-N-cyclopentyl-3-[2-(cyclopentylamino)-4-pyrimidinyl]pyrazolo[1,5-a]pyridin-7-amine

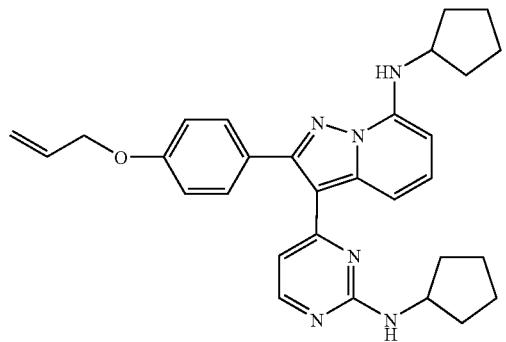

To a solution of 4-{7-(cyclopentylamino)-3-[2-(cyclopentylamino)-4-pyrimidinyl]pyrazolo[1,5-a]pyridin-2-yl}phenol (100 mg, 0.22 mmol) in N,N-dimethylformamide (5 mL) was added allyl bromide (21 μL, 0.24 mmol) and potassium carbonate (122 mg, 0.88 mmol). The mixture was heated at reflux for 3 hours. The mixture was allowed to cool to room temperature and water was added. The mixture was extracted with ethyl acetate. The ethyl acetate phase was dried (magnesium sulfate), filtered and concentrated to a solid. The residue was purified by flash chromatography (1:1 ethyl acetate:hexanes) to give 2-[4-(allyloxy)phenyl]-N-cyclopentyl-3-[2-(cyclopentylamino)-4-pyrimidinyl]pyrazolo[1,5-a]pyridin-7-amine (67 mg, 61%) as a yellow solid. $^1$H NMR (CDCl$_3$): δ 7.94 (d, 1H), 7.73 (d, 1H), 7.53 (d, 2H), 7.24 (t, 1H), 6.95 (d, 2H), 6.28 (d, 1H), 6.08–5.96 (m, 3H), 5.41 (dd, 1H), 5.27 (dd, 1H), 5.10 (d, 1H), 4.56 (d, 2H), 4.32 (m, 1H), 3.95 (m, 1H), 2.10–2.00 (m, 4H), 1.76–1.45 (m, 12H); MS m/z 495 (M+1); Anal. Calcd for C$_{30}$H$_{34}$N$_6$O: C, 72.86; H, 6.93; N 16.99. Found: C, 72.47; H, 7.05; N, 16.75.

EXAMPLE 8

Ethyl (4-{7-(cyclopentylamino)-3-[2-(cyclopentylamino)-4-pyrimidinyl]-pyrazolo[1,5-a]pyridin-2-yl}phenoxy)acetate

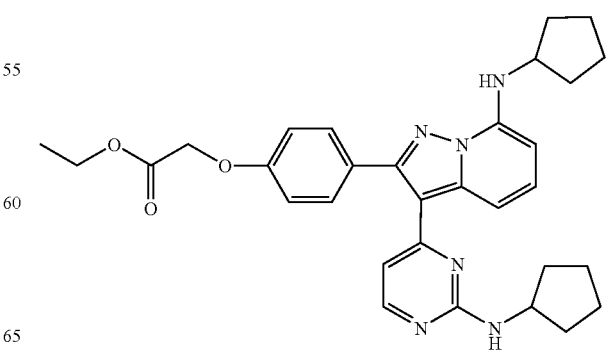

To a solution of 4-{7-(cyclopentylamino)-3-[2-(cyclopentylamino)-4-pyrimidinyl]pyrazolo[1,5-a]pyridin-2-yl}phenol (100 mg, 0.22 mmol) in acetone (10 mL) was added ethyl α-bromoacetate (49 μL, 0.44 mmol) and potassium carbonate (304 mg, 2.2 mmol). The mixture was heated to reflux for 3 hours. The reaction mixture was cooled to room temperature and water was added. The solution was extracted with ethyl acetate. The organics were dried (magnesium sulfate), filtered and concentrated, followed by purification with flash chromatography (1:1 ethyl acetate:hexanes) to give ethyl (4-{7-(cyclopentylamino)-3-[2-(cyclopentylamino)-4-pyrimidinyl]pyrazolo[1,5-a]pyridin-2-yl}phenoxy)acetate (85 mg, 71%) as a brown oil. $^1$H NMR (CDCl$_3$): δ 7.94 (d, 1H), 7.70 (d, 1H), 7.55 (d, 2H), 7.23 (t, 1H), 6.95 (d, 2H), 6.25 (d, 1H), 5.98–5.95 (m, 2H), 5.13 (d, 1H), 4.62 (s, 2H), 4.31–4.21 (m, 3H), 3.94 (m, 1H), 2.07–1.99 (m, 4H), 1.75–1.46 (m, 12H), 1.28 (t, 3H); MS m/z 541 (M+1).

EXAMPLE 9

2-(4-Butoxyphenyl)-N-cyclopentyl-3-[2-(cyclopentylamino)-4-pyrimidinyl]-pyrazolo[1,5-a]pyridin-7-amine

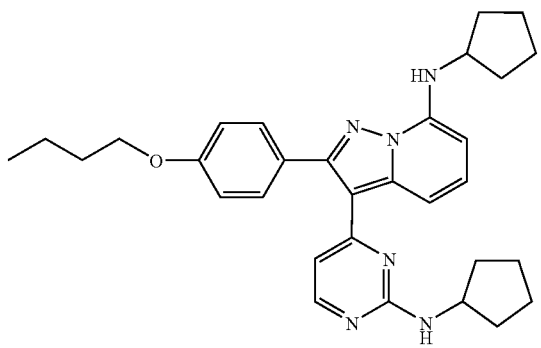

In a similar manner as described in Example 7 from 4-{7-(cyclopentylamino)-3-[2-(cyclopentylamino)-4-pyrimidinyl]pyrazolo[1,5-a]pyridin-2-yl}phenol (100 mg, 0.22 mmol) and butyl bromide was formed 2-(4-butoxyphenyl)-N-cyclopentyl-3-[2-(cyclopentylamino)-4-pyrimidinyl]pyrazolo[1,5-a]pyridin-7-amine (80 mg, 71%) as a yellow solid. $^1$H NMR (CDCl$_3$): δ 8.00 (d, 1H), 7.78 (d, 1H), 7.57 (d, 2H), 7.28 (t, 1H), 6.97 (d, 2H), 6.34 (d, 1H), 6.05 (d, 1H), 6.00 (d, 1H), 5.22 (d, 1H), 4.37 (m, 1H), 4.02 (m, 3H), 2.12–2.05 (m, 4H), 1.82–1.49 (m, 16H), 1.00 (t, 3H); MS m/z 511 (M+1).

EXAMPLE 10

N-Cyclopentyl-3-[2-(cyclopentylamino)-4-pyrimidinyl]-2-(4-isobutoxyphenyl)pyrazolo[1,5-a]pyridin-7-amine

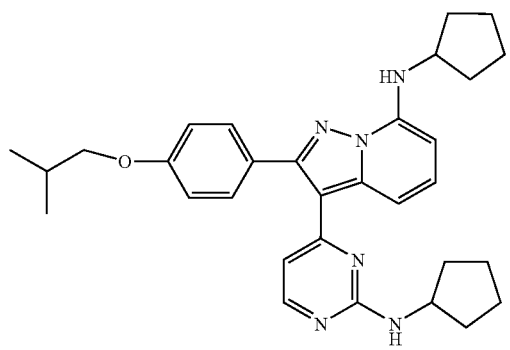

In a similar manner as described in Example 7 from 4-{7-(cyclopentylamino)-3-[2-(cyclopentylamino)-4-pyrimidinyl]pyrazolo[1,5-a]pyridin-2-yl}phenol (100 mg, 0.22 mmol) and isobutyl bromide was formed N-cyclopentyl-3-[2-(cyclopentylamino)-4-pyrimidinyl]-2-(4-isobutoxyphenyl)pyrazolo[1,5-a]pyridin-7-amine (76 mg, 68%) as a yellow foam. $^1$H NMR (CDCl$_3$): δ 8.00 (d, 1H), 7.78 (d, 1H), 7.57 (d, 2H), 7.29 (t, 1H), 6.98 (d, 2H), 6.35 (d, 1H), 6.05 (d, 1H), 6.01 (d, 1H), 5.16 (d, 1H), 4.37 (m, 1H), 4.00 (m, 1H), 3.79 (d, 2H), 2.16–2.05 (m, 5H), 1.81–1.52 (m, 12H), 1.06 (d, 6H); MS m/z 511 (M+1).

EXAMPLE 11

N-Cyclopentyl-3-[2-(cyclopentylamino)-4-pyrimidinyl]-2-[4-(cyclopropyl-methoxy)phenyl]pyrazolo[1,5-a]pyridin-7-amine

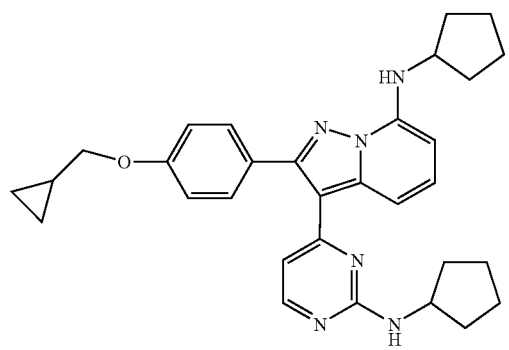

In a similar manner as described in Example 7 from 4-{7-(cyclopentylamino)-3-[2-(cyclopentylamino)-4-pyrimidinyl]pyrazolo[1,5-a]pyridin-2-yl}phenol (100 mg, 0.22 mmol) and (bromomethyl)cyclopropane was formed N-cyclopentyl-3-[2-(cyclopentylamino)-4-pyrimidinyl]-2-[4-(cyclopropylmethoxy)phenyl]-pyrazolo[1,5-a]pyridin-7-amine (48 mg, 44%) as a yellow foam. $^1$H NMR (CDCl$_3$): δ 7.99 (d, 1H), 7.77 (d, 1H), 7.57 (dd, 2H), 7.30 (t, 1H), 6.97 (d, 2H), 6.33 (d, 1H), 6.04–6.00 (m, 2H), 5.08 (d, 1H), 4.37 (m, 1H), 4.00 (m, 1H), 3.87 (d, 2H), 2.14–2.07 (m, 4H), 1.82–1.52 (m, 12H), 1.32 (m, 1H), 0.65 (m, 2H), 0.38 (m, 2H); MS m/z 509 (M+1).

EXAMPLE 12

2-[4-(Cyclobutylmethoxy)phenyl]-N-cyclopentyl-3-[2-(cyclopentylamino)-4-pyrimidinyl]pyrazolo[1,5-a]pyridin-7-amine

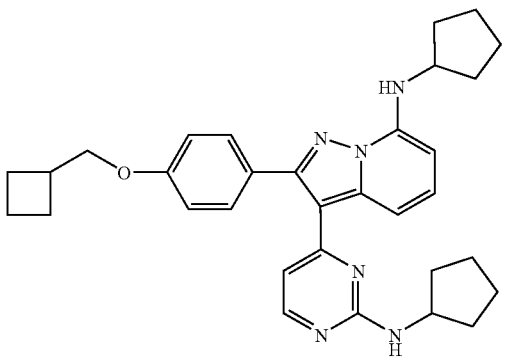

In a similar manner as described in Example 7 from 4-{7-(cyclopentylamino)-3-[2-(cyclopentylamino)-4-pyrimidinyl]pyrazolo[1,5-a]pyridin-2-yl}phenol (67 mg, 0.15 mmol) and (bromomethyl)cyclobutane was formed 2-[4-(cyclobutylmethoxy)phenyl]-N-cyclopentyl-3-[2-(cyclopentylamino)-4-pyrimidinyl]pyrazolo[1,5-a]pyridin-7-amine (50 mg, 65%) as a yellow foam. $^1$H NMR (CDCl$_3$): δ 7.99 (d, 1H), 7.78 (d, 1H), 7.57 (d, 2H), 7.30 (t, 1H), 6.98 (d, 2H), 6.34 (d, 1H), 6.05–6.00 (m, 2H), 5.13 (d, 1H), 4.37 (m, 1H), 3.99 (m, 3H), 2.82 (m, 1H), 2.20–1.50 (m, 22H); MS m/z 523 (M+1).

EXAMPLE 13

N-Cyclopentyl-3-[2-(cyclopentylamino)-4-pyrimidinyl]-2-(4-phenoxyphenyl)pyrazolo[1,5-a]pyridin-7-amine

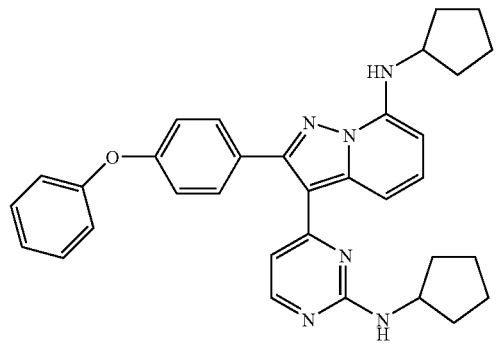

To a solution of 4-{7-(cyclopentylamino)-3-[2-(cyclopentylamino)-4-pyrimidinyl]pyrazolo[1,5-a]pyridin-2-yl}phenol (100 mg, 0.22 mmol) in dichloromethane (5 mL) was added copper (II) acetate (40 mg, 0.22 mmol), phenylboronic acid (80 mg, 0.66 mmol), triethylamine (92 µL, 0.66 mmol) and molecular sieves. The mixture was stirred at room temperature for 24 hours. Solids were removed by filtration and the filtrate was concentrated, followed by purification by flash chromatography (2:3 ethyl acetate: hexanes) to give N-cyclopentyl-3-[2-(cyclopentylamino)-4-pyrimidinyl]-2-(4-phenoxyphenyl)pyrazolo[1,5-a]pyridin-7-amine (14 mg, 12%) as a yellow foam. $^1$H NMR (CDCl$_3$): δ 8.05–6.85 (m, 12 H), 6.40 (d, 1H), 6.06 (m, 2H), 5.12 (d, 1H), 4.40 (m, 1H) 4.01 (m, 1H), 2.20–2.09 (m, 4H), 1.82–1.59 (m, 12H); MS m/z 531 (M+1).

EXAMPLE 14

2-(4-Bromophenyl)-N-butyl-3-[2-(butylamino)-4-pyrimidinyl]pyrazolo-[1,5-a]pyridin-7-amine

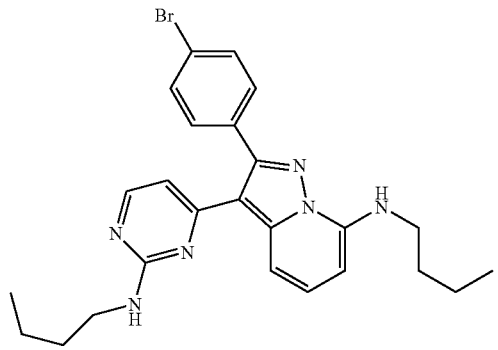

a) 1-(4-Bromophenyl)-2-(6-chloro-2-pyridinyl)ethanone

In a similar manner as described in Example 1, from ethyl 4-bromobenzoate (12.8 mL, 78.3 mmol) and 6-chloro-2-picoline (4.3 mL, 39.2 mmol), 1-(4-bromophenyl)-2-(6-chloro-2-pyridinyl)ethanone (9.6 g, 82%) was obtained as a crystalline solid existing as a keto-enol tautomeric mixture. $^1$H NMR (CDCl$_3$): for the keto tautomer δ 7.95 (d, 2H), 7.74–7.56 (m, 3H), 7.27 (m, 2H), 4.47 (s, 2H); MS m/z 310 (M+1).

b) 1-(4-Bromophenyl)-2-(6-chloro-2-pyridinyl)ethanone oxime

In a similar manner as described in Example 1, from 1-(4-bromophenyl)-2-(6-chloro-2-pyridinyl)ethanone (9.5 g, 30.6 mmol) was obtained 1-(4-bromophenyl)-2-(6-chloro-2-pyridinyl)ethanone oxime (10.0 g, 99%) as a white solid. $^1$H NMR (CDCl$_3$): δ 9.78 (broad s, 1H), 7.74–7.47 (m, 5 H), 7.21–7.17 (m, 2H), 4.39 (s, 2 H); MS m/z 325 (M+1).

c) 2-(4-Bromophenyl)-7-chloropyrazolo[1,5-a]pyridine

In a similar manner as described in Example 1, from 1-(4-bromophenyl)-2-(6-chloro-2-pyridinyl)ethanone oxime (45.2 g, 139 mmol), 2-(4-bromophenyl)-7-chloropyrazolo[1,5-a]pyridine (30.5 g, 72%) was obtained as a pale yellow crystalline solid. 1H NMR (CDCl$_3$): δ 7.85 (dd, 2 H), 7.54 (dd, 2 H), 7.46 (d, 1 H), 7.04 (m, 1 H), 6.87 (m, 2 H); MS m/z 307 (M+1).

d) 1-[2-(4-Bromophenyl)-7-chloropyrazolo[1,5-a]pyridin-3-yl]ethanone

In a similar manner as described in Example 1, from 2-(4-bromophenyl)-7-chloropyrazolo[1,5-a]pyridine (10.0 g, 32.5 mmol), 1-[2-(4-bromophenyl)-7-chloropyrazolo[1,5-a]pyridin-3-yl]ethanone (7.63 g, 67%) was obtained as pink needles. $^1$H NMR (CDCl$_3$): δ 8.37 (d, 1 H), 7.62 (d, 2 H), 7.43 (m, 3 H), 7.14 (d, 1 H), 2.13 (s, 3 H); MS m/z 349 (M+1).

e) 1-[2-(4-Bromophenyl)-7-(butylamino)pyrazolo[1,5-a]pyridin-3-yl]ethanone

In a similar manner as described in Example 1, from 1-[2-(4-bromophenyl)-7-chloropyrazolo[1,5-a]pyridin-3-yl]ethanone (2.55 g, 7.3 mmol) and butylamine, 1-[2-(4-bromophenyl)-7-(butylamino)pyrazolo[1,5-a]pyridin-3-yl]ethanone (2.15 g, 76%) was obtained as a yellow oil. $^1$H NMR (CDCl$_3$): δ 7.61 (m, 3 H), 7.43 (m, 3 H), 6.08 (d, 1 H), 6.02 (broad s, 1 H), 3.33 (q, 2 H), 2.12 (s, 3 H), 1.70 (m, 2 H), 1.44 (m, 2 H), 0.94 (t, 3 H); MS m/z 386 (M+1).

f) (2E)-1-[2-(4-Bromophenyl)-7-(butylamino)pyrazolo[1,5-a]pyridin-3-yl]-3-(dimethylamino)-2-propen-1-one In a similar manner as described in Example 1, from 1-[2-(4-bromophenyl)-7-(butylamino)pyrazolo[1,5-a]pyridin-3-yl]ethanone (5.5 g, 14.2 mmol), (2E)-1-[2-(4-bromophenyl)-7-(butylamino)pyrazolo[1,5-a]pyridin-3-yl]-3-(dimethylamino)-2-propen-1-one (5.78 g, 92%) was obtained as a brown oil. $^1$H NMR (CDCl$_3$): δ 7.57 (m, 6 H), 7.28 (t, 1 H), 5.95 (m, 2 H), 5.03 (d, 1 H), 3.32 (q, 2 H), 2.92 (broad s, 3 H), 2.52 (broad s, 3 H), 1.71 (m, 2 H), 1.44 (m, 2 H), 0.94 (t, 3 H); MS m/z 441 (M+1).

g) 2-(4-Bromophenyl)-N-butyl-3-[2-(butylamino)-4-pyrimidinyl]pyrazolo[1,5-a]pyridin-7-amine In a similar manner as described in Example 1, from (2E)-1-[2-(4-bromophenyl)-7-(butylamino)pyrazolo[1,5-a]pyridin-3-yl]-3-(dimethylamino)-2-propen-1-one (5.78 g, 13.1 mmol) and N-butylguanidine sulfate (Weiss, S.; Krommer, H. *Chem.-Zgt.* 1974, 98, 617–618) was obtained 2-(4-bromophenyl)-N-butyl-3-[2-(butylamino)-4-pyrimidinyl]pyrazolo[1,5-a]pyridin-7-amine (5.18 g, 80%) as a pale yellow solid. $^1$H NMR (CDCl$_3$): δ 7.98 (d, 1 H), 7.71 (d, 1 H), 7.56 (m, 4 H), 7.33 (t, 1 H), 6.35 (d, 1 H), 6.03 (m, 2 H), 3.46 (q, 2 H), 3.38 (q, 2 H), 1.81–1.40 (m, 8 H), 0.98 (m, 6 H); MS m/z 493 (M+1).

EXAMPLE 15

2-[1,1'-Biphenyl]-4-yl-N-butyl-3-[2-(butylamino)-4-pyrimidinyl]pyrazolo-[1,5-a]pyridin-7-amine

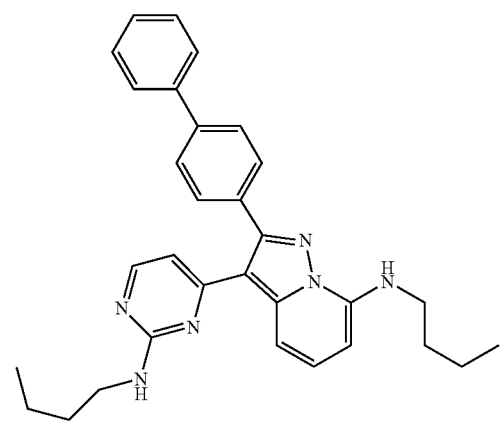

To a solution of 2-(4-Bromophenyl)-N-butyl-3-[2-(butylamino)-4-pyrimidinyl]pyrazolo-[1,5-a]pyridin-7-amine (52 mg, 0.11 mmol) in tetrahydrofuran was added phenylboronic acid (26 mg, 0.21 mmol), sodium carbonate (0.21 mL, 2 M aqueous, 0.42 mmol), and dichlorobistriphenylphosphine palladium (II) (7.5 mg, 0.01 mmol). The mixture was heated at reflux for 3.5 hours. The resultant solution was cooled to room temperature and diluted with ether and water was added. The organic layer was washed with brine. The aqueous layer was extracted with ether and the combined organics dried over magnesium sulfate. Filtration and concentration followed by flash chromatography provided 2-[1,1'-biphenyl]-4-yl-N-butyl-3-[2-(butylamino)-4-pyrimidinyl]pyrazolo[1,5-a]pyridin-7-amine (37 mg, 73%) as a yellow solid. $^1$H NMR (CDCl$_3$): δ 8.05 (d, 1 H), 7.83–7.69 (m, 7 H), 7.51 (m, 2 H), 7.43–7.33 (m, 2 H), 6.44 (d, 1 H), 6.12 (t, 1 H), 6.05 (d, 1 H), 5.16 (broad, 1 H), 3.52 (m, 2 H), 3.42 (m, 2 H), 1.84–1.43 (m, 8 H), 1.05–0.99 (m, 6 H); MS m/z 491 (M+1).

EXAMPLE 16

N-{4-[2-(4-Aminophenyl)-7-(butylamino)pyrazolo[1,5-a]pyridin-3-yl]-2-pyrimidinyl}-N-butylamine

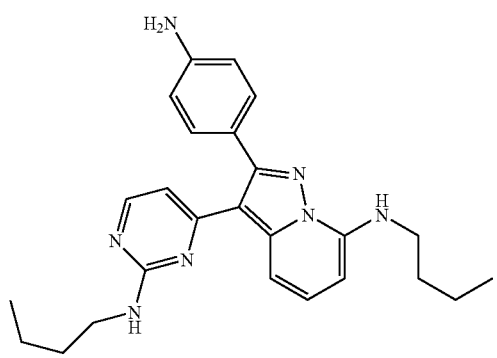

a) N-Butyl-3-[2-(butylamino)-4-pyrimidinyl]-2-{4-[(diphenylmethylene)-amino]phenyl}pyrazolo[1,5-a]pyridin-7-amine To a solution of 2-(4-bromophenyl)-N-butyl-3-[2-(butylamino)-4-pyrimidinyl]pyrazolo[1,5-a]pyridin-7-amine (1.0 g, 2.0 mmol) in toluene (20 mL) was added racemic-2,2'-bis(diphenylphosphino)-1,1'-binaphthyl (200 mg, 0.30 mmol), tris(dibenzylideneacetone)dipalladium(0) (92 mg, 0.10 mmol), diphenylimine (1.02 mL, 6.1 mmol), and sodium tert-butoxide (582 mg, 6.1 mmol). The mixture was heated to 100° C. for 50 minutes. The resultant solution was cooled to room temperature and diluted with ether and water was added. The organic layer was washed with brine. The aqueous layer was extracted with ether and the combined organics dried over magnesium sulfate. Filtration and concentration followed by flash chromatography (4:1 hexanes:ethyl acetate with 1% triethylamine) provided N-butyl-3-[2-(butylamino)-4-pyrimidinyl]-2-{4-[(diphenylmethylene)amino]phenyl}-pyrazolo[1,5-a]pyridin-7-amine (1.0 g, 84%) as a yellow solid. $^1$H NMR (CDCl$_3$): δ 7.90 (d, 1 H), 7.80–7.28 (m, 12 H), 7.19–7.16 (m, 2 H), 6.80 (d, 2 H), 6.07 (d, 1 H), 6.02 (t, 1 H), 5.97 (d, 1 H), 4.99 (t, 1 H), 3.48 (m, 2 H), 3.36 (m, 2 H), 1.80–1.43 (m, 8 H), 1.00–0.96 (m, 6 H); MS m/z 594 (M+1).

b) N-{4-[2-(4-Aminophenyl)-7-(butylamino)pyrazolo[1,5-a]pyridin-3-yl]-2-pyrimidinyl}-N-butylamine To a solution of N-butyl-3-[2-(butylamino)-4-pyrimidinyl]-2-{4-[(diphenylmethylene)-amino]phenyl}pyrazolo[1,5-a]pyridin-7-amine (1.0 g, 1.7 mmol) in tetrahydrofuran (50 mL) was added hydrochloric acid (10 mL, 4 N aqueous). The resultant solution was stirred at room temperature for 30 minutes. Ether was added and the solution was made basic by the slow addition of saturated aqueous sodium bicarbonate. The organic layer was washed with brine. The aqueous layer was extracted with ether and the combined organics dried over magnesium sulfate. Filtration and concentration followed by flash chromatography (1:1 hexanes:ethyl acetate) provided N-{4-[2-(4-aminophenyl)-7-(butylamino)pyrazolo[1,5-a]pyridin-3-yl]-2-pyrimidinyl}-N-butylamine as an orange oil. $^1$H NMR (CDCl$_3$): δ 8.02 (d, 1 H), 7.81 (d, 1 H), 7.47 (d, 2 H), 7.31 (m, 1 H), 6.77 (d, 2 H), 6.42 (d, 1 H), 6.08 (m, 1 H), 6.00 (d, 1 H), 5.18 (broad, 1 H), 3.86 (broad, 2 H), 3.53 (m, 2 H), 3.39 (m, 2 H), 1.82–1.64 (m, 4 H), 1.58–1.46 (m, 4 H), 1.04–0.99 (m, 6 H); MS m/z 430 (M+1). This material was treated with anhydrous hydrochloric acid in ether to provide the corresponding hydrochloride salt.

EXAMPLE 17

N-Butyl-3-[2-(butylamino)-4-pyrimidinyl]-2-[4-(cyclohexylamino)phenyl]-pyrazolo[1,5-a]pyridin-7-amine

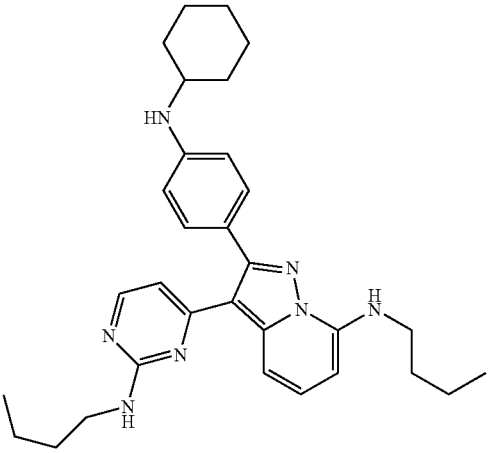

A solution of N-{4-[2-(4-aminophenyl)-7-(butylamino)pyrazolo[1,5-a]pyridin-3-yl]-2-pyrimidinyl}-N-butylamine (62 mg, 0.15 mmol) in 1,2-dichloroethane (2 mL) was treated with cyclohexanone (0.02 mL, 0.22 mmol), acetic acid (0.04 mL, 0.72 mmol), and sodium triacetoxyborohydride (61 mg, 0.29 mmol). The resultant solution was stirred at room temperature for 18 hours. Saturated aqueous sodium bicarbonate was added dropwise followed by ether. The organic layer was washed with brine. The aqueous layer was extracted with ether and the combined organics dried over magnesium sulfate. Filtration and concentration followed by flash chromatography (4:1 to 2:1 hexanes-ethyl acetate) provided N-butyl-3-[2-(butylamino)-4-pyrimidinyl]-2-[4-(cyclohexylamino)phenyl]pyrazolo[1,5-a]pyridin-7-amine (54 mg, 73%) as an orange oil. $^1$H NMR (CDCl$_3$): δ 7.94 (d, 1 H), 7.73 (d, 1 H), 7.39 (d, 2 H), 7.23 (m, 1 H), 6.59 (d, 2 H), 6.41 (d, 1 H), 6.03 (m, 1 H), 5.91 (d, 1 H), 5.11 (broad, 1 H), 3.66 (broad, 1 H), 3.44 (m, 2 H), 3.30 (m, 3 H), 2.05 (m, 2 H), 1.75–1.12 (m, 16 H), 0.95–0.92 (m, 6 H); MS m/z 512 (M+1). This material was treated with anhydrous hydrochloric acid in ether to provide the corresponding hydrochloride salt.

EXAMPLE 18

N-Butyl-3-[2-(butylamino)-4-pyrimidinyl]-2-(4-isopropenylphenyl)-pyrazolo[1,5-a]pyridin-7-amine To a cold (–78° C.) solution of 9-methoxy-9-borabicyclo[3.3.1]nonane (1 mL, 1.0 M in hexane, 1.0 mmol) in tetrahydrofuran (5 mL) was added isopropenylmagnesium bromide (2.0 mL, 0.5 M in tetrahydrofuran, 1.0 mmol) dropwise. The resultant solution was stirred at –78° C. for 5 minutes, then allowed to warm to room temperature. After 1 hour, potassium phosphate (0.33 mL, 3 M aqueous, 1.0 mmol) was added followed by N,N-dimethylformamide (5 mL), 2-(4-Bromophenyl)-N-butyl-3-[2-(butylamino)-4-pyrimidinyl]pyrazolo[1,5-a]pyridin-7-amine (100 mg, 0.20 mmol), and bis(diphenylphosphinoferrocene)palladium(II) chloride dichloromethane complex (17 mg, 0.02 mmol). The resultant solution was stirred for 72 hours at room temperature. Ether was added followed by water. The organic layer was washed with brine. The aqueous layer was extracted with ether and the combined organics dried over magnesium sulfate. Filtration and concentration followed by flash chromatography (6:1 to 4:1 to 2:1 hexanes:ethyl acetate) provided impure product. This material was taken up in tetrahydrofuran, cooled to 0° C. and 1 mL each of 10% aqueous sodium hydroxide and 30% hydrogen peroxide were added. After 30 minutes, the mixture was quenched with saturated aqueous sodium thiosulfate. Aqueous workup as reported above followed by similar chromatography provided N-butyl-3-[2-(butylamino)-4-pyrimidinyl]-2-(4-isopropenylphenyl)pyrazolo[1,5-a]pyridin-7-amine (25 mg, 27%) as an oil. $^1$H NMR (CDCl$_3$): δ 8.00 (d, 1 H), 7.76 (d, 1 H), 7.62 (d, 2 H), 7.54 (d, 2 H), 7.30 (m, 1 H), 6.35 (d, 1 H), 6.07 (m, 1 H), 5.99 (d, 1 H), 5.46 (s, 2 H), 5.22 (broad, 1 H), 5.14 (s,1 H), 3.47 (m, 2 H), 3.36 (m, 2 H), 2.20 (s, 3 H), 1.77–1.42 (m, 8 H), 1.00–0.95 (m 6 H); MS m/z 455 (M+1). This material was treated with anhydrous hydrochloric acid in ether to provide the corresponding hydrochloride salt.

EXAMPLE 19

2-(4-Anilinophenyl)-N-butyl-3-[2-(butylamino)-4-pyrimidinyl]pyrazolo[1,5-a]pyridin-7-amine

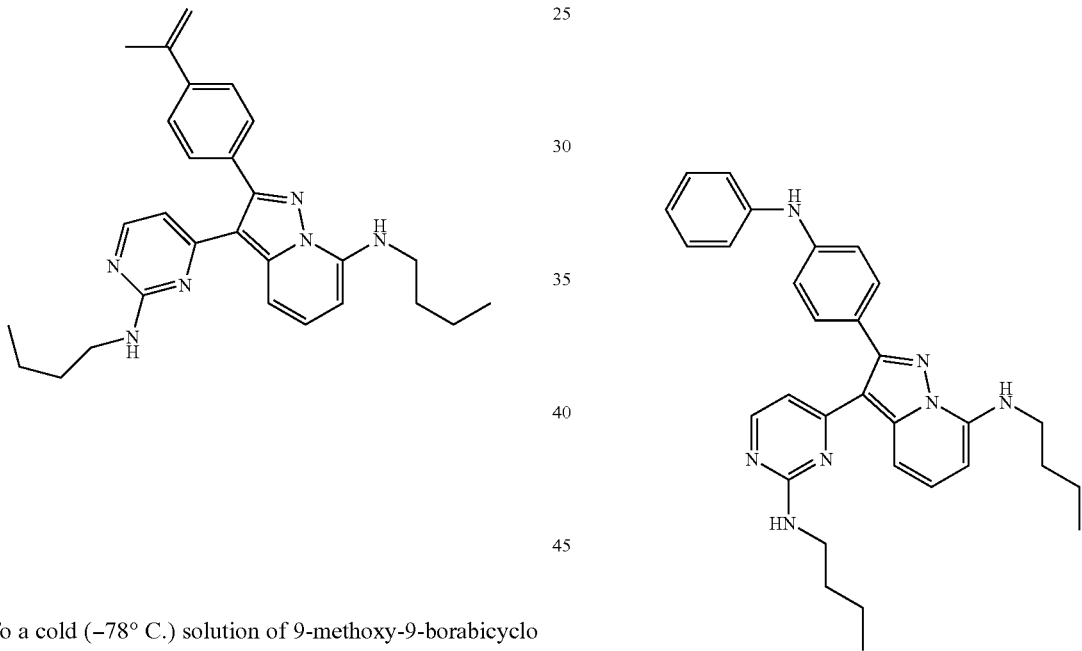

In a similar manner as described in Example 16 from N-{4-[2-(4-bromophenyl)-7-(butylamino)pyrazolo[1,5-a]pyridin-3-yl]-2-pyrimidinyl}-N-butylamine (0.25 g, 0.5 mmol) aniline and sodium t-butoxide was prepared 2-(4-anilinophenyl)-N-butyl-3-[2-(butylamino)-4-pyrimidinyl]pyrazolo[1,5-a]pyridin-7-amine (16.5 mg, 6.4%) as a yellow solid. $^1$H NMR (CDCl$_3$): δ 7.85 (broad, 1 H), 7.74 (d, 1 H), 7.49 (d, 2 H), 7.29 (m, 3 H), 7.11 (m, 4 H), 6.95 (t, 1 H), 6.40 (d, 1 H), 6.04 (t, 1 H), 6.00 (d, 1 H), 5.84 (s, 1 H), 3.49 (q, 2 H), 3.34 (q, 2 H), 1.74–1.41 (m, 8 H), 0.95 (m, 6 H); MS m/z 505 (M+1).

EXAMPLE 20

2-(4-Anilinophenyl)-N-butyl-3-[2-(butylamino)-4-pyrimidinyl]-N-phenylpyrazolo[1,5-a]pyridin-7-amine

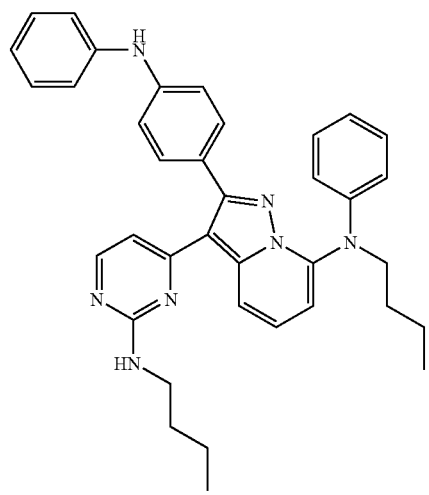

A mixture of N-{4-[2-(4-aminophenyl)-7-(butylamino)pyrazolo[1,5-a]pyridin-3-yl]-2-pyrimidinyl}-N-butylamine (50 mg, 0.12 mmol), phenylboronic acid (43 mg, 0.35 mmol), copper(II) acetate (42 mg, 0.23 mmol), triethylamine (49 μL, 0.35 mmol) and dichloromethane (1 mL) was stirred at room temperature for 60 hours, then filtered and concentrated. Flash column chromatography eluting with 3:1 hexanes:ethyl acetate afforded 2-(4-anilinophenyl)-N-butyl-3-[2-(butylamino)-4-pyrimidinyl]-N-phenylpyrazolo[1,5-a]pyridin-7-amine (29.8 mg, 44%) as a pale yellow solid. $^1$H NMR (CDCl$_3$): δ 8.18 (d, 1 H), 8.02 (d, 1 H), 7.42 (d, 2 H), 7.27–7.16 (m, 5 H), 7.09 (d, 2 H), 7.01 (d, 2 H), 6.94–6.83 (m, 4 H), 6.66 (d, 1 H), 6.47 (d, 1 H), 5.78 (s, 1 H), 5.21 (broad s, 1 H), 3.90 (m, 2 H), 3.48 (q, 2 H), 1.71–1.32 (m, 8 H), 0.95 (t, 3 H), 0.88 (t, 3 H); MS m/z 582 (M+1).

EXAMPLE 21

2-{4-[Bis(cyclopropylmethyl)amino]phenyl}-N-butyl-3-[2-(butylamino)-4-pyrimidinyl]pyrazolo[1,5-a]pyridin-7-amine and

EXAMPLE 22

N-butyl-3-[2-(butylamino)-4-pyrimidinyl]-2-{4-[(cyclopropylmethyl)amino]phenyl}pyrazolo[1,5-a]pyridin-7-amine

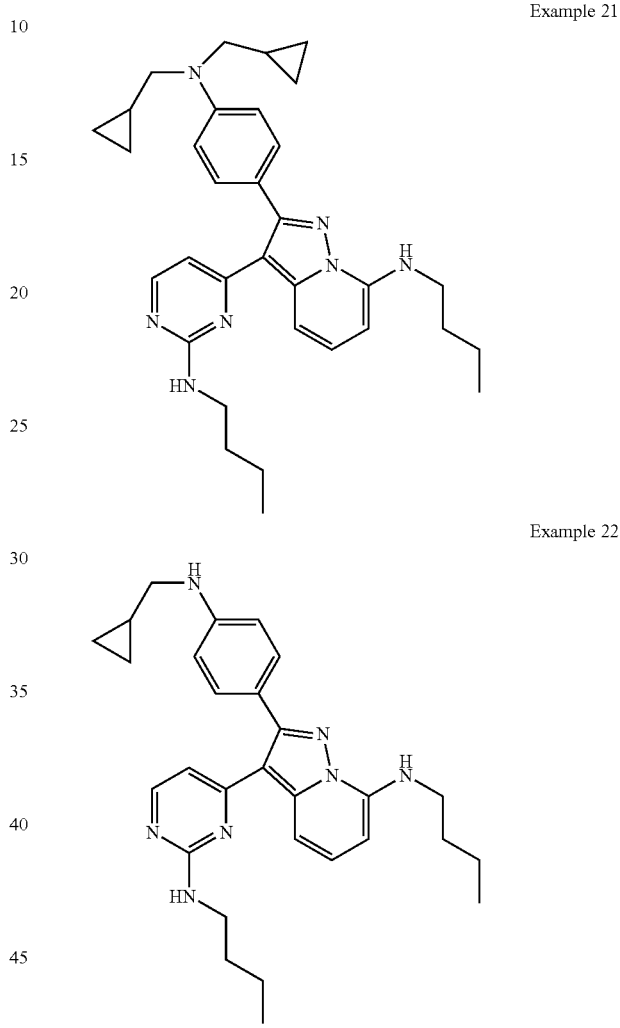

To a solution of N-{4-[2-(4-aminophenyl)-7-(butylamino)pyrazolo[1,5-a]pyridin-3-yl]-2-pyrimidinyl}-N-butylamine (64 mg, 0.15 mmol) in 1,2-dichloroethane (4 mL) was added cyclopropanecarboxaldehyde (17 μL, 0.22 mmol), acetic acid (43 μL, 0.74 mmol) and sodium triacetoxyborohydride (63 mg, 0.30 mmol). The reaction was stirred at room temperature for 15 minutes, then quenched with aqueous sodium bicarbonate. The mixture was extracted with diethyl ether. The organic layer was dried over magnesium sulfate and concentrated. Flash column chromatography eluting with a gradient of 10% to 25% ethyl acetate in hexanes afforded 2-{4-[bis(cyclopropylmethyl)amino]phenyl}-N-butyl-3-[2-(butylamino)-4-pyrimidinyl]pyrazolo[1,5-a]pyridin-7-amine (26.1 mg, 33%) as a gold solid: $^1$H NMR (CDCl$_3$): δ 7.96 (d, 1 H), 7.78 (d, 1 H), 7.50 (d, 2 H), 7.30 (t, 1 H), 6.87 (d, 2 H), 6.50 (d, 1 H), 6.08 (t, 1 H), 5.99 (d, 1 H), 3.53 (q, 2 H), 3.40–3.33 (m, 6 H), 1.79–1.46 (m, 8 H), 1.12 (m, 2 H), 0.99 (t, 6 H), 0.55 (m, 4 H), 0.26 (m, 4 H); MS m/z 538 (M+1); and N-butyl-3-[2-(butylamino)-4-pyrimidinyl]-2-{4-[(cyclopropylmethyl)amino]phenyl}pyrazolo[1,5-a]pyridin-7-amine (33.3 mg, 46%) as a yellow solid: $^1$H NMR (CDCl$_3$): δ 7.85 (d, 1 H), 7.79 (d, 1 H), 7.44 (d, 2 H), 7.33 (t, 1 H), 6.68 (d, 2 H), 6.43 (d, 1 H), 6.09 (t, 1 H), 6.02 (d, 1 H), 3.54 (q, 2 H), 3.37 (q, 2 H), 3.03 (d, 2 H), 1.80–1.43 (m, 8 H), 1.14 (m, 1 H), 0.99 (t, 6 H), 0.59 (m, 2 H), 0.28 (m, 2 H); MS m/z 484 (M+1).

EXAMPLE 23

N-Butyl-3-[2-(butylamino)-4-pyrimidinyl]-2-[4-(dimethylamino)phenyl]-pyrazolo[1,5-a]pyridin-7-amine

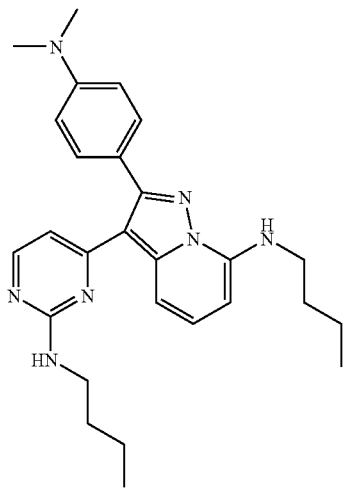

In a similar manner as described in Example 17 from N-{4-[2-(4-aminophenyl)-7-(butylamino)pyrazolo[1,5-a]pyridin-3-yl]-2-pyrimidinyl}-N-butylamine (50 mg, 0.12 mmol), formaldehyde (13 μL, 37% aqueous solution, 0.17 mmol) and sodium triacetoxyborohydride (99 mg, 0.47 mmol) was prepared N-butyl-3-[2-(butylamino)-4-pyrimidinyl]-2-[4-(dimethylamino)phenyl]pyrazolo[1,5-a]pyridin-7-amine (40.5 mg, 76%) as a pale yellow solid. $^1$H NMR (CDCl$_3$): δ 7.80 (m, 2 H), 7.50 (d, 2 H), 7.33 (t, 1 H), 6.79 (d, 2 H), 6.44 (d, 1 H), 6.10 (t, 1 H), 6.03 (d, 1 H), 3.54 (q, 2 H), 3.38 (q, 2 H), 3.03 (s, 6 H), 1.80–1.43 (m, 8 H), 0.99 (t, 6 H); MS m/z 458 (M+1).

EXAMPLE 24

2-(2-Bromophenyl)-N-cyclopentyl-3-[2-(cyclopentylamino)-4-pyrimidinyl]pyrazolo[1,5-a]pyridin-7-amine

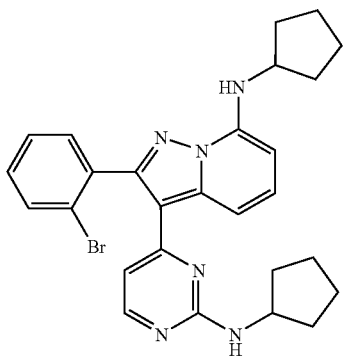

a) 1-(2-Bromophenyl)-2-(6-chloro-2-pyridinyl)ethanone

In a similar manner as described in Example 1 from ethyl 2-bromobenzoate (50.0 g, 218 mmol) and 6-chloro-2-picoline (24 mL, 218 mmol), 1-(2-bromophenyl)-2-(6-chloro-2-pyridinyl)ethanone (52.4 9, 77%) was obtained as a yellow solid. $^1$H NMR (CDCl$_3$): δ 7.53 (d, 1 H), 7.45 (d, 1 H), 7.25 (d, 1 H), 7.05 (d, 1 H), 6.97 (d, 1 H), 6.67 (d, 1H), 6.53 (d, 1H), 5.28 (s, 1H); MS m/z 310 (M+1).

b) 1-(2-Bromophenyl)-2-(6-chloro-2-pyridinyl)ethanone oxime

In a similar manner as described in Example 1 from 1-(2-bromophenyl)-2-(-6-chloro-2-pyridinyl)ethanone (52.4 g, 169 mmol) was obtained 1-(2-bromophenyl)-2-(-6-chloro-2-pyridinyl)ethanone oxime (36.5 g, 66%) as a pale yellow solid. $^1$H NMR (CDCl$_3$): δ 7.50–7.45 (m, 2H), 7.23–7.07 (m, 6H), 4.29 (s, 2H); MS m/z 325 (M+1).

c) 2-(2-Bromophenyl)-7-chloropyrazolo[1,5-a]pyridine

In a similar manner as described in Example 1 from 1-(2-bromophenyl)-2-(6-chloro-2-pyridinyl)ethanone oxime (36.5 g, 112 mmol), 2-(2-bromophenyl)-7-chloropyrazolo[1,5-a]pyridine (21.0 g, 61%) was obtained as a yellow solid. $^1$H NMR (CDCl$_3$): δ 7.83 (dd, 1H), 7.65 (d, 1H), 7.51 (d, 1H), 7.37 (t, 1H), 7.21 (m, 1H), 7.07 (m, 2H), 6.89 (d, 1H); MS m/z 307 (M+1).

d) 1-[2-(2-Bromophenyl)-7-chloropyrazolo[1,5-a]pyridin-3-yl]ethanone

In a similar manner as described in Example 1 from 2-(2-bromophenyl)-7-chloropyrazolo[1,5-a]pyridine (21.0 g, 68.3 mmol), 1-[2-(2-bromophenyl)-7-chloropyrazolo[1,5-a]pyridin-3-yl]ethanone (15.7 g, 66%) was obtained as orange needles. $^1$H NMR (CDCl$_3$): δ 8.48 (dd, 1H), 7.72 (d, 1H), 7.49–7.36 (m, 4H), 7.18 (dd, 1H), 2.06 (s, 3H); MS m/z 349 (M+1).

e) 1-[2-(2-Bromophenyl)-7-(cyclopentylamino)pyrazolo[1,5-a]pyridin-3-yl]ethanone In a similar manner as described in Example 1 from 1-[2-(2-bromophenyl)-7-chloropyrazolo[1,5-a]pyridin-3-yl]ethanone (3.00 g, 8.6 mmol), 1-[2-(2-bromophenyl)-7-(cyclopentylamino)pyrazolo[1,5-a]pyridin-3-yl]ethanone (0.93 g, 27%) was obtained as a yellow syrup. $^1$H NMR (CDCl$_3$): δ 7.73–7.68 (m, 2H), 7.43 (m, 3H), 7.35–7.31 (m, 1H), 6.12 (d, 1H), 5.98 (d, 1 H), 3.95 (m, 1 H), 2.08 (m, 2), 1.98 (s, 3H), 1.76–1.53 (m, 6H); MS m/z 398 (M+1).

f) (2E)-1-[2-(2-Bromophenyl)-7-(cyclopentylamino)pyrazolo[1,5-a]pyridin-3-yl]-3-(dimethylamino)-2-propen-1-one In a similar manner as described in Example 1 from 1-[2-(2-bromophenyl)-7-(cyclopentylamino)pyrazolo[1,5-a]pyridin-3-yl]ethanone (0.93 g, 2.3 mmol), (2E)-1-[2-(2-bromophenyl)-7-(cyclopentylamino)pyrazolo[1,5-a]pyridin-3-yl]-3-(dimethylamino)-2-propen-1-one (0.57 g, 54%) was obtained as a brown syrup. $^1$H NMR (CDCl$_3$): δ 7.78 (d, 1H), 7.66 (d, 1H), 7.53 (d, 1H), 7.46 (m, 1H), 7.39 (t, 1H), 7.31–7.22 (m, 2H), 6.02 (d, 1H), 5.85 (d, 1H), 4.80 (d, 1H), 3.95 (m, 1 H), 2.90 (broad s, 3H), 2.30 (broad s, 3H), 2.08 (m, 2H), 1.77–1.63 (m, 6H); MS m/z 455 (M+1).

g) 2-(2-Bromophenyl)-N-cyclopentyl-3-[2-(cyclopentylamino)-4-pyrimidinyl]-pyrazolo[1,5-a]pyridin-7-amine In a similar manner as described in Example 1 from (2E)-1-[2-(2-bromophenyl)-7-(cyclopentylamino)pyrazolo[1,5-a]pyridin-3-yl]-3-(dimethylamino)-2-propen-1-one (200 mg, 0.46 mmol), 2-(2-bromophenyl)-N-cyclopentyl-3-[2-(cyclopentylamino)-4-pyrimidinyl]pyrazolo[1,5-a]pyridin-7-amine (110 mg, 48%) was obtained as a yellow foam. $^1$H NMR (CDCl$_3$): δ 7.90 (m, 2H), 7.66 (d, 1H), 7.44 (m, 1H), 7.39 (t, 1H), 7.32–7.27 (m, 2H), 6.04–5.96 (m, 3H), 5.02 (m, 1H), 4.21 (m, 1H), 3.95 (m, 1H), 2.10–1.96 (m, 4H), 1.75–1.43 (m, 12H); MS m/z 517 (M+1).

EXAMPLE 25

2-(3-Bromophenyl)-N-cyclopentyl-3-[2-(cyclopentylamino)-4-pyrimidinyl]pyrazolo[1,5-a]pyridin-7-amine

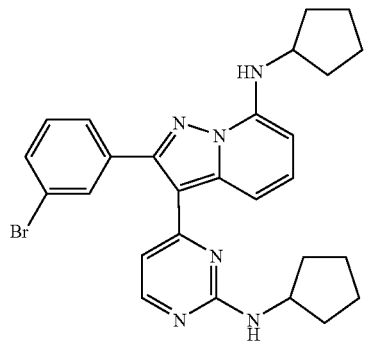

a) 1-(3-Bromophenyl)-2-(6-chloro-2-pyridinyl)ethanone

In a similar manner as described in Example 1 from ethyl 3-bromobenzoate (50.6 g, 220 mmol) and 6-chloro-2-picoline (24 mL, 220 mmol), 1-(3-bromophenyl)-2-(6-chloro-2-pyridinyl)ethanone (59.4 g, 87%) was obtained as a yellow solid. $^1$H NMR (CDCl$_3$): δ 7.96 (broad s, 1H), 7.71 (d, 1H), 7.35–7.25 (m, 3H), 6.98 (t, 1H), 6.81 (d, 1H), 6.58 (d, 1H), 5.84 (s, 1H); MS m/z 310 (M+1).

b) 1-(3-Bromophenyl)-2-(6-chloro-2-pyridinyl)ethanone oxime

In a similar manner as described in Example 1, from 1-(3-bromophenyl)-2-(6-chloro-2-pyridinyl)ethanone (59.1 g, 190 mmol) the 1-(3-bromophenyl)-2-(6-chloro-2-pyridinyl)ethanone oxime (58.3 g, 94%) was obtained as a white solid. $^1$H NMR (CDCl$_3$): δ 7.96 (s, 1H), 7.67–7.50 (m, 3H), 7.28–7.18 (m, 3H), 4.80 (b, 1H), 4.39 (s, 2H); MS m/z 325 (M+1).

c) 2-(3-Bromophenyl)-7-chloropyrazolo[1,5-a]pyridine

In a similar manner as described in Example 1 from 1-(3-bromophenyl)-2-(6-chloro-2-pyridinyl)ethanone oxime (59.1 g, 181.5 mmol), 2-(3-bromophenyl)-7-chloropyrazolo[1,5-a]pyridine (24.5 g, 44%) was obtained as a yellow solid. $^1$H NMR (CDCl$_3$): δ 8.13 (dd, 1H), 7.90 (d, 1H), 7.47 (m, 2H), 7.29 (t, 1H), 7.05 (t, 1H), 6.88 (m, 2H); MS m/z 307 (M+1).

d) 1-[2-(3-Bromophenyl)-7-chloropyrazolo[1,5-a]pyridin-3-yl]ethanone

In a similar manner as described in Example 1 from 2-(3-bromophenyl)-7-chloropyrazolo[1,5-a]pyridine (16.5 g, 53.6 mmol), 1-[2-(3-bromophenyl)-7-chloropyrazolo[1,5-a]pyridin-3-yl]ethanone (8.6 g, 46%) was obtained as pinkish needles. $^1$H NMR (CDCl$_3$): δ 8.46 (d, 1H), 7.83 (s, 1H), 7.69 (d, 1H), 7.59–7.40 (m, 3H), 7.22 (d, 1H), 2.21 (s, 3H); MS m/z 349 (M+1).

e) 1-[2-(3-Bromophenyl)-7-(cyclopentylamino)pyrazolo[1,5-a]pyridin-3-yl]ethanone In a similar manner as described in Example 1 from 1-[2-(3-bromophenyl)-7-chloropyrazolo[1,5-a]pyridin-3-yl]ethanone (3.00 g, 8.6 mmol), 1-[2-(3-bromophenyl)-7-(cyclopentylamino)pyrazolo[1,5-a]pyridin-3-yl]ethanone (1.90 g, 56%) was obtained as a yellow syrup. $^1$H NMR (CDCl$_3$): δ 7.74 (dd,1 H), 7.61–7.57 (m, 2H), 7.50 (d, 1H), 7.41 (t, 1H), 7.32 (t, 1H), 6.10 (dd, 1H), 5.99 (d, 1H), 3.95 (m, 1H), 2.12–2.05 (m, 5H), 1.78–1.63 (m, 6H); MS m/z 398 (M+1).

f) (2E)-1-[2-(3-Bromophenyl)-7-(cyclopentylamino)pyrazolo[1,5-a]pyridin-3-yl]-3-(dimethylamino)-2-propen-1-one In a similar manner as described in Example 1 from 1-[2-(3-bromophenyl)-7-(cyclopentylamino)pyrazolo[1,5-a]pyridin-3-yl]ethanone (1.90 g, 4.8 mmol), (2E)-1-[2-(3-bromophenyl)-7-(cyclopentylamino)pyrazolo[1,5-a]pyridin-3-yl]-3-(dimethylamino)-2-propen-1-one (1.87 g, 86%) was obtained as a brown syrup. $^1$H NMR (CDCl$_3$): δ 7.88 (s, 1H) 7.64–7.49 (m, 4H), 7.30–7.24 (m, 2H), 6.00 (d, 1H), 5.93 (d, 1H), 5.03 (d, 1H), 3.95 (m, 1H), 3.10–2.35 (b, 6H), 2.10–2.06 (m, 2H), 1.77–1.62 (m, 6H); MS m/z 455 (M+1).

g) 2-(3-Bromophenyl)-N-cyclopentyl-3-[2-(cyclopentylamino)-4-pyrimidinyl]-pyrazolo[1,5-a]pyridin-7-amine In a similar manner as described in Example 1 from (2E)-1-[2-(3-bromophenyl)-7-(cyclopentylamino)pyrazolo[1,5-a]pyridin-3-yl]-3-(dimethylamino)-2-propen-1-one (500 mg, 1.1 mmol), 2-(3-bromophenyl)-N-cyclopentyl-3-[2-(cyclopentylamino)-4-pyrimidinyl]pyrazolo[1,5-a]pyridin-7-amine (500 mg, 88%) was obtained as a yellow solid. $^1$H NMR (CDCl$_3$): δ 8.00 (d, 1H), 7.83 (s, 1H), 7.65 (d, 1H), 7.51 (m, 2H), 7.29–7.22 (m, 2H), 6.28 (d, 1H), 6.00 (d, 1H), 5.96 (d, 1H), 5.00 (d, 1H), 4.27 (m, 1H), 3.97 (m, 1H), 2.11–2.00 (m, 4H), 1.79–1.46 (m, 12H); MS m/z 517 (M+1).

EXAMPLE 26

4-[2-(3-Bromophenyl)-7-(1-pyrrolidinyl)pyrazolo[1,5-a]pyridin-3-yl]-N-cyclopentyl-2-pyrimidinamine

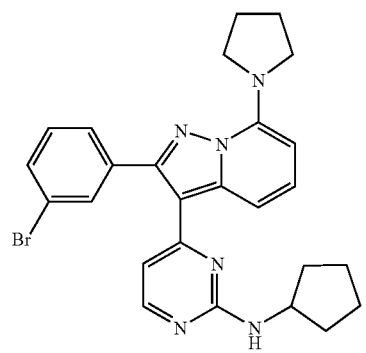

a) 1-[2-(3-Bromophenyl)-7-(1-pyrrolidinyl)pyrazolo[1,5-a]pyridin-3-yl]ethanone

In a similar manner as described in Example 1 from 1-[2-(3-bromophenyl)-7-chloropyrazolo[1,5-a]pyridin-3-yl]ethanone (3.00 g, 8.6 mmol) and pyrrolidine, 1-[2-(3-bromophenyl)-7-(1-pyrrolidinyl)pyrazolo[1,5-a]pyridin-3-yl]ethanone (3.18 g, 96%) was obtained as a yellow syrup. $^1$H NMR (CDCl$_3$): δ 7.78–7.74 (m, 2H), 7.56 (d, 1H), 7.50 (d, 1H), 7.38–7.28 (m, 2H), 6.14 (d, 1H), 3.72 (m, 4H), 2.12 (s, 3H), 1.98 (m, 4H); MS m/z 384 (M+1).

b) (2E)-1-[2-(3-Bromophenyl)-7-(1-pyrrolidinyl)pyrazolo[1,5-a]pyridin-3-yl]-3-(dimethylamino)-2-propen-1-one In a similar manner as described in Example 1 from 1-[2-(3-bromophenyl)-7-(1-pyrrolidinyl)pyrazolo[1,5-a]pyridin-3-yl]ethanone (3.1 g, 8.1 mmol), (2E)-1-[2-(3-bromophenyl)-7-(1-pyrrolidinyl)pyrazolo[1,5-a]pyridin-3-yl]-3-(dimethylamino)-2-propen-1-one (2.15 g, 61%) was obtained as a brown syrup. $^1$H NMR (CDCl$_3$): δ 7.90 (dd, 1H), 7.76 (d, 1H), 7.66 (d, 1H), 7.54 (d, 1H), 7.51 (d, 1H), 7.26–7.20 (m, 2H), 6.06 (d, 1H), 5.07 (d, 1H), 3.70 (m, 4H), 2.90 (b, 3H), 2.50 (b, 3H), 1.99 (m, 4H); MS m/z 4.39 (M+1).

c) 4-[2-(3-Bromophenyl)-7-(1-pyrrolidinyl)pyrazolo[1,5-a]pyridin-3-yl]-N-cyclopenyl-2-pyrimidinamine In a similar manner as described in Example 1 from (2E)-1-[2-(3-bromophenyl)-7-(1-pyrrolidinyl)pyrazolo[1,5-a]pyridin-3-yl]-3-(dimethylamino)-2-propen-1-one (500 mg, 1.1 mmol), 4-[2-(3-bromophenyl)-7-(1-pyrrolidinyl)pyrazolo[1,5-a]pyridin-3-yl]-N-cyclopentyl-2-pyrimidinamine (451 mg, 79%) was obtained as a yellow solid. $^1$H NMR (d$_6$-DMSO): δ 8.00 (d, 1H), 7.71 (s, 1H), 7.60 (d, 1H), 7.54 (d, 1H), 7.37 (t, 1H), 7.29 (t, 1H), 6.98 (d, 1H), 6.18 (d, 2H), 4.02 (m, 1H), 3.66 (m, 4H), 1.90 (m, 4H), 1.80–1.44 (m, 8H); MS m/z 503 (M+1); Anal. Calcd. for C$_{26}$H$_{27}$N$_6$Br: C, 62.03; H, 5.41; N, 16.69. Found: C, 61.88; H. 5.40; N, 16.40.

EXAMPLE 27

N-[3-(2-Amino-4-pyrimidinyl)-2-(3-bromophenyl)pyrazolo[1,5-a]pyridin-7-yl]-N-cyclopentylamine

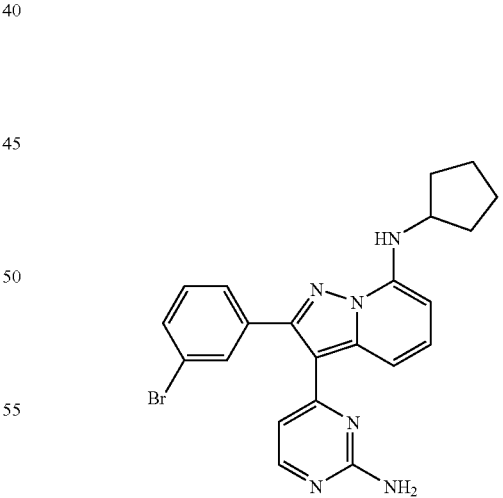

In a similar manner as described in Example 1 from (2E)-1-[2-(3-bromophenyl)-7-(cyclopentylamino)pyrazolo[1,5-a]pyridin-3-yl]-3-(dimethylamino)-2-propen-1-one (500 mg, 1.1 mmol) and guanidine sulfate (358 mg, 1.65 mmol), N-[3-(2-amino-4-pyrimidinyl)-2-(3-bromophenyl)pyrazolo[1,5-a]pyridin-7-yl]-N-cyclopentylamine (380 mg, 77%) was obtained as a yellow solid. $^1$H NMR (CDCl$_3$): δ 8.01 (d, 1H), 7.84 (s, 1H), 7.64 (d, 1H), 7.54–7.49 (m, 2H), 7.30–7.22 (m, 2H), 6.36 (d, 1H), 6.01 (d, 1H), 5.97 (d, 1H), 4.95 (broad s, 2H), 3.97 (m, 1H), 2.12 (m, 2H), 1.79–1.57 (m, 6H); MS m/z 448 (M+1); Anal. Calcd. for C$_{22}$H$_{21}$N$_6$Br: C, 58.80; H, 4.71; N,18.70. Found: C, 58.61; H, 4.75; N, 18.58.

EXAMPLE 28

4-[2-(3-Bromophenyl)-7-(1-pyrrolidinyl)pyrazolo[1,5-a]pyridin-3-yl]-2-pyrimidinamine

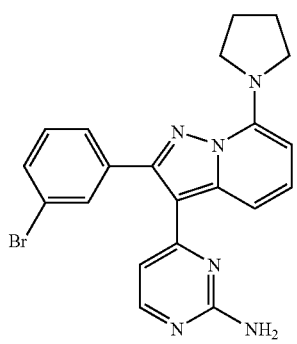

In a similar manner as described in Example 1 from (2E)-1-[2-(3-bromophenyl)-7-(1-pyrrolidinyl)pyrazolo[1,5-a]pyridin-3-yl]-3-(dimethylamino)-2-propen-1-one (500 mg, 1.1 mmol) and guanidine sulfate, 4-[2-(3-bromophenyl)-7-(1-pyrrolidinyl)pyrazolo[1,5-a]pyridin-3-yl]-2-pyrimidinamine (300 mg, 61%) was obtained as a yellow solid. $^1$H NMR (d$_6$-DMSO): δ 8.03 (d, 1H), 7.87 (d, 1H), 7.81 (s, 1H), 7.70–7.62 (m, 2H), 7.46 (t, 1H), 7.35 (t, 1H), 6.58 (broad s, 2H), 6.26 (d, 1H), 6.22 (d, 1H), 3.75 (m, 4H), 1.98 (m, 4H); MS m/z 435 (M+1); Anal. Calcd. for C$_{21}$H$_{19}$N$_6$Br: C, 57.94; H, 4.40; N. 19.31. Found: C, 57.91; H, 4.51; N, 19.07.

EXAMPLE 29

2-[1,1'-Biphenyl]-3-yl-N-cyclopentyl-3-[2-(cyclopentylamino)-4-pyrimidinyl]pyrazolo[1,5-a]pyridin-7-amine

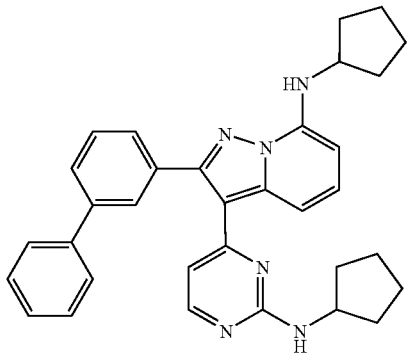

To a solution of 2-(3-bromophenyl)-N-cyclopentyl-3-[2-(cyclopentylamino)-4-pyrimidinyl]pyrazolo[1,5-a]pyridin-7-amine (100 mg, 0.19 mmol) in dimethylformamide (6 mL) was added phenylboronic acid (47 mg, 0.39 mmol), palladium (II) acetate (4.3 mg, 0.02 mmol), potassium carbonate (54 mg, 0.39 mmol) and triphenyl phosphine (30 mg, 0.08 mmol). The reaction was heated at 100° C. for 24 hours. After allowing the reaction mixture to cool to room temperature, ethyl acetate and water were added. The organic layer was separated and washed with water, then brine and dried (magnesium sulfate). Filtration and concentration, followed by purification with flash chromatography (4:6 ethyl acetate:hexanes) gave 2-[1,1'-biphenyl]-3-yl-N-cyclopentyl-3-[2-(cyclopentylamino)-4-pyrimidinyl]pyrazolo[1,5-a]pyridin-7-amine as a yellow foam (87 mg, 89%). $^1$H NMR (CDCl$_3$): δ 8.01 (d, 1H), 7.92 (s, 1H), 7.81 (d, 1H), 7.69–7.62 (m, 4H), 7.53 (t, 1H), 7.47–7.43 (m, 2H), 7.38–7.32 (m, 2H), 6.40 (d, 1H), 6.09–6.05 (m, 2H), 5.16 (m, 1H), 4.37 (m, 1H), 4.03 (m, 1H), 2.15–2.06 (m, 4H), 1.82–1.64 (m, 12H); MS m/z 515 (M+1).

EXAMPLE 30

4-[2-[1,1'-Biphenyl]-3-yl-7-(1-pyrrolidinyl)pyrazolo[1,5-a]pyridin-3-yl]-N-cyclopentyl-2-pyrimidinamine

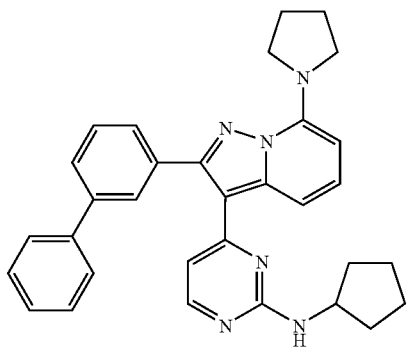

In a similar manner as described in Example 29 from 4-[2-(3-bromophenyl)-7-(1-pyrrolidinyl)pyrazolo[1,5-a]pyridin-3-yl]-N-cyclopentyl-2-pyrimidinamine (100 mg, 0.20 mmol), 4-[2-[1,1'-biphenyl]-3-yl-7-(1-pyrrolidinyl)pyrazolo[1,5-a]pyridin-3-yl]-N-cyclopentyl-2-pyrimidinamine (70 mg, 70%) was obtained as a yellow foam. $^1$H NMR (CDCl$_3$): δ 8.04 (d, 1H), 7.93 (s, 1H), 7.92 (m, 1H), 7.67–7.59 (m, 4H), 7.52–7.42 (m, 3H), 7.36 (t, 1H), 7.29–7.24 (m, 1H), 6.44 (d, 1H), 6.11 (d, 1H), 5.05 (d, 1H), 4.37 (m, 1H), 3.78 (m, 4H), 2.09–2.02 (m, 6H), 1.76–1.54 (m, 6H); MS m/z 501 (M+1).

EXAMPLE 31

N-Cyclopentyl-3-[2-(cyclopentylamino)-4-pyrimidinyl]-2-[3-(4-pyridinyl)phenyl]pyrazolo[1,5-a]pyridin-7-amine

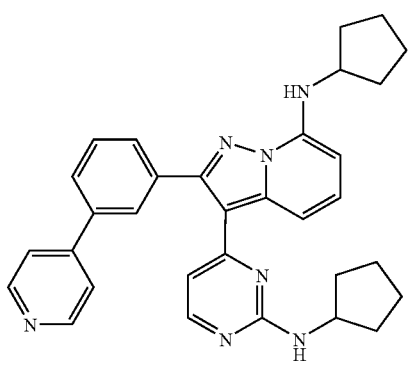

In a similar manner as described in Example 29 from 2-(3-bromophenyl)-N-cyclopentyl-3-[2-(cyclopentylamino)-4-pyrimidinyl]pyrazolo[1,5-a]pyridin-7-amine (100 mg, 0.19 mmol) and pyridine-4-boronic acid, N-cyclopentyl-3-[2-(cyclopentylamino)-4-pyrimidinyl]-2-[3-(4-pyridinyl)phenyl]pyrazolo[1,5-a]pyridin-7-amine (41 mg, 42%) was obtained as a yellow foam. $^1$H NMR (CDCl$_3$): δ 8.66 (d, 2H), 8.02 (d, 1H), 7.96 (s, 1H), 7.76–7.69 (m, 3H), 7.58–7.51 (m, 3H), 7.33 (t, 1H), 6.36 (d, 1H), 6.06–6.04 (m, 2H), 5.15 (m, 1H), 4.32 (m, 1H), 4.01 (m, 1H), 2.17–2.03 (m, 4H), 1.81–1.52 (m, 12H); MS m/z 516 (M+1).

EXAMPLE 32

N-Cyclopentyl-3-[2-(cyclopentylamino)-4-pyrimidinyl]-2-[3-(3-thienyl)phenyl]pyrazolo[1,5-a]pyridin-7-amine

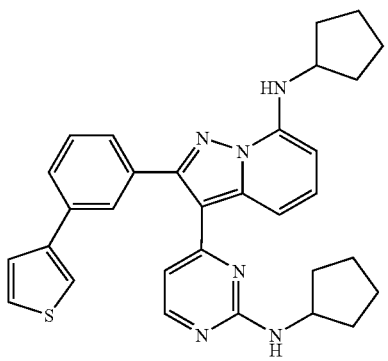

In a similar manner as described in Example 29 from 2-(3-bromophenyl)-N-cyclopentyl-3-[2-(cyclopentylamino)-4-pyrimidinyl]pyrazolo[1,5-a]pyridin-7-amine (200 mg, 0.39mmol) and thiophene-3-boronic acid, N-cyclopentyl-3-[2-(cyclopentylamino)-4-pyrimidinyl]-2-[3-(3-thienyl)phenyl]pyrazolo[1,5-a]pyridin-7-amine (94 mg, 47%) was obtained as a yellow foam. $^1$H NMR (CDCl$_3$): δ 8.00 (d, 1H), 7.92 (s. 1H), 7.81 (d, 1H), 7.67 (d, 1H), 7.57 (d, 1H), 7.49–7.42 (m, 2H), 7.40–7.34 (m, 2H), 7.32–7.27 (m, 1H), 6.38 (d, 1H), 6.09–6.03 (m, 2H), 5.22 (d, 1H), 4.36 (m, 1H), 4.00 (m, 1H), 2.15–2.05 (m, 4H), 1.82–1.56 (m, 12H); MS m/z 521 (M+1).

EXAMPLE 33

N-Cyclopentyl-3-[2-(cyclopentylamino)-4-pyrimidinyl]-2-[3-(2-thienyl)-phenyl]pyrazolo[1,5-a]pyridin-7-amine

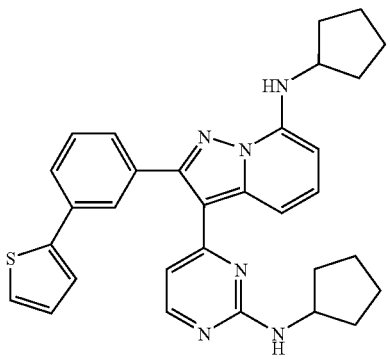

In a similar manner as described in Example 29 from 2-(3-bromophenyl)-N-cyclopentyl-3-[2-(cyclopentylamino)-4-pyrimidinyl]pyrazolo[1,5-a]pyridin-7-amine (200 mg, 0.39 mmol) and thiophene-2-boronic acid, N-cyclopentyl-3-[2-(cyclopentylamino)-4-pyrimidinyl]-2-[3-(2-thienyl)phenyl]pyrazolo[1,5-a]pyridin-7-amine (84 mg, 42%) was obtained as a yellow foam. $^1$H NMR (CDCl$_3$): δ 8.00 (d, 1H), 7.95 (s, 1H), 7.79 (d, 1H), 7.69 (d, 1H), 7.56 (d, 1H), 7.45 (t, 1H), 7.34–7.27 (m, 3H), 7.09 (m, 1H), 6.39 (d, 1H), 6.17 (m, 2H), 5.16 (m, 1H), 4.35 (m, 1H), 4.01 (m, 1H), 2.16 (m, 4H), 1.82–1.56 (m, 12H); MS m/z 521 (M+1). U16951-72

EXAMPLE 34

2-(3-Aminophenyl)-N-cyclopentyl-3-[2-(cyclopentylamino)-4-pyrimidinyl]pyrazolo[1,5-a]pyridin-7-amine

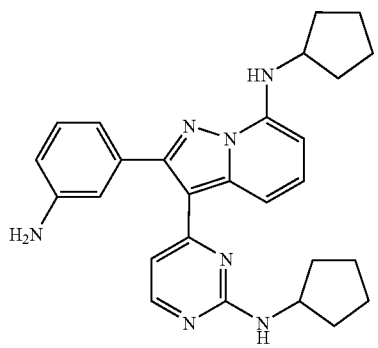

a) N-Cyclopentyl-3-[2-(cyclopentylamino)-4-pyrimidinyl]-2-{3-[(diphenylmethylene)amino]phenyl}pyrazolo[1,5-a]pyridin-7-amine To a solution of 2-(3-bromophenyl)-N-cyclopentyl-3-[2-(cyclopentylamino)-4-pyrimidinyl]pyrazolo[1,5-a]pyridin-7-amine (3.00 g, 5.8 mmol) in toluene (60 mL) was added benzophenone imine (3.15 g, 17.4 mmol), tris(dibenzylideneacetone)dipalladium (0.26 g, 0.3 mmol), rac-2,2'-bis(diphenylphosphino)-1,1'-binaphthyl (0.54 g, 0.15 mmol) and sodium tert-butoxide (1.67 g, 17.4 mmol). The reaction was heated at reflux for 5 hours, then allowed to cool to room temperature. Water and ethyl acetate were added to the reaction mixture. The phases were separated and the organic phase was washed with brine and dried (magnesium sulfate). Filtration and concentration of the filtrate followed by purification with flash chromatography (4:6 ethyl acetate:hexanes) gave N-cyclopentyl-3-[2-(cyclopentylamino)-4-pyrimidinyl]-2-{3-[(diphenylmethylene)amino]phenyl}pyrazolo[1,5-a]pyridin-7-amine (2.61 g, 73%) as a yellow solid. $^1$H NMR (CDCl$_3$): δ 7.89 (d, 1H), 7.80–7.75 (m, 3H), 7.48 (m, 1H), 7.41 (m, 2H), 7.27 (m, 5H), 7.23–7.12 (m, 4H), 7.04 (s, 1H), 6.80 (d, 1H), 6.03–5.97 (m, 3H), 4.39 (m, 1H), 4.00 (m, 1H), 2.15–2.05 (m, 4H), 1.83–1.56 (m, 12H); MS m/z 618 (M+1).

b) 2-(3-Aminophenyl)-N-cyclopentyl-3-[2-(cyclopentylamino)-4-pyrimidinyl]pyrazolo[1,5-a]pyridin-7-amine To a solution of N-cyclopentyl-3-[2-(cyclopentylamino)-4-pyrimidinyl]-2-{3-[(diphenylmethylene)amino]phenyl}pyrazolo[1,5-a]pyridin-7-amine (2.61 g, 4.22 mmol) in tetrahydrofuran (30 mL) at 0° C. was added 4N hydrochloric acid (20 mL) dropwise. Subsequently, the reaction mixture was stirred for 5 minutes. The reaction mixture was diluted with ether, then saturated aqueous bicarbonate was added slowly till the ether layer turned clear. The resulting mixture was stirred for 30 minutes. The phases were separated, the organic phase was washed with water, brine and dried (magnesium sulfate). Filtration and concentration of the filtrate to a solid, followed by recrystallization from ethyl acetate-hexanes, gave 2-(3-aminophenyl)-N-cyclopentyl-3-[2-(cyclopentylamino)-4-pyrimidinyl]pyrazolo[1,5-a]pyridin-7-amine (1.78 g, 93%) as a pale yellow solid. $^1$H NMR (CDCl$_3$): δ 7.92 (d, 1H), 7.82 (d, 1H), 7.32 (t, 1H), 7.22 (m, 2H), 7.00–6.94 (m, 2H), 6.78 (m, 1H), 6.34 (d, 1H), 6.04 (m, 2H), 4.38 (m, 1H), 4.00 (m, 1H), 3.75 (broad, 2H), 2.14–2.05 (m, 4H), 1.83–1.54 (m, 12H); MS m/z 454 (M+1).

EXAMPLE 35

N-(3-{7-(Cyclopentylamino)-3-[2-(cyclopentylamino)-4-pyrimidinyl]pyrazolo[1,5-a]pyridin-2-yl}phenyl)acetamide

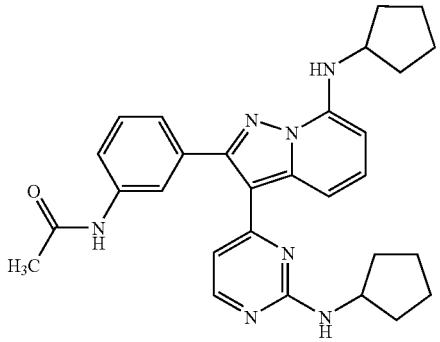

To a suspension of 2-(3-aminophenyl)-N-cyclopentyl-3-[2-(cyclopentylamino)-4-pyrimidinyl]pyrazolo[1,5-a]pyridin-7-amine (150 mg, 0.33 mmol) in dimethylformamide (10 mL) was added triethylamine (51 δL, 0.36 mmol). The reaction mixture was cooled to 0° C. and flushed with nitrogen, then acetyl chloride (26 μL, 0.36 mmol) was added dropwise. The reaction mixture was stirred at room temperature overnight. Water was added and the resulting mixture was extracted with ethyl acetate. The ethyl acetate phase was dried (magnesium sulfate), filtered and concentrated to a solid. This solid was purified by flash chromatography (95:5 chloroform:methanol) to give N-(3-{7-(cyclopentylamino)-3-[2-(cyclopentylamino)-4-pyrimidinyl]pyrazolo[1,5-a]pyridin-2-yl}phenyl)acetamide (151 mg, 92%) as a tan solid. $^1$H NMR (CDCl$_3$): δ 8.19 (s, 1H), 7.95 (d, 1H), 7.82 (d, 1H), 7.75 (d, 1H), 7.63 (s, 1H), 7.36–7.25 (m, 3H), 6.28 (d, 1H), 6.00 (m, 2H), 5.17 (d, 1H), 4.32 (m, 1H), 3.96 (m, 1H), 2.11 (s, 3H), 2.11–2.02 (m, 4H), 1.76–1.48 (m, 12H); MS m/z 496 (M+1).

EXAMPLE 36

N-(3-{7-(Cyclopentylamino)-3-[2-(cyclopentylamino)-4-pyrimidinyl]-pyrazolo[1,5-a]pyridin-2-yl}phenyl)methanesulfonamide

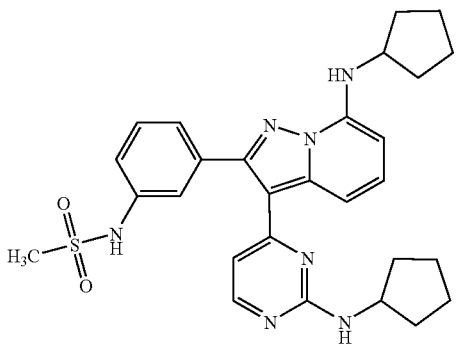

To a suspension of 2-(3-aminophenyl)-N-cyclopentyl-3-[2-(cyclopentylamino)-4-pyrimidinyl]pyrazolo[1,5-a]pyridin-7-amine (150, mg, 0.33 mmol) in N,N-dimethylformamide (5 mL) was added pyridine (40 μL, 0.49 mmol). The reaction mixture was cooled to 0° C. under nitrogen, then methanesulfonyl chloride (28 μL, 0.36 mmol) was added dropwise. After stirring at room temperature for 18 hours, the reaction mixture turned clear. Ethyl acetate and water were added and the phases separated. The organic phase was washed with water and brine, then dried over magnesium sulfate. Filtration and concentration, followed by flash chromatography (95:5 chloroform:methanol) gave N-(3-{7-(cyclopentylamino)-3-[2-(cyclopentylamino)-4-pyrimidinyl]pyrazolo[1,5-a]pyridin-2-yl}phenyl)methanesulfonamide (170 mg, 96%) as a yellow syrup. $^1$H NMR (CDCl$_3$): δ 7.93 (d, 1H), 7.66 (d, 1H), 7.42 (m, 1H), 7.35–7.25 (m, 5H), 6.25 (m, 1H), 5.99 (m, 2H), 5.62 (broad, 1H), 4.29 (m, 1H), 3.96 (m, 1H), 2.94 (s, 3H), 2.10–1.99 (m, 4H), 1.77–1.49 (m, 12H). MS m/z 532 (M+1).

EXAMPLE 37

4-[2-(3-Aminophenyl)-7-(1-pyrrolidinyl)pyrazolo[1,5-a]pyridin-3-yl]-N-cylopentyl-2-pyrimidinamine

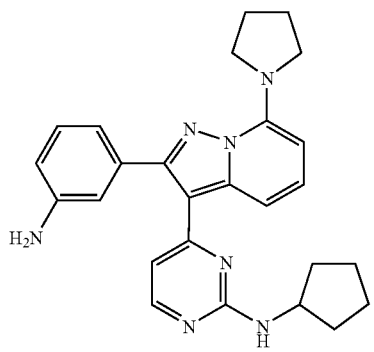

a) N-Cyclopentyl-4-{2-[3-[(diphenylmethylene)amino]phenyl]-7-(1-pyrrolidinyl)pyrazolo[1,5-a]pyridin-3-yl}-2-pyrimidinamine In a similar manner as described in Example 16 from 4-[2-(3-bromophenyl)-7-(1-pyrrolidinyl)pyrazolo[1,5-a]pyridin-3-yl]-N-cyclopentyl-2-pyrimidinamine (200 mg, 0.40 mmol), N-cyclopentyl-4-{2-[3-[(diphenylmethylene)amino]phenyl]-7-(1-pyrrolidinyl)pyrazolo[1,5-a]pyridin-3-yl}-2-pyrimidinamine (156 mg, 65%) was obtained as a yellow solid. $^1$H NMR (CDCl$_3$): δ 7.90 (m, 2H), 7.72–7.70 (m, 2H), 7.43–7.35 (m, 3H), 7.23–7.16 (m, 4H), 7.13–7.11 (m, 4H), 7.05 (s, 1H), 6.70 (m, 1H), 6.02 (m, 2H), 4.98 (d, 1H), 4.33 (m, 1H), 3.68 (m, 4H), 2.07 (m, 2H), 1.99 (m, 4H), 1.72–1.50 (m, 6H); MS m/z 604 (M+1).

b) 4-[2-(3-Aminophenyl)-7-(1-pyrrolidinyl)pyrazolo[1,5-a]pyridin-3-yl]-N-cyclopentyl-2-pyrimidinamine In a similar manner as described in Example 16 from N-cyclopentyl-4-{2-[3-[(diphenylmethylene)amino]phenyl]-7-(1-pyrrolidinyl)pyrazolo[1,5-a]pyridin-3-yl}-2-pyrimidinamine (150 mg, 0.25 mmol), 4-[2-(3-aminophenyl)-7-(1-pyrrolidinyl)-pyrazolo[1,5-a]pyridin-3-yl]-N-cyclopentyl-2-pyrimidinamine (104 mg, 95%) was obtained as a yellow foam. $^1$H NMR (CDCl$_3$): δ 7.97 (d, 1H), 7.92 (d, 1H), 7.21–7.15 (m, 2H), 7.01 (d, 1H), 6.69 (s, 1H), 6.91 (dd, 1H), 6.38 (d, 1H), 6.05 (d, 1H), 5.29 (m, 1H), 4.37 (m, 1H), 3.72 (m, 4H), 3.70 (broad, 2H), 2.07 (m, 2H), 1.98 (m, 4H), 1.74–1.53 (m, 6H); MS m/z 440 (M+1).

EXAMPLE 38

N-Cyclopentyl-3-[2-(cyclopentylamino)-4-pyrimidinyl]-2-phenylpyrazolo-[1,5-a]pyridin-7-amine

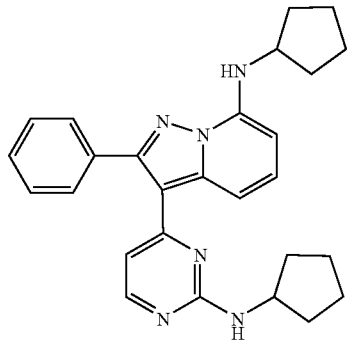

To a solution of 2-(3-bromophenyl)-N-cyclopentyl-3-[2-(cyclopentylamino)-4-pyrimidinyl]pyrazolo[1,5-a]pyridin-7-amine (100 mg, 0.19 mmol) in toluene (10 mL) was added tributyltin hydride (112 mg, 0.39 mmol) and 2,2'-azobisisobutyronitrile (9.4 mg, 0.057 mmol). After heating at reflux for 4 hours, the reaction mixture was allowed to cool to room temperature. Concentration, followed by purification with flash chromatography (40:60 ethyl acetate:hexanes) gave N-cyclopentyl-3-[2-(cyclopentylamino)-4-pyrimidinyl]-2-phenylpyrazolo[1,5-a]pyridin-7-amine as a yellow foam (39 mg, 46%). $^1$H NMR (CDCl$_3$): δ 7.98 (d, 1H), 7.78 (d, 1H), 7.64 (m, 2H), 7.45 (m, 2H), 7.33–7.26 (m, 2H), 6.27 (d, 1H), 6.04 (m, 2H), 5.12 (d, 1H), 4.35 (m, 1H), 4.00 (m, 1H), 2.09–2.03 (m, 4H), 1.81–1.59 (m, 12H). MS m/z 439 (M+1).

EXAMPLE 39

3-{7-(Cyclopentylamino)-3-[2-(cyclopentylamino)-4-pyrimidinyl]pyrazolo[1,5-a]pyridin-2-yl}benzonitrile

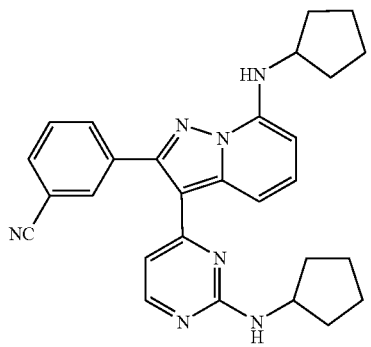

To a solution of 2-(3-bromophenyl)-N-cyclopentyl-3-[2-(cyclopentylamino)-4-pyrimidinyl]pyrazolo[1,5-a]pyridin-7-amine (500 mg, 0.97 mmol) in N,N-dimethylformamide (25 mL) was added zinc cyanide (68 mg, 0.58 mmol), tris(dibenzylidineacetone)bipalladium(0) (888 mg, 0.97 mmol) and 1,1'-bis(diphenylphosphino) ferrocene (1.29 g, 2.3 mmol). The resultant mixture was heated at 120° C. for 20 hours. After cooling to room temperature, ethyl acetate was added to the reaction mixture. The organic phase was washed with water, brine and dried over magnesium sulfate. Filtration and concentration, followed by purification with flash chromatography (40:60 ethyl acetate:hexanes) gave 3-{7-(cyclopentylamino)-3-[2-(cyclopentylamino)-4-pyrimidinyl]pyrazolo[1,5-a]pyridin-2-yl}benzonitrile (0.19 g, yield 42%) as a yellow foam. $^1$H NMR (CDCl$_3$): δ 8.07 (m, 2H), 7.89 (d, 1H), 7.70 (d, 1H), 7.62 (d, 1H), 7.52 (t, 1H), 7.33 (t, 1H), 6.33 (d, 1H), 6.06 (d, 1H), 6.00 (d, 1H), 5.16 (d, 1H), 4.25 (m, 1H), 4.02 (m, 1H), 2.15 (m, 2H), 2.03 (m, 2H), 1.85–1.51 (m, 12H). MS m/z 464 (M+1).

EXAMPLE 40

3-{7-(Cyclopentylamino)-3-[2-(cyclopentylamino)-4-pyrimidinyl]-pyrazolo[1,5-a]pyridin-2-yl}benzamide

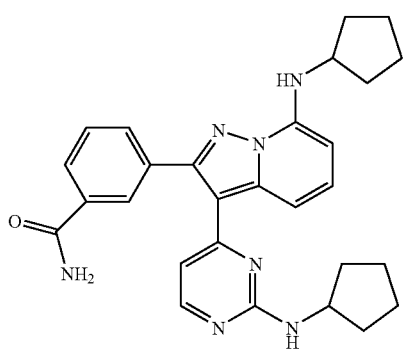

3-{7-(Cyclopentylamino)-3-[2-(cyclopentylamino)-4-pyrimidinyl]pyrazolo[1,5-a]pyridin-2-yl}benzonitrile (45 mg, 0.097 mmol) was dissolved in hot methanol (2 mL). Subsequently, the solution was cooled down to room temperature and 30% ammonium hydroxide (2 mL) was added. The reaction mixture was then cooled to 0° C., and 30% hydrogen peroxide was added. After stirring at room temperature for 8 hours, water was added and the resulting mixture extracted with ethyl acetate. The organics were dried over magnesium sulfate. Filtration and concentration, followed by purification with flash chromatography (95:5 dichloromethane:methanol), gave 3-{7-(cyclopentylamino)-3-[2-(cyclopentylamino)-4-pyrimidinyl]pyrazolo[1,5-a]pyridin-2-yl}benzamide (18 mg, 39% yield) as a yellow solid. $^1$H NMR (CDCl$_3$): δ 8.12 (s, 1H), 7.99 (d, 1H), 7.92 (d, 1H), 7.79 (d, 1H), 7.70 (d, 1H), 7.51 (t, 1H), 7.32 (t, 1H), 6.28 (d, 1H), 6.18 (broad, 1H), 6.05 (d, 1H), 6.02 (d, 1H), 5.82 (broad, 1H), 5.25 (d, 1H), 4.30 (m, 1H), 4.00 (m, 1H), 2.15 (m, 2H), 2.03 (m, 2H), 1.81–1.50 (m, 12H). MS m/z 482 (M+1).

EXAMPLE 41

3-{7-(Cyclopentylamino)-3-[2-(cyclopentylamino)-4-pyrimidinyl]pyrazolo-[1,5-a]pyridin-2-yl}benzoic acid

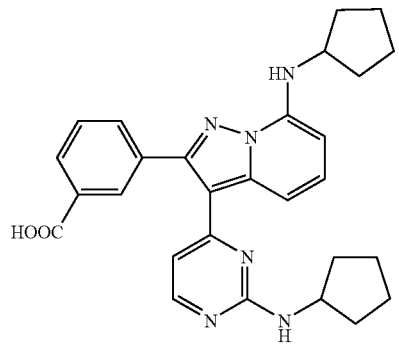

To a solution of 3-{7-(cyclopentylamino)-3-[2-(cyclopentylamino)-4-pyrimidinyl]pyrazolo[1,5-a]pyridin-2-yl}benzonitrile (50 mg, 0.1 mmol) in methanol was added 4N potassium hydroxide. After heating at 85° C. for 2 days, the reaction mixture was cooled to room temperature and acidified with 2N hydrochloric acid. The solution was extracted with ethyl acetate. The organic phases were combined and dried over magnesium sulfate. Filtration and concentration, followed by purification by flash chromatography (90:10 ethyl acetate:methanol) gave 3-{7-(cyclopentylamino)-3-[2-(cyclopentylamino)-4-pyrimidinyl]pyrazolo[1,5-a]pyridin-2-yl}benzoic acid (10 mg, 19%) as a brown foam. $^1$H NMR (CDCl$_3$): δ 8.11 (s, 1H), 8.00 (d, 1H), 7.96 (d, 1H), 7.80 (broad s, 1H), 7.64 (d, 1H), 7.46 (t, 1H), 7.37 (t, 1H), 6.98 (d, 1H), 6.57 (d, 1H), 6.21 (d, 1H), 6.11 (broad, 1H), 4.12 (m, 1H), 4.01 (m, 1H), 2.06 (m, 2H), 1.88 (m, 2H), 1.69–1.49 (m, 12H). MS m/z 483 (M+1); 481 (M−1).

EXAMPLE 42

N-{4-[2-(3-Bromo-4-methoxyphenyl)-7-(cyclopentylamino)pyrazolo[1,5-a]pyridin-3-yl]-2-pyrimidinyl}-N-cyclopentylamine

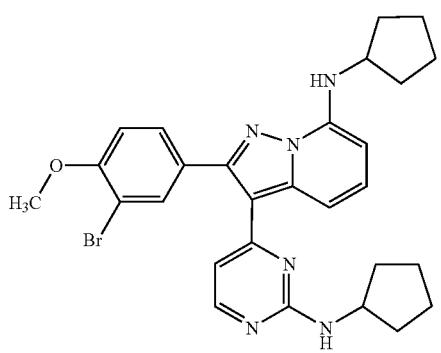

a) 1-(3-Bromo-4-methoxyphenyl)-2-(6-chloro-2-pyridinyl)ethanone

In a similar manner as described in Example 1 from ethyl 3-bromo-4-methoxybenzoate (13.6 g, 52.5 mmol) and 6-chloro-2-picoline (5.7 mL, 52.5 mmol), 1-(3-bromo-4-methoxyphenyl)-2-(6-chloro-2-pyridinyl)ethanone (15.8 g, 88%) was obtained as a yellow solid (existing as a mixture of ketone and enol tautomers). $^1$H NMR (CDCl$_3$) of the ketone: δ 8.27 (s, 1H), 8.02 (dd, 1H), 7.63 (t, 1H), 7.23 (m, 2H), 6.94 (d, 1H), 4.41 (s, 2H), 3.97 (s, 3H); MS m/z 340 (M+1).

b) 1-(3-Bromo-4-methoxyphenyl)-2-(6-chloro-2-pyridinyl)ethanone oxime

In a similar manner as described in Example 1 from 1-(3-bromo-4-methoxyphenyl)-2-(6-chloro-2-pyridinyl)ethanone (15.8 g, 49.3 mmol) was obtained 1-(3-bromo-4-methoxyphenyl)-2-(6-chloro-2-pyridinyl)ethanone oxime (12.6 g, 76%) as a white solid. $^1$H NMR (CDCl$_3$): δ 8.00 (d, 1H), 7.63 (dd, 1H), 7.54 (t, 1H), 7.19–7–7.15 (m, 2H), 6.86 (d, 1H), 4.34 (s, 2H), 3.90 (s, 3H); MS m/z 357 (M+1).

c) 2-(3-Bromo-4-methoxyphenyl)-7-chloropyrazolo[1,5-a]pyridine

To a solution of 1-(3-bromo-4-methoxyphenyl)-2-(6-chloro-2-pyridinyl)ethanone oxime (1.00 g, 2.8 mmol) in dimethoxyethane (30 mL) at 0° C. was added slowly methylsulfonyl chloride (0.24 mL, 3.08 mmol). The reaction was stirred for 15 minutes and then triethylamine (1.7 mL, 12.3 mmol) in dimethoxyethane (3 mL) was added to the reaction. Upon addition of the triethylamine a precipitate formed. Once the addition of the triethylamine solution had been completed the reaction mixture was allowed to warm to room temperature and was stirred for 1 hour. The precipitate was removed by filteration and the precipitate was washed with dimethoxyethane. To the combined filtrate was added iron (II) chloride (14 mg, 0.12 mmol) and the resulting mixture was heated at 80° C. for 15 hours. The reaction mixture was allowed to cool to room temperature. Ethyl acetate was added to dilute the mixture and the organic phase was washed with water, brine and dried (magnesium sulfate). Filtration and concentration of the filtrate, followed by flash chromatography (4:6 ethyl acetate:hexanes) gave 2-(3-bromo-4-methoxyphenyl)-7-chloropyrazolo[1,5-a]pyridine (86 mg, 9%). $^1$H NMR (CDCl$_3$): δ 8.21 (d, 1H), 7.95 (d, 1H), 7.48 (d, 1H), 7.10 (t, 1H), 6.98 (d, 1H), 6.88 (d, 1H), 6.84 (s, 1H), 3.96 (s, 3H); MS m/z 337 (M+1).

d) 1-[2-(3-Bromo-4-methoxyphenyl)-7-chloropyrazolo[1,5-a]pyridin-3-yl]ethanone In a similar manner as described in Example 1 from 2-(3-bromo-4-methoxyphenyl)-7-chloropyrazolo[1,5-a]pyridine (0.62 g, 1.83 mmol), 1-[2-(3-bromo-4-methoxyphenyl)-7-chloropyrazolo[1,5-a]pyridin-3-yl]ethanone (0.45 g, 65%) was obtained as a pink solid. $^1$H NMR (CDCl$_3$): δ 8.40 (m, 1H), 7.84 (s, 1H), 7.54 (dd, 1H), 7.46 (m, 1H), 7.16 (m, 1H), 7.03 (d, 1H), 3.99. (s, 3H), 2.20 (s, 3H); MS m/z 379 (M+1).

e) 1-[2-(3-Bromo-4-methoxyphenyl)-7-(cyclopentylamino)pyrazolo[1,5-a]pyridin-3-yl]ethanone In a similar manner as described in Example 1 from 1-[2-(3-bromo-4-methoxyphenyl)-7-chloropyrazolo[1,5-a]pyridin-3-yl]ethanone (0.51 g, 1.3 mmol), 1-[2-(3-bromo-4-methoxyphenyl)-7-(cyclopentylamino)pyrazolo[1,5-a]pyridin-3-yl]ethanone (0.24 g, 42%) was obtained as a yellow foam. $^1$H NMR (CDCl$_3$): δ 7.84 (d, 1H), 7.65 (d, 1H), 7.54 (dd, 1H), 7.44 (t, 1H), 7.02 (d, 1H), 6.15 (d, 1H), 6.04 (d, 1H), 3.98 (m, 4H), 2.19 (s, 3H), 2.13 (m, 2H), 1.82–1.64 (m, 6H); MS m/z 428 (M+1).

f) (2E)-1-[2-(3-Bromo-4-methoxyphenyl)-7-(cyclopentylamino)pyrazolo[1,5-a]pyridin-3-yl]-3-(dimethylamino)-2-propen-1-one In a similar manner as described in Example 1 from 1-[2-(3-bromo-4-methoxyphenyl)-7-(cyclopentylamino)pyrazolo[1,5-a]pyridin-3-yl]ethanone (0.24 g, 0.56 mmol), (2E)-1-[2-(3-bromo-4-methoxyphenyl)-7-(cyclopentylamino)pyrazolo[1,5-a]pyridin-3-yl]-3-(dimethylamino)-2-propen-1-one (0.13 g, 48%) was obtained as a brown syrup. $^1$H NMR (CDCl$_3$): δ 7.96 (d, 1H), 7.64 (m, 1H), 7.60–7.56 (m, 2H), 7.27 (t, 1H), 6.94 (d, 1H), 6.00–5.98 (m, 2H), 5.13 (d, 1H), 3.94 (m, 1H), 3.91 (s, 3 H), 0.92 (b, 3H), 2.55 (b, 3H), 2.08 (m, 2H), 1.78–1.64 (m, 6H); MS m/z 483 (M+1).

g) N-{4-[2-(3-Bromo-4-methoxyphenyl)-7-(cyclopentylamino)pyrazolo[1,5-a]pyridin-3-yl]-2-pyrimidinyl}-N-cyclopentylamine In a similar manner as described in Example 1 from (2E)-1-[2-(3-bromo-4-methoxyphenyl)-7-(cyclopentylamino)pyrazolo[1,5-a]pyridin-3-yl]-3-(dimethylamino)-2-propen-1-one (130 mg, 0.27 mmol), N-{4-[2-(3-bromo-4-methoxyphenyl)-7-(cyclopentylamino)pyrazolo[1,5-a]pyridin-3-yl]-2-pyrimidinyl)}-N-cyclopentylamine (84 mg, 57%) was obtained as a yellow solid. $^1$H NMR (CDCl$_3$): δ 8.03 (d, 1H), 7.93 (d, 1H), 7.71 (d, 1H), 7.54 (d, 1H), 7.30(t, 1H), 6.95 (d, 1H), 6.36 (d, 1H), 6.04–6.00 (m, 2H), 5.12 (d, 1H), 4.34 (m, 1H), 4.00 (m, 1H), 3.96 (s, 3H), 2.15–2.05 (m, 4H), 1.83–1.53 (m, 12H); MS m/z 547 (M+1).

EXAMPLE 43

2-(3-Bromo-4-chlorophenyl)-N-cyclopentyl-3-[2-(cyclopentylamino)-4-pyrimidinyl]pyrazolo[1,5-a]pyridin-7-amine

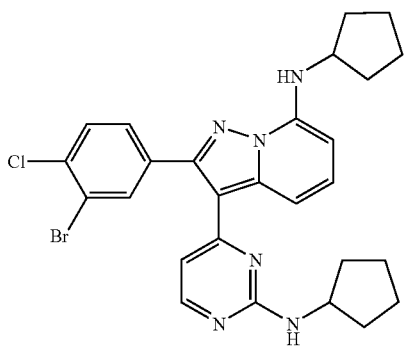

a) 1-(3-Bromo-4-chlorophenyl)-2-(6-chloro-2-pyridinyl)ethanone

In a similar manner as described in Example 1 from ethyl 3-bromo-4-chlorobenzoate (42.6 g, 171 mmol) and 6-chloro-2-picoline (18.7 mL, 171 mmol), 1-(3-bromo-4-chlorophenyl)-2-(-6-chloro-2-pyridinyl)ethanone was obtained as a pale yellow solid existing as a mixture of ketone and enol tautomers. $^1$H NMR (CDCl$_3$) of ketone: δ 8.30 (d, 1H), 7.92 (dd, 1H), 7.69–7.54 (m, 2H), 7.24 (m, 2H), 4.42 (s, 2H); MS m/z 344 (M+1).

b) 1-(3-Bromo-4-chlorophenyl)-2-(6-chloro-2-pyridinyl)ethanone oxime

In a similar manner as described in Example 1 from 1-(3-bromo-4-chlorophenyl)-2-(6-chloro-2-pyridinyl)ethanone was obtained 1-(3-bromo-4-chlorophenyl)-2-(6-chloro-2-pyridinyl)ethanone oxime (22.0 g, yield 36% for the two steps) as a white solid. $^1$H NMR (CDCl$_3$): δ 8.20 (b, 1H), 8.06 (d, 1H), 7.62–7.53 (m, 2H), 7.42 (d, 1H), 7.18–7.14 (m, 2H), 4.32 (s, 2H); MS m/z 359 (M+1).

c) 2-(3-Bromo-4-chlorophenyl)-7-chloropyrazolo[1,5-a]pyridine

In a similar manner as described in Example 1 from 1-(3-bromo-4-chlorophenyl)-2-(6-chloro-2-pyridinyl)ethanone oxime (17.57 g, 48.8 mmol) was obtained 2-(3-bromo-4-chlorophenyl)-7-chloropyrazolo[1,5-a]pyridine (13.7 g, 82%). $^1$H NMR (CDCl$_3$): δ 8.28 (d, 1H), 7.99 (dd, 1H), 7.52 (m, 2H), 7.10 (t, 1H), 6.94–6.90 (m, 2H); MS m/z 341 (M+1).

d) 1-[2-(3-Bromo-4-chlorophenyl)-7-chloropyrazolo[1,5-a]pyridin-3-yl]ethanone In a similar manner as described in Example 1 from 2-(3-bromo-4-chlorophenyl)-7-chloropyrazolo[1,5-a]pyridine (13.9 g, 40.8 mmol), 1-[2-(3-bromo-4-chlorophenyl)-7-chloropyrazolo[1,5-a]pyridin-3-yl]ethanone (12.5 g, 80%) was obtained as a tan solid. $^1$H NMR (CDCl$_3$): δ 8.40 (d, 1H), 7.92 (d, 1H), 7.61–7.44 (m, 3H), 7.19 (d, 1H), 2.21 (s, 3H); MS m/z 383 (M+1).

e) 1-[2-(3-Bromo-4-chlorophenyl)-7-(cyclopentylamino)pyrazolo[1,5-a]pyridin-3-yl]ethanone In a similar manner as described in Example 1 1-[2-(3-bromo-4-chlorophenyl)-7-chloropyrazolo[1,5-a]pyridin-3-yl]ethanone (12.5 g, 32.5 mmol), 1-[2-(3-bromo-4-chlorophenyl)-7-(cyclopentylamino)pyrazolo[1,5-a]pyridin-3-yl]ethanone was obtained as a yellow foam. $^1$H NMR (CDCl$_3$): δ 7.91 (d, 1H), 7.62–7.41 (m, 4H), 6.16 (d, 1H), 6.02 (d, 1H), 4.00 (m, 1H), 2.22 (s, 3H), 2.13 (m, 2H), 1.82–1.65 (m, 6H), MS m/z 432 (M+1).

f) (2E)-1-[2-(3-Bromo-4-chlorophenyl)-7-(cyclopentylamino)pyrazolo[1,5-a]pyridin-3-yl]-3-(dimethylamino)-2-propen-1-one In a similar manner as described in Example 1 from 1-[2-(3-bromo-4-chlorophenyl)-7-(cyclopentylamino)pyrazolo[1,5-a]pyridin-3-yl]ethanone, (2E)-1-[2-(3-bromo-4-chlorophenyl)-7-(cyclopentylamino)pyrazolo[1,5-a]pyridin-3-yl]-3-(dimethylamino)-2-propen-1-one (6.45 g, combined yield for steps e and f 41%) was obtained as a brown syrup. $^1$H NMR (CDCl$_3$): δ 8.08 (d, 1H), 7.69–7.57 (m, 3H), 7.51 (d, 1H), 7.32 (t, 1H), 6.04 (d, 1H), 5.96 (d, 1H), 5.13 (d, 1H), 4.00 (m, 1H), 3.0 (b, 3H), 2.62 (b, 3H), 2.13 (m, 2H), 1.84–1.68 (m, 6H); MS m/z 487 (M+1).

g) 2-(3-Bromo-4-chlorophenyl)-N-cyclopentyl-3-[2-(cyclopentylamino)-4-pyrimidinyl]pyrazolo[1,5-a]pyridin-7-amine In a similar manner as described in Example 1 from (2E)-1-[2-(3-bromo-4-chlorophenyl)-7-(cyclopentylamino)pyrazolo[1,5-a]pyridin-3-yl]-3-(dimethylamino)-2-propen-1-one (3.00 g, 6.15 mmol), 2-(3-bromo-4-chlorophenyl)-N-cyclopentyl-3-[2-(cyclopentylamino)-4-pyrimidinyl]pyrazolo[1.5-a]pyridin-7-amine (2.71 g, 80%) was obtained as a yellow solid. $^1$H NMR (CDCl$_3$): δ 8.08 (d, 1H), 8.02 (s, 1 H), 7.64 (d, 1H), 7.50 (m, 2H), 7.53 (t, 1H), 6.38 (d, 1H), 6.05 (d, 1H), 6.00 (d, 1H), 5.13 (d, 1H), 4.28 (m, 1H), 4.01 (m, 1H), 2.15 (m, 2H), 2.04 (m, 2H), 1.83–1.49 (m, 12H); MS m/z 551 (M+1).

EXAMPLE 44

2-(3-Amino-4-chlorophenyl)-N-cyclopentyl-3-[2-(cyclopentylamino)-4-pyrimidinyl]pyrazolo[1,5-a]pyridin-7-amine

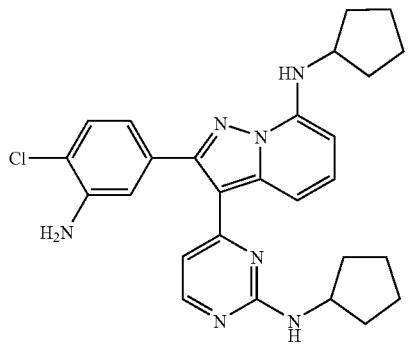

a) 2-{4-Chloro-3-[(diphenylmethylene)amino]phenyl}-N-cyclopentyl-3-[2-(cyclopentylamino)-4-pyrimidinyl]pyrazolo[1,5-a]pyridin-7-amine In a similar manner as described in Example 16 from 2-(3-bromo-4-chlorophenyl)-N-cyclopentyl-3-[2-(cyclopentylamino)-4-pyrimidinyl]pyrazolo[1,5-a]pyridin-7-amine (0.5 g, 0.91 mmol) was obtained 2-{4-chloro-3-[(diphenylmethylene)amino]phenyl}-N-cyclopentyl-3-[2-(cyclopentylamino)-4-pyrimidinyl]pyrazolo[1,5-a]pyridin-7-amine which was used directly in the next step.

b) 2-(3-Amino-4-chlorophenyl)-N-cyclopentyl-3-[2-(cyclopentylamino)-4-pyrimidinyl]pyrazolo[1,5-a]pyridin-7-amine In a similar manner as described in Example 16 from 2-{4-chloro-3-[(diphenyl-methylene)amino]phenyl}-N-cyclopentyl-3-[2-(cyclopentylamino)-4-pyrimidinyl]pyrazolo[1,5-a]pyridin-7-amine was obtained 2-(3-amino-4-chlorophenyl)-N-cyclopentyl-3-[2-(cyclopentylamino)-4-pyrimidinyl]pyrazolo[1,5-a]pyridin-7-amine (130 mg, yield 29% for 2 steps) as a yellow solid. $^1$H NMR (CDCl$_3$): δ 8.00 (d, 1H), 7.75 (d, 1H), 7.42 (m, 1H), 7.28 (m, 2H), 6.92 (d, 1H), 6.35 (d, 1H), 6.03 (m, 2H), 5.16 (d, 1H), 4.43 (m, 1H), 4.13 (broad, 2H), 3.99 (m, 1H), 2.14–2.08 (m, 4H), 1.80–1.52 (m, 12H). MS m/z488 (M+1).

EXAMPLE 45

2-[4-(Benzylamino)phenyl]-N-butyl-3-[2-(butylamino)-4-pyrimidinyl]-pyrazolo[1,5-a]pyridin-7-amine

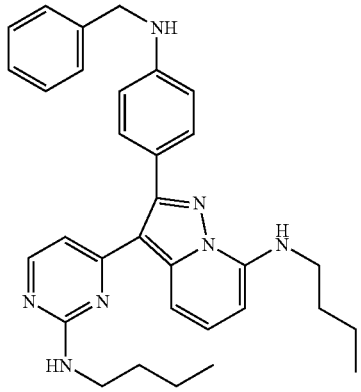

In a similar manner as described in Example 17 from N-{4-[2-(4-aminophenyl)-7-(butylamino)pyrazolo[1,5-a]pyridin-3-yl]-2-pyrimidinyl}-N-butylamine (100 mg, 0.23 mmol), and benzaldehyde (35 μL, 0.35 mmol) was prepared 2-[4-(benzylamino)phenyl]-N-butyl-3-[2-(butylamino)-4-pyrimidinyl]pyrazolo[1,5-a]pyridin-7-amine (113.6 mg, 94%) as a pale yellow foam. $^1$H NMR (CDCl$_3$): δ 7.94 (d, 1 H), 7.77 (d, 1 H), 7.46–7.26 (m, 8 H), 6.70 (d, 2 H), 6.42 (d, 1 H), 6.05 (t, 1 H), 5.99 (d, 1 H), 4.40 (d, 2 H), 4.23 (t, 1 H), 3.51 (q, 2 H), 3.36 (q, 2 H), 1.79–1.41 (m, 8 H), 0.98 (t, 6 H); MS m/z 520 (M+1).

EXAMPLE 46

N-Cyclopentyl-3-[2-(cyclopentylamino)-4-pyrimidinyl]-2-(3-methylphenyl)pyrazolo[1,5-a]pyridin-7-amine

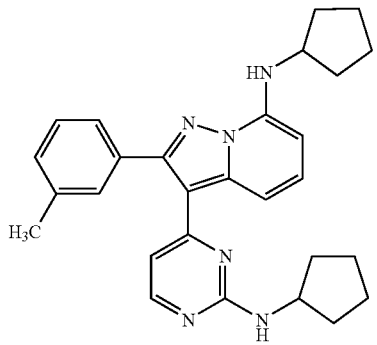

a) 2-(6-Chloro-2-pyridinyl)-1-(3-methylphenyl)ethanone

In a similar manner as described in Example 1 from ethyl 3-methylbenzoate (30 g, 183 mmol) was obtained 2-(6-chloro-2-pyridinyl)-1-(3-methylphenyl)ethanone (33.6 g, 75% yield) as a mixture of ketone and enol tautomers. This mixture was used directly in the next step.

b) 2-(6-Chloro-2-pyridinyl)-1-(3-methylphenyl)ethanone oxime

In a similar manner as described in Example 1 from 2-(6-chloro-2-pyridinyl)-1-(3-methylphenyl)ethanone (33.6 g, 137 mmol) was obtained 2-(6-chloro-2-pyridinyl)-1-(3-methylphenyl)ethanone oxime (26.1 g, 73% yield) as a white solid. $^1$H NMR (CDCl$_3$): δ 7.54–7.47 (m, 3H), 7.26–7.15 (m, 4H), 4.40 (s, 2H), 2.34 (s, 3H), MS m/z 243 (M+1).

c) 7-Chloro-2-(3-methylphenyl)pyrazolo[1,5-a]pyridine

In a similar manner as described in Example 1 from 2-(6-chloro-2-pyridinyl)-1-(3-methylphenyl)ethanone oxime (13 g, 50 mmol) was obtained 7-chloro-2-(3-methylphenyl)pyrazolo[1,5-a]pyridine (11.5 g, 99% yield) as a yellow crystalline solid. $^1$H NMR (CDCl$_3$): δ 7.86 (s, 1H), 7.79 (d, 1H), 7.48 (d, 1H), 7.34 (t, 1H), 7.20 (d, 1H), 7.05 (dd, 1H), 6.91 (s, 1H), 6.88 (d, 1H), 2.44 (s, 3H). MS m/z 243 (M+1).

d) 7-Chloro-2-(3-methylphenyl)pyrazolo[1,5-a]pyridine-3-carbaldehyde

N,N-Dimethylformamide (150 mL) was cooled to 0° C. and treated with phosphorous oxychloride (8.8 mL, 94 mmol). After the addition was complete, the mixture was warmed to room temperature and stirred for 1 hour. To this was added 7-chloro-2-(3-methylphenyl)pyrazolo[1,5-a]pyridine (16.3 g, 67 mmol) and the resultant solution was stirred overnight. Water was added, followed by dichloromethane. The aqueous layer was extracted with dichloromethane. The combined organics were washed with brine, dried over magnesium sulfate, filtered and concentrated. The residue was recrystallized from diethyl ether and hexanes to give 7-chloro-2-(3-methylphenyl)pyrazolo[1,5-a]pyridine-3-carbaldehyde (14.3 g, 79%) as a pale yellow solid. $^1$H NMR (CDCl$_3$): δ 10.11 (s, 1 H), 8.41 (dd, 1H), 7.63 (s, 1H), 7.58 (d, 1H), 7.49 (dd, 1H), 7.42 (t, 1H), 7.33 (d, 1H), 7.20 (dd, 1H), 2.45 (s, 3H); MS m/z 271 (M+1).

e) 1-[7-Chloro-2-(3-methylphenyl)pyrazolo[1,5-a]pyridin-3-yl]-2-propyn-1-ol

To a cold (−78° C.) suspension of 7-chloro-2-(3-methylphenyl)pyrazolo[1,5-a]pyridine-3-carbaldehyde (10.38 g, 36.2 mmol) in tetrahydrofuran (80 mL) was added ethynylmagnesium bromide (87 mL, 0.5 M in tetrahydrofuran, 43.4 mmol) dropwise. The reaction mixture was stirred at −78° C. for 1 hour, then at 0° C. for 2 hours. The resultant solution was poured into saturated aqueous sodium bicarbonate and extracted with ethyl acetate. The organic layer was washed with water and brine and the combined organics were dried over magnesium sulfate. Filtration and concentration followed by flash chromatography (4:1 hexanes:ethyl acetate to 7:3 hexanes:ethyl acetate) provided 1-[7-chloro-2-(3-methylphenyl)pyrazolo[1,5-a]pyridin-3-yl]-2-propyn-1-ol (11.3 g, 77%) as a yellow foam. $^1$H NMR (CDCl$_3$) δ 8.03 (d, 1H), 7.60 (s, 1H), 7.54 (d, 1H), 7.37 (t, 1H), 7.26 (d, 1H), 7.17 (dd, 1H), 6.98 (d, 1H), 2.67 (s, 1H), 2.43 (s, 3H), 2.38 (s, 1H); MS m/z 297 (M+1).

f) 1-[7-Chloro-2-(3-methylphenyl)pyrazolo[1,5-a]pyridin-3-yl]-2-propyn-1-one

To a solution of 1-[7-chloro-2-(3-methylphenyl)pyrazolo[1,5-a]pyridin-3-yl]-2-propyn-1-ol (11.3 g, 36.2 mmol) in chloroform (300 mL) was added manganese dioxide (78.9 g, 905 mmol). The reaction mixture was stirred at room temperature for 18 hours. The suspension was filtered through a pad of Celite and the filtrate was concentrated and purified by flash chromatography (7:3 hexanes:ethyl acetate). 1-[7-chloro-2-(3-methylphenyl)pyrazolo[1,5-a]pyridin-3-yl]-2-propyn-1-one (4.57 g, 41%) was obtained as a pale yellow crystalline. $^1$H NMR (CDCl$_3$) δ 8.48 (d, 1H), 7.51 (m, 3H), 7.33 (t, 1H), 7.29 (d, 1H), 8.21 (dd, 1H), 2.89 (s, 1H), 2.42 (s, 3H); MS m/z 295 (M+1).

g) 4-[7-Chloro-2-(3-methylphenyl)pyrazolo[1,5-a]pyridin-3-yl]-N-cyclopentyl-2-pyrimidinamine To a solution of 1-[7-chloro-2-(3-methylphenyl)pyrazolo[1,5-a]pyridin-3-yl]-2-propyn-1-one (4.04 g, 13.0 mmol) in N,N-dimethylformamide (100 mL) was added cyclopentyl guanidine hydrochloride (6.36 g, 39 mmol), followed by solid potassium carbonate (5.39 g, 39 mmol). The resultant solution was heated to reflux for 6 hours. Upon cooling to room temperature, ether was added followed by water. The organics were washed with brine, and the aqueous extracted with ethyl acetate. The combined organics were dried over magnesium sulfate, filtered and concentrated in vacuo. The residue was purified by silica gel flash chromatography (3:10 ethyl acetate:hexanes) to give 4-[7-chloro-2-(3-methylphenyl)pyrazolo[1,5-a]pyridin-3-yl]-N-cyclopentyl-2-pyrimidinamine (2.39 g, 43%) as a yellow foam. $^1$H NMR (CDCl$_3$) δ 8.47 (d, 1H), 7.99 (d, 1H), 7.48 (s, 1H), 7.39 (d, 1H), 7.33–7.24 (m, 3H), 7.05 (d, 1H), 6.33 (d, 1H), 5.38 (broad s, 1H), 4.36 (m, 1H), 2.40 (s, 3H), 2.10 (m, 2H), 1.78 (m, 2H), 1.67 (m, 2H), 1.58 (m, 2H); MS m/z 404 (M+1).

h) N-Cyclopentyl-3-[2-(cyclopentylamino)-4-pyrimidinyl]-2-(3-methylphenyl)-pyrazolo[1,5-a]pyridin-7-amine To a solution of 4-[7-chloro-2-(3-methylphenyl)pyrazolo[1,5-a]pyridin-3-yl]-N-cyclopentyl-2-pyrimidinamine (500 mg, 1.24 mmol) in cyclopentylamine (50 mL) was added successively racemic-2,2'-bis(diphenylphosphino)-1,1'-binaphthyl (308 mg, 0.49 mmol), cesium carbonate (0.81 g, 2.47 mmol) and palladium (II) acetate (70 mg, 0.31 mmol). The resultant mixture was heated to 95° C. for 18 hours at which time the reaction was judged complete by thin layer chromatography. The solution was cooled to room temperature and ether was added. The organic layer was washed with water and brine. The aqueous layer was extracted with ether and the combined organics dried over magnesium sulfate. Filtration and concentration, followed by flash chromatography (4:1 hexanes:ethyl acetate) provided N-cyclopentyl-3-[2-(cyclopentylamino)-4-pyrimidinyl]-2-(3-methylphenyl)pyrazolo[1,5-a]pyridin-7-amine (360 mg, 64%) as a yellow foam. $^1$H NMR (CDCl$_3$) δ 7.94 (d, 1H), 7.79 (d, 1H), 7.46 (s, 1H), 7.40 (d, 1H), 7.34–7.29 (m, 2H), 7.24 (d, 1H), 6.27 (d, 1H), 6.03 (m, 2H), 5.12 (broad s, 1H), 4.35 (m, 1H), 3.99 (m, 1H), 2.40 (s, 3H), 2.14–2.04 (m, 4H), 1.81–1.52 (m, 12H); MS m/z 453 (M+1).

EXAMPLE 47

4-[7-Chloro-2-(3-methylphenyl)pyrazolo[1,5-a]pyridin-3-yl]-N-cyclopentyl-5,6-dimethyl-2-pyrimidinamine

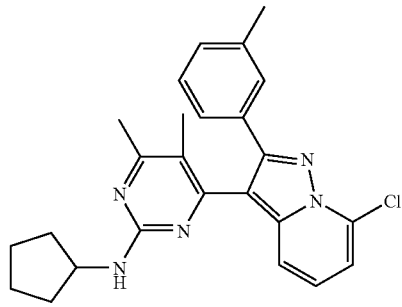

a) (2E)-1-[7-Chloro-2-(3-methylphenyl)pyrazolo[1,5-a]pyridin-3-yl]-2-methyl-2-buten-1-ol and (2Z)-1-[7-Chloro-2-(3-methylphenyl)pyrazolo[1,5-a]pyridin-3-yl]-2-methyl-2-buten-1-ol To a cold (−78 ° C.) solution of 7-chloro-2-(3-methylphenyl)pyrazolo[1,5-a]pyridine-3-carbaldehyde (592 mg, 2.19 mmol) in tetrahydrofuran (6 mL) was added 1-methyl-1-propenylmagnesium bromide (12 mL, 0.5 M in tetrahydrofuran, 6 mmol existing as a mixture of E and Z isomers). The reaction mixture was allowed to warm to −20 ° C., then poured into ice water. The aqueous mixture was extracted with ethyl acetate. The combined extracts were washed with water and brine. The organic layer was dried over magnesium sulfate. Filtration and concentration followed by flash chromatography (4:1 hexanes:ethyl acetate) provided an inseparable mixture of (2E)-1-[7-chloro-2-(3-methylphenyl)pyrazolo[1,5-a]pyridin-3-yl]-2-methyl-2-buten-1-ol and (2Z)-1-[7-chloro-2-(3-methylphenyl)pyrazolo[1,5-a]pyridin-3-yl]-2-methyl-2-buten-1-ol (650 mg, 91%) as a white gummy solid. $R_f$ 0.42 (4:1 hexanes:ethyl acetate); (for the major isomer) $^1$H NMR (CDCl$_3$) δ 7.97 (d, 1H), 7.45 (s, 1H), 7.41 (d, 1H), 7.31 (t, 1H), 7.20 (d, 1H), 7.07 (dd, 1H), 6.90 (d, 1H) 6.02 (s, 1H), 5.44 (q, 1H), 2.39 (s, 3H), 1.73 (m, 3H), 1.61 (m, 3H); MS m/z 327 (M+1).

b) (2E)-1-[7-Chloro-2-(3-methylphenyl)pyrazolo[1,5-a]pyridin-3-yl]-2-methyl-2-buten-1-one and (2Z)-1-[7-chloro-2-(3-methylphenyl)pyrazolo[1,5-a]pyridin-3-yl]-2-methyl-2-buten-1-one To a cold (0 ° C.) solution of a mixture of (2E)-1-[7-chloro-2-(3-methylphenyl)pyrazolo[1,5-a]pyridin-3-yl]-2-methyl-2-buten-1-ol and (2Z)-1-[7-chloro-2-(3-methylphenyl)pyrazolo[1,5-a]pyridin-3-yl]-2-methyl-2-buten-1-ol (640 mg, 1.96 mmol) in chloroform (70 mL) was added manganese dioxide (6.5 g, 75 mmol). The reaction mixture was warmed to room temperature and stirred 16 hours. Additional manganese dioxide (5.0 g, 57 mmol) was added and the resultant mixture was stirred at room temperature for 24 hours. The reaction mixture was filtered through a pad of Celite. The filtrate was concentrated in vacuo to provide an inseparable mixture of (2E)-1-[7-chloro-2-(3-methylphenyl)pyrazolo[1,5-a]pyridin-3-yl]-2-methyl-2-buten-1-one and (2Z)-1-[7-chloro-2-(3-methylphenyl)pyrazolo[1,5-a]pyridin-3-yl]-2-methyl-2-buten-1-one (635 mg, 100%) as a white solid. $R_f$ 0.45 (4:1 hexanes:ethyl acetate); (for the major isomer) $^1$H NMR (CDCl$_3$) δ 8.27 (d, 1H), 7.43–7.39 (m, 3H), 7.32–7.27 (m, 2H), 7.14 (d, 1H), 5.35 (q, 1H), 2.39 (s, 3H), 1.73 (m, 3H), 1.48 (m, 3H); MS m/z 325 (M+1).

c) 4-[7-Chloro-2-(3-methylphenyl)pyrazolo[1,5-a]pyridin-3-yl]-N-cyclopentyl-5,6-dimethyl-2-pyrimidinamine To a suspension of N-cyclopentylguanidine hydrochloride (261 mg, 1.60 mmol) in ethanol (2 mL) was added sodium ethoxide (530 μL, 3 M in ethanol, 1.6 mmol). The mixture was stirred at room temperature for 10 minutes. To this suspension was added a mixture of (2E)-1-[7-chloro-2-(3-methylphenyl)pyrazolo[1,5-a]pyridin-3-yl]-2-methyl-2-buten-1-one and (2Z)-1-[7-chloro-2-(3-methylphenyl)pyrazolo[1,5-a]pyridin-3-yl]-2-methyl-2-buten-1-one (200 mg, 0.616 mmol) portionwise. The reaction mixture was stirred at 70° C. for 16 hours then cooled to room temperature. Palladium on carbon (10%, 230 mg) was added and the reaction mixture was stirred at 60° C. for 24 hours. The reaction mixture was diluted with ethanol (15 mL) and filtered through Celite. The filtrate was concentrated in vacuo and chromatographed (39:1 dichloromethane:methanol) to provide 4-[7-chloro-2-(3-methylphenyl)pyrazolo[1,5-a]pyridin-3-yl]-N-cyclopentyl-5,6-dimethyl-2-pyrimidinamine (80 mg, 30%) as a light brown solid. $R_f$ 0.47 (29:1 dichloromethane:methanol); $^1$H NMR (CDCl$_3$) δ 7.60 (s, 1H), 7.55 (d, 1H), 7.32 (d, 1H), 7.21–7.11 (m, 3H), 6.96 (d, 1H), 4.99 (broad, 1H), 4.28 (m, 1H); 2.35 (s, 3H), 2.30 (s, 3H), 2.01 (m, 2H), 1.74–1.42 (9 H); MS m/z 432 (M+1).

EXAMPLE 48

N-cyclopentyl-3-[2-(cyclopentylamino)-5,6-dimethyl-4-pyrimidinyl]-2-(3-methylphenyl)pyrazolo[1,5-a]pyridin-7-amine

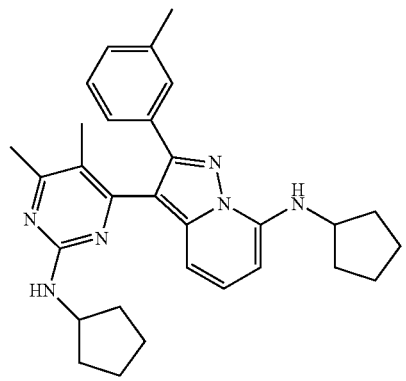

A mixture of 4-[7-chloro-2-(3-methylphenyl)pyrazolo[1,5-a]pyridin-3-yl]-N-cyclopentyl-5,6-dimethyl-2-pyrimidinamine (80 mg, 0.19 mmol) and cyclopentylamine (2 mL, 20 mmol) was heated in a sealed tube at 90° C. for 3 hours followed by 125° C. for 24 hours. The reaction mixture was cooled to room temperature and excess cyclopentylamine was removed in vacuo. The crude residue was washed with saturated aqueous sodium bicarbonate solution. The aqueous layer was extracted with ethyl acetate. The combined extracts were washed with water and brine then dried over magnesium sulfate. Filtration and concentration followed by flash chromatography (5:1 hexanes:ethyl acetate) provided N-cyclopentyl-3-[2-(cyclopentylamino)-5,6-dimethyl-4-pyrimidinyl]-2-(3-methylphenyl)pyrazolo[1,5-a]pyridin-7-amine (40 mg, 44%) as a clear oil. $R_f$ 0.32 (4:1 hexanes:ethyl acetate); $^1$H NMR (CDCl$_3$) δ 7.57 (s, 1H), 7.33 (d, 1H), 7.19–7.11 (m, 3H), 6.91 (d, 1H), 6.03 (d, 1H), 6.93 (d, 1H), 4.91 (d, 1H), 4.29 (m, 1H), 4.01 (m, 1H), 2.34 (s, 3H), 2.28 (s, 3H), 2.15 (m, 2H), 1.99 (broad, 2H), 1.87–1.40 (m, 15H); MS m/z 481 (M+1). To a solution of the product (20 mg) in ether was added 1 M HCl in ether. The precipitated solid was isolated to give the corresponding HCl salt.

EXAMPLE 49

3-[2-(Cyclopentylamino)-4-pyrimidinyl]-N-isopropyl-2-(3-methylphenyl)pyrazolo[1,5-a]pyridin-7-amine

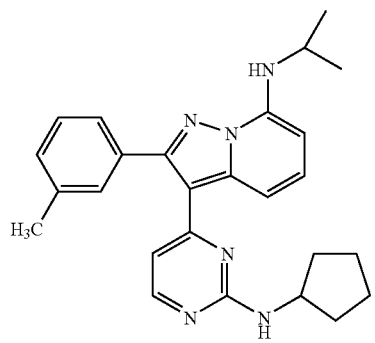

In a similar manner as described in Example 46 from 4-[7-chloro-2-(3-methylphenyl)pyrazolo[1,5-a]pyridin-3-yl]-N-cyclopentyl-2-pyrimidinamine (100 mg, 0.25 mmol) and isopropylamine was obtained 3-[2-(cyclopentylamino)-4-pyrimidinyl]-N-isopropyl-2-(3-methylphenyl)pyrazolo[1,5-a]pyridin-7-amine (36 mg, 34%) as a yellow foam. $^1$H NMR (CDCl$_3$) δ 7.97 (d, 1H), 7.79 (d, 1H), 7.47 (s, 1H), 7.41 (d, 1H), 7.34–7.23 (m, 3H), 6.28 (d, 1H), 6.00 (d, 1H), 5.98 (d, 1H), 5.14 (d, 1H), 4.35 (m, 1H), 3.85 (m, 1H), 2.40 (s, 3H), 2.07 (m, 2H), 1.75 (m, 2H), 1.66 (m, 2H), 1.56 (m, 2H), 1.36 (d, 6H); MS m/z 427 (M+1).

EXAMPLE 50

4-[7-Chloro-2-(3-methoxyphenyl)pyrazolo[1,5-a]pyridin-3-yl]-N-cyclopentyl-2-pyrimidinamine

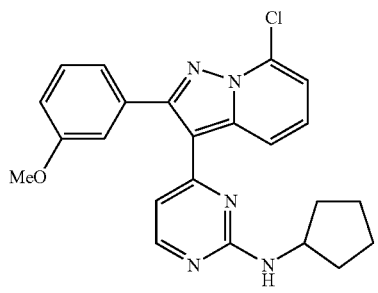

a) 2-(6-Chloro-2-pyridinyl)-1-(3-methoxyphenyl)ethanone

In a similar manner as described in Example 1 from ethyl 3-methoxybenzoate (30 g, 166 mmol) and 6-chloropicoline (21.2 g, 166 mmol) was obtained 2-(6-chloro-2-pyridinyl)-1-(3-methoxyphenyl)ethanone as a mixture of ketone and enol tautomers. This product was used directly in the next step.

b) 2-(6-Chloro-2-pyridinyl)-1-(3-methoxyphenyl)ethanone oxime

In a similar manner as described in Example 1 from 2-(6-chloro-2-pyridinyl)-1-(3-methoxyphenyl)ethanone was obtained 2-(6-chloro-2-pyridinyl)-1-(3-methoxyphenyl)ethanone oxime (33.1 g, yield for the two steps 72%) as a white solid. $^1$H NMR (CDCl$_3$) δ 8.22 (broad s, 1H), 7.52 (t, 1H), 7.34 (m, 1H), 7.26–7.25 (m, 2H), 7.17–7.05 (d, 2H), 6.90 (m, 1H), 4.36 (s, 2H), 3.81 (s, 3H); MS m/z 277.

c) 7-Chloro-2-(3-methoxyphenyl)pyrazolo[1,5-a]pyridine

In a similar manner as described in Example 1 from 2-(6-chloro-2-pyridinyl)-1-(3-methoxyphenyl)ethanone oxime (33.0 g, 119 mmol) was obtained 7-chloro-2-(3-methoxyphenyl)pyrazolo[1,5-a]pyridine (23.1 g, 75% yield) as a pale yellow solid. $^1$H NMR (CDCl$_3$) δ 7.59 (m, 2H), 7.49 (d, 1H), 7.37 (t, 1H), 7.07 (t, 1H), 6.95–6.94 (dd, 1H), 6.91 (s, 1H), 6.88 (d, 1H), 3.90 (s, 3H); MS m/z 259.

d) 7-Chloro-2-(3-methoxyphenyl)pyrazolo[1,5-a]pyridine-3-carbaldehyde

In a similar manner as described in Example 46 from 7-chloro-2-(3-methoxyphenyl)pyrazolo[1,5-a]pyridine (23 g, 88.9 mmol) was obtained 7-chloro-2-(3-methoxyphenyl)pyrazolo[1,5-a]pyridine-3-carbaldehyde (21.6 g. 84%) as a white solid. $^1$H NMR (CDCl$_3$) δ 10.13 (s, 1H), 8.40 (d, 1H), 7.52–7.42 (m, 2H), 7.35 (m, 2H), 7.21 (d, 1H), 7.06 (d, 1H), 3.89 (s, 3H); MS m/z 287.

e) 1-[7-Chloro-2-(3-methoxyphenyl)pyrazolo[1,5-a]pyridin-3-yl]-2-propyn-1-ol In a similar manner as described in Example 46 from 7-chloro-2-(3-methoxyphenyl)pyrazolo[1,5-a]pyridine-3-carbaldehyde (17.25 g, 60.1 mmol) and ethynylmagnesium bromide was obtained 1-[7-chloro-2-(3-methoxyphenyl)pyrazolo[1,5-a]pyridin-3-yl]-2-propyn-1-ol (19.0 g, 100%). $^1$H NMR (CDCl$_3$) δ 8.02 (d, 1H), 7.38–7.32 (m, 3H), 7.17 (t, 1H), 6.98–6.97 (d, 2H), 5.82 (m, 1H), 3.86 (s, 3H), 2.67 (s, 1H), 2.53 (d, 1H); MS m/z 313.

f) 1-[7-Chloro-2-(3-methoxyphenyl)pyrazolo[1,5-a]pyridin-3-yl]-2-propyn-1-one In a similar manner as described in Example 46 from 1-[7-chloro-2-(3-methoxyphenyl)pyrazolo[1,5-a]pyridin-3-yl]-2-propyn-1-ol (19 g, 60.8 mmol) was obtained 1-[7-chloro-2-(3-methoxyphenyl)pyrazolo[1,5-a]pyridin-3-yl]-2-propyn-1-one (14.4 g, yield 76%) as an orange colored solid. $^1$H NMR (CDCl$_3$) δ 8.47 (d, 1H), 7.52 (t, 1H), 7.36 (t, 1H), 7.29–7.21 (m, 3H), 7.02 (dd, 1H), 3.86 (s, 3H), 2.92 (s, 1H); MS m/z 311.

g) 4-[7-Chloro-2-(3-methoxyphenyl)pyrazolo[1,5-a]pyridin-3-yl]-N-cyclopentyl-2-pyrimidinamine In a similar manner as described in Example 46 from 1-[7-chloro-2-(3-methoxyphenyl)pyrazolo[1,5-a]pyridin-3-yl]-2-propyn-1-one (1.0 g, 3.2 mmol) and cyclopentyl guanidine hydrochloride was obtained 4-[7-chloro-2-(3-methoxyphenyl)pyrazolo[1,5-a]pyridin-3-yl]-N-cyclopentyl-2-pyrimidinamine (0.34 g, yield 25%) as a pale yellow foam. $^1$H NMR (CDCl$_3$) δ 8.52 (d, 1H), 8.05 (d, 1H), 7.43–7.23 (m, 4H), 7.11 (d, 1H), 7.03 (dd, 1H), 6.40 (d, 1H), 5.45 (broad s, 1H), 4.40 (m, 1H), 3.86 (s. 3H), 2.10 (m, 2H), 1.85–1.59 (m, 6H); MS m/z 420.

EXAMPLE 51

N-Cyclopentyl-3-[2-(cyclopentylamino)-4-pyrimidinyl]-2-(3-methoxyphenyl)pyrazolo[1,5-a]pyridin-7-amine

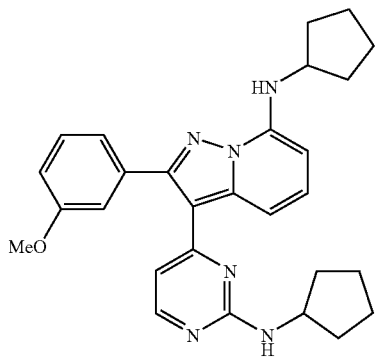

In a similar manner as described in Example 1 from 4-[7-chloro-2-(3-methoxyphenyl)pyrazolo[1,5-a]pyridin-3-yl]-N-cyclopentyl-2-pyrimidinamine (500 mg, 1.19 mmol) and cyclopentylamine was obtained N-cyclopentyl-3-[2-(cyclopentylamino)-4-pyrimidinyl]-2-(3-methoxyphenyl)pyrazolo[1,5-a]pyridin-7-amine (389 mg, yield 70%) as a yellow foam. $^1$H NMR (CDCl$_3$) δ 7.92 (d, 1H), 7.79 (d, 1H), 7.38–7.30 (m, 2H), 7.21–7.18 (m, 2H), 6.99 (d, 1H), 6.30 (d, 1H), 6.04 (m, 2H), 5.38 (broad s, 1H), 4.36 (m, 1H), 4.00 (m, 1H), 3.82 (s, 3H), 2.14–2.06 (m, 4H), 1.82–1.57 (m, 12H); MS m/z 469.

EXAMPLE 52

3-[2-(Cyclopentylamino)-4-pyrimidinyl]-N-isopropyl-2-(3-methoxyphenyl)pyrazolo[1,5-a]pyridin-7-amine

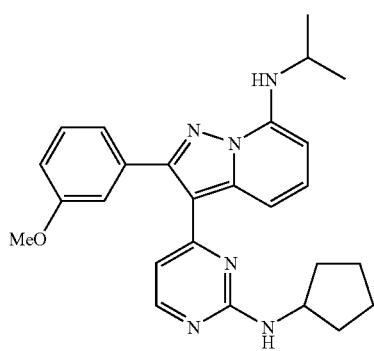

In a similar manner as described in Example 1 from 4-[7-chloro-2-(3-methoxyphenyl)pyrazolo[1,5-a]pyridin-3-yl]-N-cyclopentyl-2-pyrimidinamine (150 mg, 0.36 mmol) and isopropylamine was obtained 3-[2-(cyclopentylamino)-4-pyrimidinyl]-N-isopropyl-2-(3-methoxyphenyl)pyrazolo[1,5-a]pyridin-7-amine (98 mg, yield 62%) as a yellow foam. $^1$H NMR (CDCl$_3$) δ 7.93 (s,1H), 7.78 (d, 1H), 7.38–7.31 (m, 2H), 7.22–7.18 (m, 2H), 6.99 (d, 1H), 6.30 (d, 1H), 6.03 (d, 1H), 5.96 (d, 1H), 5.30 (broad s, 1H), 4.36 (m, 1H), 3.85 (m, 1H), 3.82 (s, 3H), 2.10–2.06 (m, 2H), 1.76–1.53 (m, 6H), 1.37 (d, 6H); MS m/z 443.

EXAMPLE 53

3-[2-(Cyclopentylamino)-4-pyrimidinyl]-2-(3-methoxyphenyl)-N,N-dimethylpyrazolo[1,5-a]pyridin-7-amine

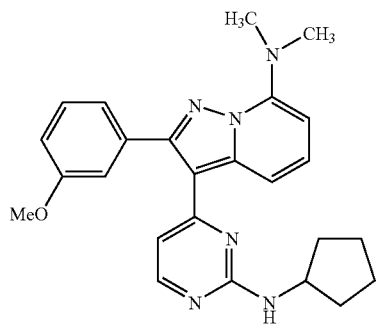

To a solution of 4-[7-chloro-2-(3-methoxyphenyl)pyrazolo[1,5-a]pyridin-3-yl]-N-cyclopentyl-2-pyrimidinamine (60 mg, 0.14 mmol) in N,N-dimethylformamide (10 mL) was added dimethylamine (7 mL 40% in water). The solution was heated in a steal bomb at 100° C. for 3 days. The bomb was cooled to room temperature and ethyl acetate was added to the reaction mixture. The organics were washed with water, brine and dried over magnesium sulfate. Filtration and concentration followed by purification with flash chromatography (95:5-dichloromethane: methanol) gave 3-[2-(cyclopentylamino)-4-pyrimidinyl]-2-(3-methoxyphenyl)-N,N-dimethylpyrazolo[1,5-a]pyridin-7-amine (43 mg, 70%) as a yellow foam. $^1$H NMR (CDCl$_3$) δ 8.11 (d, 1H), 7.95 (s, 1H), 7.35–7.30 (m, 2H), 7.24–7.21 (m, 2H), 6.97 (dd, 1H), 6.36 (d, 1H), 6.32 (d, 1H), 5.40 (broad s, 1H), 4.37 (m, 1H), 3.80 (s, 3H), 3.12 (s, 6H), 2.11–2.06 (m, 2H), 1.77–1.56 (m, 6H); MS m/z 429.

EXAMPLE 54

3-{7-(Cyclopentylamino)-3-[2-(cyclopentylamino)-4-pyrimidinyl]pyrazolo[1,5-a]pyridin-2-yl}phenol

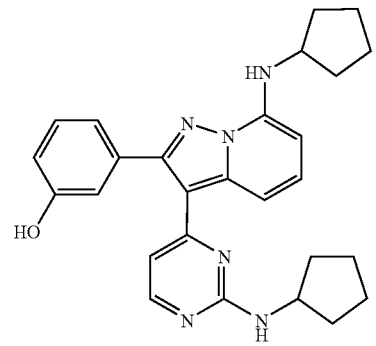

In a similar manner as described in Example 4 from N-cyclopentyl-3-[2-(cyclopentylamino)-4-pyrimidinyl]-2-(3-methoxyphenyl)pyrazolo[1,5-a]pyridin-7-amine (150 mg, 0.32 mmol) was obtained 3-{7-(cyclopentylamino)-3-[2-(cyclopentylamino)-4-pyrimidinyl]pyrazolo[1,5-a]pyridin-2-yl}phenol (126 mg, yield 87%) as a yellow foam. ¹H NMR (CDCl₃) δ 7.83 (d, 1H), 7.77 (d, 1H), 7.35–7.28 (m, 2H), 7.21 (d, 1H), 7.06 (s, 1H), 6.95 (dd, 1H), 6.39 (d, 1H), 6.05–6.02 (m, 2H), 5.29 (s, 1H), 5.22 (m, 1H), 4.31 (m, 1H), 3.99 (m, 1H), 2.12–1.98 (m, 4H), 1.80–1.46 (m, 12H); MS m/z 455.

EXAMPLE 55

N-Cyclopentyl-3-[2-(cyclopentylamino)-4-pyrimidinyl]-2-[3-(cyclopropylmethoxy)phenyl]pyrazolo[1,5-a]pyridin-7-amine

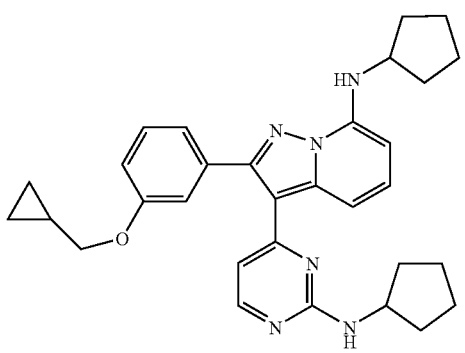

To a solution of 3-{7-(cyclopentylamino)-3-[2-(cyclopentylamino)-4-pyrimidinyl]pyrazolo[1,5-a]pyridin-2-yl}phenol (400 mg, 0.88 mmol) in acetonitrile (80 mL) was added cesium carbonate (315 mg, 0.97 mmol) and (bromomethyl)-cyclopropane (0.26 mL, 2.64 mmol). The reaction mixture was heated at reflux for 6 hours. After the reaction was cooled to room temperature, ethyl acetate was added and the organic phase was washed with water, brine and dried over magnesium sulfate. Filtration and concentration followed by purification with silica gel chromatography (3:2 hexanes/ethyl acetate) gave N-cyclopentyl-3-[2-(cyclopentylamino)-4-pyrimidinyl]-2-[3-(cyclopropylmethoxy)phenyl]pyrazolo[1,5-a]pyridin-7-amine (320 mg, 71%) as yellow solid. ¹H NMR (CDCl₃): δ 7.97 (d, 1H), 7.78 (d, 1H), 7.33 (m, 2H), 7.18 (m, 2H), 6.98 (m, 1H), 6.30 (d, 1H), 6.02 (m, 2H), 5.08 (d, 1), 4.35 (m, 1H), 3.99 (m, 1H), 3.80 (d, 2H), 2.014 (m, 4H), 1.83–1.55 (m, 12H), 1.22 (m, 1H), 0.61 (m, 2H), 0.35 (m, 2H). MS m/z 509 (M+1).

EXAMPLE 56

N-Cyclopentyl-3-[2-(cyclopentylamino)-4-pyrimidinyl]-2-(3-fluorophenyl)pyrazolo[1,5-a]pyridin-7-amine

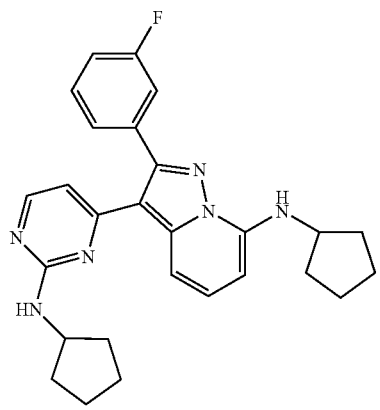

In a similar manner as described for above examples the title compound was prepared as a yellow solid. $R_f$ 0.43 (99:1 dichloromethane:methanol); ¹H NMR (CDCl₃): δ 8.06 (d, 1H), 7.76 (d, 1H), 7.47–7.30 (m, 4H), 7.17 (m, 1H), 6.35 (d, 1H), 6.10–6.04 (m, 2H), 5.15 (d, 1H), 4.36 (m, 1H), 4.05 (m, 1H), 2.21–2.07 (m, 4H), 1.88–1.54 (m, 12H), MS m/z 457 (M+1).

EXAMPLE 57

2-(3-Chlorophenyl)-N-cyclopentyl-3-[2-(cyclopentylamino)-4-pyrimidinyl]pyrazolo[1,5-a]pyridin-7-amine

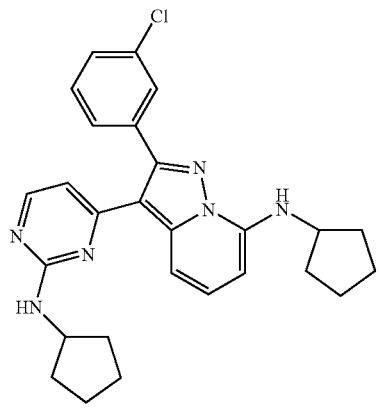

In a similar manner as described for above examples the title compound was prepared as a yellow solid. $R_f$ 0.48 (49:1 dichloromethane:methanol); ¹H NMR (DMSO-d₆) δ 8.02 (d, 1H), 7.73–7.67 (br, 2H), 7.56–7.44 (m, 2H), 7.36 (t, 1H), 7.01 (d, 1H), 6.61 (d, 1H), 6.22–6.17 (m, 2H), 4.09 (br, 1H), 3.98 (m, 1H), 2.04 (m, 2H), 1.84 (m, 2H), 1.72–1.48 (m, 12H); MS m/z 473 (M+1). Anal. Calcd for $C_{27}H_{29}ClN_6$: C, 68.56; H, 6.18; N, 17.77. Found: C, 68.55; H, 6.20; N, 17.64.

EXAMPLE 58

N-Cyclopentyl-3-[2-(cyclopropylamino)-4-pyrimidinyl]-2-(4-methoxyphenyl)pyrazolo[1,5-a]pyridin-7-amine

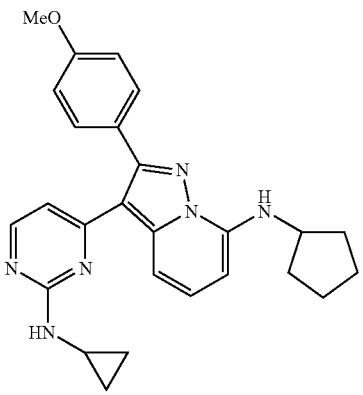

In a similar manner as described in Example 1 from (2E)-1-[7-(cyclopentylamino)-2-(4-methoxyphenyl)pyrazolo[1,5-a]pyridin-3-yl]-3-(dimethylamino)-2-propen-1-one (0.25 g, 0.62 mmol) and N-cyclopropylguanidine sulfate was obtained N-cyclopentyl-3-[2-(cyclopropylamino)-4-pyrimidinyl]-2-(4-methoxyphenyl)pyrazolo[1,5-a]pyridin-7-amine (0.11 g, 41%) as a light yellow solid. $^1$H NMR (CDCl$_3$): δ 7.95 (m, 2 H), 7.57 (d, 2 H), 7.31 (t, 1 H), 6.90 (d, 2 H), 6.37 (d, 1 H), 6.04 (m, 2H), 4.00 (m, 1 H), 3.87 (s, 3 H), 2.87 (m, 1 H), 2.12 (m, 2 H), 1.82–1.55 (m, 6 H), 0.87 (m, 2 H), 0.64 (m, 2 H); MS m/z 441 (M+1).

EXAMPLE 59

3-[2-(Cyclopentylamino)-4-pyrimidinyl]-2-(4-methoxyphenyl)-N-[2-(4-morpholinyl)ethyl]pyrazolo[1,5-a]pyridin-7-amine

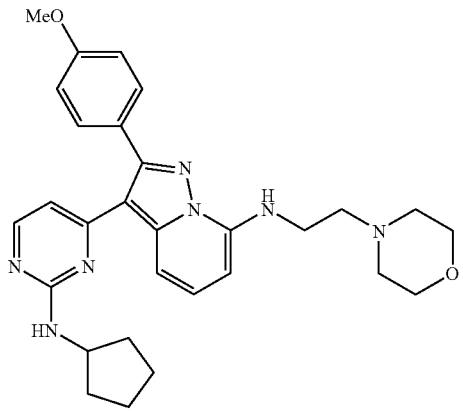

a) 7-Chloro-2-(4-methoxyphenyl)pyrazolo[1,5-a]pyridine-3-carbaldehyde

In a similar manner as described in Example 46 from 7-chloro-2-(4-methoxyphenyl)pyrazolo[1,5-a]pyridine (5.0 g, 19.3 mmol) was obtained 7-chloro-2-(4-methoxyphenyl)pyrazolo[1,5-a]pyridine-3-carbaldehyde (5.11 g, 92%) as a pale yellow crystalline solid. $^1$H NMR (CDCl$_3$): δ 10.14 (s, 1 H), 8.40 (d, 1 H), 7.78 (d, 2 H), 7.50 (t, 1 H), 7.21 (d, 1 H), 7.08 (d, 2 H), 3.91 (s, 3 H); MS m/z 287 (M+1).

b) 1-[7-Chloro-2-(4-methoxyphenyl)pyrazolo[1,5-a]pyridin-3-yl]-2-propyn-1-ol

In a similar manner as described in Example 46 from 7-chloro-2-(4-methoxyphenyl)pyrazolo[1,5-a]pyridine-3-carbaldehyde (5.11 g, 17.8 mmol) and ethynylmagnesium bromide (89 mL, 0.5 M in tetrahydrofuran, 44.6 mmol) at 0° C. was obtained 1-[7-chloro-2-(4-methoxyphenyl)pyrazolo[1,5-a]pyridin-3-yl]-2-propyn-1-ol (5.22 g, 94%) as an off-white solid. $^1$H NMR (CDCl$_3$): δ 8.02 (d, 1 H), 7.73 (d, 2 H), 7.18 (t, 1 H), 7.02 (d, 2 H), 6.97 (d, 1 H), 5.79 (m, 1 H), 3.87 (s, 3 H), 2.68 (m, 1 H), 2.25 (d, 1H).

c) 1-[7-Chloro-2-(4-methoxyphenyl)pyrazolo[1,5-a]pyridin-3-yl]-2-propyn-1-one

In a similar manner as described in Example 46 from 1-[7-chloro-2-(4-methoxyphenyl)pyrazolo[1,5-a]pyridin-3-yl]-2-propyn-1-ol (5.22 g, 16.7 mmol) and manganese dioxide (58.0 g, 668 mmol) in dichloromethane (250 mL) was obtained 1-[7-chloro-2-(4-methoxyphenyl)pyrazolo[1,5-a]pyridin-3-yl]-2-propyn-1-one (3.46 g, 67%) as a gold solid. $^1$H NMR (CDCl$_3$): δ 8.47 (d, 1 H), 7.67 (d, 2 H), 7.50 (t, 1 H), 7.20 (d, 1 H), 6.98 (d, 2 H), 3.87 (s, 3 H), 2.97 (s, 1 H); MS m/z 333 (M+1).

d) 4-[7-Chloro-2-(4-methoxyphenyl)pyrazolo[1,5-a]pyridin-3-yl]-N-cyclopentyl-2-pyrimidinamine To a mixture of 1-[7-chloro-2-(4-methoxyphenyl)pyrazolo[1,5-a]pyridin-3-yl]-2-propyn-1-one (1.57 g, 5.0 mmol) and N-cyclopentylguanidine hydrochloride (1.07 g, 6.6 mmol) in ethanol (50 mL) was added sodium ethoxide (2.5 mL, 21 wt % in ethanol, 6.6 mmol). The resulting suspension was stirred overnight at room temperature, then diluted with water and extracted with ethyl acetate. The organic extracts were washed with brine and dried over magnesium sulfate. Filtration and concentration followed by flash chromatography (7:3 to 3:2 hexanes-ethyl acetate) provided 4-[7-chloro-2-(4-methoxyphenyl)pyrazolo[1,5-a]pyridin-3-yl]-N-cyclopentyl-2-pyrimidinamine (1.77 g, 83%) as a pale yellow solid. $^1$H NMR (CDCl$_3$): δ 8.44 (d, 1 H), 8.05 (d, 1 H), 7.60 (d, 2 H), 7.28 (m, 1 H), 7.06–6.96 (m, 3 H), 6.38 (d, 1 H), 5.31 (broad, 1 H), 4.38 (m, 1 H), 3.88 (s, 3 H), 2.12 (m, 2 H), 1.84–1.53 (m, 6 H); MS m/z 420 (M+1).

e) 3-[2-(Cyclopentylamino)-4-pyrimidinyl]-2-(4-methoxyphenyl)-N-[2-(4-morpholinyl)ethyl]pyrazolo[1,5-a]pyridin-7-amine A mixture of 4-[7-chloro-2-(4-methoxyphenyl)pyrazolo[1,5-a]pyridin-3-yl]-N-cyclopentyl-2-pyrimidinamine (150 mg, 0.36 mmol) and 4-(2-aminoethyl)morpholine (3 mL, 21.2 mmol) was heated at 140° C. for 4 hours. Concentration of the reaction mixture followed by flash chromatography (3:1 ethyl acetate-hexane to ethyl acetate) provided 3-[2-(cyclopentylamino)-4-pyrimidinyl]-2-(4-methoxyphenyl)-N-[2-(4-morpholinyl)ethyl]pyrazolo[1,5-a]pyridin-7-amine (135 mg, 74%) as a pale yellow foam. $^1$H NMR (CDCl$_3$): δ 8.01 (d, 1 H), 7.78 (d, 1 H), 7.61 (d, 2 H), 7.30 (t, 1 H), 6.99 (d, 2 H), 6.52 (t, 1 H), 6.36 (d, 1 H), 5.98 (d, 1 H), 5.08 (d, 1 H), 4.37 (m, 1 H), 3.88 (s, 3 H), 3.76 (m, 4 H), 3.46 (q, 2 H), 2.76 (t, 2 H), 2.54 (m, 4 H), 2.12–1.52 (m, 8 H); MS m/z 514 (M+1).

EXAMPLE 60

3-[2-(Cyclopentylamino)-4-pyrimidinyl]-N-cyclopropyl-2-(4-methoxyphenyl)pyrazolo[1,5-a]pyridin-7-amine

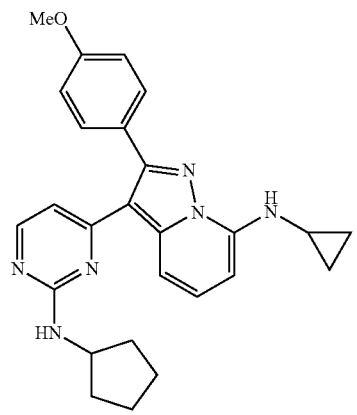

To a solution of 4-[7-chloro-2-(4-methoxyphenyl)pyrazolo[1,5-a]pyridin-3-yl]-N-cyclopentyl-2-pyrimidinamine (0.39 g, 0.93 mmol) in toluene (20 mL) was added successively racemic-BINAP (34.7 mg, 0.06 mmol), cesium carbonate (0.91 g, 2.8 mmol), cyclopropylamine (0.64 mL, 9.3 mmol) and palladium (II) acetate (8.3 mg, 0.04 mmol). The resultant mixture was heated under reflux for 8 hours. After cooling to room temperature the reaction mixture was partitioned between ether and water. The organic layer was washed with brine and dried over magnesium sulfate. Filtration and concentration followed by flash chromatography (3:1 hexanes-ethyl acetate) provided 3-[2-(cyclopentylamino)-4-pyrimidinyl]-N-cyclopropyl-2-(4-methoxyphenyl)pyrazolo-[1,5-a]pyridin-7-amine (0.30 g, 73%) as a pale yellow solid. $^1$H NMR (CDCl$_3$): δ 7.95 (d, 1 H), 7.85 (d, 1 H), 7.56 (d, 2 H), 7.36 (t, 1 H), 6.99 (d, 2 H), 6.40 (d, 1 H), 6.33 (m, 2 H), 4.38 (m, 1 H), 3.88 (s, 3 H), 2.68 (m, 1 H), 2.09 (m, 2H), 1.81–1.57 (m, 6 H), 0.89 (m, 2 H), 0.75 (m, 2 H); MS m/z 441 (M+1).

EXAMPLE 61

N-Cyclopentyl-4-[2-(4-methoxyphenyl)-7-(4-morpholinyl)pyrazolo[1,5-a]pyridin-3-yl]-2-pyrimidinamine

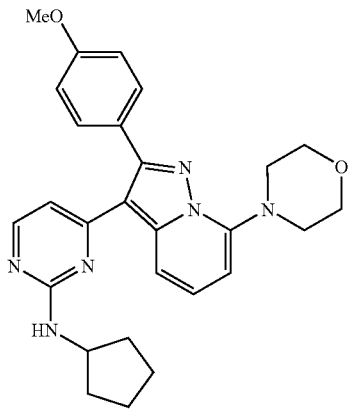

A mixture of 4-[7-chloro-2-(4-methoxyphenyl)pyrazolo[1,5-a]pyridin-3-yl]-N-cyclopentyl-2-pyrimidinamine (75 mg, 0.18 mmol) and morpholine (5 mL, 57 mmol) was heated at 120° C. for 4 hours, then cooled and concentrated. Flash chromatography (3:1 to 1:3 hexanes-ethyl acetate) afforded N-cyclopentyl-4-[2-(4-methoxyphenyl)-7-(4-morpholinyl)pyrazolo[1,5-a]pyridin-3-yl]-2-pyrimidinamine (72 mg, 86%) as a yellow solid. $^1$H NMR (CDCl$_3$): δ 8.14 (d, 1 H), 7.93 (broad, 1 H), 7.58 (d, 2 H), 7.33 (t, 1 H), 6.97 (d, 2 H), 6.35 (m, 2 H), 4.38 (m, 1 H), 3.99 (m, 4 H), 3.87 (s, 3 H), 3.50 (m, 4 H), 2.08 (m, 2 H), 1.79–1.54 (m, 6 H); MS m/z 471 (M+1).

EXAMPLE 62

3-[2-(Cyclopentylamino)-4-pyrimidinyl]-N-(2-methoxyethyl)-2-(4-methoxyphenyl)pyrazolo[1,5-a]pyridin-7-amine

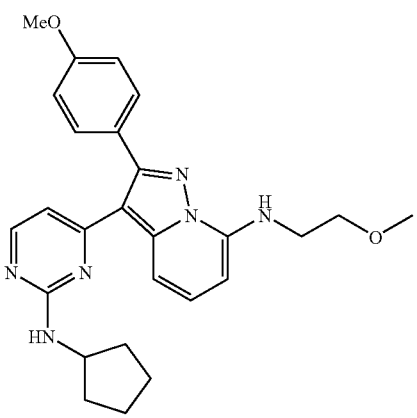

A mixture of 4-[7-chloro-2-(4-methoxyphenyl)pyrazolo[1,5-a]pyridin-3-yl]-N-cyclopentyl-2-pyrimidinamine (75 mg, 0.18 mmol) and 2-methoxyethylamine (5 mL, 58 mmol) was heated at 90° C. for 72 hours, then cooled and concentrated. Flash chromatography (1:1 to 1:3 hexanes-ethyl acetate) provided 3-[2-(cyclopentylamino)-4-pyrimidinyl]-N-(2-methoxyethyl)-2-(4-methoxyphenyl)pyrazolo[1,5-a]pyridin-7-amine (80.4 mg, 98%) as an off-white solid. $^1$H NMR (CDCl$_3$): δ 7.98 (d, 1 H), 7.81 (d, 1 H), 7.59 (d, 2 H), 7.31 (t, 1 H), 6.99 (d, 2 H), 6.35–6.29 (m, 2 H), 6.03 (d, 1 H), 5.15 (broad, 1 H), 4.38 (m, 1 H), 3.89 (s, 3 H), 3.72 (t, 2 H), 3.57 (q, 2 H), 3.43 (s, 3 H), 2.09 (m, 2 H), 1.80–1.53 (m, 6 H); MS m/z 459 (M+1).

EXAMPLE 63

N-Cyclopropyl-4-[2-(4-methoxyphenyl)-7-(4-morpholinyl)pyrazolo[1,5-a]pyridin-3-yl]-2-pyrimidinamine

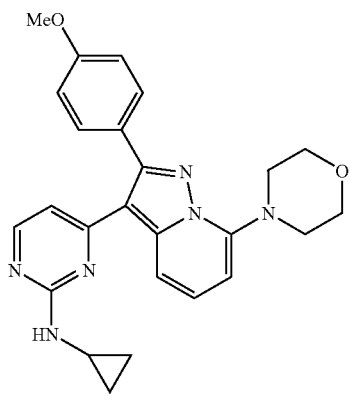

a) 4-[7-Chloro-2-(4-methoxyphenyl)pyrazolo[1,5-a]pyridin-3-yl]-N-cyclopropyl-2-pyrimidinamine In a similar manner as described in examples above from 1-[7-chloro-2-(4-methoxyphenyl)pyrazolo[1,5-a]pyridin-3-yl]-2-propyn-1-one (1.80 g, 5.8 mmol) and N-cyclopropylguanidine sulfate (1.50 g, 7.5 mmol) was prepared 4-[7-chloro-2-(4-methoxyphenyl)pyrazolo[1,5-a]pyridin-3-yl]-N-cyclopropyl-2-pyrimidinamine (1.31 g, 58%) as a yellow solid. $^1$H NMR (CDCl$_3$): δ 8.61 (broad, 1 H), 8.09 (broad, 1 H), 7.59 (d, 2 H), 7.28–7.23 (m, 1 H), 7.03 (d, 1 H), 6.98 (d, 2 H), 6.43 (d, 1 H), 5.41 (broad, 1 H), 3.87 (s, 3 H), 2.86 (m, 1 H), 0.88 (m, 2 H), 0.65 (m, 2 H); MS m/z 392 (M+1).

b) N-Cyclopropyl-4-[2-(4-methoxyphenyl)-7-(4-morpholinyl)pyrazolo[1,5-a]pyridin-3-yl]-2-pyrimidinamine A mixture of 4-[7-chloro-2-(4-methoxyphenyl)pyrazolo[1,5-a]pyridin-3-yl]-N-cyclopropyl-2-pyrimidinamine (75 mg, 0.19 mmol) and morpholine (2 mL, 23 mmol) was heated in a sealed tube at 140° C. for 4 hours. After cooling to room temperature, the mixture was concentrated. Flash chromatography (1:1 to 1:3 hexanes-ethyl acetate) provided N-cyclopropyl-4-[2-(4-methoxyphenyl)-7-(4-morpholinyl)pyrazolo[1,5-a]pyridin-3-yl]-2-pyrimidinamine (78.4 mg, 92%) as an off-white solid. $^1$H NMR (CDCl$_3$): δ 8.29 (d, 1 H), 8.08 (d, 1 H), 7.61 (d, 2 H), 7.31 (t, 1 H), 6.98 (d, 2 H), 6.45 (d, 1 H), 6.33 (d, 1 H), 5.40 (broad, 1 H), 4.00 (m, 4 H), 3.89 (d, 3 H), 3.51 (m, 4 H), 2.88 (m, 1 H), 0.89 (m, 2 H), 0.65 (m, 2 H); MS m/z 443 (M+1).

EXAMPLE 64

3-[2-(Cyclopropylamino)-4-pyrimidinyl]-N-(2-methoxyethyl)-2-(4-methoxyphenyl)pyrazolo[1,5-a]pyridin-7-amine

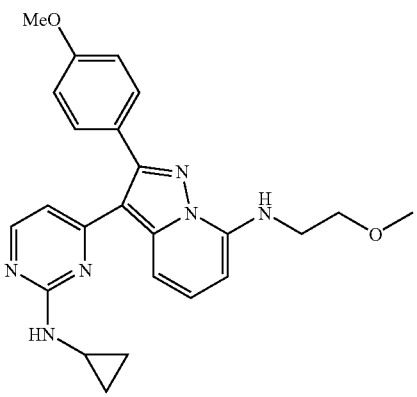

A mixture of 4-[7-chloro-2-(4-methoxyphenyl)pyrazolo[1,5-a]pyridin-3-yl]-N-cyclopropyl-2-pyrimidinamine (75 mg, 0.19 mmol) and 2-methoxyethylamine (5 mL, 58 mmol) was heated in a sealed tube at 140° C. for 24 hours. After cooling to room temperature, the mixture was concentrated. Flash chromatography (1:1 to 1:3 hexanes-ethyl acetate) provided 3-[2-(cyclopropylamino)-4-pyrimidinyl]-N-(2-methoxyethyl)-2-(4-methoxyphenyl)pyrazolo[1,5-a]pyridin-7-amine (77.7 mg, 95%) as a yellow solid. $^1$H NMR (CDCl$_3$): δ 8.03 (d, 1 H), 7.96 (d, 1 H), 7.60 (d, 2 H), 7.31 (t, 1 H), 7.00 (d, 2 H), 6.41 (d, 1 H), 6.31 (t, 1 H), 6.04 (d, 1 H), 5.40 (broad, 1 H), 3.89 (s, 3 H), 3.72 (t, 2 H), 3.57 (q, 2 H), 3.43 (s, 3 H), 2.88 (m, 1 H), 0.88 (m, 2 H), 0.64 (m, 2 H); MS m/z 431 (M+1).

EXAMPLE 65

3-[2-(Cyclopropylamino)-4-pyrimidinyl]-2-(4-methoxyphenyl)-N-[2-(4-morpholinyl)ethyl]pyrazolo[1,5-a]pyridin-7-amine

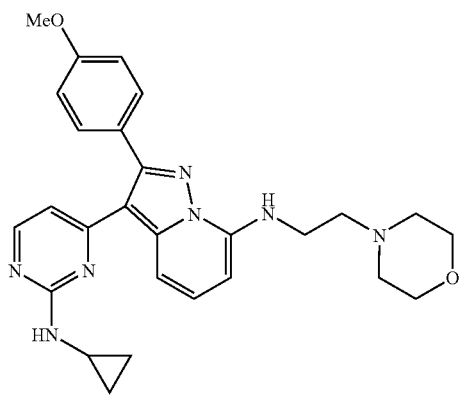

In a similar manner as described in Example 64 from 4-[7-chloro-2-(4-methoxyphenyl)pyrazolo[1,5-a]pyridin-3-yl]-N-cyclopropyl-2-pyrimidinamine (75 mg, 0.19 mmol) was prepared 3-[2-(cyclopropylamino)-4-pyrimidinyl]-2-(4- methoxyphenyl)-N-[2-(4-morpholinyl)ethyl]pyrazolo[1,5-a]pyridin-7-amine (74.5 mg, 80%) as a light yellow foam. ¹H NMR (CDCl₃): δ 8.05 (d, 1 H), 7.93 (d, 1 H), 7.61 (d, 2 H), 7.31 (t, 1 H), 7.00 (d, 2 H), 6.52 (t, 1 H), 6.42 (d, 1 H), 6.00 (d, 1 H), 5.32 (broad, 1 H), 3.89 (s,3 H), 3.76 (m, 4 H), 3.46 (q, 2 H), 2.88 (m, 1 H), 2.77 (t, 2 H), 2.55 (m, 4 H), 0.88 (m, 2 H), 0.64 (m, 2 H); MS m/z 486 (M+1).

EXAMPLE 66

N-Cyclopropyl-3-[2-(cyclopropylamino)-4-pyrimidinyl]-2-(4-methoxyphenyl)pyrazolo[1,5-a]pyridin-7-amine

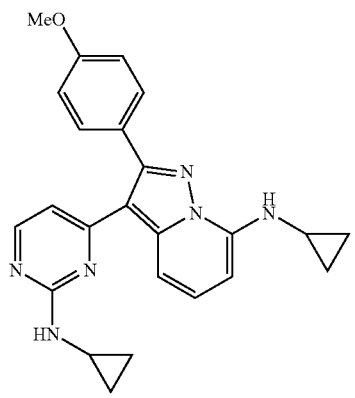

a) 1-[7-(Cyclopropylamino)-2-(4-methoxyphenyl)pyrazolo[1,5-a]pyridin-3-yl]ethanone In a similar manner as described in Example 1 from 1-[7-chloro-2-(4-methoxyphenyl)pyrazolo[1,5-a]pyridin-3-yl]ethanone (1.15 g, 3.8 mmol) was prepared 1-[7-(cyclopropylamino)-2-(4-methoxyphenyl)pyrazolo[1,5-a]pyridin-3-yl]ethanone (1.22 g, 99%) as a thick yellow oil. ¹H NMR (CDCl₃): δ 7.77 (d, 1 H), 7.53–7.45 (m, 3 H), 7.03 (d, 2 H), 6.50 (d, 1 H), 6.37 (broad, 1 H), 3.89 (s, 3 H), 2.67 (m, 1 H), 2.15 (s, 3 H), 0.89 (m, 2 H), 0.74 (m, 2 H); MS m/z 322 (M+1).

b) (2E)-1-[7-(Cyclopropylamino)-2-(4-methoxyphenyl)pyrazolo[1,5-a]pyridin-3-yl]-3-(dimethylamino)-2-propen-1-one A solution of 1-[7-(cyclopropylamino)-2-(4-methoxyphenyl)pyrazolo[1,5-a]pyridin-3-yl]ethanone (1.22 g, 3.8 mmol) in N,N-dimethylformamide di-tert-butyl acetal (8 mL, 33 mmol) was heated under reflux for 4 hours. After cooling to room temperature, the reaction mixture was diluted with water and extracted with ethyl acetate. The organics were washed with water and brine, then dried over magnesium sulfate. Filtration and concentration followed by flash chromatography (1:1 hexanes-ethyl acetate to ethyl acetate) provided (2E)-1-[7-(cyclopropylamino)-2-(4-methoxyphenyl)pyrazolo[1,5-a]pyridin-3-yl]-3-(dimethylamino)-2-propen-1-one (1.19 g, 83%) as a gold foam. ¹H NMR (CDCl₃): δ 7.73 (d, 1 H), 7.62 (d, 2 H), 7.34 (t, 1 H), 6.97 (d, 2 H), 6.37 (d, 1 H), 6.29 (s, 1 H), 5.13 (d, 1 H), 3.85 (s, 3 H), 2.95 (broad, 3 H), 2.65 (m, 1 H), 2.50 (broad, 3 H), 0.86 (m, 2 H), 0.72 (m, 2 H); MS m/z 377 (M+1).

c) N-Cyclopropyl-3-[2-(cyclopropylamino)-4-pyrimidinyl]-2-(4-methoxyphenyl)pyrazolo[1,5-a]pyridin-7-amine In a similar manner as described in Example 1 from (2E)-1-[7-(cyclopropylamino)-2-(4-methoxyphenyl)pyrazolo[1,5-a]pyridin-3-yl]-3-(dimethylamino)-2-propen-1-one (1.19 g, 3.2 mmol) and N-cyclopropylguanidine sulfate (1.25 g, 6.3 mmol) was prepared N-cyclopropyl-3-[2-(cyclopropylamino)-4-pyrimidinyl]-2-(4-methoxyphenyl)pyrazolo[1,5-a]pyridin-7-amine (0.71 g, 55%) as a light yellow foam. ¹H NMR (CDCl₃): δ 8.04 (d, 1 H), 7.99 (d, 1 H), 7.57 (d, 2 H), 7.34 (t, 1 H), 6.99 (d, 2 H), 6.39 (m, 2 H), 6.33 (s, 1 H), 5.31 (s, 1 H), 3.89 (s, 3 H), 2.88 (m, 1 H), 2.68 (m, 1 H), 0.88 (m, 4 H), 0.75 (m, 2 H), 0.64 (m, 2 H); MS m/z 413 (M+1).

EXAMPLE 67

4-[3-[2-(Cyclopentylamino)-4-pyrimidinyl]-7-(cyclopropylamino)pyrazolo[1,5-a]pyridin-2-yl]phenol

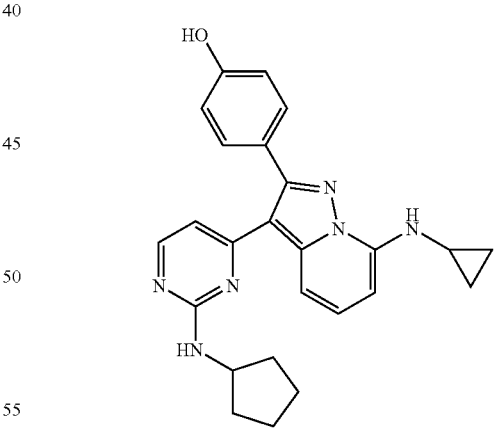

In a similar manner as described in Example 4 from 3-[2-(cyclopentylamino)-4-pyrimidinyl]-N-cyclopropyl-2-(4-methoxyphenyl)pyrazolo[1,5-a]pyridin-7-amine (0.24 g. 0.54 mmol) was prepared 4-[3-[2-(cyclopentylamino)-4-pyrimidinyl]-7-(cyclopropylamino)pyrazolo[1,5-a]pyridin-2-yl]phenol (0.17 g, 72%) as a gold foam. ¹H NMR (CDCl₃): δ 7.96 (d, 1 H), 7.82 (d, 1 H), 7.50 (d, 2 H), 7.35 (t, 1 H), 6.91 (d, 2 H), 6.39 (d, 1 H), 6.32 (m, 2 H), 5.13 (d, 1 H), 4.38 (m, 1 H), 2.68 (m, 1 H), 2.09 (m, 2 H), 1.80–1.53 (m, 6 H), 0.89 (m, 2 H), 0.75 (m, 2 H); MS m/z 427 (M+1).

EXAMPLE 68

4-{7-(Cyclopentylamino)-3-[2-(cyclopropylamino)-4-pyrimidinyl]-pyrazolo[1,5-a]pyridin-2-yl}phenol

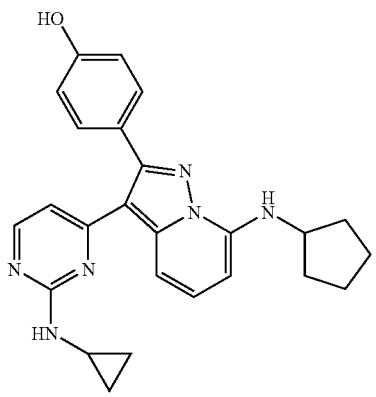

In a similar manner as described in Example 4 from N-cyclopentyl-3-[2-(cyclopropylamino)-4-pyrimidinyl]-2-(4-methoxyphenyl)pyrazolo[1,5-a]pyridin-7-amine (0.19 g, 0.43 mmol) was prepared 4-{7-(cyclopentylamino)-3-[2-(cyclopropylamino)-4-pyrimidinyl]pyrazolo[1,5-a]pyridin-2-yl}phenol (0.12 g, 67%) as a gold foam. $^{1}$H NMR (CDCl$_{3}$): δ 7.97 (d, 1 H), 7.89 (d, 1 H), 7.51 (d, 2 H), 7.32 (t, 1 H), 6.94 (d, 2 H), 6.37 (d, 1 H), 6.05 (d, 2 H), 5.42 (s, 1 H), 4.01 (m, 1 H), 2.87 (m, 1 H), 2.14 (m, 2 H), 1.83–1.55 (m, 6 H), 0.89 (m, 2 H), 0.65 (m, 2 H); MS m/z 427 (M+1).

EXAMPLE 69

4-{7-(Cyclopropylamino)-3-[2-(cyclopropylamino)-4-pyrimidinyl]-pyrazolo[1,5-a]pyridin-2-yl}phenol

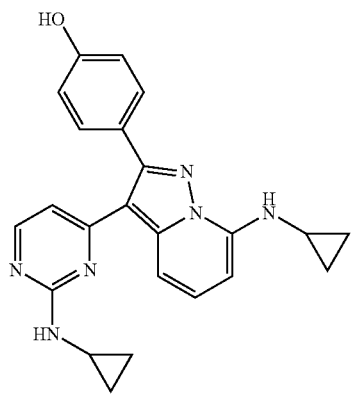

In a similar manner as described in Example 4 from N-cyclopropyl-3-[2-(cyclopropylamino)-4-pyrimidinyl]-2-(4-methoxyphenyl)pyrazolo[1,5-a]pyridin-7-amine (0.33 g, 0.80 mmol) was prepared 4-{7-(cyclopropylamino)-3-[2-(cyclopropylamino)-4-pyrimidinyl]pyrazolo[1,5-a]pyridin-2-yl}phenol (0.18 9, 56%) as a gold foam. $^{1}$H NMR (CDCl$_{3}$): δ 7.98 (m, 2 H), 7.51 (d, 2 H), 7.36 (t, 1 H), 6.93 (d, 2 H), 6.42–6.34 (m, 3 H), 5.45 (broad, 1 H), 2.88 (m, 1 H), 2.68 (m, 1 H), 0.89 (m, 4 H), 0.76 (m, 2 H), 0.65 (m, 2 H); MS m/z 399 (M+1).

EXAMPLE 70

3-[2-(Cyclopentylamino)-4-pyrimidinyl]-N-cyclopropyl-2-[4-(cyclopropylmethoxy)phenyl]pyrazolo[1,5-a]pyridin-7-amine

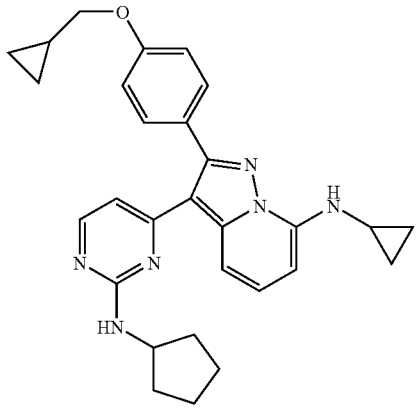

To a solution of 4-[3-[2-(cyclopentylamino)-4-pyrimidinyl]-7-(cyclopropylamino)pyrazolo[1,5-a]pyridin-2-yl]phenol (146 mg, 0.34 mmol) in N,N-dimethylformamide (3 mL) was added cesium carbonate (0.22 g, 0.68 mmol) and (bromomethyl)cyclopropane (66 μL, 0.68 mmol). The reaction was stirred for 1 hour at room temperature, then partitioned between water and ethyl acetate. The organic layer was washed with brine and dried over magnesium sulfate. Filtration and concentration followed by flash chromatography (3:1 to 1:1 hexanes-ethyl acetate) provided 3-[2-(cyclopentylamino)-4-pyrimidinyl]-N-cyclopropyl-2-[4-(cyclopropylmethoxy)phenyl]pyrazolo[1,5-a]pyridin-7-amine (90.4 mg, 55%) as an off-white solid. $^{1}$H NMR (CDCl$_{3}$): δ 7.99 (d, 1 H), 7.84 (d, 1 H), 7.55 (d, 2 H), 7.34 (t, 1 H), 6.98 (d, 2 H), 6.39–6.32 (m, 3 H), 5.08 (broad, 1 H), 4.37 (m, 1 H), 3.87 (d, 2 H), 2.68 (m, 1 H), 2.10 (m, 2 H), 1.80–1.27 (m, 6 H), 0.89 (m, 2 H), 0.78–0.65 (m, 4 H), 0.39 (m, 2 H); MS m/z 481 (M+1).

EXAMPLE 71

2-[4-(Allyloxy)phenyl]-N-cyclopentyl-3-[2-(cyclopropylamino)-4-pyrimidinyl]pyrazolo[1,5-a]pyridin-7-amine

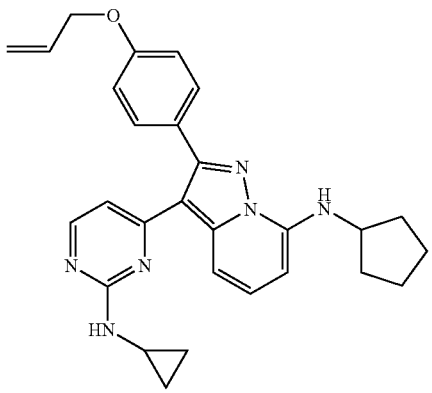

In a similar manner as described in Example 70 from 4-{7-(cyclopentylamino)-3-[2-(cyclopropylamino)-4-pyrimidinyl]pyrazolo[1,5-a]pyridin-2-yl}phenol (90 mg, 0.21 mmol) and allyl bromide (37 μL, 0.42 mmol) was prepared 2-[4-(allyloxy)phenyl]-N-cyclopentyl-3-[2-(cyclopropylamino)-4-pyrimidinyl]pyrazolo[1,5-a]pyridin-7-amine (76.8 mg, 78%) as a pale yellow solid. $^1$H NMR (CDCl$_3$): δ 7.97–7.94 (m, 2 H), 7.57 (d, 2 H), 7.34 (t, 1 H), 7.02 (d, 2 H), 6.39 (d, 1 H), 6.16–6.04 (m, 3 H), 5.47 (dd, 1 H), 5.33 (dd, 1 H), 4.62 (d, 2 H), 4.02 (m, 1 H), 2.89 (m, 1 H), 2.16 (m, 2 H), 1.83–1.69 (m, 6 H), 0.89 (m, 2 H), 0.67 (m, 2 H); MS m/z 467 (M+1).

EXAMPLE 72

N-Cyclopropyl-3-[2-(cyclopropylamino)-4-pyrimidinyl]-2-[4-(cyclopropylmethoxy)phenyl]pyrazolo[1,5-a]pyridin-7-amine

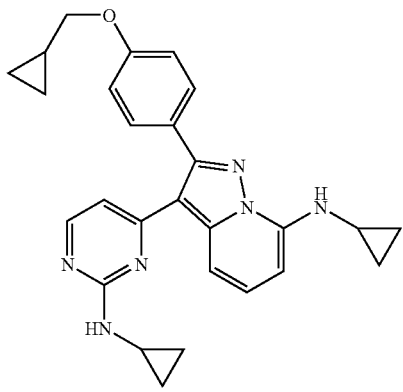

In a similar manner as described in Example 70 from 4-{7-(cyclopropylamino)-3-[2-(cyclopropylamino)-4-pyrimidinyl]pyrazolo[1,5-a]pyridin-2-yl}phenol (102 mg, 0.25 mmol) was prepared N-cyclopropyl-3-[2-(cyclopropylamino)-4-pyrimidinyl]-2-[4-(cyclopropylmethoxy)phenyl]pyrazolo[1,5-a]pyridin-7-amine (78 mg, 68%) as a pale yellow solid. $^1$H NMR (CDCl$_3$): δ 8.00–7.96 (m, 2 H), 7.53 (d, 2 H), 7.34 (t, 1 H), 6.97 (d, 2 H), 6.40–6.33 (m, 3 H), 5.55 (broad, 1 H), 3.86 (d, 2 H), 2.87 (m, 1 H), 2.66 (m, 1 H), 1.31 (m, 1 H), 0.87 (m, 4 H), 0.74 (m, 2 H), 0.66 (m, 4 H), 0.38 (m, 2 H); MS m/z 453 (M+1).

EXAMPLE 73

2-[4-(Allyloxy)phenyl]-N-cyclopropyl-3-[2-(cyclopropylamino)-4-pyrimidinyl]pyrazolo[1,5-a]pyridin-7-amine

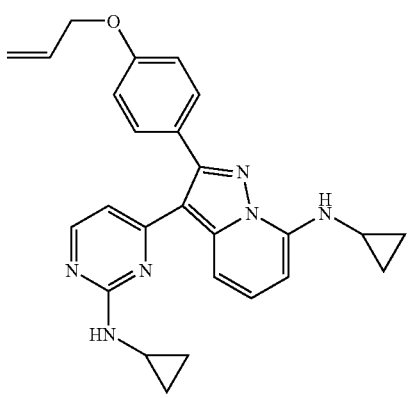

In a similar manner as described in Example 70 from 4-{7-(cyclopropylamino)-3-[2-(cyclopropylamino)-4-pyrimidinyl]pyrazolo[1,5-a]pyridin-2-yl}phenol (60 mg, 0.15 mmol) and allyl bromide (26 μL, 0.30 mmol) was prepared 2-[4-(allyloxy)phenyl]-N-cyclopropyl-3-[2-(cyclopropylamino)-4-pyrimidinyl]pyrazolo[1,5-a]pyridin-7-amine (47 mg, 71%) as a pale yellow foam. $^1$H NMR (CDCl$_3$): δ 8.00–7.97 (m, 2 H), 7.54 (d, 2 H), 7.35 (t, 1 H), 7.00 (d, 2 H), 6.41–6.33 (m, 3 H), 6.09 (m, 1 H), 5.62 (broad, 1 H), 5.45 (dd, 1 H), 5.32 (d, 1 H), 4.60 (d, 2 H), 2.87 (m, 1 H), 2.67 (m, 1 H), 0.87 (m, 4 H), 0.74 (m, 2 H), 0.65 (m, 2 H); MS m/z 439 (M+1).

EXAMPLE 74

N-Butyl-3-[2-(butylamino)pyrimidin-4-yl]-2-{4-[(4-methoxybenzyl)-amino]phenyl}pyrazolo[1,5-a]pyridin-7-amine

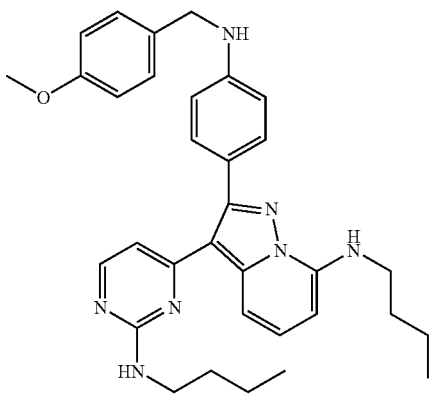

In a similar manner as described above from N-{4-[2-(4-aminophenyl)-7-(butylamino)pyrazolo[1,5-a]pyridin-3-yl]-2-pyrimidinyl}-N-butylamine (100 mg, 0.23 mmol), and p-methoxybenzaldehyde (42 µL, 0.35 mmol) was prepared N-butyl-3-[2-(butylamino)pyrimidin-4-yl]-2-{4-[(4-methoxybenzyl)amino]phenyl}pyrazolo[1,5-a]pyridin-7-amine (113 mg, 94%) as a pale yellow foam. $^1$H NMR (CDCl$_3$): δ 7.92 (broad, 1 H), 7.79 (d, 1 H), 7.46 (d, 2 H), 7.34–7.29 (m, 3 H), 6.91 (d, 2 H), 6.71 (d, 2 H), 6.44 (d, 1 H), 6.07 (t, 1 H), 6.01 (d, 1 H), 4.33 (d, 2 H), 4.16 (t, 1 H), 3.83 (s, 3 H), 3.53 (q, 2 H), 3.38 (q, 2 H), 1.80–1.45 (m, 8 H), 0.99 (t, 6 H); MS m/z 550 (M+1).

EXAMPLE 75

N-Butyl-3-[2-(butylamino)pyrimidin-4-yl]-2-(4-morpholin-4-ylphenyl)pyrazolo[1,5-a]pyridin-7-amine

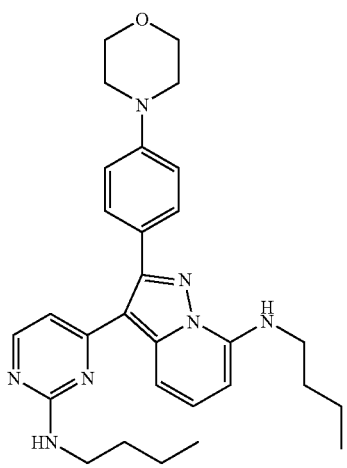

In a similar manner as described above from N-{4-[2-(4-bromophenyl)-7-(butylamino)pyrazolo[1,5-a]pyridin-3-yl]-2-pyrimidinyl}-N-butylamine (100 mg, 0.20 mmol) was prepared N-butyl-3-[2-(butylamino)pyrimidin-4-yl]-2-(4-morpholin-4-ylphenyl)pyrazolo[1,5-a]pyridin-7-amine (23.5 mg, 23%) as a yellow solid. $^1$H NMR (CDCl$_3$): δ 7.88 (broad, 1 H), 7.74 (d, 1 H), 7.51 (d, 2 H), 7.28 (t, 1 H), 6.94 (d, 2 H), 6.34 (d, 1 H), 6.02 (t, 1 H), 5.97 (d, 1 H), 3.86 (m, 4 H), 3.47 (q, 2 H), 3.33 (q, 2 H), 3.21 (m, 4 H), 1.74–1.41 (m, 8 H), 0.94 (t, 6 H); MS m/z 500 (M+1).

EXAMPLE 76

2-(3-Bromophenyl)-N-cyclopentyl-3-[2-(cyclopropylamino)-4-pyrimidinyl]pyrazolo[1,5-a]pyridin-7-amine

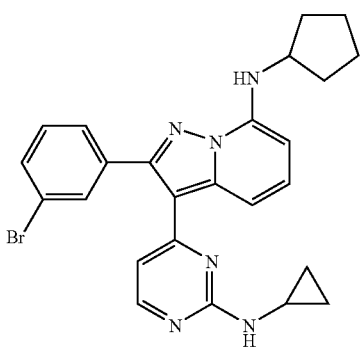

In a similar manner as described in Example 46 from (2E)-1-[2-(3-bromophenyl)-7-(cyclopentylamino)pyrazolo[1,5-a]pyridin-3-yl]-3-(dimethylamino)-2-propen-1-one (0.38 g, 0.84 mmol), 2-(3-bromophenyl)-N-cyclopentyl-3-[2-(cyclopropylamino)-4-pyrimidinyl]pyrazolo[1,5-a]pyridin-7-amine (0.19 g, 47%) was obtained as a yellow crystalline solid. $^1$H NMR (DMSO-d$_6$): δ 8.01 (d, 1H), 7.84 (d, 1H), 7.81 (s, 1H), 7.67 (d, 1H), 7.59 (d, 1H), 7.44–7.35 (m, 2H), 7.28 (s, 1H), 6.63 (d, 1H), 6.21 (m, 2H), 4.00 (m, 1H), 2.68 (m, 1H), 2.07–2.03 (m, 2H), 1.74–1.56 (m, 6H), 0.67–0.63 (m, 2H), 0.49–0.46 (m, 2H); MS m/z 489 (M+1).

EXAMPLE 77

2-(3-Bromophenyl)-3-[2-(cyclopentylamino)-4-pyrimidinyl]-N-cyclopropylpyrazolo[1,5-a]pyridin-7-amine

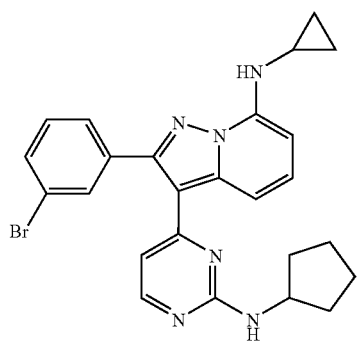

a) 2-(3-Bromophenyl)-7-chloropyrazolo[1,5-a]pyridine-3-carbaldehyde

A solution of N,N-Dimethylformamide (150 mL) and 2-(3-bromophenyl)-7-chloropyrazolo[1,5-a]pyridine (10.3 g, 33 mmol) was cooled to 0° C. and treated with phosphorous oxychloride (4.7 mL, 50 mmol). After the addition was complete, the mixture was warmed to room temperature and the resultant solution was stirred over the weekend. Water was added, followed by dichloromethane. The aqueous layer was extracted with dichloromethane. The combined organics were washed with brine, dried over magnesium sulfate, filtered and concentrated. The residue was washed with diethyl ether and hexanes to give 2-(3-bromophenyl)-7-chloropyrazolo[1,5-a]pyridine-3-carbaldehyde (10.6 g, 96%) as a fluffy white solid. $^1$H NMR (DMSO-d$_6$): δ 10.09 (s, 1 H), 8.37 (d, 1 H), 8.11 (d, 1H), 7.95 (d, 1H), 7.80 (m, 2 H), 7.65 (d, 1 H), 7.55 (m, 1 H).

b) 1-[2-(3-Bromophenyl)-7-chloropyrazolo[1,5-a]pyridin-3-yl]-2-propyn-1-ol

In a similar manner as described in Example 46 from 2-(3-bromophenyl)-7-chloropyrazolo[1,5-a]pyridine-3-carbaldehyde (1.0 g, 2.9 mmol) and ethynylmagnesium bromide (6.4 mL, 0.5 M in tetrahydrofuran, 3.2 mmol) at 0 ° C., was obtained 1-[2-(3-bromophenyl)-7-chloropyrazolo[1,5-a]pyridin-3-yl]-2-propyn-1-ol (0.68 g, 68%) as a white solid. $^1$H NMR (DMSO-d$_6$): δ 8.04 (m, 2 H), 7.87 (d, 1 H), 7.67 (d, 1 H), 7.49 (t, 1 H), 7.38–7.29 (m, 2 H), 6.27 (bs, 1 H), 5.69 (s, 1 H), 3.49 (d, 1 H).

c) 1-[2-(3-Bromophenyl)-7-chloropyrazolo[1,5-a]pyridin-3-yl]-2-propyn-1-one

In a similar manner as described in Example 46 from 1-[2-(3-bromophenyl)-7-chloropyrazolo[1,5-a]pyridin-3-yl]-2-propyn-1-ol (1.0 g, 2.8 mmol) was obtained 1-[2-(3-bromophenyl)-7-chloropyrazolo[1,5-a]pyridin-3-yl]-2-propyn-1-one (0.45 g, 45%) as a yellow solid. $^1$H NMR (DMSO-d$_6$): δ 8.41 (dd, 1 H), 7.88–7.62 (m, 5 H), 7.46 (m, 1 H), 4.65 (s, 1 H).

d) 4-[2-(3-Bromophenyl)-7-chloropyrazolo[1,5-a]pyridin-3-yl]-N-cyclopentyl-2-pyrimidinamine In a similar manner as described in Example 46 from 1-[2-(3-bromophenyl)-7-chloropyrazolo[1,5-a]pyridin-3-yl]-2-propyn-1-one (1.0 g, 2.8 mmol), N-cyclopentylguanidine hydrochloride and sodium ethoxide (4.1 mL, 21 wt % in ethanol, 3.6 mmol) at room temperature was obtained 4-[2-(3-bromophenyl)-7-chloropyrazolo[1,5-a]pyridin-3-yl]-N-cyclopentyl-2-pyrimidinamine (0.60 g, 46%) as a yellow crystalline solid. MS m/z 469 (M+1).

e) 2-(3-Bromophenyl)-3-[2-(cyclopentylamino)-4-pyrimidinyl]-N-cyclopropylpyrazolo[1,5-a]pyridin-7-amine In a similar manner as described in Example 1 from 4-[2-(3-bromophenyl)-7-chloropyrazolo[1,5-a]pyridin-3-yl]-N-cyclopentyl-2-pyrimidinamine (0.1 g, 0.21 mmol) and cyclopropylamine was obtained 3-[2-(butylamino)-4-pyrimidinyl]-N-cyclopropyl-2-(4-fluorophenyl)pyrazolo[1,5-a]pyridin-7-amine2-(3-bromophenyl)-3-[2-(cyclopentylamino)-4-pyrimidinyl]-N-cyclopropylpyrazolo[1,5-a]pyridin-7-amine (0.02 g mg, 24%) as a yellow crystalline solid. $^1$H NMR (CDCl$_3$): δ 8.08 (d, 1 H), 7.89 (s, 1 H), 7.80 (d, 1 H), 7.58 (m, 2 H), 7.36 (m, 2 H), 6.43 (d, 1 H), 6.35 (m, 2 H), 5.08 (d, 1H), 4.34 (m, 1 H), 2.72 (m, 1 H), 2.12 (m, 2 H), 1.79–1.55 (m, 6 H), 0.93 (m, 2 H), 0.81 (m, 2 H); MS m/z 489 (M+1).

EXAMPLE 78

2-(3-Bromophenyl)-N-cyclopropyl-3-[2-(cyclopropylamino)-4-pyrimidinyl]pyrazolo[1,5-a]pyridin-7-amine

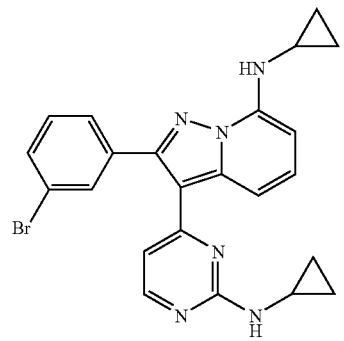

a) 4-[2-(3-Bromophenyl)-7-chloropyrazolo[1,5-a]pyridin-3-yl]-N-cyclopropyl-2-pyrimidinamine In a similar manner as described in Example 46 from 1-[2-(3-bromophenyl)-7-chloropyrazolo[1,5-a]pyridin-3-yl]-2-propyn-1-one (0.45 g, 1.25 mmol), N-cyclopropylguanidine sulfate and sodium ethoxide (0.61 mL, 21 wt % in ethanol, 1.6 mmol) at room temperature was obtained 4-[2-(3-bromophenyl)-7-chloropyrazolo[1,5-a]pyridin-3-yl]-N-cyclopropyl-2-pyrimidinamine (0.21 g, 39%) as a pale yellow solid. $^1$H NMR (CDCl$_3$): δ 8.57 (d, 1 H), 8.12 (d, 1 H), 7.86 (t, 1 H), 7.57 (m, 2 H), 7.28 (m, 2 H), 7.06 (d, 1 H), 6.37 (d, 1 H), 5.38 (bs, 1 H), 2.84 (m, 1 H), 0.88 (m, 2 H), 0.63 (m, 2 H); MS m/z 440 (M+1).

b) 2-(3-Bromophenyl)-N-cyclopropyl-3-[2-(cyclopropylamino)-4-pyrimidinyl]pyrazolo[1,5-a]pyridin-7-amine In a similar manner as described in Example 46 from 4-[2-(3-bromophenyl)-7-chloropyrazolo[1.5-a]pyridin-3-yl]-N-cyclopropyl-2-pyrimidinamine (0.2 g, 0.45 mmol) and cyclopropylamine was obtained 2-(3-bromophenyl)-N-cyclopropyl-3-[2-(cyclopropylamino)-4-pyrimidinyl]pyrazolo[1,5-a]pyridin-7-amine (0.04 g, 21%) as a yellow crystalline solid. $^1$H NMR (CDCl$_3$): δ 8.07 (d, 1 H), 7.90 (d, 1 H), 7.85 (t, 1 H), 7.55 (m, 2 H), 7.36–7.27 (m, 2 H), 6.38 (m, 2 H), 6.30 (s, 1 H), 5.30 (s, 1H), 2.80 (m, 1 H), 2.68 (m, 1 H), 0.89–0.60 (m, 8 H); MS m/z 461 (M+1).

EXAMPLE 79

Methyl N-[3-[2-(cyclopentylamino)pyrimidin-4-yl]-2-(4-methoxyphenyl)pyrazolo[1,5-a]pyridin-7-yl]glycinate

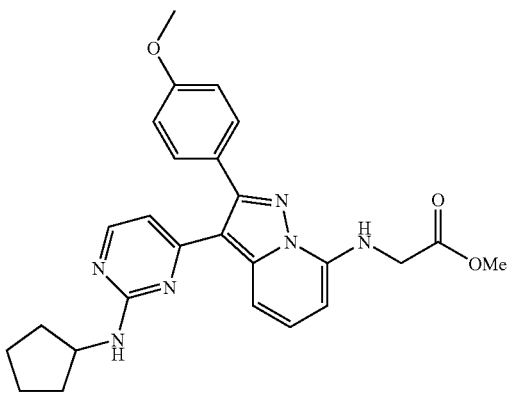

In a similar manner as described for above examples the title compound was prepared as a tan solid. $^1$H NMR (CDCl$_3$): δ 8.00 (d, 1 H), 7.82 (d, 1 H), 7.59 (d, 2 H), 7.27 (m, 1 H), 6.96 (d, 2 H), 6.58 (t, 1 H), 6.34 (d, 1 H), 5.89 (d, 1 H), 5.10 (d, 1 H), 4.35 (m, 1 H), 6.16 (d, 2 H), 3.86 (s, 3 H), 3.80 (s, 3 H), 2.07 (m, 2 H), 1.75–1.51 (m, 6 H); MS m/z 473 (M+1).

EXAMPLE 80

5-[(3aS,4S,6a R)-2-Oxohexahydro-1H-thieno[3,4-d]imidazol-4-yl]-N-(4-{7-(butylamino)-3-[2-(butylamino)pyrimidin-4-yl]pyrazolo[1,5-a]pyridin-2-yl}phenyl)pentanamide

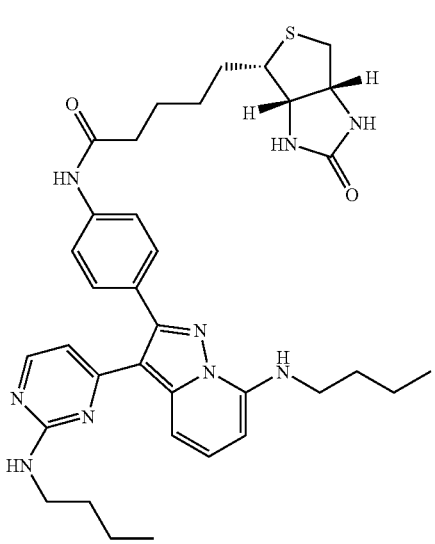

To a cold (0° C.) solution of thionyl chloride (1 mL) was added solid d-(+)-biotin (100 mg, 0.41 mmol). The resulting mixture was warmed to room temperature and stirred for 1 hour. The excess thionyl chloride and other volatiles were removed under vacuum (<0.1 mm Hg) resulting in a solid residue. To this residue at 0° C. was added N,N-dimethylformamide (3 mL) followed by 2-(4-aminophenyl)-N-butyl-3-[2-(butylamino)pyrimidin-4-yl]pyrazolo[1,5-a]pyridin-7-amine (70 mg, 0.16 mmol) in 2 mL of N,N-dimethylformamide. The resultant solution was stirred at room temperature for 1 hour at which time the reaction appeared to be complete by analytical methods. The solution was stirred an additional 72 hours. Ethyl acetate and saturated aqueous sodium bicarbonate were added and the layers separated. The organic layer was washed with brine. The aqueous layer was extracted with ethyl acetate and the combined organics were dried over sodium sulfate. Filtration and concentration followed by flash chromatography (8% methanol in dichloromethane) provided 5-[(3aS,4S,6aR)-2-oxohexahydro-1H-thieno[3,4-d]imidazol-4-yl]-N-(4-{7-(butylamino)-3-[2-(butylamino)pyrimidin-4-yl]pyrazolo[1,5-a]pyridin-2-yl}phenyl)pentanamide (30 mg, 28%) as a yellow solid. $^1$H NMR (DMSO-d$_6$): δ 10.00 (s, 1 H), 7.90 (d, 1 H), 7.66 (m, 3 H), 7.46 (d, 2 H), 7.29 (t, 1 H), 6.99–6.94 (m, 2 H), 6.40 (s, 1 H), 6.32 (s, 1 H), 6.11–6.09 (m, 2 H), 6.25 (m, 1 H), 4.09 (m, 1 H), 3.47–3.06 (m, 4 H), 2.77 (m, 1 H), 2.53 (m, 1 H), 2.44 (m, 1 H), 2.97 (m, 2 H), 1.62–1.27 (m, 14 H), 0.89–0.83 (m, 6 H); MS m/z 656 (M+1).

EXAMPLE 81

N-[3-[2-(Cyclopentylamino)pyrimidin-4-yl]-2-(4-methoxyphenyl)-pyrazolo[1,5-a]pyridin-7-yl]butane-1,4-diamine

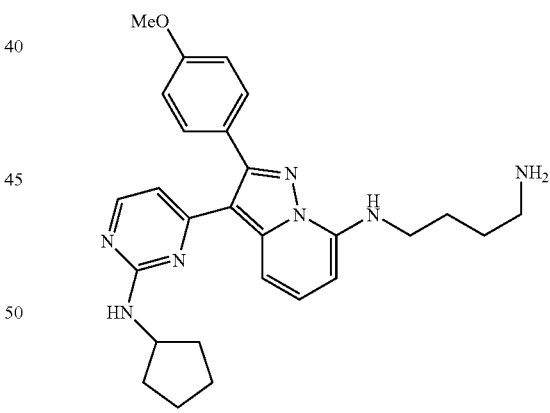

In a similar manner as described for above examples the title compound was prepared as a yellow solid. $^1$H NMR (CDCl$_3$): δ 7.99 (d, 1 H), 7.77 (d, 1 H), 7.58 (d, 2 H), 7.30 (m, 1 H), 6,97 (d, 2 H), 6.34 (d, 1 H), 6.17 (m, 1 H), 5.98 (d, 1 H), 5.27 (m, 1 H), 4.82 (broad, 2 H), 4.36 (m, 1 H), 3.87 (s, 3 H), 3.38 (m, 2 H), 2.83–2.78 (m, 2 H), 2.09 (m 2 H), 1.83–1.52 (m, 10 H); MS m/z 472 (M+1).

EXAMPLE 82

5-[(3aS,4S,6aR)-2-Oxohexahydro-1H-thieno[3,4-d]
imidazol-4-yl]-N-(4-{[3-[2-(cyclopentylamino)pyri-
midin-4-yl]-2-(4-methoxyphenyl)pyrazolo[1,5-a]
pyridin-7-yl]amino}butyl)pentanamide

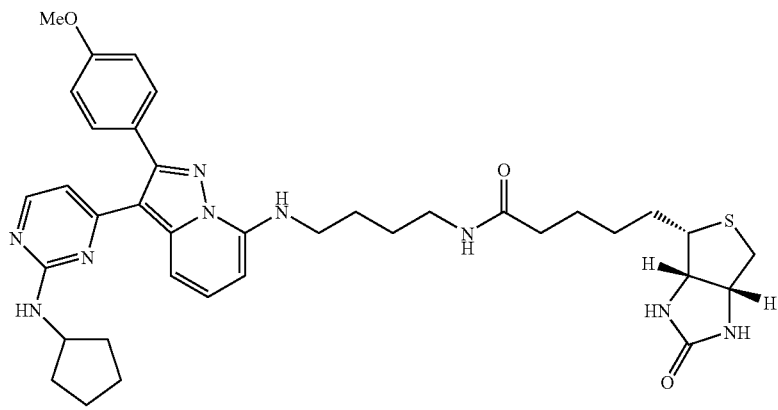

To a cold (0° C.) solution of N-[3-[2-(cyclopentylamino) pyrimidin-4-yl]-2-(4-methoxyphenyl)pyrazolo[1,5-a]pyridin-7-yl]butane-1,4-diamine (33 mg, 0.07 mmol) in N,N-dimethylformamide (3 mL) was added triethylamine (0.03 mL, 0.21 mmol) and d-biotin-N-hydroxysuccinimide ester (27 mg, 0.08 mmol). The resultant mixture was warmed to room temperature and stirred for 30 minutes. A subsequent 5 mg of d-biotin-N-hydroxysuccinimide ester was added and the mixture was stirred an additional 30 minutes. Water was added and the layers were separated. The organic layer was washed with saturated aqueous sodium bicarbonate and then brine. The aqueous layer was extracted with dichloromethane and the combined organics were dried over sodium sulfate. Filtration and concentration followed by flash chromatography (5% to 8% methanol in dichloromethane) provided 5-[(3aS,4S,6aR)-2-oxohexahydro-1H-thieno[3,4-d]imidazol-4-yl]-N-(4-{[3-[2-(cyclopentylamino)-pyrimidin-4-yl]-2-(4-methoxyphenyl)pyrazolo[1,5-a]pyridin-7-yl]amino}butyl)-pentanamide (25 mg, 51%) as a yellow solid. $^1$H NMR (CDCl$_3$): δ 7.98 (d, 1 H), 7.80 (d, 1 H), 7.58 (d, 2 H), 7.32 (m, 1 H), 7.00 (d, 2 H), 6.60 (s,1 H), 6.39 (m, 1 H), 6.33 (d, 1 H), 6.18 (m, 1 H), 6.02 (m, 1 H), 5.72 (s, 1 H), 5.62 (broad, 1 H), 4.44–4.31 (m, 2 H), 4.19 (m, 1 H), 3.89 (s, 3 H), 3.39 (m, 2 H), 3.28 (m, 2 H), 3.06 (m, 1 H), 2.95 (m, 2 H), 2.77 (dd, 1 H), 2.58 (d, 1 H), 2.20–2.05 (m, 4 H), 1.82–1.54 (m, 12 H), 1.39 (m, 2 H); MS m/z 698 (M+1).

EXAMPLE 83

3-[2-(Cyclopentylamino)pyrimidin-4-yl]-2-(4-methoxyphenyl)pyrazolo-[1,5-a]pyridin-7-amine

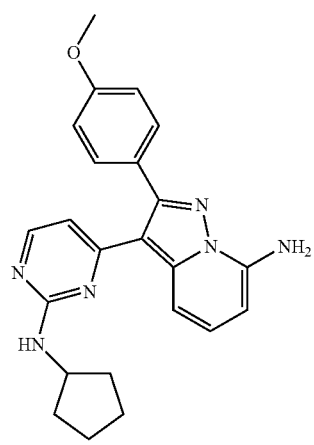

To a solution of 4-[7-chloro-2-(4-methoxyphenyl)pyrazolo[1,5-a]pyridin-3-yl]-N-cyclopentylpyrimidin-2-amine (100 mg, 0.24 mmol) in 1-methyl-2-pyrrolidinone (3 mL) was added sodium azide (200 mg, 3.1 mmol). The resulting suspension was heated at 80° C. until the reaction was judged complete by thin layer chromatography. The mixture was cooled to room temperature and water and ether were added. The organic layer was washed with brine. The aqueous layer was extracted with ether and the combined organics were dried over sodium sulfate. Filtration and concentration followed by flash chromatography (2:1 to 1:1 hexanes-ethyl acetate) provided 3-[2-(cyclopentylamino)pyrimidin-4-yl]-2-(4-methoxyphenyl)pyrazolo[1,5-a]pyridin-7-amine (50 mg, 52%) as a yellow powder. $^1$H NMR (CDCl$_3$): δ 8.03 (d, 1 H), 7.87 (d, 1 H), 7.62 (d, 2 H), 7.27 (m, 1 H), 7.01 (d, 2 H), 6.37 (d, 1 H), 6.17 (d, 1 H), 5.39 (s, 2 H), 5.19 (d, 1 H), 4.39 (m, 1 H), 3.90 (s, 3 H), 2.10 (m, 2 H), 1.82–1.54 (m, 6 H); MS m/z 401(M+1).

EXAMPLE 84

N,N''-di-tert-butoxycarbonyl-N'-(4-{[3-[2-(cyclopentylamino)pyrimidin-4-yl]-2-(4-methoxyphenyl)pyrazolo[1,5-a]pyridin-7-yl]amino}butyl)guanidine

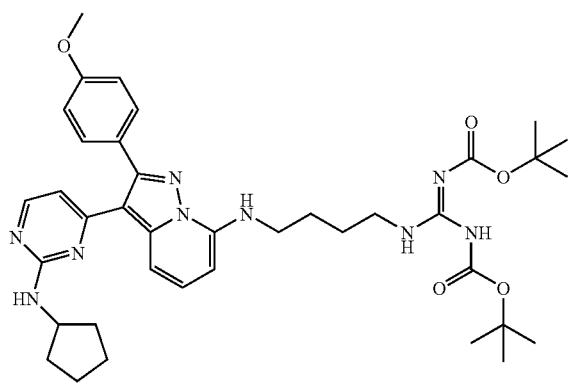

To a cold (0° C.) solution of N-[3-[2-(cyclopentylamino) pyrimidin-4-yl]-2-(4-methoxyphenyl)pyrazolo[1,5-a]pyridin-7-yl]butane-1,4-diamine (43 mg, 0.09 mmol) in dichloromethane (3 mL) was added triethylamine (0.03 mL, 0.18 mmol) and N,N-di-boc-N'-triflylguanidine (see Goodman et. al. *Journal of Organic Chemistry* 1998, 63, 3804). The resultant solution was warmed to room temperature and stirred overnight. Saturated aqueous sodium bicarbonate and ether were added. The organic layer was washed with brine. The aqueous layer was extracted with ether and the combined organics were dried over sodium sulfate. Filtration and concentration followed by flash chromatography (2:1 to 1:1 hexanes-ethyl acetate) provided N,N''-di-tert-butoxycarbonyl-N'-(4-{[3-[2-(cyclopentylamino)pyrimidin-4-yl]-2-(4-methoxyphenyl)pyrazolo[1,5-a]pyridin-7-yl]amino}butyl) guanidine (42 mg, 65%). $^1$H NMR (CDCl$_3$): δ 11.54 (s, 1 H), 8.40 (m, 1 H), 8.02 (m, 1 H), 7.80 (d, 1 H), 7.61 (d, 2 H), 7.33 (m, 1 H), 7.01 (d, 2 H), 6.36 (d, 1 H), 6.11 (m, 1 H), 6.02 (d, 1 H), 5.12 (m, 1 H), 4.39 (m, 1 H), 3.89 (s, 3 H), 3.56–3.42 (m, 4 H), 2.14–2.06 (m, 2 H), 1.90–1.50 (m, 10 H), 1.53 (s, 9 H), 1.52 (s, 9 H); MS m/z 714 (M+1).

EXAMPLE 85

N-(4-{[3-[2-(Cyclopentylamino)pyrimidin-4-yl]-2-(4-methoxyphenyl)pyrazolo[1,5-a]pyridin-7-yl]amino}butyl)guanidine

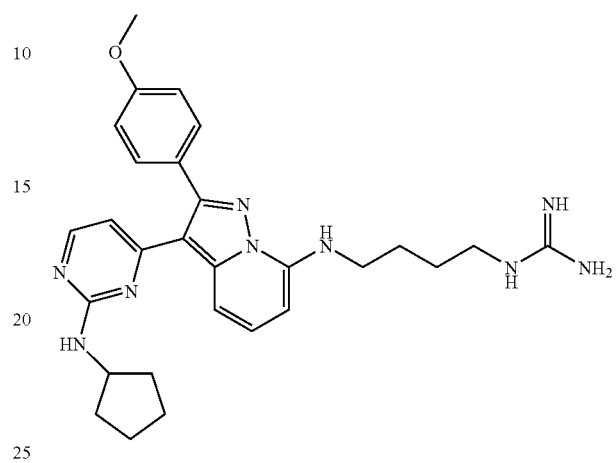

To a solution of N,N''-di-tert-butoxycarbonyl-N'-(4-{[3-[2-(cyclopentylamino)-pyrimidin-4-yl]-2-(4-methoxyphenyl)pyrazolo[1,5-a]pyridin-7-yl]amino}butyl)-guanidine (42 mg, 0.06 mmol) in dichloromethane (8 mL) was added trifluoroacetic acid (2 mL). The resultant solution was stirred for 8 hours and then concentrated in vacuo. The residue was dissolved in dichloromethane and saturated aqueous sodium bicarbonate was added. The organic layer was washed with brine. The aqueous layer was extracted with dichloromethane and the combined organics were dried over sodium sulfate. Filtration and concentration provided N-(4-{[3-[2-(cyclopentylamino)pyrimidin-4-yl]-2-(4-methoxyphenyl)pyrazolo[1,5-a]pyridin-7-yl]amino}butyl)guanidine (10 mg, 33%) as a yellow solid. MS m/z 514 (M+1).

EXAMPLE 86

N-(4-{[3-[2-(Cyclopentylamino)pyrimidin-4-yl]-2-(4-methoxyphenyl)pyrazolo[1,5-a]pyridin-7-yl]amino}butyl)methanesulfonamide

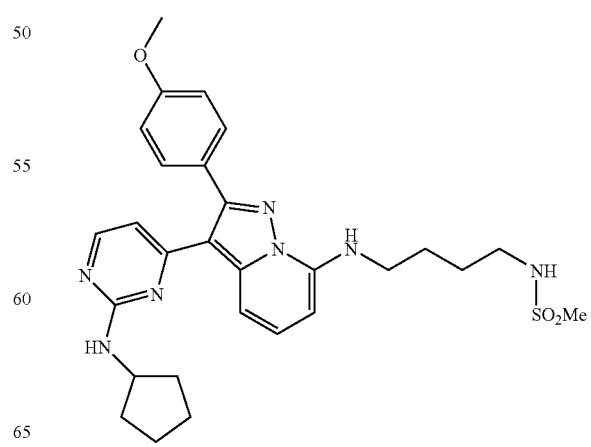

To a cold (0° C.) solution of N-[3-[2-(cyclopentylamino)
pyrimidin-4-yl]-2-(4-methoxyphenyl)pyrazolo[1,5-a]pyridin-7-yl]butane-1,4-diamine (21 mg, 0.04 mmol) in dichloromethane (3 mL) was added triethylamine (0.02 mL, 0.13 mmol) and methanesulfonyl chloride (0.05 mL). The resultant solution was stirred at 0° C. for 1 hour and saturated aqueous sodium bicarbonate was added. The organic layer was washed with brine. The aqueous layer was extracted with dichloromethane and the combined organics were dried over sodium sulfate. Filtration and concentration followed by flash chromatography (5% methanol in dichloromethane) provided N-(4-{[3-[2-(Cyclopentylamino)pyrimidin-4-yl]-2-(4-methoxyphenyl)pyrazolo[1,5-a]pyridin-7-yl]amino}butyl)methanesulfonamide (25 mg, 99%) a yellow solid. $^1$H NMR (CDCl$_3$): δ 8.01 (d, 1 H), 7.79 (d, 1 H), 7.59 (d, 2 H), 7.32 (m, 1 H), 7.01 (d, 2 H), 6.34 (d, 1 H), 6.13 (m, 1 H), 6.00 (d, 1 H), 5.34 (d, 1 H), 5.02 (m, 1 H), 4.38 (m, 1 H), 3.90 (s, 3 H), 3.38 (m, 2 H), 3.13 (m, 2 H), 2.94 (s, 3 H), 2.14–2.06 (m, 2 H), 1.82–1.54 (m, 10 H); MS m/z 550 (M+1).

EXAMPLE 87

N-{[(4-{[3-[2-(Cyclopentylamino)pyrimidin-4-yl]-2-(4-methoxyphenyl)pyrazolo[1,5-a]pyridin-7-yl]amino}butyl)amino]carbonyl}-4-methylbenzenesulfonamide

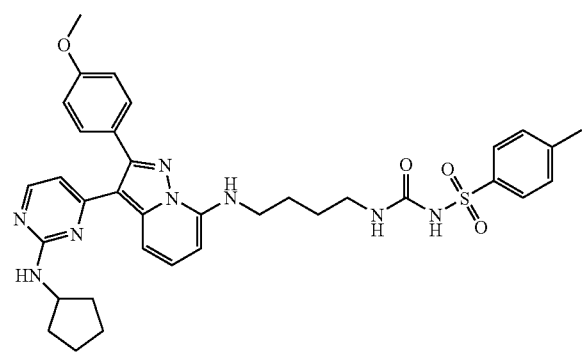

To a cold (0° C.) solution of N-[3-[2-(cyclopentylamino)pyrimidin-4-yl]-2-(4-methoxyphenyl)pyrazolo[1,5-a]pyridin-7-yl]butane-1,4-diamine (28 mg, 0.05 mmol) in dichloromethane (5 mL) was added triethylamine (0.1 mL) and p-tolylsulfonyl isocyanate (0.012 mL, 0.08 mmol). The resultant solution was stirred at 0° C. for 1 hour and saturated aqueous sodium bicarbonate was added. The organic layer was washed with brine. The aqueous layer was extracted with dichloromethane and the combined organics were dried over sodium sulfate. Filtration and concentration followed by flash chromatography (5% methanol in dichloromethane) and recrystallization from dichloromethane-ether provided N-{[(4-{[3-[2-(cyclopentylamino)pyrimidin-4-yl]-2-(4-methoxyphenyl)pyrazolo[1,5-a]pyridin-7-yl]amino}butyl)amino]carbonyl}-4-methylbenzenesulfonamide (14 mg, 35%) as a yellow solid. $^1$H NMR (CDCl$_3$): δ 8.03 (m, 1 H), 7.84–7.76 (m, 3 H), 7.58 (d, 2 H), 7.36–7.26 (m, 5 H), 7.01 (d, 2 H), 6.66 (m, 1 H), 6.34 (m 1 H), 6.04 (m, 2 H), 4.36 (m, 1 H), 3.91 (s, 3 H), 3.38–3.30 (m, 4 H), 2.36 (s, 3 H), 2.07 (m, 2 H), 1.82–1.54 (m, 10 H); MS m/z 669 (M+1).

EXAMPLE 88

4-[(4-{[3-[2-(Cyclopentylamino)pyrimidin-4-yl]-2-(4-methoxyphenyl)pyrazolo[1,5-a]pyridin-7-yl]amino}butyl)amino]-4-oxobutanoic acid

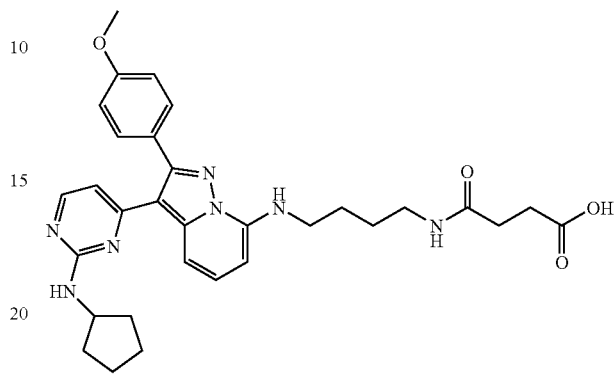

To a solution of N-[3-[2-(cyclopentylamino)pyrimidin-4-yl]-2-(4-methoxyphenyl)pyrazolo[1,5-a]pyridin-7-yl]butane-1,4-diamine (25 mg, 0.05 mmol) in dichloromethane (4 mL) was added succinic anhydride (6 mg, 0.6 mmol). The resultant solution was stirred overnight and then ether was added. The precipitated solids were recovered by filtration to give 4-[(4-{[3-[2-(cyclopentylamino)pyrimidin-4-yl]-2-(4-methoxyphenyl)pyrazolo[1,5-a]pyridin-7-yl]amino}butyl)amino]-4-oxobutanoic acid (31 mg, 99%) as a white solid. $^1$H NMR (CDCl$_3$/CD$_3$OD): δ 7.71 (m, 2 H), 7.47 (d, 2 H), 7.32 (m, 1 H), 6.97 (d, 2 H), 6.15 (d, 1 H), 6.04 (d, 1 H), 4.30 (m, 1 H), 3.88 (s, 3 H), 3.38–3.27 (m, 4 H), 2.62 (m, 2 H), 2.45 (m, 2 H), 2.10–2.00 (m, 2 H), 1.84–1.55 (m, 10 H); MS m/z 572 (M+1).

EXAMPLE 89

Diethyl 4-{[3-[2-(cyclopentylamino)pyrimidin-4-yl]-2-(4-methoxyphenyl)pyrazolo[1,5-a]pyridin-7-yl]amino}butylamidophosphate

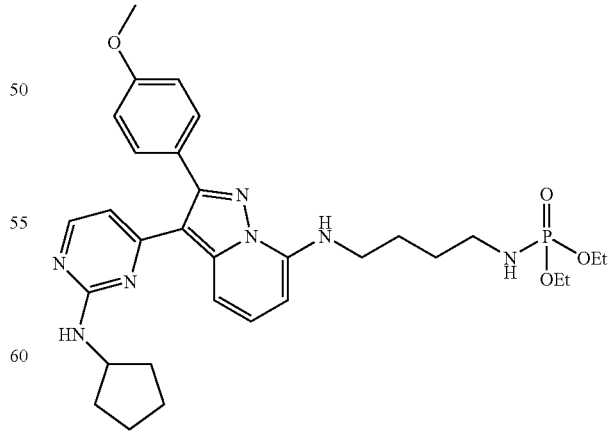

To a cold (0° C.) solution of N-[3-[2-(cyclopentylamino)pyrimidin-4-yl]-2-(4-methoxyphenyl)pyrazolo[1,5-a]pyridin-7-yl]butane-1,4-diamine (21 mg, 0.04 mmol) in dichloromethane (3 mL) was added triethylamine (0.1 mL), and diethyl chlorophosphate (0.1 mL of a stock solution prepared from 0.1 mL of diethyl chlorophosphate in 3 mL of dichloromethane). The resultant solution was stirred for 3 hours at 0° C. and then quenched by the addition of saturated aqueous sodium bicarbonate. The organic layer was washed with brine. The aqueous layer was extracted with dichloromethane and the combined organics were dried over sodium sulfate. Filtration and concentration followed by flash chromatography (5% methanol in dichloromethane) provided diethyl 4-{[3-[2-(cyclopentylamino)pyrimidin-4-yl]-2-(4-methoxyphenyl)pyrazolo[1,5-a]pyridin-7-yl]amino}butylamidophosphate (22 mg, 81%) as a yellow solid. $^1$H NMR (CDCl$_3$): δ 7.98 (d, 1 H), 7.76 (d, 1 H), 7.55 (d, 2 H), 7.28 (m, 1 H), 6.96 (d, 2 H), 6.31 (d, 1 H), 6.06 (m, 1 H), 5.97 (d, 1 H), 5.11 (d, 1 H), 4.34 (m, 1 H), 4.09–3.98 (m, 4 H), 3.86 (s, 3 H), 3.37 (m, 2 H), 2.95 (m, 2 H), 2.64 (m, 1 H), 2.11–1.48 (m, 12 H), 1.31–1.27 (m, 6 H); MS m/z 608 (M+1).

EXAMPLE 90

4-{[3-[2-(Cyclopentylamino)pyrimidin-4-yl]-2-(4-methoxyphenyl)-pyrazolo[1,5-a]pyridin-7-yl]amino}butan-1-ol

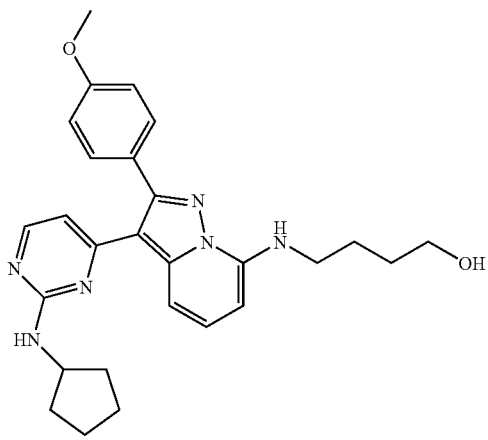

In a similar manner as described for above examples the title compound was prepared as a yellow foam. $^1$H NMR (CDCl$_3$): δ 7.98 (d, 1 H), 7.75 (d, 1 H), 7.56 (d, 2 H), 7.29 (m, 1 H), 6.97 (d, 2 H), 6.31 (d, 1 H), 6.12 (m, 1 H), 5.99 (d, 1 H), 5.04 (d, 1 H), 4.35 (m, 1 H), 3.86 (s, 3 H), 3.71 (m, 2 H), 3.42 (m, 2 H), 2.07 (m, 2 H), 1.86 (m, 2 H), 1.76–1.49 (m, 8 H); MS m/z 473 (M+1).

EXAMPLE 91

Dibenzyl 4-{[3-[2-(cyclopentylamino)pyrimidin-4-yl]-2-(4-methoxyphenyl)pyrazolo[1,5-a]pyridin-7-yl]amino}butyl phosphate

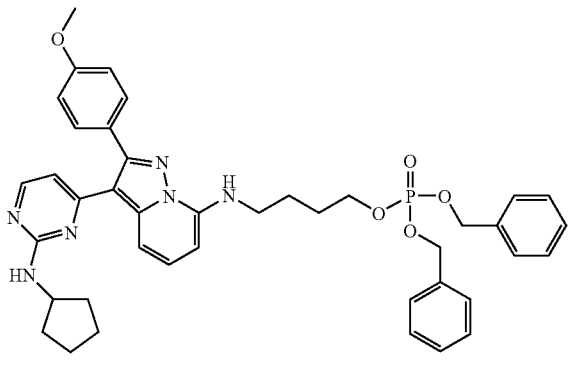

To a room temperature solution of 4-{[3-[2-(cyclopentylamino)pyrimidin-4-yl]-2-(4-methoxyphenyl)pyrazolo[1,5-a]pyridin-7-yl]amino}butan-1-ol (22 mg, 0.05 mmol) in dichloromethane (5 mL) was added 1-H-tetrazole (7 mg, 0.1 mmol) and dibenzyl N,N-diisopropylphosphoramidate (0.32 mL of a stock solution prepared from 0.2 mL of dibenzyl N,N-diisopropylphosphoramidate in 3.2 mL of dichloromethane). The resultant solution was stirred at room temperature for 1 hour and then cooled to 0° C. Iodobenzene diacetate (16.5 mg, 0.05 mmol) was added and the mixture was stirred for 20 minutes. Saturated aqueous sodium thiosulfate and saturated aqueous sodium bicarbonate were added and the layers separated. The organic layer was washed with brine. The aqueous layer was extracted with dichloromethane and the combined organics were dried over sodium sulfate. Filtration and concentration followed by flash chromatography (1:4 hexanes-ethyl acetate) provided dibenzyl 4-{[3-[2-(cyclopentylamino)pyrimidin-4-yl]-2-(4-methoxyphenyl)pyrazolo[1,5-a]pyridin-7-yl]amino}butyl phosphate (18 mg, 53%). $^1$H NMR (CDCl$_3$): δ 8.03 (d, 1 H), 7.81 (d, 1 H), 7.61 (d, 2 H), 7.38–7.32 (m, 11 H), 7.01 (d, 2 H), 6.36 (d, 1 H), 6.06 (m, 1 H), 5.98 (d, 1 H), 5.13–5.01 (m, 5 H), 4.40 (m, 1 H), 4.05 (m, 2 H), 3.91 (s, 3 H), 3.37 (m, 2 H), 2.16–1.54 (m, 12 H); MS m/z 733 (M+1).

EXAMPLE 92

4-{[3-[2-(Cyclopentylamino)pyrimidin-4-yl]-2-(4-methoxy-phenyl)pyrazolo[1,5-a]pyridin-7-yl]amino}butyl phosphate diammonium salt

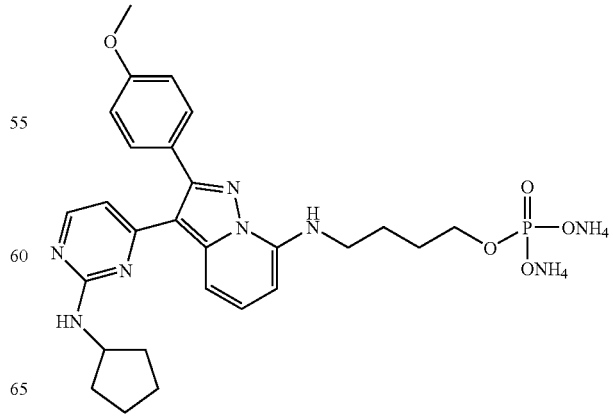

A solution of dibenzyl 4-{[3-[2-(cyclopentylamino)pyrimidin-4-yl]-2-(4-methoxyphenyl)pyrazolo[1,5-a]pyridin-7-yl]amino}butyl phosphate (55 mg, 0.07 mmol) in methanol (10 mL) was treated with a catalytic amount of palladium on carbon. This mixture was placed under a hydrogen atmosphere (48 psi) for 14 hours. The catalyst was removed by filtration through Celite with ammonia in ethanol as eluent. The filtrate was concentrated in vacuo and the residue was triturated with methanol/ether to provide 4-{[3-[2-(cyclopentylamino)pyrimidin-4-yl]-2-(4-methoxyphenyl)pyrazolo[1,5-a]pyridin-7-yl]amino}butyl phosphate as its diammonium salt. $^1$H NMR (DMSO-$d_6$): δ 10.89 (broad, 2 H), 7.93 (d, 1 H), 7.77 (broad, 1 H), 7.50 (d, 2 H), 7.34 (t, 1 H), 7.09–7.01 (m, 4 H), 6.16 (m, 2 H), 4.15 (m, 1 H), 3.84 (m, 2 H), 3.80 (s, 3 H), 3.36 (m, 2 H), 1.92–1.50 (m, 12 H); HRMS m/z 553.2357 (calcd for $C_{27}H_{33}N_6O_5P$ free base 552.2250) (M+1).

EXAMPLE 93

2-(3-Azidophenyl)-N-cyclopentyl-3-[2-(cyclopentylamino)pyrimidin-4-yl]pyrazolo[1,5-a]pyridin-7-amine

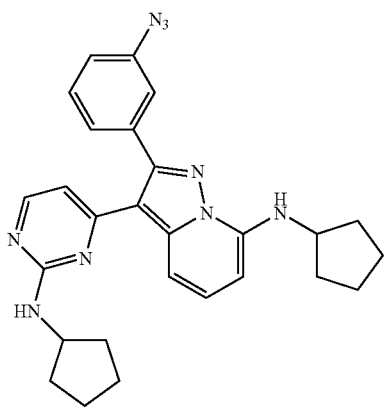

This reaction was performed in a dark environment. To a cold (0–5° C.) solution of 2-(3-aminophenyl)-N-cyclopentyl-3-[2-(cyclopentylamino)pyrimidin-4-yl]pyrazolo[1,5-a]pyridin-7-amine (46 mg, 0.10 mmol) in acetic acid (3 mL) was added sodium nitrite (0.31 mL of a 25 mg/mL aqueous stock solution, 7.7 mg, 0.11 mmol). The mixture turned dark and was stirred for 20 minutes at 0° C. Sodium azide was then added and the mixture was stirred for 20 minutes, allowed to warm to room temperature and stirred for an additional 10 minutes. Ether was added and the mixture was neutralized with sodium bicarbonate. Aqueous workup was followed by drying over sodium sulfate. Filtration and concentration followed by flash chromatography (4:1 to 2:1 hexanes-ethyl acetate) provided 2-(3-azidophenyl)-N-cyclopentyl-3-[2-(cyclopentylamino)pyrimidin-4-yl]pyrazolo[1,5-a]pyridin-7-amine (25 mg, 52%) as a yellow solid. $^1$H NMR (CDCl$_3$): δ 8.05 (d, 1 H), 7.75 (d, 1 H), 7.45–7.42 (m, 3 H), 7.36 (t, 1 H), 7.13 (m, 1 H), 6.33 (d, 1 H), 6.10–6.03 (m, 2 H), 5.10 (d, 1 H), 4.36 (m, 1 H), 4.05 (m, 1 H), 2.20–1.54 (m, 16 H); MS m/z 480 (M+1); IR 2109 cm$^{-1}$.

EXAMPLE 94

3-[2-(Cyclopentylamino)-4-pyrimidinyl]-2-(4-methoxyphenyl)-N-[2-oxo-2-(1-pyrrolidinyl)ethyl]pyrazolo[1,5-a]pyridin-7-amine

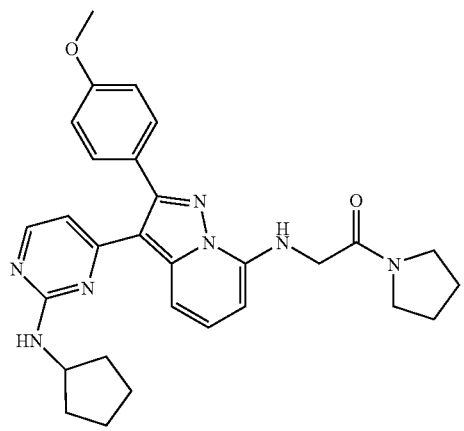

In a similar manner as described for above examples the title compound was prepared as a yellow solid. $R_f$ 0.15 (1:2 hexanes:ethyl acetate); $^1$H NMR (CDCl$_3$): δ 8.02 (d, 1H), 7.79 (d, 1H), 7.65 (d, 2H), 7.28 (m, 1H), 7.07 (t, 1H), 6.97 (d, 2H), 6.40 (d, 1H), 5.91 (d, 1H), 5.11 (d, 1H), 4.38 (m, 1H), 4.06 (d, 2H), 3.88 (s, 3H), 3.59 (t, 2H), 3.49 (t, 2H), 2.13–2.01 (m, 4H), 1.92 (m, 2H), 1.82–1.51 (m, 6H); MS m/z 512 (M+1).

EXAMPLE 95

N-(2-{[3-[2-(Cyclopentylamino)-4-pyrimidinyl]-2-(4-methoxy-phenyl)pyrazolo[1,5-a]pyridin-7-yl]amino}ethyl)methanesulfonamide

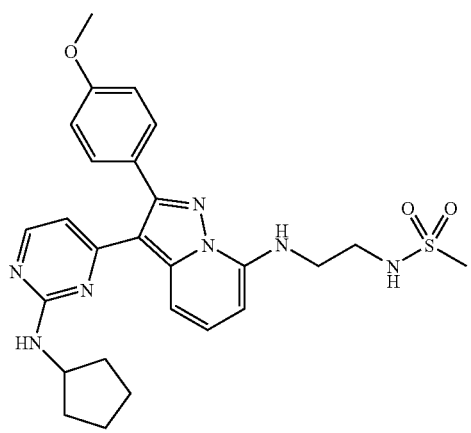

In a similar manner as described for above examples the title compound was prepared as a yellow solid. $R_f$ 0.33 (39:1 dichloromethane:methanol); $^1$H NMR (CDCl$_3$): δ 7.82 (br, 1H), 7.73 (d, 1H), 7.46 (d, 2H), 7.27 (m, 1H), 6.94 (d, 2H), 6.25 (t, 1H), 6.12–6.08 (m, 2H), 5.50 (br, 1H), 4.30 (m, 1H), 3.88 (s, 3H), 3.58 (m, 2H), 3.38 (m, 2H), 2.95 (s, 3H), 2.06 (m, 2H), 1.81–1.56 (m, 6H); MS m/z 522 (M+1).

EXAMPLE 96

N'-[3-[2-(Cyclopentylamino)-4-pyrimidinyl]-2-(4-methoxyphenyl)pyrazolo[1,5-a]pyridin-7-yl]-1,2-ethanediamine

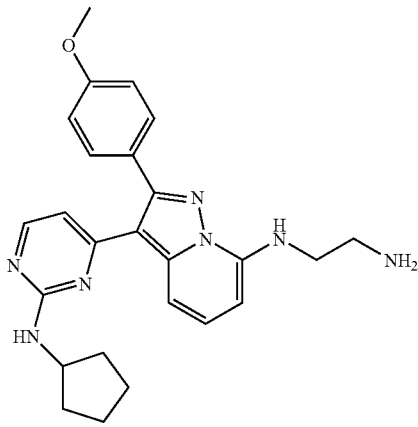

In a similar manner as described for above examples the title compound was prepared as a light yellow solid. $^1$H NMR (CDCl$_3$): δ 8.01 (d, 1H), 7.80 (d, 1H), 7.59 (d, 2H), 7.32 (d, 1H), 6.99 (d, 2H), 6.35–6.30 (m, 2H), 6.03 (d, 1H), 5.11 (d, 1H), 4.37 (m, 1H), 3.87 (s, 3H), 3.45 (m, 2H), 3.07 (t, 2H), 2.09 (m, 2H), 1.78–1.44 (m, 6H); MS m/z 444 (M+1).

EXAMPLE 97

N-Cyclopentyl-4-[2-(3-fluorophenyl)-7-(4-morpholinyl)pyrazolo[1,5-a]pyridin-3-yl]-2-pyrimidinamine

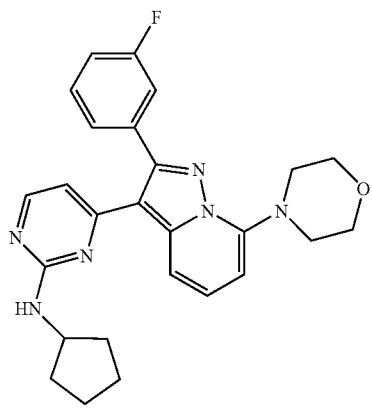

In a similar manner as described for above examples the title compound was prepared as a pale yellow solid. R$_f$ 0.47 (99:1 dichloromethane:methanol); $^1$H NMR (CDCl$_3$) δ 8.11–8.09 (m, 2H), 7.49–7.30 (m, 4H), 7.15 (t, 1 H), 6.40–6.35 (m, 2H), 5.28 (d, 1H), 4.36 (m, 1H), 4.03 (m, 4H), 3.52 (m, 4H), 2.10 (m, 2H), 1.81–1.50 (m, 6H); MS m/z 459 (M+1). Anal. Calcd for C$_{26}$H$_{27}$FN$_6$O: C, 68.10; H, 5.93; N, 18.33. Found: C, 68.07; H, 6.00; N, 18.18.

EXAMPLE 98

N-Cyclopentyl-3-[2-(cyclopentylamino)-4-pyrimidinyl]-2-[3-(trifluoromethyl)phenyl]pyrazolo[1,5-a]pyridin-7-amine

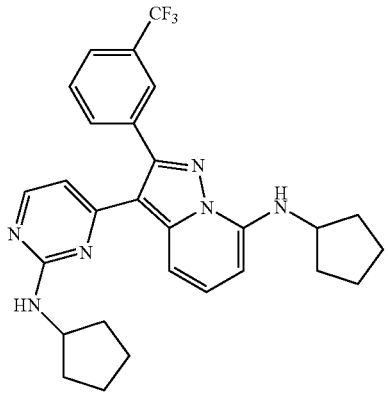

In a similar manner as described for above examples the title compound was prepared as a light yellow solid. R$_f$ 0.22 (4:1 hexanes:ethyl acetate); $^1$H NMR (300 MHz, CDCl$_3$) δ 8.06–8.02 (m, 2H), 7.84 (d, 1H), 7.71–7.67 (m, 2H), 7.55 (t, 1H), 7.34 (t, 1H), 6.32 (d, 1H), 6.07 (d, 1H), 6.03 (d, 1H), 5.08 (d, 1H), 4.28 (m, 1H), 4.03 (m, 1H), 2.17 (m, 2H), 2.04 (m, 2H), 1.86–1.51 (m, 12H); MS m/z 507 (M+1).

EXAMPLE 99

2-(3-Chlorophenyl)-N-cyclopropyl-3-[2-(cyclopropylamino)-4-pyrimidinyl]pyrazolo[1,5-a]pyridin-7-amine

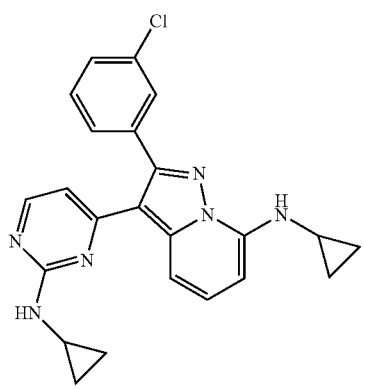

In a similar manner as described for above examples the title compound was prepared as a yellowish-orange solid. $^1$H NMR (CDCl$_3$): δ 8.07 (d, 1H) 7.92 (d, 1H), 7.69 (s, 1H), 7.50 (d, 1H), 7.42–7.34 (m, 3H), 6.41 (d, 1H), 6.37 (d, 1H), 6.30 (s, 1H), 5.35 (s, 1H), 2.84 (m, 1H), 2.68 (m, 1H), 0.90–0.82 (m, 4H), 0.76 (m, 2H), 0.61 (m, 2H); MS m/z 417 (M+1).

EXAMPLE 100

2-(3-Chlorophenyl)-N-cyclopentyl-3-[2-(cyclopropylamino)-4-pyrimidinyl]pyrazolo[1,5-a]pyridin-7-amine

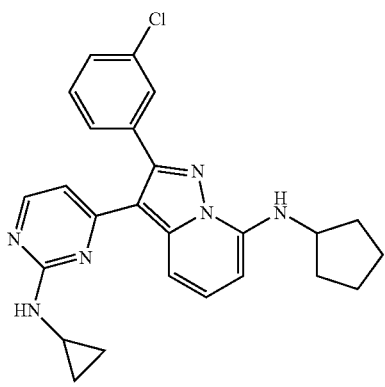

In a similar manner as described for above examples the title compound was prepared as a yellow solid. $R_f$ 0.18 (4:1 hexanes:ethyl acetate); $^1$H NMR (CDCl$_3$): δ 8.07 (d, 1H), 7.85 (d, 1H), 7.71 (s, 1H), 7.52 (d, 1H), 7.42–7.27 (m, 3H), 6.36 (d, 1H), 6.03 (d, 1H), 6.00 (d, 1H), 5.56 (s, 1H), 3.99 (m, 1H), 2.81 (m, 1H), 2.13 (m, 2H), 1.82–1.65 (m, 6H), 0.82 (m, 2H), 0.59 (m, 2H); MS m/z 445 (M+1).

EXAMPLE 101

2-(3-Chlorophenyl)-3-[2-(cyclopentylamino)-4-pyrimidinyl]-N-cyclopropylpyrazolo[1,5-a]pyridin-7-amine

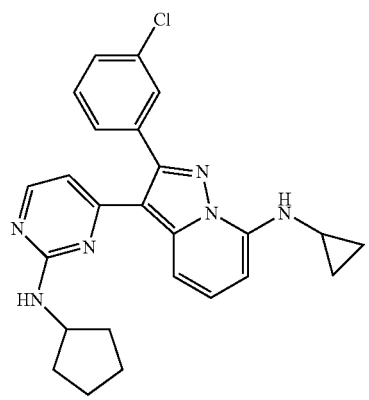

In a similar manner as described for above examples the title compound was prepared as a yellow solid. $R_f$ 0.26 (4:1 hexanes:ethyl acetate); $^1$H NMR (CDCl$_3$) δ 8.03 (d, 1H), 7.76 (d, 1H), 7.68 (s, 1H), 7.49 (d, 1H), 7.41–7.33 (m, 3H), 6.40 (d, 1H), 6.32–6.30 (m, 2H), 5.10 (d, 1H), 4.31 (m, 1H), 2.67 (m, 1H), 2.05 (m, 2H), 1.78–1.50 (m, 6H), 0.89 (m, 2H), 0.75 (m, 2H); MS m/z 445 (M+1). Anal. Calcd for C$_{25}$H$_{25}$ClN$_6$: C, 67.48; H, 5.66; N, 18.89. Found: C, 67.48; H, 5.80; N, 18.62.

EXAMPLE 102

N-Cyclopentyl-3-[2-(cyclopropylamino)-4-pyrimidinyl]-2-(3-fluorophenyl)pyrazolo[1,5-a]pyridin-7-amine

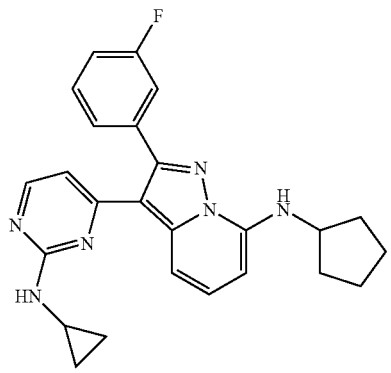

In a similar manner as described for above examples the title compound was prepared as a yellow solid. $R_f$ 0.19 (4:1 hexanes:ethyl acetate); $^1$H NMR (CDCl$_3$): δ 8.11 (d, 1H), 7.90 (d, 1H), 7.48–7.30 (m, 4H), 7.18 (t, 1H), 6.40 (d, 1H), 6.09 (d, 1H), 6.04 (d, 1H), 5.41 (s, 1H), 4.05 (m, 1H), 2.88 (m, 1H), 2.18 (m, 2H), 1.88–1.69 (m, 6H), 0.89 (m, 2H), 0.65 (m, 2H); MS m/z 429 (M+1).

EXAMPLE 103

4-[2-(3-Chlorophenyl)-7-(4-morpholinyl)pyrazolo[1,5-a]pyridin-3-yl]-N-cyclopentyl-2-pyrimidinamine

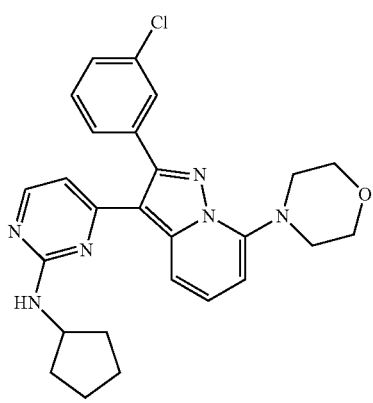

In a similar manner as described for above examples the title compound was prepared as a white solid. $R_f$ 0.49 (99:1 dichloromethane:methanol); $^1$H NMR (DMSO-d$_6$): δ 8.06 (d, 1H), 7.63 (s, 1H), 7.54–7.42 (m, 5H), 7.10 (d, 1H), 6.55 (d, 1H), 6.23 (br, 1H), 4.10 (br, 1H), 3.83 (m, 4H), 3.43 (m, 4H), 1.85 (m, 2H), 1.67 (m, 2H), 1.53–1.45 (m, 4H); MS m/z 475 (M+1). Anal. Calcd for C$_{26}$H$_{27}$ClN$_6$O: C, 65.75; H, 5.73; N, 17.69. Found: C, 65.67; H, 5.83; N, 17.64.

EXAMPLE 104

2-(3-Chlorophenyl)-3-[2-(cyclopentylamino)-4-pyrimidinyl]-N-(2-methoxyethyl)pyrazolo[1,5-a]pyridin-7-amine

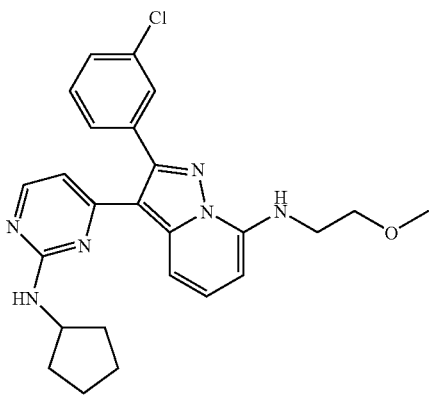

In a similar manner as described for above examples the title compound was prepared as a yellow solid. $R_f$ 0.41 (99:1 dichloromethane:methanol); $^1$H NMR (CDCl$_3$): δ 8.02 (d, 1H), 7.77–7.71 (m, 2H), 7.53 (d, 1H), 7.44–7.32 (m, 3H), 6.34 (d, 1H), 6.30 (t, 1H), 6.08 (d, 1H), 5.28 (br, 1H), 4.34 (m, 1H), 3.73 (t, 2H), 3.59 (m, 2H), 3.44 (s, 3H), 2.07 (m, 2H), 1.80–1.52 (m, 6H); MS m/z 463 (M+1). Anal. Calcd for C$_{25}$H$_{27}$ClN$_6$O: C, 64.86; H, 5.88; N, 18.15. Found: C, 65.03; H, 6.07; N, 18.05.

EXAMPLE 105

3-[2-(Cyclopentylamino)-4-pyrimidinyl]-N-cyclopropyl-2-(3-fluorophenyl)pyrazolo[1,5-a]pyridin-7-amine

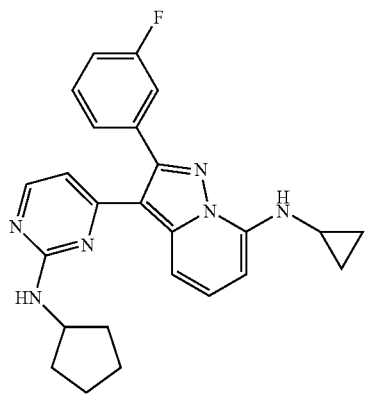

In a similar manner as described for above examples the title compound was prepared as a yellow solid. $R_f$ 0.76 (99:1 dichloromethane:methanol); $^1$H NMR (CDCl$_3$): δ 8.02 (d, 1H), 7.80 (d, 1H), 7.45–7.37 (m, 4H), 7.15 (m, 1H), 6.42 (d, 1H), 6.34–6.32 (m, 2H), 5.20 (br, 1H), 4.34 (m, 1H), 2.69 (m, 1H), 2.07 (m, 2H), 1.80–1.52 (m, 6H), 0.90 (m, 2H), 0.77 (m, 2H); MS m/z 429 (M+1). Anal. Calcd for C$_{25}$H$_{25}$FN$_6$: C, 70.07; H, 5.88; N, 19.61. Found: C, 69.98; H, 5.98; N, 19.35.

EXAMPLE 106

3-[2-(Cyclopentylamino)-4-pyrimidinyl]-2-(3-fluorophenyl)-N-(2-methoxyethyl)pyrazolo[1,5-a]pyridin-7-amine

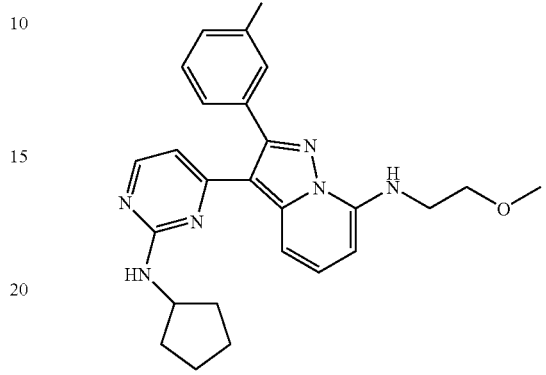

In a similar manner as described for above examples the title compound was prepared as a yellow solid. $R_f$ 0.33 (99:1 dichloromethane:methanol); $^1$H NMR (CDCl$_3$): δ 8.06 (d, 1H), 7.79 (d, 1H), 7.49–7.30 (m, 4H), 7.17 (t, 1H), 6.37–6.30 (m, 2H), 6.09 (d, 1H), 5.18 (br, 1H), 4.37 (m, 1H), 3.75 (m, 2H), 3.61 (m, 2H), 3.47 (s, 3H), 2.10 (m, 2H), 1.81–1.52 (m, 6H); MS m/z 447 (M+1). Anal. Calcd for C$_{25}$H$_{27}$FN$_6$O: C, 67.25; H, 6.09; N, 18.82. Found: C, 67.20; H, 6.09; N, 18.64.

EXAMPLE 107

Biological Activity

In the following example, "MEM" means Minimal Essential Media; "FBS" means Fetal Bovine Serum; "NP40" and "Igepal" are detergents; "MOI" means Multiplicity of Infection; "NaOH" means sodium hydroxide; "MgCl$_2$" means magnesium chloride; "dATP" means deoxyadenosine 5' triphosphate; "dUTP" means deoxyuridine 5' triphosphate; "dCTP" means dexoxycytidine 5' triphosphate; "dGTP" means deoxyguanosine 5' triphosphate; "GuSCN" means Guanidinium thiocyanate; "EDTA" means ethylenediamine tetraacetic acid; "TE" means Tris-EDTA; "SCC" means sodium chloride/sodium citrate; "APE" means a solution of ammonia acetate, ammonia phosphate, EDTA; "PBS" means phosphate buffered saline; and "HRP" means horseradish peroxidase.

a) Tissue Culture and HSV Infection.

Vero 76 cells were maintained in MEM with Earle's salts, L-glutamine, 8% FBS (Hyclone, A-1111-L) and 100 units/mL Penicillin-100 μg/mL Streptomycin. For assay conditions, FBS was reduced to 2%. Cells are seeded into 96-well tissue culture plates at a density of 5×10$^4$ cells/well after being incubated for 45 min at 37° C. in the presence of HSV-1 or HSV-2 (MOI=0.001). Test compounds are added to the wells and the plates are incubated at 37° C. for 40–48 hours. Cell lysates are prepared as follows: media was removed and replaced with 150 μL/well 0.2 N NaOH with 1% Igepal CA 630 or NP-40. Plates were incubated up to 14 days at room temperature in a humidified chamber to prevent evaporation.

(b) Preparation of Detection DNA.

For the detection probe, a gel-purified, digoxigenin-labeled, 710-bp PCR fragment of the HSV UL-15 sequence was utilized. PCR conditions included 0.5 μM primers, 180 μM dTTP, 20 μM dUTP-digoxigenin (Boehringer Mannheim 1558706), 200 μM each of dATP, dCTP, and dGTP, 1×PCR Buffer II (Perkin Elmer), 2.5 mM MgCl$_2$, 0.025 units/μL of AmpliTaq Gold polymerase (Perkin Elmer), and 5 ng of gel-purified HSV DNA per 100 μL Extension conditions were 10 min at 95° C., followed by 30 cycles of 95° C. for 1 min, 55° C. for 30 sec, and 72° C. for 2 min. The amplification was completed with a 10-min incubation at 72° C. Primers were selected to amplify a 728 bp probe spanning a section of the HSV1 UL15 open reading frame (nucleotides 249–977). Single-stranded transcripts were purified with Promega M13 Wizard kits. The final product was mixed 1:1 with a mixture of 6 M GuSCN, 100 mM EDTA and 200 μg/mL herring sperm DNA and stored at 4° C.

(c) Preparation of Capture Plates.

The capture DNA plasmid (HSV UL13 region in pUC) was linearized by cutting with Xba I, denatured for 15 min at 95° C. and diluted immediately into Reacti-Bind DNA Coating Solution (Pierce, 17250, diluted 1:1 with TE buffer, pH 8) at 1 ng/μL 75 μL/well were added to Corning (#3922 or 9690) white 96-well plates and incubated at room temperature for at least 4 hrs before washing twice with 300 μL/well 0.2×SSC/0.05% Tween-20 (SSC/T buffer). The plates were then incubated overnight at room temperature with 150 μL/well 0.2 N NaOH, 1% IGEPAL and 10 μg/mL herring sperm DNA.

d) Hybridization.

Twenty-seven (27) μL of cell lysate was combined with 45 μL of hybridization solution (final concentration: 3M GuSCN, 50 mM EDTA, 100 μg/ml salmon sperm DNA, 5×Denhardt's solution, 0.25×APE, and 5 ng of the digoxigenin-labeled detection probe). APE is 1.5 M NH$_4$-acetate, 0.15 M NH$_4$H$_2$ phosphate, and 5 mM EDTA adjusted to pH 6.0. Mineral oil (50 μL) was added to prevent evaporation. The hybridization plates were incubated at 95° C. for 10 minutes to denature the DNA, then incubated at 42° C. overnight. The wells were washed 6× with 300 μL/well SSC/T buffer then incubated with 75 μL/well anti-digoxigenin-HRP-conjugated antibody (Boehringer Mannheim 1207733, 1:5000 in TE) for 30 min at room temperature. The wells were washed 6× with 300 μL/well with PBS/0.05% Tween-20 before 75 μL/well SuperSignal LBA substrate (Pierce) was added. The plates were incubated at room temperature for 30 minutes and chemiluminescence was measured in a Wallac Victor reader.

e) Results.

The following results were obtained for HSV-1.

| Example No. | IC$_{50}$ (μM) |
| --- | --- |
| 1 | 0.3 |
| 2 | 0.6 |
| 3 | 5 |
| 4 | 1 |
| 5 | 2 |
| 6 | 5 |
| 7 | 0.15 |
| 8 | 3 |
| 9 | 3 |
| 10 | 0.9 |
| 11 | 0.3 |
| 12 | 2 |
| 13 | 1 |
| 15 | 1 |
| 16 | 1 |
| 17 | 1.5 |
| 18 | 9 |
| 19 | 0.5 |
| 20 | 16 |
| 21 | 15 |
| 22 | 0.6 |
| 23 | 2 |
| 24 | 0.9 |
| 25 | 0.2 |
| 26 | 0.6 |
| 27 | 1.5 |
| 28 | 5 |
| 29 | 3 |
| 30 | 0.8 |
| 31 | 2 |
| 32 | 0.6 |
| 33 | 0.8 |
| 34 | 0.6 |
| 35 | 2 |
| 36 | 3 |
| 37 | 3.0 |
| 38 | 0.3 |
| 39 | 0.5 |
| 40 | 2.5 |
| 41 | 3.5 |
| 42 | 1.4 |
| 43 | 0.5 |
| 44 | 1.8 |
| 45 | 22 |
| 46 | 0.2 |
| 48 | >40 |
| 49 | 0.5 |
| 50 | 2.5 |
| 51 | 0.21 |
| 52 | 0.56 |
| 53 | 1.1 |
| 54 | 0.65 |
| 55 | 0.1 |
| 56 | 0.2 |
| 57 | 0.2 |
| 58 | 0.4 |
| 59 | 0.4 |
| 60 | 0.4 |
| 61 | 0.2 |
| 62 | 0.1 |
| 63 | 1.2 |
| 64 | 0.3 |
| 65 | 0.5 |
| 66 | 1.3 |
| 67 | 0.3 |
| 68 | 1.2 |
| 69 | 2.3 |
| 70 | 0.6 |
| 71 | 0.5 |
| 72 | 1.4 |
| 73 | 2.0 |
| 75 | 27 |
| 79 | 2.5 |
| 81 | 0.6 |
| 82 | 0.4 |
| 83 | 0.7 |
| 85 | 4 |
| 86 | 0.6 |
| 87 | 1 |
| 88 | 9 |
| 89 | 0.8 |
| 90 | 0.2 |
| 92 | 0.3 |
| 93 | 0.7 |
| 94 | 6.2 |
| 95 | 0.3 |
| 96 | 1.1 |

-continued

| Example No. | IC$_{50}$ (µM) |
|---|---|
| 97 | 0.7 |
| 98 | 0.3 |
| 99 | 0.5 |
| 100 | 0.3 |
| 101 | 0.2 |
| 102 | 0.7 |
| 103 | 0.5 |
| 104 | 0.2 |
| 105 | 0.6 |
| 106 | 0.2 |

The results demonstrate that the compounds of the present invention are useful for the treatment and prophylaxis of herpes viral infections.

The invention claimed is:

1. A compound of formula (I):

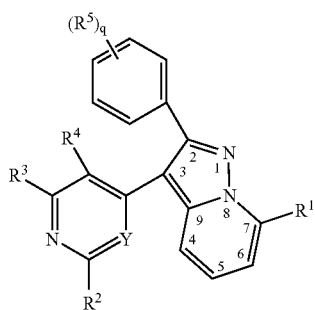

I wherein:
R$^1$ is selected from the group consisting of halo, —NR$^7$R$^8$, Ay, —NR$^7$Ay, Het, —NHR$^{10}$Het, —NHHet and —NHR$^{10}$Ay;
each R$^7$ and R$^8$ are the same or different and are independently selected from the group consisting of H, alkyl, cycloalkyl, alkenyl, cycloalkenyl, —R$^{10}$cycloalkyl, —R$^{10}$OR$^9$, —NR$^9$R$^{11}$, —R$^{10}$NR$^9$R$^{11}$, —R$^{10}$C(O)R$^9$, —C(O)R$^9$, —C(O)R$^{10}$Ay, —C(O)R$^{10}$Het, —CO$_2$R$^9$, —R$^{10}$CO$_2$R$^9$, —C(O)NR$^9$R$^{11}$, —R$^{10}$C(O)NR$^9$R$^{11}$, —R$^{10}$C(O)Ay, —R$^{10}$C(O)Het, —C(S)NR$^9$R$^{11}$, —R$^{10}$C(S)NR$^9$R$^{11}$, —R$^{10}$NHC(NH)NR$^9$R$^{11}$, —R$^{10}$NHC(O)R$^{10}$Het, —R$^{10}$NHC(O)R$^{10}$CO$_2$R$^9$, —R$^{10}$NHC(NCO$_2$R$^9$) NHCO$_2$R$^9$, —R$^{10}$NHC(O)NHSO$_2$R$^9$, —R$^{10}$NHC(O)NHSO$_2$Ay, —R$^{10}$NHC(O)NHSO$_2$Het, —R$^{10}$C(NH)NR$^9$R$^{11}$, —C(NH)NR$^9$R$^{11}$, —SO$_2$NR$^9$R$^{11}$, —R$^{10}$SO$_2$NR$^9$R$^{11}$, —R$^{10}$NHSO$_2$R$^9$, —SO$_2$R$^{10}$, —R$^{10}$SO$_2$R$^{10}$, —R$^{10}$NHCOR$^9$, —R$^{10}$SO$_2$NHCOR$^9$, —R$^{10}$NHP(O)(OR$^9$)$_2$, —R$^{10}$OP(O)(OR$^9$)$_2$ and —R$^{10}$OP(O)(OR$^{10}$Ay)$_2$;

each R$^9$ and R$^{11}$ are the same or different and are independently selected from the group consisting of H, alkyl, cycloalkyl, —R$^{10}$cycloalkyl, —R$^{10}$OH, —R$^{10}$(OR$^{10}$)$_w$ where w is 1–10, and —R$^{10}$NR$^{10}$R$^{10}$;

each R$^{10}$ is the same or different and is independently selected from the group consisting of alkyl, cycloalkyl, alkenyl, cycloalkenyl and alkynyl;
Ay is aryl;
Het is a 5- or 6-membered heterocyclic or heteroaryl group;

R$^2$ is selected from the group consisting of halo, alkyl, cycloalkyl, alkenyl, cycloalkenyl, —NR$^7$R$^8$, —OR$^7$, —OAy, —S(O)$_n$R$^9$, —S(O)$_n$Ay, —R$^{10}$NR$^7$R$^8$, —R$^{10}$NR$^7$Ay, Ay, Het, —NHHet, —NHR$^{10}$Het, —OHet and —OR$^{10}$Het;
n is 0, 1 or 2;
Y is N;
R$^3$ and R$^4$ are the same or different and are each independently selected from the group consisting of H, halo, alkyl, cycloalkyl, alkenyl, Ay, —OR$^7$, —OAy, —R$^{10}$OR$^7$, —R$^{10}$OAy, —NR$^7$R$^8$, —NR$^7$Ay, —R$^{10}$NR$^7$R$^8$, —R$^{10}$NR$^7$Ay, —C(O)R$^7$, —C(O)Ay, —CO$_2$R$^7$, —CO$_2$Ay, —SO$_2$NHR$^9$, Het, —NHHet and —NHR$^{10}$Het;
q is 0, 1, 2, 3, 4 or 5; and
each R$^5$ is the same or different and is independently selected from the group consisting of halo, alkyl, alkenyl, alkynyl, cycloalkyl, cycloalkenyl, —R$^{10}$cycloalkyl, Ay, —NHR$^{10}$Ay, Het, —NHHet, —NHR$^{10}$Het, —OR$^7$, —OAy, —OHet, —R$^{10}$OR$^9$, —NR$^7$R$^8$, —NR$^7$Ay, —R$^{10}$NR$^7$R$^8$, —R$^{10}$NR$^7$Ay, —R$^{10}$C(O)R$^9$, —C(O)R$^9$, —CO$_2$R$^9$, —R$^{10}$CO$_2$R$^9$, —C(O)NR$^7$R$^8$, —C(O)Ay, —C(O)NR$^7$Ay, —C(O) Het, —C(O)NHR$^{10}$Het —R$^{10}$C(O)NR$^9$R$^{11}$, —C(S) NR$^9$R$^{11}$, —R$^{10}$C(S)NR$^9$R$^{11}$, —R$^{10}$NHC(NH)NR$^9$R$^{11}$, —C(NH)NR$^7$R$^8$, —C(NH)NR$^7$Ay, —R$^{10}$C(NH) NR$^9$R$^{11}$, —S(O)$_2$NR$^7$R$^8$, —S(O)$_2$NR$^7$Ay, —R$^{10}$SO$_2$NHCOR$^9$, —R$^{10}$SO$_2$NR$^9$R$^{11}$, —R$^{10}$SO$_2$R$^9$, —S(O)$_n$R$^9$, cyano, nitro and azido; or
two adjacent R$^5$ groups together with the atoms to which they are bonded form a C$_{5-6}$ cycloalkyl or aryl; wherein when q is 1 and R$^5$ is in the para position, R$^5$ is not halo; and
or a pharmaceutically acceptable salt thereof.

2. The compound according to claim 1 wherein R$^1$ is selected from the group consisting of —NR$^7$R$^8$, Ay, —NR$^7$Ay, Het, —NHR$^{10}$Het, —NHHet and —NHR$^{10}$Ay.

3. The compound according to claim 1 wherein R$^1$ is selected from the group consisting of —NR$^7$R$^8$ and Het.

4. The compound according to claim 1 wherein R$^2$ is selected from the group consisting of —NR$^7$R$^8$, —OR$^7$, —OAy, —S(O)$_n$R$^9$, —S(O)$_n$Ay, —R$^{10}$NR$^7$R$^8$, —R$^{10}$NR$^7$Ay, Ay, Het, —NHR$^{10}$Het, —NHHet, —OHet and —OR$^{10}$Het.

5. The compound according to claim 1 wherein R$^2$ is selected from the group consisting of —NR$^7$R$^8$ and Het.

6. The compound according to claim 1 wherein R$^3$ and R$^4$ are the same or different and are each independently selected from the group consisting of H, halo, alkyl, —OR$^7$, —R$^{10}$OR$^7$, —NR$^7$R$^8$, —R$^{10}$NR$^7$R$^8$, —CO$_2$R$^7$ and Ay.

7. The compound according to claim 1 wherein R$^3$ and R$^4$ are each H.

8. The compound according to claim 1 wherein q is 0 or 1.

9. The compound according to claim 1 wherein each R$^5$ is the same or different and is independently selected from the group consisting of halo, alkyl, alkenyl, —OR$^7$, —CO$_2$R$^9$, —NR$^7$R$^8$, —C(O)NR$^7$R$^8$, Ay, —NHR$^{10}$Ay, Het, —S(O)$_2$NR$^7$R$^8$, cyano, nitro and azido.

10. The compound according to claim 1 wherein each R$^5$ is the same or different and is independently selected from the group consisting of halo, alkyl, —OR$^7$, —NR$^7$R$^8$ and cyano.

11. A compound selected from the group consisting of:
N-Cyclopentyl-3-[2-(cyclopentylamino)-4-pyrimidinyl]-2-(4-methoxyphenyl)-pyrazolo[1,5-a]pyridin-7-amine, N-Cyclopentyl-4-[2-(4-methoxyphenyl)-7-(1-pyrrolidinyl)pyrazolo[1,5-a]pyridin-3-yl]-2-pyrimidinamine, 4-[2-(4-Methoxyphenyl)-7-(1-pyrrolidinyl)pyrazolo[1,5-a]pyridin-3-yl]-2-pyrimidinamine, 4-{7-(Cyclopentylamino)-3-[2-(cyclopentylamino)-4-pyrimidinyl]pyrazolo-[1,5-a]pyridin-2-yl}phenol, 4-[3-[2-(Cyclopentylamino)-4-pyrimidinyl]-7-(1-pyrrolidinyl)pyrazolo[1,5-a]pyridin-2-yl]phenol, 4-[3-(2-Amino-4-pyrimidinyl)-7-(1-pyrrolidinyl)pyrazolo[1,5-a]pyridin-2-yl]phenol, 2-[4-(Allyloxy)phenyl]-N-cyclopentyl-3-[2-(cyclopentylamino)-4-pyrimidinyl]pyrazolo-[1,5-a]pyridin-7-amine, Ethyl (4-{7-(cyclopentylamino)-3-[2-(cyclopentylamino)-4-pyrimidinyl]-pyrazolo[1,5-a]pyridin-2-yl}phenoxy)acetate, 2-(4-Butoxyphenyl)-N-cyclopentyl-3-[2-(cyclopentylamino)-4-pyrimidinyl]pyrazolo[1,5-a]pyridin-7-amine, N-Cyclopentyl-3-[2-(cyclopentylamino)-4-pyrimidinyl]-2-(4-isobutoxyphenyl)pyrazolo-[1,5-a]pyridin-7-amine, N-Cyclopentyl-3-[2-(cyclopentylamino)-4-pyrimidinyl]-2-[4-(cyclopropyl-methoxy)-phenyl]pyrazolo[1,5-a]pyridin-7-amine, 2-[4-(Cyclobutylmethoxy)phenyl]-N-cyclopentyl-3-[2-(cyclopentylamino)-4-pyrimidinyl]pyrazolo[1,5-a]pyridin-7-amine, N-Cyclopentyl-3-[2-(cyclopentylamino)-4-pyrimidinyl]-2-(4-phenoxyphenyl)-pyrazolo[1,5-a]pyridin-7-amine, 2-[1,1'-Biphenyl]-4-yl-N-butyl-3-[2-(butylamino)-4-pyrimidinyl]pyrazolo-[1,5-a]pyridin-7-amine, N-{4-[2-(4-Aminophenyl)-7-(butylamino)pyrazolo[1,5-a]pyridin-3-yl]-2-pyrimidinyl}-N-butylamine, N-Butyl-3-[2-(butylamino)-4-pyrimidinyl]-2-[4-(cyclohexylamino)phenyl]-pyrazolo[1,5-a]pyridin-7-amine, N-Butyl-3-[2-(butylamino)-4-pyrimidinyl]-2-(4-isopropenylphenyl)-pyrazolo[1,5-a]pyridin-7-amine, 2-(4-Anilinophenyl)-N-butyl-3-[2-(butylamino)-4-pyrimidinyl]pyrazolo[1,5-a]pyridin-7-amine, 2-(4-Anilinophenyl)-N-butyl-3-[2-(butylamino)-4-pyrimidinyl]-N-phenylpyrazolo[1,5-a]pyridin-7-amine, 2-{4-[Bis(cyclopropylmethyl)amino]phenyl}-N-butyl-3-[2-(butylamino)-4-pyrimidinyl]pyrazolo[1,5-a]pyridin-7-amine, N-butyl-3-[2-(butylamino)-4-pyrimidinyl]-2-{4-[(cyclopropylmethyl)amino]phenyl}-pyrazolo[1,5-a]pyridin-7-amine, N-Butyl -3-[2-(butylamino)-4-pyrimidinyl]-2-[4-(dimethylamino)phenyl]-pyrazolo[1,5-a]pyridin-7-amine, 2-(2-Bromophenyl)-N-cyclopentyl-3-[2-(cyclopentylamino)-4-pyrimidinyl]pyrazolo[1,5-a]pyridin-7-amine, 2-(3-Bromophenyl)-N-cyclopentyl-3-[2-(cyclopentylamino)-4-pyrimidinyl]pyrazolo[1,5-a]pyridin-7-amine, 4-[2-(3-Bromophenyl)-7-(1-pyrrolidinyl)pyrazolo[1,5-a]pyridin-3-yl]-N-cyclopentyl-2-pyrimidinamine, N-[3-(2-Amino-4-pyrimidinyl)-2-(3-bromophenyl)pyrazolo[1,5-a]pyridin-7-yl]-N-cyclopentylamine, 4-[2-(3-Bromophenyl)-7-(1-pyrrolidinyl)pyrazolo[1,5-a]pyridin-3-yl]-2-pyrimidinamine, 2-[1,1'-Biphenyl]-3-yl-N-cyclopentyl-3-[2-(cyclopentylamino)-4-pyrimidinyl]pyrazolo-[1,5-a]pyridin-7-amine, 4-[2-[1,1'-Biphenyl]-3-yl-7-(1-pyrrolidinyl)pyrazolo[1,5-a]pyridin-3-yl]-N-cyclopentyl-2-pyrimidinamine, N-Cyclopentyl -3-[2-(cyclopentylamino)-4-pyrimidinyl]-2-[3-(4-pyridinyl)phenyl]-pyrazolo[1,5-a]pyridin-7-amine, N-Cyclopentyl-3-[2-(cyclopentylamino)-4-pyrimidinyl]-2-[3-(3-thienyl)phenyl]pyrazolo-[1,5-a]pyridin-7-amine, N-Cyclopentyl-3-[2-(cyclopentylamino)-4-pyrimidinyl]-2-[3-(2-thienyl)-phenyl]pyrazolo[1,5-a]pyridin-7-amine, 2-(3-Aminophenyl)-N-cyclopentyl-3-[2-(cyclopentylamino)-4-pyrimidinyl]pyrazolo[1,5-a]pyridin-7-amine, N-(3-{7-(Cyclopentylamino)-3-[2-(cyclopentylamino)-4-pyrimidinyl]pyrazolo[1,5-a]pyridin-2-yl}phenyl)acetamide, N-(3-{7-(Cyclopentylamino)-3-[2-(cyclopentylamino)-4-pyrimidinyl]-pyrazolo[1,5-a]pyridin-2-yl}phenyl)methanesulfonamide, 4-[2-(3-Aminophenyl)-7-(1-pyrrolidinyl)pyrazolo[1,5-a]pyridin-3-yl]-N-cyclopentyl-2-pyrimidinamine, N-cyclopentyl-3-[2-(cyclopentylamino)-4-pyrimidinyl]-2-phenylpyrazolo-[1,5-a]pyridin-7-amine, 3-{7-(Cyclopentylamino)-3-[2-(cyclopentylamino)-4-pyrimidinyl]pyrazolo[1,5-a]pyridin-2-yl}benzonitrile, 3-{7-(Cyclopentylamino)-3-[2-(cyclopentylamino)-4-pyrimidinyl]-pyrazolo[1,5-a]pyridin-2-yl}benzamide, 3-{7-(Cyclopentylamino)-3-[2-(cyclopentylamino)-4-pyrimidinyl]pyrazolo-[1,5-a]pyridin-2-yl}benzoic acid, N-{4-[2-(3-Bromo-4-methoxyphenyl)-7-(cyclopentylamino)pyrazolo[1,5-a]pyridin-3-yl]-2-pyrimidinyl}-N-cyclopentylamine, 2-(3-Bromo-4-chlorophenyl)-N-cyclopentyl-3-[2-(cyclopentylamino)-4-pyrimidinyl]-pyrazolo[1,5-a]pyridin-7-amine, 2-(3-Amino-4-chlorophenyl)-N-cyclopentyl-3-[2-(cyclopentylamino)-4-pyrimidinyl]pyrazolo[1,5-a]pyridin-7-amine, 2-[4-(Benzylamino)phenyl]-N-butyl-3-[2-(butylamino)-4-pyrimidinyl]-pyrazolo[1,5-a]pyridin-7-amine, N-Cyclopentyl-3-[2-(cyclopentylamino)-4-pyrimidinyl]-2-(3-methylphenyl)pyrazolo[1,5-a]pyridin-7-amine, 4-[7-Chloro-2-(3-methylphenyl)pyrazolo[1,5-a]pyridin-3-yl]-N-cyclopentyl-5,6-dimethyl-2-pyrimidinamine, N-cyclopentyl-3-[2-(cyclopentylamino)-5,6-dimethyl-4-pyrimidinyl]-2-(3-methylphenyl)pyrazolo[1,5-a]pyridin-7-amine, 3-[2-(Cyclopentylamino)-4-pyrimidinyl]-N-isopropyl-2-(3-methylphenyl)pyrazol[1,5-a]pyridin-7-amine, 4-[7-Chloro-2-(3-methoxyphenyl)pyrazolo[1,5-a]pyridin-3-yl]-N-cyclopentyl-2-pyrimidinamine, N-Cyclopentyl-3-[2-(cyclopentylamino)-4-pyrimidinyl]-2-(3-methoxyphenyl)pyrazolo[1,5-a]pyridin-7-amine, 3-[2-(Cyclopentylamino)-4-pyrimidinyl]-N-isopropyl-2-(3-methoxyphenyl)pyrazolo[1,5-a]pyridin-7-amine, 3-[2-(Cyclopentylamino)-4-pyrimidinyl]-2-(3-methoxyphenyl)-N,N-dimethylpyrazolo[1,5-a]pyridin-7-amine, 3-{7-(Cyclopentylamino)-3-[2-(cyclopentylamino)-4-pyrimidinyl]pyrazolo[1,5-a]pyridin-2-yl}phenol, N-Cyclopentyl-3-[2-(cyclopentylamino)-4-pyrimidinyl]-2-[3-(cyclopropylmethoxy)phenyl]pyrazolo[1,5-a]pyridin-7-amine, N-Cyclopentyl-3-[2-(cyclopentylamino)-4-pyrimidinyl]-2-(3-fluorophenyl)pyrazolo[1,5-a]pyridin-7-amine, 2-(3-Chlorophenyl)-N-cyclopentyl-3-[2-(cyclopentylamino)-4-pyrimidinyl]pyrazolo[1,5-a]pyridin-7-amine, N-Cyclopentyl-3-[2-(cyclopropylamino)-4-pyrimidinyl]-2-(4-methoxyphenyl)pyrazolo[1,5-a]pyridin-7-amine,
3-[2-(Cyclopentylamino)-4-pyrimidinyl]-2-(4-methoxyphenyl)-N-[2-(4-morpholinyl)ethyl]pyrazolo[1,5-a]pyridin-7-amine,
3-[2-(Cyclopentylamino)-4-pyrimidinyl]-N-cyclopropyl-2-(4-methoxyphenyl)pyrazolo[1,5-a]pyridin-7-amine,
N-Cyclopentyl-4-[2-(4-methoxyphenyl)-7-(4-morpholinyl)pyrazolo[1,5-a]pyridin-3-yl]-2-pyrimidinamine,
3-[2-(Cyclopentylamino)-4-pyrimidinyl]-N-(2-methoxyethyl)-2-(4-methoxyphenyl)pyrazolo[1,5-a]pyridin-7-amine,
N-Cyclopropyl-4-[2-(4-methoxyphenyl)-7-(4-morpholinyl)pyrazolo[1,5-a]pyridin-3-yl]-2-pyrimidinamine,
3-[2-(Cyclopropylamino)-4-pyrimidinyl]-N-(2-methoxyethyl)-2-(4-methoxyphenyl)pyrazolo[1,5-a]pyridin-7-amine,
3-[2-(Cyclopropylamino)-4-pyrimidinyl]-2-(4-methoxyphenyl)-N-[2-(4-morpholinyl)ethyl]pyrazolo[1,5-a]pyridin-7-amine,
N-Cyclopropyl-3-[2-(cyclopropylamino)-4-pyrimidinyl]-2-(4-methoxyphenyl)pyrazolo[1,5-a]pyridin-7-amine,
4-[3-[2-(Cyclopentylamino)-4-pyrimidinyl]-7-(cyclopropylamino)pyrazolo[1,5-a]pyridin-2-yl]phenol,
4-{7-(Cyclopentylamino)-3-[2-(cyclopropylamino)-4-pyrimidinyl]pyrazolo[1,5-a]pyridin-2-yl}phenol,
4-{7-(Cyclopropylamino)-3-[2-(cyclopropylamino)-4-pyrimidinyl]pyrazolo[1,5-a]pyridin-2-yl}phenol,
3-[2-(Cyclopentylamino)-4-pyrimidinyl]-N-cyclopropyl-2-[4-(cyclopropylmethoxy)phenyl]pyrazolo[1,5-a]pyridin-7-amine,
2-[4-(Allyloxy)phenyl]-N-cyclopentyl-3-[2-(cyclopropylamino)-4-pyrimidinyl]pyrazolo[1,5-a]pyridin-7-amine,
N-Cyclopropyl-3-[2-(cyclopropylamino)-4-pyrimidinyl]-2-[4-(cyclopropylmethoxy)phenyl]pyrazolo[1,5-a]pyridin-7-amine,
2-[4-(Allyloxy)phenyl]-N-cyclopropyl-3-[2-(cyclopropylamino)-4-pyrimidinyl]pyrazolo[1,5-a]pyridin-7-amine,
N-Butyl-3-[2-(butylamino)pyrimidin-4-yl]-2-{4-[(4-methoxybenzyl)amino]phenyl}pyrazolo[1,5-a]pyridin-7-amine,
N-Butyl-3-[2-(butylamino)pyrimidin-4-yl]-2-(4-morpholin-4-yl phenyl)pyrazolo[1,5-a]pyridin-7-amine,
2-(3-Bromophenyl)-N-cyclopentyl-3-[2-(cyclopropylamino)-4-pyrimidinyl]pyrazolo[1,5-a]pyridin-7-amine,
2-(3-Bromophenyl)-3-[2-(cyclopentylamino)-4-pyrimidinyl]-N-cyclopropylpyrazolo[1,5-a]pyridin-7-amine,
2-(3-Bromophenyl)-N-cyclopropyl-3-[2-(cyclopropylamino)-4-pyrimidinyl]pyrazolo[1,5-a]pyridin-7-amine,
Methyl N-[3-[2-(cyclopentylamino)pyrimidin-4-yl]-2-(4-methoxyphenyl)pyrazolo[1,5-a]pyridin-7-yl]glycinate,
5-[(3aS,4S,6aR)-2-Oxohexahydro-1H-thieno[3,4-d]imidazol-4-yl]-N-(4-{7-(butylamino)-3-[2-(butylamino)pyrimidin-4-yl]pyrazolo[1,5-a]pyridin-2-yl}phenyl)pentanamide,
N-[3-[2-(Cyclopentylamino)pyrimidin-4-yl]-2-(4-methoxyphenyl)pyrazolo[1,5-a]pyridin-7-yl]butane-1,4-diamine,
5-[(3aS,4S,6aR)-2-Oxohexahydro-1H-thieno[3,4-d]imidazol-4-yl]-N-(4-{[3-[2-(cyclopentylamino)pyrimidin-4-yl]-2-(4-methoxyphenyl)pyrazolo[1,5-a]pyridin-7-yl]amino}butyl)pentanamide,
3-[2-(Cyclopentylamino)pyrimidin-4-yl]-2-(4-methoxyphenyl)pyrazolo[1,5-a]pyridin-7-amine,
N,N'-di-tert-butoxycarbonyl-N-(4-{[3-[2-(cyclopentylamino)pyrimidin-4-yl]-2-(4-methoxyphenyl)pyrazolo[1,5-a]pyridin-7-yl]amino}butyl)guanidine,
N-(4-{[3-[2-(Cyclopentylamino)pyrimidin-4-yl]-2-(4-methoxyphenyl)pyrazolo[1,5-a]pyridin-7-yl]amino}butyl)guanidine,
N-(4-{[3-[2-(Cyclopentylamino)pyrimidin-4-yl]-2-(4-methoxyphenyl)pyrazolo[1,5-a]pyridin-7-yl]amino}butyl)methanesulfonamide,
N-{[(4-{[3-[2-(Cyclopentylamino)pyrimidin-4-yl]-2-(4-methoxyphenyl)pyrazolo[1,5-a]pyridin-7-yl]amino}butyl)amino]carbonyl}-4-methylbenzenesulfonamide,
4-[(4-{[3-[2-(Cyclopentylamino)pyrimidin-4-yl]-2-(4-methoxyphenyl)pyrazolo[1,5-a]pyridin-7-yl]amino}butyl)amino]-4-oxobutanoic acid,
Diethyl 4-{[3-[2-(cyclopentylamino)pyrimidin-4-yl]-2-(4-methoxyphenyl)pyrazolo[1,5-a]pyridin-7-yl]amino}butylamidophosphate,
4-{[3-[2-(Cyclopentylamino)pyrimidin-4-yl]-2-(4-methoxyphenyl)pyrazolo[1,5-a]pyridin-7-yl]amino}butan-1-ol,
Dibenzyl 4-{[3-[2-(cyclopentylamino)pyrimidin-4-yl]-2-(4-methoxyphenyl)pyrazolo[1,5-a]pyridin-7-yl]amino}butyl phosphate,
4-{[3-[2-(Cyclopentylamino)pyrimidin-4-yl]-2-(4-methoxyphenyl)pyrazolo[1,5-a]pyridin-7-yl]amino}butyl phosphate diammonium salt,
2-(3-Azidophenyl)-N-cyclopentyl-3-[2-(cyclopentylamino)pyrimidin-4-yl]pyrazolo[1,5-a]pyridin-7-amine,
3-[2-(Cyclopentylamino)-4-pyrimidinyl]-2-(4-methoxyphenyl)-N-[2-oxo-2-(1-pyrrolidinyl)ethyl]pyrazolo[1,5-a]pyridin-7-amine,
N-(2-{[3-[2-(Cyclopentylamino)-4-pyrimidinyl]-2-(4-methoxyphenyl)pyrazolo[1,5-a]pyridin-7-yl]amino}ethyl)methanesulfonamide,
$N^1$-[3-[2-(Cyclopentylamino)-4-pyrimidinyl]-2-(4-methoxyphenyl)pyrazolo[1,5-a]pyridin-7-yl]-1,2-ethanediamine,
N-Cyclopentyl-4-[2-(3-fluorophenyl)-7-(4-morpholinyl)pyrazolo[1,5-a]pyridin-3-yl]-2-pyrimidinamine,
N-Cyclopentyl-3-[2-(cyclopentylamino)-4-pyrimidinyl]-2-[3-(trifluoromethyl)phenyl]pyrazolo[1,5-a]pyridin-7-amine,
2-(3-Chlorophenyl)-N-cyclopropyl-3-[2-(cyclopropylamino)-4-pyrimidinyl]pyrazolo[1,5-a]pyridin-7-amine,
2-(3-Chlorophenyl)-N-cyclopentyl-3-[2-(cyclopropylamino)-4-pyrimidinyl]pyrazolo[1,5-a]pyridin-7-amine,
2-(3-Chlorophenyl)-3-[2-(cyclopentylamino)-4-pyrimidinyl]-N-cyclopropylpyrazolo[1,5-a]pyridin-7-amine,
N-Cyclopentyl-3-[2-(cyclopropylamino)-4-pyrimidinyl]-2-(3-fluorophenyl)pyrazolo[1,5-a]pyridin-7-amine,
4-[2-(3-Chlorophenyl)-7-(4-morpholinyl)pyrazolo[1,5-a]pyridin-3-yl]-N-cyclopentyl-2-pyrimidinamine,
2-(3-Chlorophenyl)-3-[2-(cyclopentylamino)-4-pyrimidinyl]-N-(2-methoxyethyl)pyrazolo[1,5-a]pyridin-7-amine,
3-[2-(Cyclopentylamino)-4-pyrimidinyl]-N-cyclopropyl-2-(3-fluorophenyl)pyrazolo[1,5-a]pyridin-7-amine,
3-[2-(Cyclopentylamino)-4-pyrimidinyl]-2-(3-fluorophenyl)-N-(2-methoxyethyl)pyrazolo[1,5-a]pyridin-7-amine, and pharmaceutically acceptable salts thereof.

12. A pharmaceutical composition comprising a compound according to claim 1.

13. The pharmaceutical composition according to claim 12 further comprising a pharmaceutically acceptable carrier or diluent.

14. The pharmaceutical composition according to claim 12 further comprising an antiviral agent selected from the group consisting of aciclovir and valaciclovir.

15. A method for the treatment of a herpes viral infection selected from HSV-1 and HSV-2 in an animal, said method comprising administering to the animal a therapeutically effective amount of a compound according to claim 1.

16. A method for the treatment of a condition or disease associated with a herpes viral infection selected from HSV-1 and HSV-2 in an animal, comprising administering to the animal a therapeutically effective amount of a compound according to claim 1.

17. A process for preparing the compound according to claim 1 wherein R² is selected from the group consisting of alkyl, cycloalkyl, alkenyl, cycloalkenyl, —NR⁷R⁸, —OR⁷, Ay, —OAy, —S(O)ₙR⁹, —S(O)ₙAy, —R¹⁰NR⁷R⁸, —R¹⁰NR⁷Ay, Het, —NHHet, —NHR¹⁰Het, —OHet, and —OR¹⁰Het, and R³ and R⁴ are H, said process comprising reacting a compound of formula (IX):

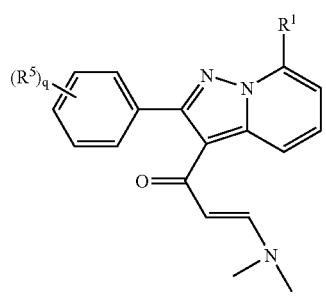

IX with an amine of formula (X):

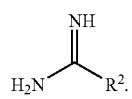

X

18. A process for preparing the compound according to claim 1 wherein R² is selected from the group consisting of alkyl, cycloalkyl, alkenyl, cycloalkenyl, —NR⁷R⁸, —OR⁷, Ay, —OAy, —S(O)ₙR⁹, —S(O)ₙAy, —R¹⁰NR⁷R⁸, —R¹⁰NR⁷Ay, Het, —NHHet, —NHR¹⁰Het, —OHet, and —OR¹⁰Het; R³ is selected from the group consisting of H, alkyl, cycloalkyl, alkenyl, —R¹⁰OR⁷, —R¹⁰OAy, —NR⁷R⁸ where R⁷ and R⁸ are not H, Ay, —NR⁷Ay where R⁷ is not H, —R¹⁰NR⁷R⁸, —R¹⁰NR⁷Ay, —C(O)R⁷, —C(O)Ay, —CO₂R⁷, —CO₂Ay, —SO₂NHR⁹ and Het; and R⁴ is H, said process comprising reacting a compound of formula (XVI):

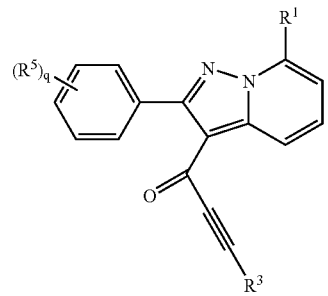

XVI with an amine of formula (X):

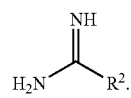

X

19. A process for preparing the compound according to claim 1 wherein and R² is selected from the group consisting of alkyl, cycloalkyl, alkenyl, cycloalkenyl, —NR⁷R⁸, —OR⁷, Ay, —OAy, —S(O)ₙR⁹, —S(O)ₙAy, —R¹⁰NR⁷R⁸, —R¹⁰NR⁷Ay, Het, —NHHet, —NHR¹⁰Het, —OHet, and —OR¹⁰Het, said process comprising the steps of:

a) reacting a compound of formula (XX):

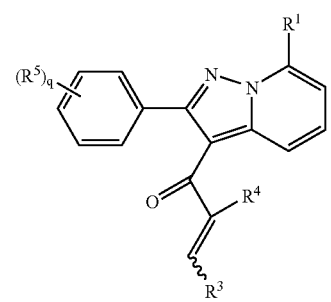

XX with an amine of formula (X):

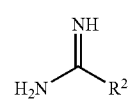

X to prepare an intermediate compound; and b) oxidizing the intermediate compound.

20. A process for preparing the compound according to claim 1, said process comprising reacting a compound of formula (XXII):

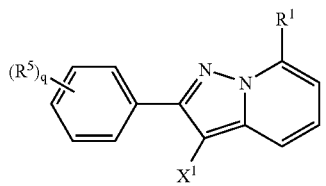

XXII wherein $X^1$ is chloro, bromo or iodo;

with a compound of formula XXIV:

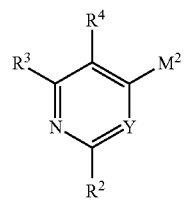

XXIV wherein $M^2$ is selected from the group consisting of —$B(OH)_2$, —$B(ORa)_2$, —$B(Ra)_2$, —$Sn(Ra)_3$, Zn-halide, ZnRa, and Mg-halide where Ra is alkyl or cycloalkyl and halide is halo.

* * * * *